US009433687B2

(12) United States Patent
Geles et al.

(10) Patent No.: US 9,433,687 B2
(45) Date of Patent: Sep. 6, 2016

(54) ANTI-NOTCH3 ANTIBODIES AND ANTIBODY-DRUG CONJUGATES

(71) Applicant: Pfizer Inc., New York, NY (US)

(72) Inventors: Kenneth G. Geles, Nyack, NY (US); Yijie Gao, Chestnut Hill, MA (US); Puja Sapra, River Edge, NJ (US); Lioudmila Gennadievna Tchistiakova, Stoneham, MA (US); Bin-Bing Stephen Zhou, Rohnert Park, CA (US)

(73) Assignee: Pfizer Inc., New York, NY (US)

( * ) Notice: Subject to any disclaimer, the term of this patent is extended or adjusted under 35 U.S.C. 154(b) by 123 days.

(21) Appl. No.: 14/073,273

(22) Filed: Nov. 6, 2013

(65) Prior Publication Data

US 2014/0127211 A1 May 8, 2014

Related U.S. Application Data

(60) Provisional application No. 61/889,744, filed on Oct. 11, 2013, provisional application No. 61/723,772, filed on Nov. 7, 2012.

(51) Int. Cl.

| C07K 16/18 | (2006.01) |
| C07K 16/28 | (2006.01) |
| C07K 16/30 | (2006.01) |
| A61K 39/395 | (2006.01) |
| A61K 47/48 | (2006.01) |
| C07K 16/32 | (2006.01) |
| A61K 39/00 | (2006.01) |

(52) U.S. Cl.
CPC ....... *A61K 47/48438* (2013.01); *A61K 39/395* (2013.01); *A61K 47/48561* (2013.01); *A61K 47/48569* (2013.01); *A61K 47/48584* (2013.01); *A61K 47/48592* (2013.01); *A61K 47/48638* (2013.01); *A61K 47/48715* (2013.01); *C07K 16/28* (2013.01); *C07K 16/32* (2013.01); *A61K 39/3955* (2013.01); *A61K 2039/505* (2013.01); *C07K 16/2866* (2013.01); *C07K 16/30* (2013.01); *C07K 2316/96* (2013.01); *C07K 2317/24* (2013.01); *C07K 2317/51* (2013.01); *C07K 2317/515* (2013.01); *C07K 2317/56* (2013.01); *C07K 2317/565* (2013.01); *C07K 2317/732* (2013.01); *C07K 2317/75* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 4,816,397 A | 3/1989 | Boss et al. |
| 4,816,567 A | 3/1989 | Cabilly et al. |
| 5,225,539 A | 7/1993 | Winter et al. |
| 5,545,806 A | 8/1996 | Lonberg et al. |
| 5,569,825 A | 10/1996 | Lonberg et al. |
| 5,585,089 A | 12/1996 | Queen et al. |
| 5,591,828 A | 1/1997 | Bosslet et al. |
| 5,616,462 A | 4/1997 | Joutel et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,840,699 A | 11/1998 | Sakakibara et al. |
| 5,985,837 A | 11/1999 | Ritter et al. |
| 6,124,431 A | 9/2000 | Sakakibara et al. |
| 6,180,370 B1 | 1/2001 | Queen et al. |
| 6,537,775 B1 | 3/2003 | Tournier-Lasserve et al. |
| 6,884,869 B2 | 4/2005 | Senter et al. |
| 7,022,500 B1 | 4/2006 | Queen et al. |
| 7,521,425 B2 | 4/2009 | Bradshaw et al. |
| 7,750,116 B1 | 7/2010 | Doronina et al. |
| 2004/0058414 A1 | 3/2004 | Queen et al. |
| 2005/0026831 A1 | 2/2005 | Bodmer et al. |
| 2005/0137130 A1 | 6/2005 | Bodmer et al. |
| 2006/0263774 A1 | 11/2006 | Clark et al. |
| 2007/0224201 A1 | 9/2007 | Wu et al. |
| 2008/0226621 A1* | 9/2008 | Fung ............ C07K 14/705 424/130.1 |
| 2013/0129753 A1* | 5/2013 | Doroski ............ C07K 7/02 424/179.1 |

FOREIGN PATENT DOCUMENTS

| EP | 0 171 496 B1 | 2/1986 |
| EP | 0 173 494 A2 | 3/1986 |
| EP | 0 184 187 A2 | 6/1986 |
| EP | 0 404 097 A2 | 12/1990 |
| EP | 0 695 758 B1 | 2/1996 |
| EP | 0 780 478 A1 | 6/1997 |
| WO | 86/01533 A1 | 3/1986 |
| WO | 87/02671 A1 | 5/1987 |
| WO | 93/11161 A1 | 6/1993 |
| WO | 94/07474 A1 | 4/1994 |
| WO | 95/09864 A1 | 4/1995 |
| WO | 96/33212 A1 | 10/1996 |
| WO | 97/34631 A1 | 9/1997 |
| WO | 98/05775 A1 | 2/1998 |
| WO | 00/20576 A2 | 4/2000 |

(Continued)

OTHER PUBLICATIONS

Lee et al. Molecular cloning of agonistic and antagonistic monoclonal antibodies against human 4-1BB. Eur J Immunogenet 29: 449-452, 2002.*
Richter et al. Antagonistic TNF receptor one-specific antibody (ATROSAB): receptor binding and in vitro bioactivity. PLOS One 8(8): e72156, 2013, 13 pages.*
Rimm et al. Identification of functional regions on the tail of Acanthamoeba myosin-II using recombinant fusion protein. I. High resolution epitope mapping and characterization of monoclonal antibody binding sites. J Cell Biol 111(6 Pt 1): 2405-2416, 1990.*
Paes et al, "Atomic-Level Mapping of Antibody Epitopes on a GPCR", J. Am. Chem. Soc. 131:6952-6954 (2009).
Palanki et al, "Development of novel linkers to conjugate pharmacophores to a carrier antibody", Bioorganic & Medicinal Chemistry Letters 22:4249-4253 (2012).

(Continued)

*Primary Examiner* — Bridget E Bunner
(74) *Attorney, Agent, or Firm* — Carol A. McKeever

(57) ABSTRACT

The present invention provides for anti-Notch3 antibodies, anti-Notch3 antibody-drug conjugates and methods for preparing and using the same.

64 Claims, 28 Drawing Sheets

(56) References Cited

FOREIGN PATENT DOCUMENTS

| | | |
|---|---|---|
| WO | 01/18032 A2 | 3/2001 |
| WO | 03/020934 A1 | 3/2003 |
| WO | 03/041735 A2 | 5/2003 |
| WO | 2004/001004 A2 | 12/2003 |
| WO | 2005/054434 A2 | 6/2005 |
| WO | 2005/081711 A2 | 9/2005 |
| WO | 2006/015375 A2 | 2/2006 |
| WO | 2006/053063 A2 | 5/2006 |
| WO | 2007/008848 A2 | 1/2007 |
| WO | 2007/061988 A2 | 5/2007 |
| WO | 2007/103114 A2 | 9/2007 |
| WO | 2008/051797 A2 | 5/2008 |
| WO | 2008/052187 A2 | 5/2008 |
| WO | 2008/057144 A2 | 5/2008 |
| WO | 2008/076960 A2 | 6/2008 |
| WO | 2008/136848 A2 | 11/2008 |
| WO | 2009/036167 A1 | 3/2009 |
| WO | 2009/048967 A1 | 4/2009 |
| WO | 2009/117531 A1 | 9/2009 |
| WO | 2009/124931 A2 | 10/2009 |
| WO | 2010/005566 A2 | 1/2010 |
| WO | 2010/005567 A2 | 1/2010 |
| WO | 2010/129304 A2 | 11/2010 |
| WO | 2010/141249 A2 | 12/2010 |
| WO | 2010/146550 A1 | 12/2010 |
| WO | 2011/041336 A2 | 4/2011 |
| WO | 2011/140295 A2 | 11/2011 |
| WO | 2012/007896 A1 | 1/2012 |
| WO | 2012/058137 A2 | 5/2012 |
| WO | 2012/059882 A2 | 5/2012 |
| WO | 2012/064697 A2 | 5/2012 |
| WO | 2012/080891 A1 | 6/2012 |
| WO | 2012/080926 A2 | 6/2012 |
| WO | 2012/112792 A2 | 8/2012 |
| WO | 2012/131527 A1 | 10/2012 |
| WO | 2013/072813 A2 | 5/2013 |
| WO | 2013/093809 A1 | 6/2013 |

OTHER PUBLICATIONS

Pettit et al, "The Absolute Configuration and Synthesis of Natural (--)-Dolastatin 101", J. Am. Chem. Soc. 111:5463-5465 (1989).
Pettit et al, "Antineoplastic agents 365. Dolastatin 10 SAR probes", Anti-Cancer Drug Design 13:243-277 (1998).
Pettit et al, "Antineoplastic Agents. 592. Highly Effective Cancer Cell Growth Inhibitory Structural Modifications of Dolastatin 10", Journal of Natural Products 74:962-968 (2011).
Ploscariu et al, "Single Molecule Studies of Force-Induced S2 Site Exposure in the Mammalian Notch Negative Regulatory Domain", The Journal of Physical Chemistry B 118(18):4761-4770 (2014).
Plückthun, "Antibodies from *Escherichia coli*", The Pharmacology of Monoclonal Antibodies, Chapter 11, 113:269-315 (1994).
Presta, "Antibody engineering", Current Opinion in Structural Biology 2:593-596 (1992).
Quan et al, "The Rise of Antibodies as Therapeutics", n Anti-IgE and Allergic Disease, Chapter 20, pp. 427-469 (2002).
Radtke et al, "The Role of Notch in Tumorigenesis: Oncogene or Tumour Suppressor?", Nature Reviews—Cancer 3:756-767 (2003).
Rand et al, "Calcium Depletion Dissociates and Activates Heterodimeric Notch Receptors", Molecular and Cellular Biology 20(5):1825-1835 (2000).
Reedijk et al, "High-level Coexpression of JAG1 and NOTCH1 is Observed in Human Breast Cancer and is Associated with Poor Overall Survival", Cancer Research 65:8530-8537 (2005).
Ridgway et al, "Inhibition of Dll4 signalling inhibits tumour growth by deregulating angiogenesis", Nature 444:1083-1087 (2006).
Riechmann et al, "Reshaping human antibodies for therapy", Nature 332:323-329 (1988).
Rockberg et al, "Epitope Mapping of Antibodies Using Bacterial Surface Display", Nature Methods 5(12):1039-1045 (2008).
Roy et al, "The multifaceted role of Notch in cancer", Current Opinion in Genetics & Development 17:52-59 (2007).

Said et al, "Involucrin in Lung Tumors: A Specific Marker for Squamos Differentiation", Laboratory Investigation 49(5):563-568 (1983).
Sanchez-Irizarry et al, "Notch Subunit Heterodimerization and Prevention of Ligand-Independent Proteolytic Activation Depend, Respectively, on a Novel Domain and the LNR Repeats", Molecular and Cellular Biology 24 (21):9265-9273 (2004).
Schroeter et al, "Notch-1 signalling requires ligand-induced proteolytic release of intracellular domain", Nature 393:382-386 (1998).
Shaw et al, "Mouse/Human Chimeric Antibodies to a Tumor-Associated Antigen: Biologic Activity of the Four Human IgG Subclasses", J. Natl. Cancer Inst. 80(19):1553-1559 (1988).
Siedlecki et al, "Array Synthesis of Novel Lipodepsipeptide", Bioorganic & Medicinal Chemistry Letters 13:4245-4249 (2003).
Stephenson et al, "Direct observation of proteolytic cleavage at the S2 site upon forced unfolding of the Notch negative regulatory region", Proceedings of the National Academy of Sciences USA 109(41):E2757-E2765 (2012).
Sun et al, "Chimeric antibody with human constant regions and mouse variable regions directed against carcinoma-associated antigen 17-1A", Proceedings of the National Academy of Sciences USA 84:214-218 (1987).
Teng et al, "Construction and testing of mouse-human heteromyelomas for human monoclonal antibody production", Proceedings of the National Academy of Sciences USA 80:7308-7312 (1983).
Tiyanont et al, "Insights into Notch3 Activation and Inhibition Mediated by Antibodies Directed against Its Negative Regulatory Region", Journal of Molecular Biology 425(17):3192-3204 (2013).
Tun et al, "Recognition Sequence of a Highly Conserved DNA Binding Protein RBP-Jx", Nucleic Acids Research 22 (6):965-971 (1994).
van Es et al, "Notch/y-secretase inhibition turns proliferative cells in intestinal crypts and adenomas into goblet cells", Nature 435:959963 (2005).
Vardar et al, "Nuclear Magnetic Resonance Structure of a Prototype Lin12-Notch Repeat Module from Human Notch1", Biochemistry 42:7061-7067 (2003).
Verhoeyen et al, "Reshaping Human Antibodies: Grafting an Antilysozyme Activity", 239(#4847):1534-1536 (1988).
Weng et al, "Activating Mutations of NOTCH1 in Human T Cell Acute Lymphoblastic Leukemia", Science 306 (#5694):269-271 (2004).
Wood et al, "The synthesis and in vivo assembly of functional antibodies in yeast", Nature 314:446-449 (1985).
Zoller et al, "Oligonucleotide-directed mutagenesis using M13-derived vectors: an efficient and general procedure for the production of point mutations in any fragment of DNA", Nucleic Acids Research 10(20):6487-6500 (1982).
Doronina et al, "Enhanced Activity of Monomethylauristatin F through Monoclonal Antibody Delivery: Effects of Linker Technology on Efficacy and Toxicity", Bioconjugate Chemistry 17(1):114-124 (2006).
Doronina et al, "Novel Peptide Linkers for Highly Potent Antibody—Auristatin Conjugate", Bioconjugate Chemistry 19(10):1960-1963 (2008).
Gordon et al, "Structural basis for autoinhibition of Notch", Nature: Structural & Molecular Biology 14(4):295-300 (2007).
Li et al, "Modulation of Notch Signaling by Antibodies Specific for the Extracellular Negative Regulatory Region of NOTCH3", Journal of Biological Chemistry 283(12):8046-8054 (2008).
PCT International Search Report and Written Opinion for PCT/IB2013/059893 issued Mar. 3, 2014.
Wu et al, "Therapeutic antibody targeting of individual Notch receptors", Nature 464(7291):1052-1058 (2010).
Andresen, "Development of peptide microarrays for epitope mapping of antibodies against the human TSH receptor", Journal of Immunological Methods 315:11-18 (2006).
Aste-Amézaga et al, "Characterization of Notch1 Antibodies That Inhibit Signaling of Both Normal and Mutated Notch1 Receptors", PLoS One 5(2):e9094 (2010).

(56) References Cited

OTHER PUBLICATIONS

Aster et al, "The Folding and Structural Integrity of the First LIN-12 Module of Human Notch1 Are Calcium-Dependent", Biochemistry 38:4736-4742 (1999).
Beidler et al, "Cloning and High Level Expression of a Chimeric Antibody with Specificty for Human Carcinoembryonic Antigen", The Journal of Immunology 141(11):4053-4060 (1988).
Better et al, "*Escherichia coli* Secretion of an Active Chimeric Antibody Fragment", Science 240:1041-1043 (1988).
Bray et al, "Notch signalling: a simple pathway becomes complex", Nature Reviews: Molecular Cell Biology 7 (9):678-689 (2006).
Chen et al, "Force-Induced Unfolding Simulations of the Human Notch1 Negative Regulatory Region: Possible Roles of the Heterodimerization Domain in Mechanosensing", PLoS One 6(7):e22837 (2011).
Chothia et al, "Canonical Structures for the Hypervariable Regions of Immunoglobulins", Journal of Molecular Biology 196:901-917 (1987).
Dhungana et al, "Epitope Mapping by Proteolysis of Antigen-Antibody Complexes", Methods in Molecular Biology 524:87-101 (2009).
Domenga et al, "Notch3 is required for arterial identity and maturation of vascular smooth muscle cells", Genes and Development 18(22):2730-2735 (2004).
Efstratiadis et al, "Notch, Myc and Breast Cancer", Cell Cycle 6(4):418-429 (2007).
Falk et al, "Generation of anti-Notch antibodies and their application in blocking Notch signalling in neural stem cells", Methods 58(1):69-78 (2012).
Garner et al, "Effect of Z-DNA on Nucleosome Placement", Journal of Molecular Biology 196:581-590 (1987).
Goodson, "Dental Applications", Medical Applications of Controlled Release, supra, 2:115-138 (1984).
Gordon et al, "Structure of the Notch1-negative regulatory region: implications for normal activation and pathogenic signaling in T-ALL", Blood 113(18):4381-4390 (2009).
Harrison et al, "The Manufacturing Process for Recombinant Factor IX", Seminars in Hematology 35(2 Suppl 2) 4-10 (1998).
Hellström et al, "Dll4 signalling through Notch1 regulates formation of tip cells during angiogenesis", Nature 445:776-780 (2007).
Holliger et al, "'Diabodies': Small bivalent and bispecific antibody fragments", Proceedings of the National Academy of Sciences USA 90:6444-6448 (1993).
Hoogenboom et al, "By-passing Immunisation: Human Antibodies from Synthetic Repertoires of Germline VH Gene Segments Rearranged in Vitro", Journal of Molecular Biology 227:381-388 (1992).
Hu et al, "Overexpression of Activated Murine Notch1 and Notch3 in Transgenic Mice Blocks Mammary Gland Development and Induces Mammary Tumors", American Journal of Pathology 168(3):973-990 (2006).
Jeffries et al, "Characterization of a High-Molecular-Weight Notch Complex in the Nucleus of Notchic-Transformed RKE Cells and in a Human T-Cell Leukemia Cell Line", Molecular and Cellular Biology 22(11):3927-3941 (2002).
Jespers et al, "Guiding the Selection of Human Antibodies from Phage Display Repertoires to a Single Epitope of an Antigen", Bio/Technology 12:899-903 (1994).
Jia et al, "Lysosome-dependent degradation of Notch3", The International Journal of Biochemistry & Cell Biology 41(12):2594-2598 (2009).
Jones et al, "Replacing the complementarity-determining regions in a human antibody with those from a mouse", Nature 321(6069):522-525 (1986).
Kabat, "Origins of Antibody Complementarity and Specificity—Hypervariable Regions and the Minigene Hypothesis", The Journal of Immunology 125(3):961-969 (1980).
Kang et al, "Bacterial cell surface display for epitope mapping of hepatitis C virus core antigen", FEMS Microbiology Letters 226:347-353 (2003).
Kidd et al, "Structure and distribution of the Notch protein in developing *Drosophila*", Genes & Development 3 (8):1113-1129 (1989).
Kipriyanov et al, "Generation and production of engineered antibodies" Molecular Biotechnology 26(1):39-60 (2004).
Klinakis et al, "Myc is a Notch1 transcriptional target and a requisite for Notch1-induced mammary tumorigenesis in mice", Proceedings of the National Academy of Sciences USA 103(24):9262-9267 (2006).
Kozbor et al, "The production of monoclonal antibodies from human lymphocytes", Immunology Today 4(3):72-79 (1983.
Kunkel, "Rapid and efficient site-specific mutagenesis without phenotypic selection", Proceedings of the National Academy of Sciences USA 82(2):488-492 (1985).
Laguzza et al, "New Antitumor Monoclonal Antibody-Vinca Conjugates LY203725 and Related Compounds: Design, Preparation, and Representative in Vivo Activity", J. Med. Chem. 32(3):548-555 (1989).
Langer, "New Methods of Drug Delivery", Science 249:1527-1533 (1990).
Lee et al, "Epitope Mapping of CCR5 Reveals Multiple Conformational States and Distinct but Overlapping Structures Involved in Chemokine and Coreceptor Function", The Journal of Biological Chemistry 274(14):9617-9626 (1999).
Lehmann et al, "Identification of human triple-negative breast cancer subtypes and preclinical models for selection of targeted therapies", The Journal of Clinical Investigation 121(7):2750-2767 (2011).
Levy et al, "Fine and Domain-level Epitope Mapping of Botulinum Neurotoxin Type A Neutralizing Antibodies by Yeast Surface Display", Journal of Molecular Biology 365:196-210 (2007).
Liu et al, "Chimeric mouse-human IgG1 antibody that can mediate lysis of cancer cells", Proceedings of the National Academy of Sciences USA 84:3439-3443 (1987).
Liu et al, "Production of a Mouse-Human Chimeric Monoclonal Antibody to CD20 with Potent Fc-Dependent Biologic Activity", The Journal of Immunology 139(10):3521-3526 (1987).
Lonberg et al, "Human Antibodies from Transgenic Mice", International Reviews of Immunology 13(1):65-93 (1995).
Malecki et al, "Leukemia-Associated Mutations within the NOTCH1 Heterodimerization Domain Fall into at Least Two Distinct Mechanistic Classes", Molecular and Cellular Biology 26(12):4642-4651 (2006).
Miyazaki et al, "Synthesis and Antitumor Activity of Novel Dolastatin 10 Analogs", Chem. Pharm. Bull. 43 (10)1706-1718 (1995).
Morikawa et al, "Two E-Rosette-Forming Lymphoid Cell Lines", Int. J. Cancer 21:166-170 (1978).
Morrison, "Transfectomas Provide Novel Chimeric Antibodies", Science 229:1202-1207 (1985).
Mumm et al, "A Ligand-Induced Extracellular Cleavage Regulates γ-Secretase-like Proteolytic Activation of Notch1", Molecular Cell 5:197-206 (2000).
Nakatsu et al, "Angiogenic sprouting and capillary lumenn formation modeled by human umbilical vein endothelial cells (HUVEC) in fibrin gels: the role of fibroblasts and Angiopoietin-1", Microvascular Research 66:102-112 (2003).
Nam et al, "Notch signaling as a therapeutic target", Current Opinion in Chemical Biology 6:501-509 (2002).
Nishimura et al, "Recombinant Human-Mouse Chimeric Monoclonal Antibody Specific for Common Acute Lymphocytic Leukemia Antigen", Cancer Research 47:999-1005 (1987).
Ol et al, "Chimeric Antibodies", BioTechniques 4(3):214-221 (1986).
Olsson et al, "Human-Human Monoclonal Antibody—Producing Hybridomas: Technical Aspects", Methods in Enzymology 92:3-16 (1983).
Osipo et al, "ErbB-2 Inhibition Activates Notch-1 and Sensitizes Breast Cancer Cells to a γ-Secretase Inhibitor", Oncogene 27:5019-5032 (2008).

\* cited by examiner

Schematic diagram of recombinant Notch3 NRR protein immunogen with Avi- and his- tags.

FIG. 2

SEQ ID NO: 1 Human Notch3 NRR recombinant protein amino acid sequence
APEVSEEPRCPRAACQAKRGDQRCDRECNSPGCWDGGDCSLSVGDPWRQCEALQCWRLFNNSRC
DPACSSPACLYDNFDCHAGGRERTCNPVYEKYCADHFADGRCDQGCNTEECGWDGLDCASEVPALLA
RGVLVLTVLLPPEELLRSSADFLQRLSAILRTSLRFRLDAHGQAMVFPYHRPSPGSEPRARRELAPEVIGS
VVVMLEIDNRLCLQSPENDHCFPDAQSAADYLGALSAVERLDFPYPLRDVRGEPLEPPEPSVPgggsgggIndi
feaqkiewheggpphhhhhh

SEQ ID NO: 2 Human Notch3 NRR recombinant protein nucleotide sequence
GCACCCGAGGTCTCGGAGGAGCCGCGGTGCCCGCGCGCCGCCTGCCAGGCCAAGCGCGGGGACC
AGCGCTGCGACCGCGAGTGCAACAGCCCAGGCTGCGGCTGGGACGGCGGCGACTGCTCGCTGAG
CGTGGGCGACCCCTGGCGGCAATGCGAGGCGCTGCAGTGCTGGCGCCTCTTCAACAACAGCCGCT
GCGACCCCGCCTGCAGCTCGCCCGCCTGCCTCTACGACAACTTCGACTGCCACGCCGGTGGCCGC
GAGCGCACTTGCAACCCGGTGTACGAGAAGTACTGCGCCGACCACTTTGCCGACGGCCGCTGCGA
CCAGGGCTGCAACACGGAGGAGTGCGGCTGGGATGGGCTGGATTGTGCCAGCGAGGTGCCGGCC
CTGCTGGCCCGCGGCGTGCTGGTGCTCACAGTGCTGCTGCCGCCGGAGGAGCTACTGCGTTCCAG
CGCCGACTTTCTGCAGCGGCTCAGCGCCATCCTGCGCACCTCGCTGCGCTTCCGCCTGGACGCGC
ACGGCCAGGCCATGGTCTTCCCTTACCACCGGCCTAGTCCTGGCTCCGAACCCCGGGCCCGTCGG
GAGCTGGCCCCCGAGGTGATCGGCTCGGTAGTAATGCTGGAGATTGACAACCGGCTCTGCCTGCA
GTCGCCTGAGAATGATCACTGCTTCCCCGATGCCCAGAGCGCCGCTGACTACCTGGGAGCGTTGTC
AGCGGTGGAGCGCCTGGACTTCCCGTACCCACTGCGGGACGTGCGGGGGGAGCCGCTGGAGCCT
CCAGAACCCAGCGTCCCGggaggggaagcggaggcggactgaacgacatcttcgaggctcagaaaatcgaatggcacgaaggt
ggcccaccacatcatcatcatcac

SEQ ID NO: 3 Mouse Notch3 NRR recombinant protein amino acid sequence
APEVPEEPRCPRAACQAKRGDQNCDRECNTPGCWDGGDCSLNVDDPWRQCEALQCWRLFNNSRC
DPACSSPACLYDNFDCYSGGRDRTCNPVYEKYCADHFADGRCDQGCNTEECGWDGLDCASEVPALLA
RGVLVLTVLLPPEELLRSSADFLQRLSAILRTSLRFRLDARGQAMVFPYHRPSPGSESRVRRELGPEVIG
SVVVMLEIDNRLCLQSAENDHCFPDAQSAADYLGALSAVERLDFPYPLRDVRGEPLEAPEQSVPgggsgggI
ndifeaqkiewheggpphhhhhh

SEQ ID NO: 4 Mouse Notch3 NRR recombinant protein nucleotide sequence
GCCCCTGAGGTCCCCGAGGAGCCACGGTGCCCGCGAGCGGCTTGCCAGGCCAAGCGAGGGGACC
AGAACTGCGATCGTGAGTGCAACACCCCAGGCTGTGGCTGGGATGGCGGTGACTGCTCACTGAAC
GTGGACGACCCCTGGAGGCAGTGTGAGGCACTGCAGTGCTGGCGTCTCTTCAACAACAGCCGGTG
TGACCCGGCCTGCAGCTCTCCAGCCTGCCTCTATGACAACTTTGACTGCTACTCTGGTGGCCGCGA
CCGCACCTGCAACCCTGTTTATGAGAAGTACTGCGCCGACCACTTTGCAGATGGCCGTTGTGACCA
GGGCTGCAACACTGAGGAATGCGGCTGGGATGGGCTGGACTGTGCCAGCGAGGTCCCGGCCCTTT
TGGCCCGAGGGGTTCTGGTCCTCACAGTTCTTCTGCCTCCTGAAGAGTTGCTGCGCTCCAGTGCCG
ACTTTCTGCAGCGACTCAGCGCTATTCTGCGCACCTCACTGCGCTTCCGCTTGGACGCACGTGGCC
AGGCCATGGTCTTCCCCTATCACCGGCCAAGCCCTGGCTCTGAATCCCGGGTCCGTCGTGAGCTGG
GTCCTGAGGTGATCGGCTCTGTGGTGATGCTGGAGATTGACAACCGGCTCTGTCTGCAGTCAGCTG
AGAATGACCACTGCTTCCCTGATGCCCAGAGTGCTGCTGACTACCTGGGAGCCTTGTCAGCAGTGG
AGCGACTTGATTTCCCATACCCACTTCGGGATGTGCGAGGAGAGCCGCTGGAGGCCCCAGAGCAGA
GCGTGCCAggaggggaagcggaggcggactgaacgacatcttcgaggctcagaaaatcgaatggcacgaaggtggcccaccacatca
tcatcatcatcac

FIG. 3

SEQ ID NO: 5 r28 VH amino acid sequence (CDRs underlined)
EVQLVESGGGLVQPGRSLTLSCVAS<u>GFTFRDYGMT</u>WIRQAPGKGLTWVA<u>YISSGSNYIYYAEAVKG</u>RFTI
SRDNAKNTLYLQMTSLRSEDTALYFCTR<u>RGPFVLDA</u>WGQGASVTVSS

SEQ ID NO: 6 r28 VH nucleotide sequence
GAGGTGCAACTGGTGGAGTCTGGAGGAGGCTTAGTGCAGCCTGGAAGGTCCCTGACACTCTCCTGT
GTAGCCTCTGGATTCACTTTCAGGGACTATGGAATGACCTGGATTCGCCAGGCTCCAGGGAAGGGG
CTGACATGGGTTGCATATATTAGTAGTGGTAGCAATTACATCTATTATGCAGAAGCGGTGAAGGGCC
GATTCACCATCTCCAGAGACAATGCCAAGAACACCCTGTACCTGCAAATGACCAGTCTGAGGTCTGA
AGACACTGCCTTGTATTTTTGTACAAGACGAGGCCCGTTTGTTTTGGATGCCTGGGGTCAAGGAGCT
TCAGTCACTGTCTCCTCA

SEQ ID NO: 7 r28 VL amino acid sequence (CDRs underlined)
DIQMTQSPSFLSASVGDRVTINC<u>KASQSINRYLH</u>WFQQKLGEAPKLLIY<u>NANGLQT</u>GIPSRFSGSGSGTD
FTLTISSLQSEDVATYFC<u>LQHNTWPDT</u>FGAGTKLELK

SEQ ID NO: 8 r28 VL nucleotide sequence
GACATCCAGATGACCCAGTCTCCTTCATTCCTGTCTGCATCTGTGGGAGACAGAGTCACTATCAACT
GCAAAGCAAGTCAGAGTATTAACAGGTACTTACACTGGTTTCAGCAGAAACTTGGAGAAGCTCCCAA
ACTCCTGATATATAATGCAAACGGTTTGCAAACGGGCATCCCATCAAGGTTCAGTGGCAGTGGATCT
GGTACTGATTTCACACTTACCATCAGCAGCCTGCAGTCTGAAGATGTTGCCACATATTTCTGCTTGCA
GCATAATACGTGGCCGGACACGTTTGGCGCTGGGACCAAGCTGGAACTGAA

SEQ ID NO: 9 r75 VH amino acid sequence (CDRs underlined)
QVKLLQSGAALVKPGASVKMSCKAS<u>GYAFTDYWVT</u>WVKQSHGKSLEWIG<u>EISPNSGGTNFNEKFKG</u>KA
TLTVDKSTSTAYMELSRLTSEDSAIYYCTR<u>GEIRYNWFAY</u>WGQGTLVTVSS

SEQ ID NO: 10 r75 VH nucleotide sequence
CAGGTCAAGCTGCTGCAGTCTGGGGCTGCACTGGTGAAGCCTGGAGCCTCTGTGAAGATGTCTTGC
AAAGCTTCTGGTTATGCATTCACTGACTACTGGGTGACCTGGGTGAAGCAGAGTCATGGAAAGAGCC
TTGAGTGGATTGGGGAAATTTCTCCTAACAGTGGTGGTACTAACTTCAATGAAAAGTTCAAGGGCAA
GGCCACATTGACTGTAGACAAATCCACCAGCACAGCCTATATGGAGCTCAGCAGATTGACATCTGAG
GACTCTGCAATCTATTACTGTACAAGAGGGGAAATCCGTTACAATTGGTTTGCTTACTGGGGCCAAG
GCACTCTGGTCACTGTCTCCTCA

SEQ ID NO: 11 r75 VL amino acid sequence (CDRs underlined)
DIQMTQSPSSLSASVGDRVTITC<u>KASQNVGNNIA</u>WYQQKPGKAPKLLIY<u>YASNRYT</u>GVPSRFSGSGYGT
DFTLTISSLQPEDFATYYC<u>QRLYNSPFT</u>FGGGTKVEIK

SEQ ID NO: 12 r75 VL nucleotide sequence
AACATTGTGATGACCCAGTCTCCCAAATCCATGTCCATATCAGTAGGAGACAGGGTCACCATGAACT
GCAAGGCCAGTCAGAATGTGGGTAATAATATAGCCTGGTATCAACAGAAACCAGGGCAGTCTCCTAA
ACTGTTGATCTACTATGCATCTAACCGGTACACTGGGGTCCCTGATCGCTTCACAGGCGGTGGATAT
GGGACAGATTTCACTCTCACCATCAATAGTATGCAAGCTGAAGATGCAGCCTTTTATTACTGTCAGCG
TCTTTACAATTCTCCATTCACGTTCGGCTCAGGGACGAAGTTGGAAATAAAG

FIG. 4A

SEQ ID NO: 13  hu28 VH 1.0  amino acid sequence
EVQLVESGGGLVQPGGSLRLSCAASGFTFRDYGMTWVRQAPGKGLEWVAYISSGSNYIYYAEAVKGRF
TISRDNAKNSLYLQMNSLRAEDTAVYYCARRGPFVLDAWGQGTLVTVSS

SEQ ID NO: 14  hu28 VH 1.0 nucleotide sequence
GAGGTGCAGCTGGTGGAGTCTGGGGGAGGCTTGGTCCAGCCTGGGGGGTCCCTGAGACTCTCCTG
TGCAGCCTCTGGATTCACTTTCAGGGACTATGGAATGACCTGGGTCCGCCAGGCTCCAGGGAAGGG
GCTGGAGTGGGTGGCCTATATTAGTAGTGGTAGCAATTACATCTATTATGCAGAAGCGGTGAAGGGC
CGATTCACCATCTCCAGAGACAACGCCAAGAACTCACTGTATCTGCAAATGAACAGCCTGAGAGCCG
AGGACACGGCTGTGTATTACTGTGCGAGACGAGGCCCGTTTGTTTTGGATGCCTGGGGCCAGGGAA
CCCTGGTCACCGTCTCCTCA

SEQ ID NO: 15  hu28 VH 1.0 CDR1 amino acid sequence-Kabat
DYGMT

SEQ ID NO: 16  hu28 VH 1.0 CDR1 amino acid sequence-Chothia
GFTFRDY

SEQ ID NO: 17  hu28 VH 1.0 CDR1 nucleotide sequence-Kabat
GACTATGGAATGACC

SEQ ID NO: 18  hu28 VH 1.0 CDR1 nucleotide sequence-Chothia
GGATTCACTTTCAGGGACTAT

SEQ ID NO: 19   hu28 VH 1.0 CDR2 amino acid sequence-Kabat
YISSGSNYIYYAEAVKG

SEQ ID NO: 20  hu28 VH 1.0 CDR2 amino acid sequence-Chothia
SSGSNY

SEQ ID NO: 21  hu28 VH 1.0 CDR2 nucleotide sequence-Kabat
TATATTAGTAGTGGTAGCAATTACATCTATTATGCAGAAGCGGTGAAGGGC

SEQ ID NO: 22  hu28 VH 1.0 CDR2 nucleotide sequence-Chothia
AGTAGTGGTAGCAATTAC

SEQ ID NO: 23   hu28 VH 1.0 CDR3 amino acid sequence-Kabat and Chothia
RGPFVLDA

SEQ ID NO: 24  hu28 VH 1.0 CDR3 nucleotide sequence-Kabat and Chothia
CGAGGCCCGTTTGTTTTGGATGCC

FIG. 4B

SEQ ID NO: 25 hu28 VL 1.0 amino acid sequence
DIQMTQSPSSLSASVGDRVTITCKASQSINRYLHWYQQKPGKAPKLLIYNANGLQTGVPSRFSGSGSGTD
FTLTISSLQPEDFATYYCLQHNTWPDTFGGGTKVEIK

SEQ ID NO: 26 hu28 VL 1.0 nucleotide sequence
GACATCCAGATGACCCAGTCTCCATCCTCCCTGTCTGCATCTGTAGGAGACAGAGTCACCATCACTT
GCAAAGCAAGTCAGAGTATTAACAGGTACTTACACTGGTATCAGCAGAAACCAGGGAAAGCCCCTAA
GCTCCTGATCTATAATGCAAACGGTTTGCAAACGGGGGTCCCATCAAGGTTCAGTGGCAGTGGATCT
GGGACAGATTTCACTCTCACCATCAGCAGTCTGCAACCTGAAGATTTTGCAACTTACTACTGTTTGCA
GCATAATACGTGGCCGGACACGTTTGGCGGAGGGACCAAGGTGGAGATCAAA

SEQ ID NO: 27 hu28 VL 1.0 CDR1 amino acid sequence-Kabat and Chothia
KASQSINRYLH

SEQ ID NO: 28 hu28 VL 1.0 CDR1 nucleotide sequence-Kabat and Chothia
AAAGCAAGTCAGAGTATTAACAGGTACTTACAC

SEQ ID NO: 29 hu28 VL 1.0 CDR2 amino acid sequence-Kabat and Chothia
NANGLQT

SEQ ID NO: 30 hu28 VL 1.0 CDR2 nucleotide sequence-Kabat and Chothia
AATGCAAACGGTTTGCAAACG

SEQ ID NO: 31 hu28 VL 1.0 CDR3 amino acid sequence-Kabat and Chothia
LQHNTWPDT

SEQ ID NO: 32 hu28 VL 1.0 CDR3 nucleotide sequence-Kabat and Chothia
TTGCAGCATAATACGTGGCCGGACACGTTT

FIG. 4C

SEQ ID NO: 33  hu28 HC 1.0 amino acid sequence-Human IgG1
EVQLVESGGGLVQPGGSLRLSCAASGFTFRDYGMTWVRQAPGKGLEWVAYISSGSNYIYYAEAVKGRF
TISRDNAKNSLYLQMNSLRAEDTAVYYCARRGPFVLDAWGQGTLVTVSSASTKGPSVFPLAPSSKSTSG
GTAALGCLVKDYFPEPVTVSWNSGALTSGVHTFPAVLQSSGLYSLSSVVTVPSSSLGTQTYICNVNHKPS
NTKVDKKVEPKSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFFLYSKLTVDKS
RWQQGNVFSCSVMHEALHNHYTQKSLSLSPG

SEQ ID NO: 34  hu28 HC 1.0 nucleotide sequence
GAGGTGCAGCTGGTGGAGTCTGGGGGAGGCTTGGTCCAGCCTGGGGGGTCCCTGAGACTCTCCTG
TGCAGCCTCTGGATTCACTTTCAGGGACTATGGAATGACCTGGGTCCGCCAGGCTCCAGGGAAGGG
GCTGGAGTGGGTGGCCTATATTAGTAGTGGTAGCAATTACATCTATTATGCAGAAGCGGTGAAGGGC
CGATTCACCATCTCCAGAGACAACGCCAAGAACTCACTGTATCTGCAAATGAACAGCCTGAGAGCCG
AGGACACGGCTGTGTATTACTGTGCGAGACGAGGCCCGTTTGTTTTGGATGCCTGGGGCCAGGGAA
CCCTGGTCACCGTCTCCTCAGCGTCGACCAAGGGCCCATCGGTCTTCCCCCTGGCACCCTCCTCCA
AGAGCACCTCTGGGGGCACAGCGGCCCTGGGCTGCCTGGTCAAGGACTACTTCCCCGAACCGGTG
ACGGTGTCGTGGAACTCAGGCGCCCTGACCAGCGGCGTGCACACCTTCCCGGCTGTCCTACAGTC
CTCAGGACTCTACTCCCTCAGCAGCGTGGTGACCGTGCCCTCCAGCAGCTTGGGCACCCAGACCTA
CATCTGCAACGTGAATCACAAGCCCAGCAACACCAAGGTGGACAAGAAAGTTGAGCCCAAATCTTGT
GACAAAACTCACACATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCACATGCGTGGTGGTG
GACGTGAGCCACGAAGACCCTGAGGTCAAGTTCAACTGGTACGTGGACGGCGTGGAGGTGCATAAT
GCCAAGACAAAGCCGCGGGAGGAGCAGTACAACAGCACGTACCGTGTGGTCAGCGTCCTCACCGT
CCTGCACCAGGACTGGCTGAATGGCAAGGAGTACAAGTGCAAGGTCTCCAACAAAGCCCTCCCAGC
CCCCATCGAGAAACCATCTCCAAAGCCAAAGGGCAGCCCCGAGAACCACAGGTGTACACCCTGCC
CCCATCCCGGGAGGAGATGACCAAGAACCAGGTCAGCCTGACCTGCCTGGTCAAAGGCTTCTATCC
CAGCGACATCGCCGTGGAGTGGGAGAGCAATGGGCAGCCGGAGAACAACTACAAGACCACGCCTC
CCGTGCTGGACTCCGACGGCTCCTTCTTCCTCTATAGCAAGCTCACCGTGGACAAGAGCAGGTGGC
AGCAGGGGAACGTCTTCTCATGCTCCGTGATGCATGAGGCTCTGCACAACCACTACACGCAGAAGA
GCCTCTCCCTGTCCCCGGGT

SEQ ID NO: 35  hu28 LC 1.0 amino acid sequence-Human kappa
DIQMTQSPSSLSASVGDRVTITCKASQSINRYLHWYQQKPGKAPKLLIYNANGLQTGVPSRFSGSGSGTD
FTLTISSLQPEDFATYYCLQHNTWPDTFGGGTKVEIKRTVAAPSVFIFPPSDEQLKSGTASVVCLLNNFYP
REAKVQWKVDNALQSGNSQESVTEQDSKDSTYSLSSTLTLSKADYEKHKVYACEVTHQGLSSPVTKSFN
RGEC

SEQ ID NO: 36  hu28 LC 1.0 nucleotide sequence
GACATCCAGATGACCCAGTCTCCATCCTCCCTGTCTGCATCTGTAGGAGACAGAGTCACCATCACTT
GCAAAGCAAGTCAGAGTATTAACAGGTACTTACACTGGTATCAGCAGAAACCAGGGAAAGCCCCTAA
GCTCCTGATCTATAATGCAAACGGTTTGCAAACGGGGGTCCCATCAAGGTTCAGTGGCAGTGGATCT
GGGACAGATTTCACTCTCACCATCAGCAGTCTGCAACCTGAAGATTTTGCAACTTACTACTGTTTGCA
GCATAATACGTGGCCGGACACGTTTGGCGGAGGGACCAAGGTGGAGATCAAA
CGGACCGTGGCCGCTCCTTCCGTGTTCATCTTCCCCCCTTCCGACGAGCAGCTGAAGTCTGGCACC
GCCTCTGTGGTGTGTCTGCTGAACAACTTCTACCCCCGGGAGGCCAAGGTGCAGTGGAAGGTGGAC
AACGCTCTGCAGTCCGGCAACTCCCAGGAGTCTGTGACCGAGCAGGACTCCAAGGACAGCACCTAC
TCCCTGTCCTCTACCCTGACCCTGTCCAAGGCCGACTACGAGAAGCACAAGGTGTACGCCTGTGAG
GTGACCCACCAGGGCCTGTCCTCCTGTGACCAAGTCCTTCAACCGGGGCGAGTGC

FIG. 5A

SEQ ID NO: 37  hu75 VH 1.9 amino acid sequence
EVQLVESGGGLVQPGGSLRLSCAASGYAFTDYWMTWVRQAPGKGLEWVAEISPNSGGTNFNEKFKGR
FTISVDNAKNSLYLQMNSLRAEDTAVYYCARGEIRYNWFAYWGQGTLVTVSS

SEQ ID NO: 38  hu75 VH 1.9 nucleotide sequence
GAGGTGCAGCTGGTGGAGTCTGGGGGAGGCTTGGTCCAGCCTGGGGGGTCCCTGAGACTCTCCTG
TGCAGCCTCTGGTTATGCATTCACTGACTACTGGATGACCTGGGTCCGCCAGGCTCCAGGGAAGGG
GCTGGAGTGGGTGGCCGAAATTTCTCCTAACAGTGGTGGTACTAACTTCAATGAAAAGTTCAAGGGC
CGATTCACCATCTCCGTTGACAACGCCAAGAACTCACTGTATCTGCAAATGAACAGCCTGAGAGCCG
AGGACACGGCTGTGTATTACTGTGCGAGAGGGGAAATCCGTTACAATTGGTTTGCTTACTGGGGCCA
GGGAACCCTGGTCACCGTCTCCTCA

SEQ ID NO: 39  hu75 VH 1.9 CDR1 amino acid sequence-Kabat
DYWMT

SEQ ID NO: 40  hu75 VH 1.9 CDR1 amino acid sequence-Chothia
GYAFTDY

SEQ ID NO: 41  hu75 VH 1.9 CDR1 nucleotide sequence-Kabat
GACTACTGGATGACC

SEQ ID NO: 42  hu75 VH 1.9 CDR1 nucleotide sequence-Chothia
GGTTATGCATTCACTGACTAC

SEQ ID NO: 43   hu75 VH 1.9 CDR2 amino acid sequence-Kabat
EISPNSGGTNFNEKFKG

SEQ ID NO: 44  hu75 VH 1.9 CDR2 amino acid sequence-Chothia
SPNSGG

SEQ ID NO: 45  hu75 VH 1.9 CDR2 nucleotide sequence-Kabat
GAAATTTCTCCTAACAGTGGTGGTACTAACTTCAATGAAAAGTTCAAGGGC

SEQ ID NO: 46  hu75 VH 1.9 CDR2 nucleotide sequence-Chothia
TCTCCTAACAGTGGTGGT

SEQ ID NO: 47  hu75 VH 1.9 CDR3 amino acid sequence-Kabat and Chothia
GEIRYNWFAY

SEQ ID NO: 48  hu75 VH 1.9 CDR3 nucleotide sequence-Kabat and Chothia
GGGGAAATCCGTTACAATTGGTTTGCTTAC

FIG. 5B

SEQ ID NO: 49 hu75 VL 1.3 amino acid sequence
DIQMTQSPSSLSASVGDRVTITCKASQNVGNNIAWYQQKPGKAPKLLIYYASNRYTGVPSRFSGSGYGT
DFTLTISSLQPEDFATYYCQRLYNSPFTFGGGTKVEIK

SEQ ID NO: 50 hu75 VL 1.3 nucleotide sequence
GACATCCAGATGACCCAGTCTCCATCCTCCCTGTCTGCATCTGTAGGAGACAGAGTCACCATCACTT
GCAAGGCCAGTCAGAATGTGGGTAATAATATAGCCTGGTATCAGCAGAAACCAGGGAAAGCCCCTA
AGCTCCTGATCTATTATGCATCTAACCGGTACACTGGGGTCCCATCAAGGTTCAGTGGCAGTGGATA
TGGGACAGATTTCACTCTCACCATCAGCAGTCTGCAACCTGAAGATTTTGCAACTTACTACTGTCAGC
GTCTTTACAATTCTCCATTCACGTTCGGCGGAGGGACCAAGGTGGAGATCAAA

SEQ ID NO: 51 hu75 VL 1.3 CDR1 amino acid sequence-Kabat and Chothia
KASQNVGNNIA

SEQ ID NO: 52 hu75 VL 1.3 CDR1 nucleotide sequence-Kabat and Chothia
AAGGCCAGTCAGAATGTGGGTAATAATATAGCC

SEQ ID NO: 53 hu75 VL 1.3 CDR2 amino acid sequence-Kabat and Chothia
YASNRYT

SEQ ID NO: 54 hu75 VL 1.3 CDR2 nucleotide sequence-Kabat and Chothia
TATGCATCTAACCGGTACACT

SEQ ID NO: 55 hu75 VL 1.3 CDR3 amino acid sequence-Kabat and Chothia
QRLYNSPFT

SEQ ID NO: 56 hu75 VL 1.3 CDR3 nucleotide sequence-Kabat and Chothia
CAGCGTCTTTACAATTCTCCATTCACGTTC

FIG. 5C

SEQ ID NO: 57  hu75 HC 1.9 amino acid sequence-Human IgG1
EVQLVESGGGLVQPGGSLRLSCAASGYAFTDYWMTWVRQAPGKGLEWVAEISPNSGGTNFNEKFKGR
FTISVDNAKNSLYLQMNSLRAEDTAVYYCARGEIRYNWFAYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNHK
PSNTKVDKKVEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKTTPPVLDSDGSFFLYSKLTVDK
SRWQQGNVFSCSVMHEALHNHYTQKSLSLSPG

SEQ ID NO: 58  hu75 HC 1.9 nucleotide sequence
GAGGTGCAGCTGGTGGAGTCTGGGGGAGGCTTGGTCCAGCCTGGGGGGTCCCTGAGACTCTCCTG
TGCAGCCTCTGGTTATGCATTCACTGACTACTGGATGACCTGGGTCCGCCAGGCTCCAGGGAAGGG
GCTGGAGTGGGTGGCCGAAATTTCTCCTAACAGTGGTGGTACTAACTTCAATGAAAAGTTCAAGGGC
CGATTCACCATCTCCGTTGACAACGCCAAGAACTCACTGTATCTGCAAATGAACAGCCTGAGAGCCG
AGGACACGGCTGTGTATTACTGTGCGAGAGGGGAAATCCGTTACAATTGGTTTGCTTACTGGGGCCA
GGGAACCCTGGTCACCGTCTCCTCAGCGTCGACCAAGGGCCCATCGGTCTTCCCCCTGGCACCCTC
CTCCAAGAGCACCTCTGGGGGCACAGCGGCCCTGGGCTGCCTGGTCAAGGACTACTTCCCCGAAC
CGGTGACGGTGTCGTGGAACTCAGGCGCCCTGACCAGCGGCGTGCACACCTTCCCGGCTGTCCTA
CAGTCCTCAGGACTCTACTCCCTCAGCAGCGTGGTGACCGTGCCCTCCAGCAGCTTGGGCACCCAG
ACCTACATCTGCAACGTGAATCACAAGCCCAGCAACACCAAGGTGGACAAGAAAGTTGAGCCCAAAT
CTTGTGACAAAACTCACACATGCCCACCGTGCCCAGCACCTGAACTCCTGGGGGGACCGTCAGTCT
TCCTCTTCCCCCCAAAACCCAAGGACACCCTCATGATCTCCCGGACCCCTGAGGTCACATGCGTGG
TGGTGGACGTGAGCCACGAAGACCCTGAGGTCAAGTTCAACTGGTACGTGGACGGCGTGGAGGTG
CATAATGCCAAGACAAAGCCGCGGGAGGAGCAGTACAACAGCACGTACCGTGTGGTCAGCGTCCTC
ACCGTCCTGCACCAGGACTGGCTGAATGGCAAGGAGTACAAGTGCAAGGTCTCCAACAAAGCCCTC
CCAGCCCCCATCGAGAAAACCATCTCCAAAGCCAAAGGGCAGCCCCGAGAACCACAGGTGTACACC
CTGCCCCCATCCCGGGAGGAGATGACCAAGAACCAGGTCAGCCTGACCTGCCTGGTCAAAGGCTTC
TATCCCAGCGACATCGCCGTGGAGTGGGAGAGCAATGGGCAGCCGGAGAACAACTACAAGACCAC
GCCTCCCGTGCTGGACTCCGACGGCTCCTTCTTCCTCTATAGCAAGCTCACCGTGGACAAGAGCAG
GTGGCAGCAGGGGAACGTCTTCTCATGCTCCGTGATGCATGAGGCTCTGCACAACCACTACACGCA
GAAGAGCCTCTCCCTGTCCCCGGGT

SEQ ID NO: 59  hu75 LC 1.3 amino acid sequence-Human kappa
DIQMTQSPSSLSASVGDRVTITCKASQNVGNNIAWYQQKPGKAPKLLIYYASNRYTGVPSRFSGSGYGT
DFTLTISSLQPEDFATYYCQRLYNSPFTFGGGTKVEIKRTVAAPSVFIFPPSDEQLKSGTASVVCLLNNFYP
REAKVQWKVDNALQSGNSQESVTEQDSKDSTYSLSSTLTLSKADYEKHKVYACEVTHQGLSSPVTKSFN
RGEC

SEQ ID NO: 60  hu28 LC 1.3 nucleotide sequence
GACATCCAGATGACCCAGTCTCCATCCTCCCTGTCTGCATCTGTAGGAGACAGAGTCACCATCACTT
GCAAGGCCAGTCAGAATGTGGGTAATAATATAGCCTGGTATCAGCAGAAACCAGGGAAAGCCCCTA
AGCTCCTGATCTATTATGCATCTAACCGGTACACTGGGGTCCCATCAAGGTTCAGTGGCAGTGGATA
TGGGACAGATTTCACTCTCACCATCAGCAGTCTGCAACCTGAAGATTTTGCAACTTACTACTGTCAGC
GTCTTTACAATTCTCCATTCACGTTCGGCGGAGGGACCAAGGTGGAGATCAAACGGACCGTGGCCG
CTCCTTCCGTGTTCATCTTCCCCCCTTCCGACGAGCAGCTGAAGTCTGGCACCGCCTCTGTGGTGTG
TCTGCTGAACAACTTCTACCCCGGGAGGCCAAGGTGCAGTGGAAGGTGGACAACGCTCTGCAGTC
CGGCAACTCCCAGGAGTCTGTGACCGAGCAGGACTCCAAGGACAGCACCTACTCCCTGTCCTCTAC
CCTGACCCTGTCCAAGGCCGACTACGAGAAGCACAAGGTGTACGCCTGTGAGGTGACCCACCAGG
GCCTGTCCTCTCCTGTGACCAAGTCCTTCAACCGGGGCGAGTGC

FIG. 6

| antibody | ch28 | ch75 |
|---|---|---|
| Notch3-NRR —Ⓐ—Ⓑ—Ⓒ—[hd1]—[hd2] | 2.06 | 1.72 |
| Notch1-NRR —Ⓐ—Ⓑ—Ⓒ—[hd1]—[hd2] | - | - |
| —Ⓐ—Ⓑ—Ⓒ—[hd1]—[hd2] | - | - |
| —Ⓐ—Ⓑ—Ⓒ—[hd1]—[hd2] | 0.15 | - |
| —Ⓐ—Ⓑ—Ⓒ—[hd1]—[hd2] | 0.54 | 2.37 |
| —Ⓐ—Ⓑ—Ⓒ—[hd1]—[hd2] | - | 0.80 |
| —Ⓐ—Ⓑ—Ⓒ—[hd1]—[hd2] | - | - |
| —Ⓐ—Ⓑ—Ⓒ—[hd1]—[hd2] | 0.5 | - |
| —Ⓐ—Ⓑ—Ⓒ—[hd1]—[hd2] | - | - |

Recombinant human Notch1 NRR and Notch3 NRR domain swap chimeric constructs for epitope mapping of anti-Notch3 ch28 and ch75 antibodies.

Western blot analysis of Notch3 positive and negative cell lines using the D11B8 antibody.

a) 0 hr

Cell membrane localization of anti-Notch3 antibody hu75-Alexa 488 and labeling of acidic vesicles with pHrodoTM red dextran in MDA-MB-468 breast cancer cells at hour 0.

b) 5 hr

Intracellular trafficking of anti-Notch3 antibody hu75-Alexa 488 and co-localization with pHrodoTM red dextran in MDA-MB-468 breast cancer cells at hour 5 (arrows).

c) 0 hr

Cell membrane localization of anti-Notch3 antibody hu28-DyLight650 and labeling of acidic vesicles with pHrodoTM red dextran (intracellular puncta) in MDA-MB-468 breast cancer cells at hour 0.

d) 8 hr

Intracellular trafficking of anti-Notch3 antibody hu28-DyLight650 and co-localization with pHrodoTM red dextran in MDA-MB-468 breast cancer cells at hour 8 (arrows).

Pearson's correlation coefficient demonstrating the degree of overlap or co-localization of hu28-DyLight650 and pHrodoTM red dextran fluorescent labels in MDA-MB-468 cells over time.

Western blot analysis of S2-cleavage assay using HCC2429 and MDA-MB-468 cells treated with humanized anti-Notch3 antibodies. M.W. = molecular weight.

Treatment of OVCAR3 ovarian cancer cells with anti-Notch3 hu28-vc0101 disrupts microtubules (stained with anti-alpha-tubulin antibody) in mitotic cells that were identified by phospho-Histone H3 staining.

Western blot analysis of Notch3-ECD from xenografts harvested from 2-3 mice (M).

Efficacy of anti-Notch3 hu28-vc0101 and hu75-vc0101 at a dose of 3 mg/kg compared to Cisplatin at a dose of at 5 mg/kg in the 37622A1 NSCLC patient derived xenografts model.

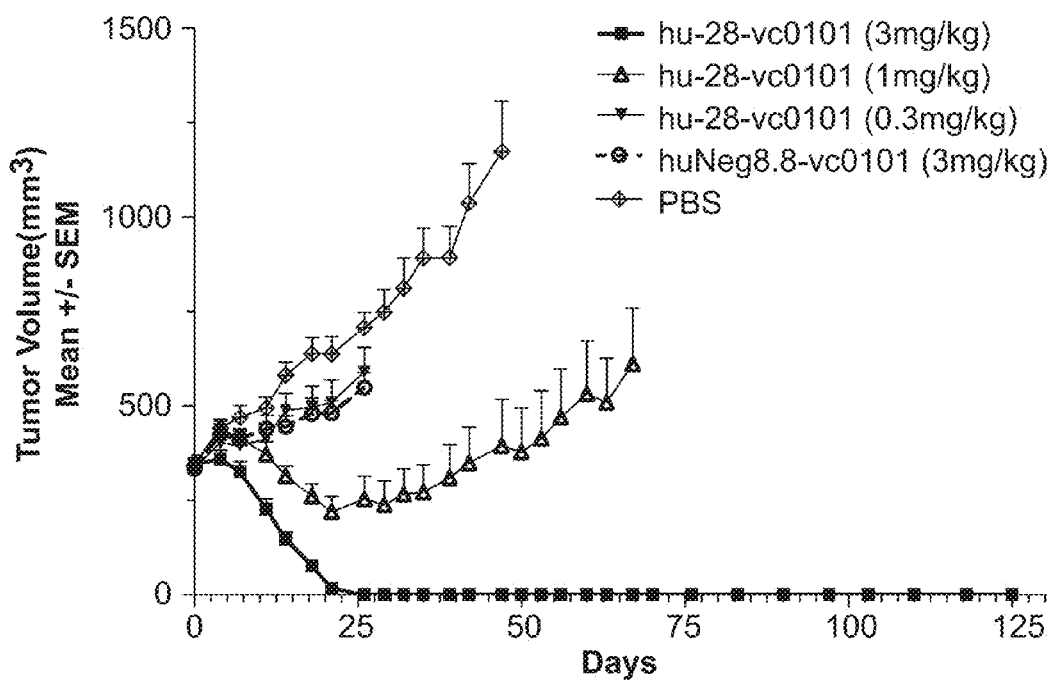
Efficacy of anti-Notch3 hu28-vc0101 in the MDA-MB-468 breast model.
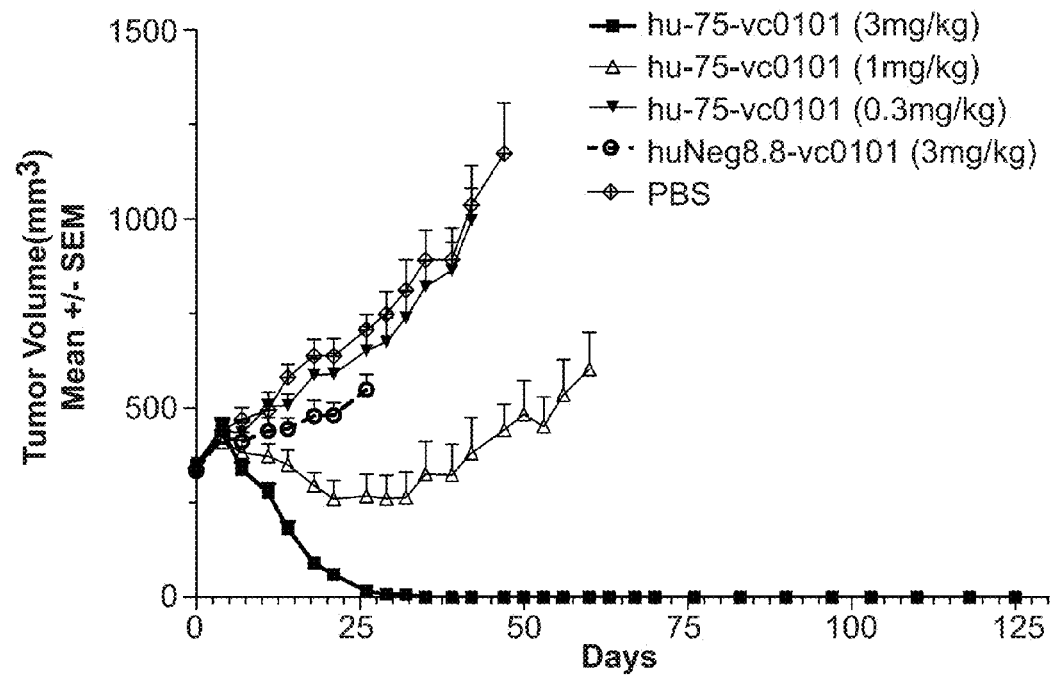
Efficacy of anti-Notch3 hu75-vc0101 in the MDA-MB-468 breast model.

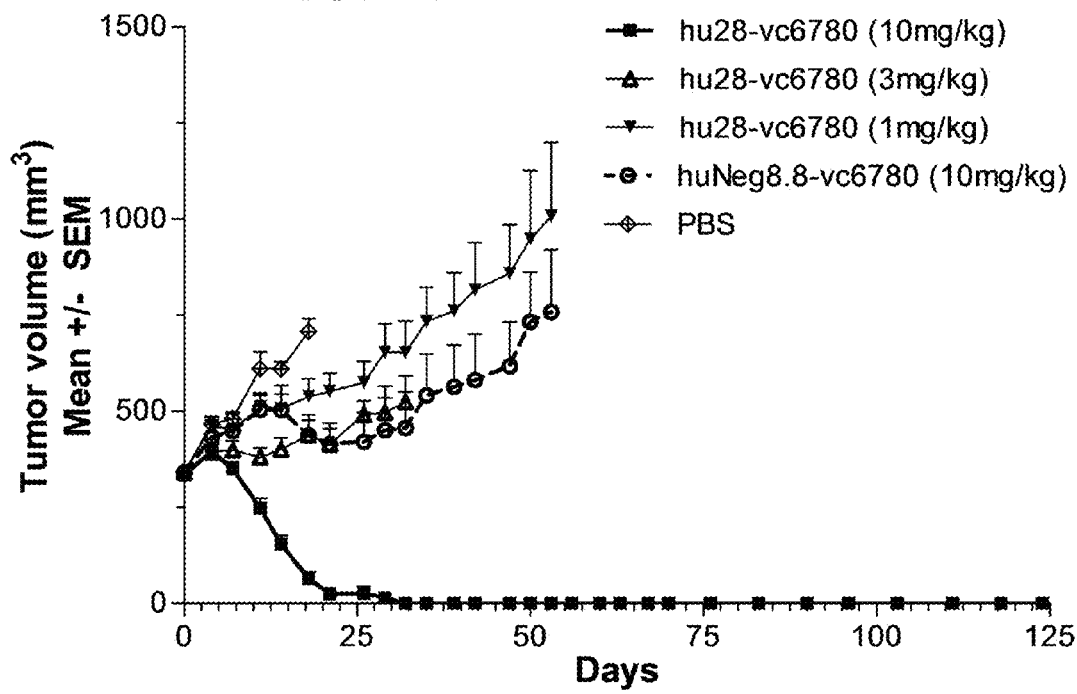
Efficacy of anti-Notch3 hu28-vc6780 in the MDA-MB-468 breast model.
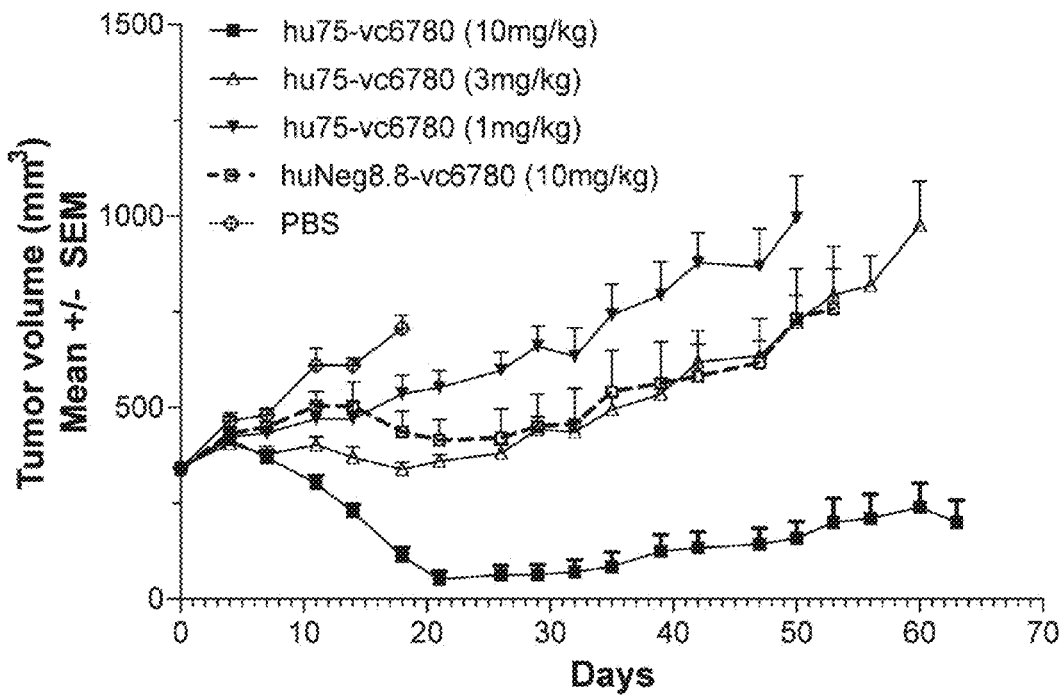
Efficacy of anti-Notch3 hu75-vc6780 in the MDA-MB-468 breast model.

Efficacy of anti-Notch3 hu28-vc0101 in the OVCAR3 ovarian model.

FIG. 16A  Efficacy of rat-human chimeric anti-Notch3 ADCs dosed at 5mg/kg in HCC2429 lung xenografts HCC2429 Lung xenografts, tumor volume (mm³ +/- SEM)

| Day | PBS | ch28-mc0101 | ch28-mc3377 | ch28-me0131 | ch28-MALPEG6C2-0131 | ch75-mc0131 | ch28-vc0101 | ch28-vc6780 | ch75-vc0101 | ch75-vc6780 | huNeg8.8-mc0131 | huNeg8.8-mc3377 | huNeg8.8-me0131 | huNeg8.8-vc0101 | huNeg8.8-vc6780 |
|---|---|---|---|---|---|---|---|---|---|---|---|---|---|---|---|
| -2 | 198 ±44 | 195 ±37 | 195 ±39 | 196 ±39 | 196 ±47 | 195 ±35 | 195 ±26 | 195 ±33 | 195 ±25 | 205 ±35 | 195 ±43 | 175 ±47 | 195 ±42 | 196 ±41 | 195 ±43 |
| 2 | 503 ±106 | 457 ±73 | 525 ±101 | 458 ±90 | 505 ±128 | 483 ±96 | 395 ±54 | 378 ±77 | 450 ±48 | 420 ±66 | 603 ±119 | 546 ±140 | 543 ±115 | 602 ±127 | 516 ±117 |
| 4 | 838 ±187 | 506 ±96 | 654 ±136 | 504 ±112 | 638 ±192 | 522 ±125 | 298 ±46 | 329 ±73 | 366 ±47 | 430 ±92 | 845 ±149 | 714 ±186 | 746 ±168 | 766 ±191 | 759 ±177 |
| 6 | 1008 ±229 | 562 ±126 | 789 ±156 | 600 ±152 | 750 ±207 | 634 ±158 | 259 ±33 | 319 ±79 | 318 ±48 | 474 ±108 | 1117 ±171 | 939 ±243 | 1016 ±225 | 1000 ±262 | 988 ±229 |
| 9 | 1618 ±265 | 652 ±133 | 1186 ±253 | 787 ±177 | 1020 ±213 | 620 ±129 | 177 ±24 | 280 ±72 | 217 ±30 | 502 ±125 | 1773 ±264 | 1348 ±284 | 1506 ±367 | 1372 ±385 | 1449 ±304 |
| 11 | 1605± 228 | 761 ±166 | 1458 ±314 | 941 ±199 | 1302 ±257 | 737 ±162 | 169 ±22 | 290 ±77 | 196 ±30 | 601 ±155 | 1986 ±170 | 1608 ±259 | 1475 ±283 | 1331 ±399 | 1582 ±316 |
| 13 | 2033± 293 | 865 ±176 | 1534 ±339 | 1096 ±264 | 1599 ±274 | 802 ±184 | 122 ±15 | 293 ±88 | 166 ±33 | 735 ±196 | 2535 ±228 | 2257 ±350 | 1831 ±400 | - | - |
| 16 | - | 917 ±207 | - | 949 ±190 | 1556 ±300 | 878 ±200 | 97 ±13 | 266 ±105 | 120 ±26 | 781 ±210 | - | - | - | - | - |
| 19 | - | 1222 ±275 | - | 1322 ±276 | 1966 ±414 | 1051 ±247 | 88 ±14 | 484 ±171 | 102 ±28 | 770 ±153 | - | - | - | - | - |
| 23 | - | 1694 ±401 | - | - | - | 1354 ±340 | 79 ±25 | 496 ±238 | 72 ±25 | 855 ±156 | - | - | - | - | - |
| 26 | - | - | - | - | - | - | 77 ±47 | 658 ±329 | 64 ±26 | 1159 ±253 | - | - | - | - | - |
| 30 | - | - | - | - | - | - | 109 ±86 | 533 ±290 | 36 ±20 | 1270 ±205 | - | - | - | - | - |
| 33 | - | - | - | - | - | - | 138 ±128 | 775 ±411 | 36 ±34 | 1628 ±309 | - | - | - | - | - |
| 37 | - | - | - | - | - | - | 210 ±199 | - | 46 ±45 | - | - | - | - | - | - |
| 40 | - | - | - | - | - | - | 323 ±311 | - | 58 ±57 | - | - | - | - | - | - |
| 44 | - | - | - | - | - | - | 17 ±17 | - | 108 ±107 | - | - | - | - | - | - |
| 51 | - | - | - | - | - | - | 43 ±43 | - | 201 ±200 | - | - | - | - | - | - |
| 58 | - | - | - | - | - | - | 82 ±82 | - | 0±0 | - | - | - | - | - | - |
| 65 | - | - | - | - | - | - | 138 ±138 | - | 0±0 | - | - | - | - | - | - |
| 73 | - | - | - | - | - | - | 301 ±301 | - | 0±0 | - | - | - | - | - | - |
| 79 | - | - | - | - | - | - | - | - | 0±0 | - | - | - | - | - | - |
| 89 | - | - | - | - | - | - | - | - | 0±0 | - | - | - | - | - | - |
| 96 | - | - | - | - | - | - | - | - | 0±0 | - | - | - | - | - | - |

FIG. 16B Efficacy of rat-human chimeric anti-Notch3 ADCs dosed at 5mg/kg in MDA-MB-468 breast xenografts MDA-MB-468 Breast xenografts, tumor volume (mm³ ± SEM)

| Day | PBS | ch75-mc3377 | ch75-me0131 | ch75-MALPEG6 C2-0131 | ch75-mc0131 | huNeg8.8-mc0131 | huNeg8.8-mc3377 | huNeg8.8-me0131 |
|---|---|---|---|---|---|---|---|---|
| -1 | 303 ±10 | 304 ±19 | 303 ±18 | 308 ±22 | 305 ±14 | 306 ±14 | 302 ±15 | 306 ±21 |
| 2 | 344 ±14 | 315 ±26 | 348 ±21 | 375 ±16 | 354 ±7 | 340 ±16 | 363 ±25 | 343 ±26 |
| 5 | 360 ±17 | 339 ±25 | 339 ±16 | 325 ±23 | 346 ±14 | 349 ±19 | 366 ±19 | 349 ±31 |
| 8 | 439 ±28 | 340 ±20 | 352 ±21 | 346 ±27 | 368 ±15 | 437 ±35 | 431 ±25 | 421 ±36 |
| 12 | 533 ±41 | 337 ±22 | 311 ±26 | 312 ±31 | 350 ±18 | 492 ±27 | 449 ±30 | 486 ±41 |
| 15 | 542 ±40 | 304 ±23 | 291 ±22 | 271 ±18 | 322 ±22 | 543 ±42 | 484 ±48 | 523 ±35 |
| 19 | 608 ±46 | 234 ±20 | 228 ±25 | 204 ±20 | 283 ±19 | 552 ±37 | 516 ±26 | 542 ±45 |
| 22 | 644 ±34 | 240 ±20 | 210 ±26 | 156 ±21 | 261 ±22 | 602 ±38 | 561 ±38 | 586 ±47 |
| 26 | 707 ±58 | 256 ±22 | 169 ±14 | 127 ±14 | 252 ±25 | 615 ±65 | 604 ±34 | 664 ±52 |
| 29 | 785 ±72 | 278 ±33 | 191 ±18 | 119 ±16 | 285 ±27 | 701 ±58 | 641 ±42 | 695 ±57 |
| 33 | 822 ±78 | 320 ±45 | 203 ±23 | 133 ±22 | 315 ±31 | 755 ±80 | 737 ±57 | 759 ±66 |
| 36 | 840 ±87 | 308 ±53 | 220 ±18 | 119 ±20 | 320 ±30 | 798 ±55 | 865 ±54 | 788 ±81 |
| 40 | 894 ±80 | 346 ±51 | 276 ±39 | 143 ±20 | 367 ±41 | 882 ±90 | 946 ±69 | 853 ±77 |
| 44 | 1040 ±104 | 373 ±49 | 312 ±34 | 162 ±29 | 421 ±29 | 1050 ±109 | 1055 ±54 | 1002 ±82 |
| 48 | 1174 ±146 | 459 ±69 | 362 ±58 | 193 ±31 | 455 ±42 | 1138 ±131 | 1148 ±36 | 1066 ±92 |
| 51 | 1266 ±144 | 539 ±83 | 418 ±49 | 237 ±31 | 563 ±48 | 1301 ±127 | 1368 ±57 | 1164 ±98 |
| 54 | 1244 ±155 | 543 ±80 | 422 ±45 | 220 ±37 | 592 ±52 | 1288 ±134 | 1321 ±56 | 1206 ±139 |
| 57 | 1366 ±161 | 607 ±99 | 474 ±85 | 260 ±36 | 665 ±56 | 1380 ±151 | 1530 ±23 | 1143 ±117 |
| 61 | 1492 ±129 | 659 ±100 | 497 ±80 | 275 ±36 | 690 ±52 | 1330 ±149 | 1607 ±39 | - |
| 64 | - | 718 ±117 | 519 ±93 | 363 ±45 | 758 ±64 | 1420 ±160 | 1580 ±47 | - |
| 68 | - | - | 636 ±117 | 369 ±48 | - | 1552 ±198 | 1550 ±71 | - |
| 71 | - | - | 706 ±102 | 377 ±65 | - | - | - | - |
| 78 | - | - | 906 ±137 | 511 ±74 | - | - | - | - |

FIG. 16C Efficacy of rat-human chimeric anti-Notch3 ADCs dosed at 5mg/kg in MDA-MB-468 breast xenograft MDA-MB-468 Breast xenografts, tumor volume (mm³ ± SEM)

| Day | PBS | ch28-mc0131 | ch28-mc3377 | ch28-me0131 | ch28-MALPEG6 C2-0131 | ch75-mc0131 | ch28-vc0101 | ch28-vc6780 | ch75-vc0101 | ch75-vc6780 | huNeg8.8-mc0131 | huNeg8.8-mc3377 | huNeg8.8-me0131 | huNeg8.8-vc0101 | huNeg8.8-vc6780 |
|---|---|---|---|---|---|---|---|---|---|---|---|---|---|---|---|
| -1 | 309 ±11 | 314 ±12 | 313 ±20 | 314 ±15 | 311 ±22 | 307 ±19 | 313 ±22 | 309 ±20 | 312 ±7 | 308 ±8 | 313 ±21 | 310 ±15 | 308 ±22 | 312 ±18 | 312 ±19 |
| 4 | 396 ±20 | 358 ±19 | 321 ±20 | 329 ±19 | 331 ±26 | 337 ±16 | 303 ±21 | 325 ±18 | 328 ±21 | 341 ±17 | 353 ±27 | 333 ±19 | 358 ±27 | 333 ±27 | 375 ±17 |
| 8 | 414 ±25 | 315 ±18 | 297 ±17 | 306 ±14 | 295 ±25 | 315 ±14 | 241 ±24 | 303 ±21 | 297 ±23 | 323 ±21 | 384 ±33 | 391 ±26 | 398 ±32 | 349 ±22 | 383 ±16 |
| 11 | 452 ±31 | 262 ±15 | 237 ±15 | 256 ±12 | 238 ±22 | 324 ±22 | 149 ±17 | 249 ±25 | 219 ±16 | 306 ±25 | 422 ±33 | 408 ±31 | 422 ±40 | 350 ±35 | 420 ±20 |
| 18 | 578 ±48 | 143 ±11 | 121 ±10 | 173 ±21 | 115 ±9 | 257 ±28 | 38 ±8 | 143 ±18 | 108 ±12 | 257 ±35 | 496 ±45 | 479 ±40 | 537 ±56 | 310 ±61 | 486 ±19 |
| 21 | 615 ±46 | 107 ±9 | 119 ±10 | 145 ±19 | 68 ±6 | 214 ±27 | 24 ±7 | 14 ±2±21 | 70 ±10 | 232 ±43 | 499 ±47 | 569 ±49 | 572 ±55 | 275 ±66 | 548 ±39 |
| 28 | 729 ±69 | 113 ±16 | 132 ±15 | 95 ±18 | 26 ±10 | 171 ±24 | 14 ±7 | 168 ±25 | 37 ±11 | 258 ±50 | 584 ±51 | 638 ±72 | 638 ±61 | 251 ±66 | 616 ±28 |
| 35 | 835 ±87 | 131 ±25 | 191 ±20 | 127 ±19 | 15 ±8 | 206 ±29 | 7 ±5 | 176 ±33 | 26 ±9 | 340 ±58 | 662 ±64 | 758 ±101 | 772 ±86 | 279 ±72 | 730 ±57 |
| 39 | 968 ±103 | 179 ±37 | 234 ±19 | 148 ±33 | 32 ±12 | 267 ±36 | 0 ±0 | 229 ±41 | 13 ±9 | 400 ±74 | 702 ±56 | 882 ±110 | 881 ±114 | 361 ±99 | 860 ±65 |
| 42 | 1004 ±112 | 168 ±35 | 256 ±22 | 174 ±37 | 32 ±13 | 255 ±38 | 0 ±0 | 242 ±41 | 10 ±8 | 420 ±72 | 753 ±75 | 945 ±123 | 926 ±115 | 362 ±90 | 888 ±49 |
| 46 | 1140 ±126 | 191 ±43 | 290 ±27 | 188 ±48 | 44 ±16 | 293 ±35 | 0 ±0 | 243 ±41 | 11 ±8 | 442 ±77 | 834 ±77 | 1016 ±148 | 1022 ±135 | 377 ±101 | 965 ±102 |
| 49 | 1211 ±92 | 233 ±56 | 333 ±33 | 207 ±45 | 37 ±17 | 334 ±46 | 0 ±0 | 295 ±52 | 7 ±7 | 495 ±86 | 896 ±90 | 1114 ±150 | 1060 ±130 | 439 ±115 | 1038 ±128 |
| 57 | 1402 ±112 | 298 ±67 | 447 ±37 | 272 ±59 | 72 ±28 | 400 ±53 | 0 ±0 | 369 ±65 | 13 ±13 | 652 ±110 | 1093 ±106 | 1356 ±189 | 1329 ±175 | 448 ±90 | 1275 ±143 |
| 60 |  | 328 ±169 | 513 ±42 | 335 ±67 | 69 ±28 | 472 ±59 | 0 ±0 | 373 ±61 | 25 ±16 | 688 ±118 | 1108 ±97 | 1296 ±158 | 1249 ±166 | 582 ±157 |  |
| 63 |  | 320 ±70 | 516 ±44 | 354 ±67 | 67 ±29 | 498 ±58 | 0 ±0 | 415 ±76 | 21 ±14 | 709 ±114 | 1092 ±113 | 1376 ±137 | 1332 ±160 | 579 ±148 |  |
| 67 |  | 379 ±85 | 538 ±49 | 371 ±77 | 85 ±37 | 563 ±63 | 0 ±0 | 462 ±94 | 21 ±15 | 798 ±136 | 1203 ±121 |  |  | 655 ±165 |  |
| 74 |  | 434 ±96 | 682 ±57 | 382 ±47 | 114 ±47 |  | 0 ±0 | 499 ±91 | 42 ±27 | 928 ±143 |  |  |  |  |  |
| 77 |  | 470 ±113 |  | 423 ±42 | 122 ±51 |  | 0 ±0 |  | 45 ±26 |  |  |  |  |  |  |
| 84 |  |  |  |  | 177 ±72 |  | 0 ±0 |  | 67 ±37 |  |  |  |  |  |  |
| 98 |  |  |  |  | 162 ±75 |  | 0 ±0 |  | 55 ±37 |  |  |  |  |  |  |
| 104 |  |  |  |  |  |  | 0 ±0 |  |  |  |  |  |  |  |  |
| 112 |  |  |  |  |  |  | 0 ±0 |  |  |  |  |  |  |  |  |
| 117 |  |  |  |  |  |  | 0 ±0 |  |  |  |  |  |  |  |  |
| 126 |  |  |  |  |  |  | 0 ±0 |  |  |  |  |  |  |  |  |

FIG. 16D  Efficacy of rat-human chimeric anti-Notch3 ADCs dosed at 5mg/kg in N87 gastric xenograft N87 Gastric xenografts, tumor volume (mm³ ± SEM)

| Day | PBS | ch28-mc0131 | ch28-vc0101 | ch28-vc6780 | ch75-vc0101 | ch75-vc6780 | huNeg8.8-vc0101 | huNeg8.8-vc6780 |
|---|---|---|---|---|---|---|---|---|
| -1 | 388 ±16 | 391 ±11 | 394 ±16 | 388 ±17 | 391 ±8 | 385 ±18 | 394 ±18 | 393 ±16 |
| 3 | 315 ±48 | 669 ±35 | 558 ±20 | 484 ±72 | 596 ±38 | 631 ±31 | 722 ±60 | 711 ±31 |
| 6 | 907 ±56 | 583 ±41 | 488 ±48 | 522 ±41 | 611 ±27 | 672 ±40 | 745 ±76 | 733 ±43 |
| 11 | 1335 ±67 | 623 ±50 | 313 ±26 | 416 ±48 | 437 ±29 | 568 ±74 | 858 ±112 | 1019 ±46 |
| 14 | 1260 ±85 | 452 ±48 | 208 ±21 | 297 ±52 | 275 ±18 | 447 ±87 | 771 ±124 | 988 ±86 |
| 18 | 1393 ±101 | 468 ±55 | 183 ±20 | 285 ±65 | 228 ±17 | 419 ±91 | 727 ±167 | 997 ±88 |
| 21 | 1701 ±117 | 528 ±61 | 189 ±25 | 314 ±80 | 221 ±28 | 462 ±121 | 775 ±180 | 1202 ±156 |
| 25 | - | 531 ±72 | 194 ±30 | 305 ±84 | 224 ±44 | 430 ±131 | 579 ±112 | 1151 ±119 |
| 28 | - | 579 ±78 | 173 ±26 | 291 ±88 | 230 ±56 | 427 ±133 | 570 ±133 | 1247 ±137 |
| 31 | - | 597 ±75 | 176 ±32 | 349 ±110 | 256 ±62 | 458 ±148 | 646 ±148 | 1310 ±160 |
| 35 | - | 671 ±89 | 214 ±45 | 380 ±121 | 326 ±72 | 490 ±177 | 685 ±163 | 1465 ±237 |
| 39 | - | 762 ±98 | 256 ±53 | 406 ±133 | 416 ±109 | 514 ±190 | 791 ±186 | - |
| 42 | - | 894 ±118 | 279 ±55 | 470 ±217 | 497 ±123 | 611 ±230 | 892 ±5%& | - |
| 46 | - | 873 ±115 | 279 ±58 | 493 ±158 | 549 ±156 | 603 ±225 | 912 ±248 | - |
| 50 | - | 1020 ±149 | 341 ±80 | 573 ±179 | 630 ±187 | 806 ±285 | - | - |
| 55 | - | 1055 ±153 | 374 ±83 | 560 ±174 | 715 ±207 | 600 ±238 | - | - |
| 62 | - | 1193 ±207 | 379 ±85 | 653 ±204 | 806 ±253 | 649 ±254 | - | - |
| 69 | - | - | 490 ±106 | 773 ±254 | - | 788 ±313 | - | - |
| 77 | - | - | 534 ±126 | 720 ±269 | - | - | - | - |
| 83 | - | - | 627 ±156 | - | - | - | - | - |
| 90 | - | - | 813 ±197 | - | - | - | - | - |
| 95 | - | - | 903 ±207 | - | - | - | - | - |
| 101 | - | - | 901 ±213 | - | - | - | - | - |

FIG. 16E  Efficacy of rat-human chimeric anti-Notch3 ADCs dosed at 5mg/kg in N87 gastric xenografts N87 Gastric xenografts, tumor volume (mm³ ± SEM)

| Day | PBS | ch28-mc0131 | ch28-m(H2O)c-0131 | ch75-mc0131 | ch75-m(H2O)c-0131 |
|---|---|---|---|---|---|
| -1 | 372 ±8 | 371 ±18 | 371 ±17 | 364 ±12 | 373 ±15 |
| 4 | 589 ±28 | 473 ±41 | 469 ±41 | 461 ±33 | 497 ±34 |
| 7 | 706 ±56 | 479 ±39 | 446 ±34 | 466 ±28 | 484 ±35 |
| 11 | 837 ±71 | 442 ±37 | 391 ±29 | 468 ±33 | 414 ±28 |
| 14 | 959 ±98 | 395 ±43 | 303 ±24 | 430 ±33 | 337 ±20 |
| 18 | 1069 ±106 | 328 ±36 | 231 ±27 | 424 ±41 | 279 ±14 |
| 21 | 1252 ±123 | 337 ±48 | 232 ±29 | 448 ±42 | 268 ±13 |
| 25 | 1230 ±112 | 324 ±55 | 230 ±38 | 422 ±45 | 271 ±11 |
| 28 | 1352 ±132 | 363 ±62 | 256 ±41 | 487 ±52 | 266 ±17 |
| 32 | - | 381 ±66 | 255 ±49 | 530 ±56 | 298 ±22 |
| 35 | - | 419 ±85 | 283 ±52 | 541 ±56 | 307 ±21 |
| 39 | - | 453 ±87 | 315 ±65 | 570 ±55 | 358 ±23 |
| 42 | - | 522 ±108 | 347 ±71 | 619 ±66 | 388 ±34 |
| 46 | - | 559 ±119 | 381 ±87 | 629 ±68 | 432 ±41 |
| 49 | - | 637 ±139 | 418 ±96 | 697 ±87 | 447 ±48 |
| 53 | - | 681 ±149 | 441 ±107 | 755 ±91 | 484 ±52 |
| 56 | - | 713 ±167 | 479 ±113 | 753 ±90 | 512 ±55 |
| 63 | - | 783 ±192 | 542 ±139 | 869 ±112 | 563 ±70 |
| 70 | - | 847 ±219 | 535 ±148 | 827 ±107 | 579 ±86 |
| 77 | - | 1081 ±273 | 726 ±191 | 1041 ±139 | 788 ±110 |
| 84 | - | - | 855 ±230 | 1172 ±165 | 872 ±131 |
| 91 | - | - | 722 ±194 | 1332 ±194 | 1015 ±169 |
| 98 | - | - | 757 ±204 | - | 1125 ±198 |

FIG. 17A

SEQ ID NO: 61 hu28 HC 1.0 L443C amino acid sequence
EVQLVESGGGLVQPGGSLRLSCAASGFTFRDYGMTWVRQAPGKGLEWVAYISSGSNYIYYAEAVKGRF
TISRDNAKNSLYLQMNSLRAEDTAVYYCARRGPFVLDAWGQGTLVTVSSASTKGPSVFPLAPSSKSTSG
GTAALGCLVKDYFPEPVTVSWNSGALTSGVHTFPAVLQSSGLYSLSSVVTVPSSSLGTQTYICNVNHKPS
NTKVDKKVEPKSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFFLYSKLTVDKS
RWQQGNVFSCSVMHEALHNHYTQKSLSCSPG

SEQ ID NO: 62 hu28 HC 1.0 L443C nucleotide sequence
GAGGTGCAGCTGGTGGAGTCTGGGGGAGGCTTGGTCCAGCCTGGGGGGTCCCTGAGACTCTCCTG
TGCAGCCTCTGGATTCACTTTCAGGGACTATGGAATGACCTGGGTCCGCCAGGCTCCAGGGAAGGG
GCTGGAGTGGGTGGCCTATATTAGTAGTGGTAGCAATTACATCTATTATGCAGAAGCGGTGAAGGGC
CGATTCACCATCTCCAGAGACAACGCCAAGAACTCACTGTATCTGCAAATGAACAGCCTGAGAGCCG
AGGACACGGCTGTGTATTACTGTGCGAGACGAGGCCCGTTTGTTTTGGATGCCTGGGGCCAGGGAA
CCCTGGTCACCGTCTCCTCAGCGTCGACCAAGGGCCCATCGGTCTTCCCCCTGGCACCCTCCTCCA
AGAGCACCTCTGGGGGCACAGCGGCCCTGGGCTGCCTGGTCAAGGACTACTTCCCCGAACCGGTG
ACGGTGTCGTGGAACTCAGGCGCCCTGACCAGCGGCGTGCACACCTTCCCGGCTGTCCTACAGTC
CTCAGGACTCTACTCCCTCAGCAGCGTGGTGACCGTGCCCTCCAGCAGCTTGGGCACCCAGACCTA
CATCTGCAACGTGAATCACAAGCCCAGCAACACCAAGGTGGACAAGAAAGTTGAGCCCAAATCTTGT
GACAAAACTCACACATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCACATGCGTGGTGGTG
GACGTGAGCCACGAAGACCCTGAGGTCAAGTTCAACTGGTACGTGGACGGCGTGGAGGTGCATAAT
GCCAAGACAAAGCCGCGGGAGGAGCAGTACAACAGCACGTACCGTGTGGTCAGCGTCCTCACCGT
CCTGCACCAGGACTGGCTGAATGGCAAGGAGTACAAGTGCAAGGTCTCCAACAAAGCCCTCCCAGC
CCCCATCGAGAAAACCATCTCCAAAGCCAAAGGGCAGCCCCGAGAACCACAGGTGTACACCCTGCC
CCCATCCCGGGAGGAGATGACCAAGAACCAGGTCAGCCTGACCTGCCTGGTCAAAGGCTTCTATCC
CAGCGACATCGCCGTGGAGTGGGAGAGCAATGGGCAGCCGGAGAACAACTACAAGACCACGCCTC
CCGTGCTGGACTCCGACGGCTCCTTCTTCCTCTATAGCAAGCTCACCGTGGACAAGAGCAGGTGGC
AGCAGGGGAACGTCTTCTCATGCTCCGTGATGCATGAGGCTCTGCACAACCACTACACGCAGAAGA
GCCTCTCCTGCTCCCCGGGT

SEQ ID NO: 63 hu28 LC 1.0 κK183C amino acid sequence
DIQMTQSPSSLSASVGDRVTITCKASQSINRYLHWYQQKPGKAPKLLIYNANGLQTGVPSRFSGSGSGTD
FTLTISSLQPEDFATYYCLQHNTWPDTFGGGTKVEIKRTVAAPSVFIFPPSDEQLKSGTASVVCLLNNFYP
REAKVQWKVDNALQSGNSQESVTEQDSKDSTYSLSSTLTLSCADYEKHKVYACEVTHQGLSSPVTKSFN
RGEC

SEQ ID NO: 64 hu28 LC 1.0 κK183C nucleotide sequence
GACATCCAGATGACCCAGTCTCCATCCTCCCTGTCTGCATCTGTAGGAGACAGAGTCACCATCACTT
GCAAAGCAAGTCAGAGTATTAACAGGTACTTACACTGGTATCAGCAGAAACCAGGGAAAGCCCCTAA
GCTCCTGATCTATAATGCAAACGGTTTGCAAACGGGGGTCCCATCAAGGTTCAGTGGCAGTGGATCT
GGGACAGATTTCACTCTCACCATCAGCAGTCTGCAACCTGAAGATTTTGCAACTTACTACTGTTTGCA
GCATAATACGTGGCCGGACACGTTTGGCGGAGGGACCAAGGTGGAGATCAAACGAACTGTGGCTG
CACCATCTGTCTTCATCTTCCCGCCATCTGATGAGCAGTTGAAATCTGGAACTGCCTCTGTTGTGTGC
CTGCTGAATAACTTCTATCCCAGAGAGGCCAAAGTACAGTGGAAGGTGGATAACGCCCTCCAATCGG
GTAACTCCCAGGAGAGTGTCACAGAGCAGGACAGCAAGGACAGCACCTACAGCCTCAGCAGCACCC
TGACGCTGAGCTGCGCAGACTACGAGAAACACAAAGTCTACGCCTGCGAAGTCACCCATCAGGGCC
TGAGCTCGCCCGTCACAAAGAGCTTCAACAGGGGAGAGTGT

FIG. 17B

SEQ ID NO: 65 hu28 HC 1.0 L443C/K392C amino acid sequence
EVQLVESGGGLVQPGGSLRLSCAASGFTFRDYGMTWVRQAPGKGLEWVAYISSGSNYIYYAEAVKGRF
TISRDNAKNSLYLQMNSLRAEDTAVYYCARRGPFVLDAWGQGTLVTVSSASTKGPSVFPLAPSSKSTSG
GTAALGCLVKDYFPEPVTVSWNSGALTSGVHTFPAVLQSSGLYSLSSVVTVPSSSLGTQTYICNVNHKPS
NTKVDKKVEPKSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYCTTPPVLDSDGSFFLYSKLTVDKS
RWQQGNVFSCSVMHEALHNHYTQKSLSCSPG SEQ ID NO: 66 hu28 HC 1.0 L443C/K392C nucleotide sequence
GAGGTGCAGCTGGTGGAGTCTGGGGGAGGCTTGGTCCAGCCTGGGGGGTCCCTGAGACTCTCCTG
TGCAGCCTCTGGATTCACTTTCAGGGACTATGGAATGACCTGGGTCCGCCAGGCTCCAGGGAAGGG
GCTGGAGTGGGTGGCCTATATTAGTAGTGGTAGCAATTACATCTATTATGCAGAAGCGGTGAAGGGC
CGATTCACCATCTCCAGAGACAACGCCAAGAACTCACTGTATCTGCAAATGAACAGCCTGAGAGCCG
AGGACACGGCTGTGTATTACTGTGCGAGACGAGGCCCGTTTGTTTTGGATGCCTGGGGCCAGGGAA
CCCTGGTCACCGTCTCCTCAGCGTCGACCAAGGGCCCATCGGTCTTCCCCCTGGCACCCTCCTCCA
AGAGCACCTCTGGGGGCACAGCGGCCCTGGGCTGCCTGGTCAAGGACTACTTCCCCGAACCGGTG
ACGGTGTCGTGGAACTCAGGCGCCCTGACCAGCGGCGTGCACACCTTCCCGGCTGTCCTACAGTC
CTCAGGACTCTACTCCCTCAGCAGCGTGGTGACCGTGCCCTCCAGCAGCTTGGGCACCCAGACCTA
CATCTGCAACGTGAATCACAAGCCCAGCAACACCAAGGTGGACAAGAAAGTTGAGCCCAAATCTTGT
GACAAAACTCACACATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCACATGCGTGGTGGTG
GACGTGAGCCACGAAGACCCTGAGGTCAAGTTCAACTGGTACGTGGACGGCGTGGAGGTGCATAAT
GCCAAGACAAAGCCGCGGGAGGAGCAGTACAACAGCACGTACCGTGTGGTCAGCGTCCTCACCGT
CCTGCACCAGGACTGGCTGAATGGCAAGGAGTACAAGTGCAAGGTCTCCAACAAAGCCCTCCCAGC
CCCCATCGAGAAAACCATCTCCAAAGCCAAAGGGCAGCCCCGAGAACCACAGGTGTACACCCTGCC
CCCATCCCGGGAGGAGATGACCAAGAACCAGGTCAGCCTGACCTGCCTGGTCAAAGGCTTCTATCC
CAGCGACATCGCCGTGGAGTGGGAGAGCAATGGGCAGCCGGAGAACAACTACTGCACCACGCCTC
CCGTGCTGGACTCCGACGGCTCCTTCTTCCTCTATAGCAAGCTCACCGTGGACAAGAGCAGGTGGC
AGCAGGGGAACGTCTTCTCATGCTCCGTGATGCATGAGGCTCTGCACAACCACTACACGCAGAAGA
GCCTCTCCTGCTCCCCGGGT

US 9,433,687 B2

ANTI-NOTCH3 ANTIBODIES AND ANTIBODY-DRUG CONJUGATES

RELATED APPLICATIONS

This application claims the benefits of U.S. Provisional Application No. 61/723,772 filed Nov. 7, 2012 and U.S. Provisional Application No. 61/889,744 filed Oct. 11, 2013, which are hereby incorporated by reference in their entireties.

SEQUENCE LISTING

This application is being filed electronically via EFS-Web and includes an electronically submitted sequence listing in .txt format. The .txt file contains a sequence listing entitled "PC071980A_Sequence_Listing.txt" created on Oct. 11, 2013, and having a size of 61 KB. The sequence listing contained in this .txt file is part of the specification and is incorporated herein by reference in its entirety.

FIELD OF THE INVENTION

The present invention relates to anti-Notch3 antibodies and anti-Notch3 antibody-drug conjugates. The present invention further relates to methods of using such antibodies and antibody-drug conjugates for the treatment of cancer.

BACKGROUND

Notch signaling is triggered by extracellular receptor and ligand interactions. Notch receptors control normal cellular proliferation, differentiation, and death in multicellular organisms through a signaling cascade that is triggered by ligand-induced proteolysis. After furin-like protease cleavage at site S1, the mature Notch heterodimer is translocated into the cell membrane where it is held in an auto-inhibited state by a juxtamembrane Negative Regulatory Region (NRR) consisting of three Lin12/Notch repeats (LNR-A, B, C) and the heterodimerization (HD) domain. The HD domain is divided into N-terminal (HD1) and C-terminal (HD2) halves after cleavage at site S1. Through an uncertain mechanism, binding of ligands of the Delta/Serrate/Lag-2 (DSL) family to the extracellular EGF-repeat region relieves this inhibition and induces two additional cleavage events. First, ADAM-type metalloproteinase mediate cleavage at site S2 near the C-terminal region of the HD-2 domain, thereby releasing the extracellular domain (ECD) from the cell surface which then undergoes trans-endocytosis into the ligand-expressing cell. Next, gamma-secretase mediates cleavage at site S3 within the transmembrane domain which releases the intracellular domain of Notch (Notch-ICD) from the membrane, permitting it to translocate to the nucleus and activate the transcription of target genes (Bray, S., Nature Reviews Molecular Cell Biology, 2006, volume 7, 678-689).

The X-ray crystal structure of the human Notch2-NRR domain in an auto-inhibited conformation revealed extensive interactions between the LNR repeats and heterdimerization domains within the NRR burying the metalloprotease S2 site, suggesting that a substantial conformational movement is necessary to expose the site during activation by ligand (Gordon, W. R., et. al, Nature Structural & Molecular Biology, 2007, volume 14, 295-300). Studies suggest that stabilization of the interactions within the NRR may prevent ligand-induced Notch activation. The availability of structural information on the Notch auto-inhibited conformation provided new opportunities for the development of therapeutics, particularly antibodies that target Notch signaling. (Li, K., et. al, Journal of Biological Chemistry, 2008, volume 283, 8046-8054; Aste-Amezaga, M, et. al, PLOS ONE, 2010, volume 5, e9094; Wu, Y., et. al, Nature, 2010, volume 464, 1052-1057).

In mammalian cells, there are four known Notch receptors. Notch-1, -2, -3 and -4 have broad, overlapping patterns of expression in embryonic and adult tissues, and fulfill non-redundant roles during hematopoietic stem cell specification, T cell development, intestinal crypt cell specification and vascular development. Notch3 is expressed primarily in vascular smooth muscle cells (vSMC), various thymocyte subpopulations and the developing nervous system. Consistent with its restricted tissue distribution, targeted deletion of murine Notch3 does not lead to embryonic lethality like Notch1 and Notch2 deletion. Instead, Notch3-null mice are viable, but have defects in the maturation and differentiation of vSMCs (Domenga, V., et. al, Genes and Development, 2004, volume 18, 2730-2735).

Notch activation is oncogenic in many contexts; constitutively active, intracellular forms of all four Notch homologues function as oncogenes in vitro and in transgenic mouse models. Recent studies indicate that Notch3 is often amplified and overexpressed in various human solid tumors and the over-expression of developmental signaling pathways, such as Notch3, in human cancers implicates them as key mediators of tumorigenesis. Several strategies are in development to block Notch signaling for therapeutic purposes in cancer; however there is still a need in the art for more potent and efficacious anti-Notch targeted therapies for the treatment of cancer.

Antibody-drug conjugates (ADCs) combine the specificity and targeting of high affinity antibodies with the cytotoxicity of a therapeutic agent, such as cytotoxic agents, biological response modifiers, enzymes, apoptosis-inducing agents, and radioisotopes. Release of therapeutic agents from the antibody can require trafficking and localization of the antibody-drug conjugate to lysosomes and both Notch3-ECD and Notch3-ICD undergo lysosomal degradation, thus antibodies that bind Notch3 are expected to traffic to the lysosome (Jia L, et. al, International Journal of Biochemistry and Cell Biology, 2009, volume 41, 2594-2598). The present invention provides novel anti-Notch3 antibodies and anti-body-drug conjugates that fulfill an unmet clinical need in the diagnosis and therapeutic use in the treatment of cancer.

SUMMARY

The present invention provides for anti-Notch3 antibodies and antibody-drug conjugates (ADCs). The present invention also provides for methods of using such anti-Notch3 antibodies and antibody-drug conjugates for the treatment of cancer.

In one embodiment, the present invention provides for isolated antibodies, or antigen-binding fragment thereof, that bind to Notch3, having a CDR1, a CDR2, and a CDR3 of SEQ ID NO: 13 and, a light chain variable region having a CDR1, a CDR2, and a CDR3 of SEQ ID NO: 25.

In another embodiment, the present invention provides for isolated antibodies, or antigen-binding fragment thereof, that bind to Notch3, wherein the antibody or antigen-binding fragment: (a) internalizes into a cell, (b) does not inhibit Notch3 signaling, or (c) does not activate Notch3 signaling. In a further embodiment, the present invention provides for isolated antibodies, or antigen-binding fragment thereof, that bind to Notch3, wherein the antibody or antigen-binding fragment: (a) binds to the LNR-C and HD-1 domains of the Notch3 NRR, (b) does not maintain the Notch3 NRR in an auto-inhibitory conformation, or (c) does not inhibit S2-cleavage.

In a further embodiment, the present invention provides for isolated antibodies, or antigen-binding fragment thereof, that bind to Notch3, having: (a) a heavy chain CDR1 comprising SEQ ID NO: 15 or 16; (b) a heavy chain CDR2 comprising SEQ ID NO: 19 or 20; (c) a heavy chain CDR3 comprising SEQ ID NO: 23; (d) a light chain CDR1 comprising SEQ ID NO: 27; (e) a light chain CDR2 comprising SEQ ID NO: 29; and, (f) a light chain CDR3 comprising SEQ ID NO: 31.

The present invention also provides for isolated antibodies, or antigen-binding fragment thereof, that bind to Notch3, having a heavy chain variable region amino acid sequence that is at least 90% identical to SEQ ID NO: 13 or a light chain variable region amino acid sequence that is at least 90% identical to SEQ ID NO: 25.

The present invention also provides for isolated antibodies, or antigen-binding fragment thereof, that bind to Notch3 having a heavy chain variable region amino acid sequence of SEQ ID NO: 13 and isolated antibodies, or antigen-binding fragment thereof, that bind to Notch3 having a light chain variable region amino acid sequence of SEQ ID NO: 25. The present invention also provides for isolated antibodies, or antigen-binding fragment thereof, that bind to Notch3 having a heavy chain amino acid sequence of SEQ ID NO: 33 and isolated antibodies, or antigen-binding fragment thereof, that bind Notch3 having a light chain amino acid sequence of SEQ ID NO: 35.

In another embodiment, the present invention provides for isolated antibodies, or antigen-binding fragment thereof, that bind to Notch3, having a heavy chain variable region comprising a CDR1, a CDR2, and a CDR3 of SEQ ID NO: 37 and, a light chain variable region having a CDR1, a CDR2, and a CDR3 of SEQ ID NO: 49.

In further embodiment, the present invention provides for isolated antibodies, or antigen-binding fragment thereof, that bind to Notch3, having: (a) a heavy chain CDR1 comprising SEQ ID NO: 39 or 40; (b) a heavy chain CDR2 comprising SEQ ID NO: 43 or 44; (c) a heavy chain CDR3 comprising SEQ ID NO: 47; (d) a light chain CDR1 comprising SEQ ID NO: 51; (e) a light chain CDR2 comprising SEQ ID NO: 53; and, (f) a light chain CDR3 comprising SEQ ID NO: 55.

The present invention also provides for isolated antibodies, or antigen-binding fragment thereof, that bind to Notch3, having a heavy chain variable region amino acid sequence that is at least 90% identical to SEQ ID NO: 37 or a light chain variable region amino acid sequence that is at least 90% identical to SEQ ID NO: 49.

The present invention also provides for isolated antibodies, or antigen-binding fragment thereof, that bind to Notch3 having a heavy chain variable region amino acid sequence of SEQ ID NO: 37 and isolated antibodies, or antigen-binding fragment thereof, that bind to Notch3 having a light chain variable region amino acid sequence of SEQ ID NO: 49. The present invention also provides for isolated antibodies, or antigen-binding fragment thereof, that bind to Notch3 having a heavy chain amino acid sequence of SEQ ID NO: 57 and isolated antibodies, or antigen-binding fragment thereof, that bind to Notch3 having a light chain amino acid sequence of SEQ ID NO: 59.

The invention further provides for isolated antibodies that compete with an antibody, or antigen-binding fragment thereof, of the present invention for specific binding to Notch3.

The present invention further provides for antibody-drug conjugates having a cytotoxic agent conjugated to any antibody, or antigen-binding fragment thereof, of the present invention.

In another embodiment, the present invention provides for antibody-drug conjugates of the formula: Ab-(L-D)p, or a pharmaceutically acceptable salt thereof wherein; Ab is an antibody, or antigen-binding fragment thereof, that binds to Notch3; L-D is a linker-drug moiety, wherein L is a linker, and D is a drug; and p is an integer from 1 to about 12.

In a further embodiment, the present invention provides antibody-drug conjugates of the formula: Ab-(L-D)p, or a pharmaceutically acceptable salt thereof wherein; Ab is any antibody, or antigen-binding fragment thereof, of the present invention; L-D is a linker-drug moiety, wherein L is a linker, and D is a drug; and p is an integer from 1 to about 12.

In another embodiment, the present invention provides antibody-drug conjugates wherein L is selected from the group consisting of vc, mc, me and MalPeg6C2.

In another embodiment, the present invention provides antibody-drug conjugates wherein D is selected from the group consisting of: (a) 0101 (2-Methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide), (b) 6780 (2-methylalanyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide), (c) 0131 (2-methyl-L-prolyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt), (d) 3377 (N,2-dimethylalanyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide, trifluoroacetic acid salt), and (e) 8261 (2-Methylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide).

The present invention further provides for antibody-drug conjugates wherein L-D is selected from the group consisting of:

vc0101 having the formula:

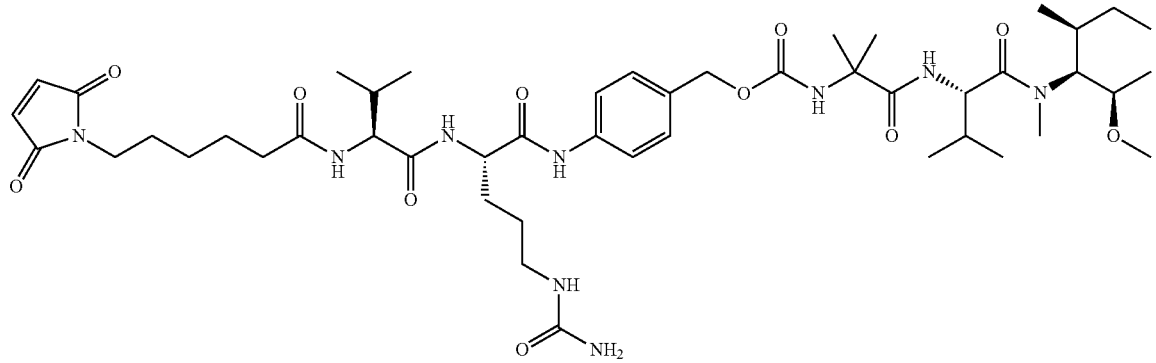

-continued

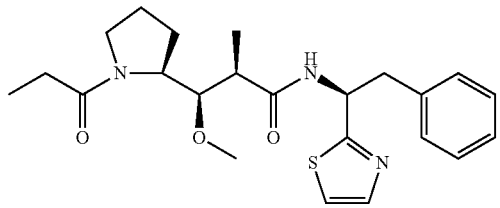

and vc6780 having the formula:

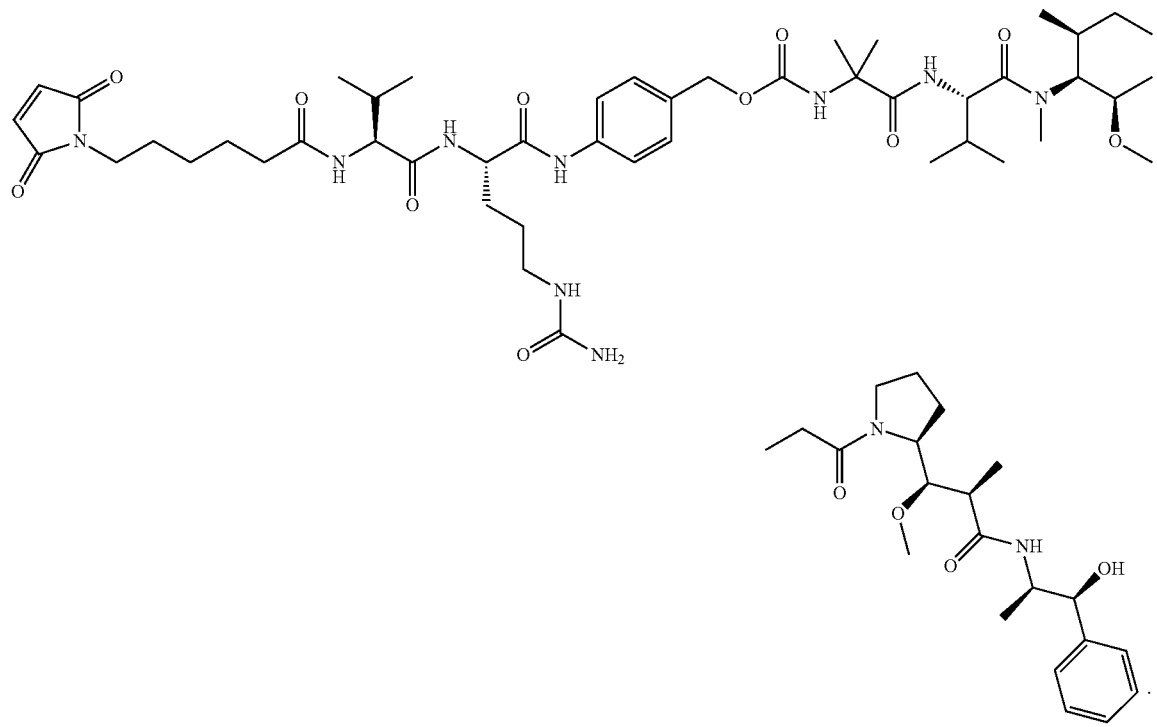

In another embodiment, the present invention provides for antibody-drug conjugates, wherein Ab comprises (a) a heavy chain variable region having a CDR1, a CDR2, and a CDR3 of SEQ ID NO: 13; and, (b) a light chain variable region having a CDR1, a CDR2, and a CDR3 of SEQ ID NO: 25.

The present invention further provides for antibody-drug conjugates, wherein Ab comprises (a) a heavy chain CDR1 comprising SEQ ID NO: 15; (b) a heavy chain CDR2 comprising SEQ ID NO: 19; (c) a heavy chain CDR3 comprising SEQ ID NO: 23; (d) a light chain CDR1 comprising SEQ ID NO: 27; (e) a light chain CDR2 comprising SEQ ID NO: 29; and, (f) a light chain CDR3 comprising SEQ ID NO: 31.

In another embodiment, the present invention provides for antibody-drug conjugates, wherein Ab comprises (a) a heavy chain variable region comprising a CDR1, a CDR2, and a CDR3 of SEQ ID NO: 37; and, (b) a light chain variable region comprising a CDR1, a CDR2, and a CDR3 of SEQ ID NO: 49.

The present invention further provides for antibody-drug conjugates, wherein Ab comprises (a) a heavy chain CDR1 comprising SEQ ID NO: 39; (b) a heavy chain CDR2 comprising SEQ ID NO: 43; (c) a heavy chain CDR3 comprising SEQ ID NO: 47; (d) a light chain CDR1 comprising SEQ ID NO: 51; (e) a light chain CDR2 comprising SEQ ID NO: 53; and, (f) a light chain CDR3 comprising SEQ ID NO: 55.

The present invention further provides for antibody-drug conjugates, wherein Ab comprises an engineered human IgG1 heavy chain constant domain (Cγ) polypeptide selected from the group consisting of: (a) one amino acid substitution at position L443 as set forth in SEQ ID NO: 61 and (b) two amino acid substitutions at positions L443 and K392 as set forth in SEQ ID NO: 65, according to the EU index of Kabat.

The present invention further provides for antibody-drug conjugates, wherein Ab comprises an engineered human kappa light chain constant domain (CK) polypeptide having one amino acid substitution at position κK183 as set forth in SEQ ID NO: 63, according to the EU index of Kabat.

The present invention further provides a pharmaceutical composition having any antibody, or antigen-binding fragment thereof, of the present invention or any antibody-drug conjugate of the present invention and a pharmaceutically acceptable carrier.

Further, the present invention provides for a method of treating a condition associated with Notch3 expression in a patient in need thereof, comprising administering to the patient any antibody-drug conjugate or a pharmaceutical composition of the present invention. The present invention also provides for a method of treating cancer, wherein the cancer is a solid tumor cancer. Further, the present invention provides for methods treating solid tumor cancers including, but not limited to, lung cancer, breast cancer, ovarian cancer, stomach cancer, esophageal cancer, cervical cancer, head and neck cancer, bladder cancer, liver cancer, skin cancer and sarcoma. The present invention also provides for methods of treating cancer, wherein the cancer is a blood cancer including, but limited to, T-cell malignancies, T-cell leukemia, T-cell lymphoma, T-cell acute lymphoblastic leukemia, multiple myeloma, B-cell malignancies, myeloid malignancies, acute myeloid leukemia and chronic myeloid leukemia.

The present invention provides any antibody-drug conjugate or pharmaceutical composition of the present invention for use in therapy. The present invention further provides for use in a therapy, wherein the cancer is a solid tumor cancer. The present invention also provides for use in therapy wherein the solid tumor cancers includes but is not limited lung cancer, breast cancer, ovarian cancer, stomach cancer, esophageal cancer, cervical cancer, head and neck cancer, bladder cancer, liver cancer, skin cancer and sarcoma. The present invention also provides for use in a therapy, wherein the cancer is a blood cancer including, but not limited to, T-cell malignancies, T-cell leukemia, T-cell lymphoma, T-cell acute lymphoblastic leukemia, multiple myeloma, B-cell malignancies, myeloid malignancies, acute myeloid leukemia and chronic myeloid leukemia. The invention further provides for use of any antibody-drug conjugate of the present invention in the manufacture of a medicament for therapy. The invention further provides the use of any antibody-drug conjugate of the present invention, wherein said use is for the treatment of a Notch3 expressing cancer.

The invention further provides a nucleic acid that encodes Notch3 antibodies, or antibody-binding fragments thereof, of the present invention, a vector comprising said nucleic acid, and a host cell comprising said vector. The invention also provides a process for producing Notch3 antibodies of the present invention wherein said process comprises cultivating the host cell comprising the above mentioned vector and recovering the antibody from the cell culture.

In another embodiment, the invention provides a process for producing antibody-drug conjugates of the present invention comprising: linking L to D; conjugating the L-D to an antibody recovered from the culture of the present invention; and purifying the antibody-drug conjugate.

The invention further provides for antibody-drug conjugates having antibody, or antigen-binding fragments thereof, of the present invention that specifically binding to Notch3.

In a further embodiment, the present invention provides a method for predicting whether a subject with cancer will respond to any antibody-drug conjugates of the present invention by determining whether a biological sample from the subject expresses Notch3.

The invention further provides a process of determining the level of Notch3 in a biological sample comprising the steps of: contacting a sample from a subject suspected to have cancer with any antibody, or antigen-binding fragment thereof, of the present invention; determining the cell surface levels of Notch3 on the sample; and comparing the cell surface levels of Notch3 with that of a reference subject or standard.

BRIEF DESCRIPTION OF THE DRAWINGS

FIG. 2 shows the amino acid and nucleotide sequences of purified human and mouse Notch3 NRR recombinant proteins.

FIG. 3 shows the amino acid and nucleotide sequences of r28 and r75 antibody variable regions (CDRs underlined).

FIGS. 4A through 4C show the amino acid and nucleotide sequences of [A] hu28 VH 1.0 and CDRs (Kabat and Chothia), [B] hu28 VL 1.0 and CDRs (Kabat and Chothia), and [C] hu28 HC 1.0 and LC 1.0.

FIGS. 5A through 5C show the amino acid and nucleotide sequences of [A] hu75 VH 1.9 and CDRs (Kabat and Chothia), [B] hu75 VL 1.3 and CDRs (Kabat and Chothia), and [C] hu75 HC 1.9 and LC 1.3.

FIG. 6 shows recombinant human Notch1 NRR and Notch3 NRR domain swap chimeric constructs for epitope mapping of the anti-Notch3 antibodies ch28 and ch75.

FIGS. 13A and 13B show [A] the efficacy of anti-Notch3 hu28-vc0101 in the MDA-MB-468 breast model and [B] the efficacy of anti-Notch3 hu75-vc0101 in the MDA-MB-468 breast model.

FIGS. 14A and 14B show [A] the efficacy of anti-Notch3 hu28-vc6780 in the MDA-MB-468 breast model and [B] the efficacy of anti-Notch3 hu75-vc6780 in the MDA-MB-468 breast model.

FIGS. 16A through 16E show [A] the efficacy of rat-human chimeric anti-Notch3 antibody-drug conjugates dosed at 5 mg/kg in HCC2429 lung xenografts; [B and C] the efficacy of rat-human chimeric anti-Notch3 antibody-drug conjugates dosed at 5 mg/kg in MDA-MB-468 breast xenografts; [D and E] the efficacy of rat-human chimeric anti-Notch3 antibody-drug conjugates dosed at 5 mg/kg in N87 gastric xenografts.

FIGS. 17A and 17B show the amino acid and nucleotide sequences of [A] single cysteine mutants hu28 HC 1.0 L443C and hu28 LC 1.0 κK183C and [B] double cysteine mutants hu28 HC 1.0 L443C/K392C.

DETAILED DESCRIPTION OF THE INVENTION

Figure 1:
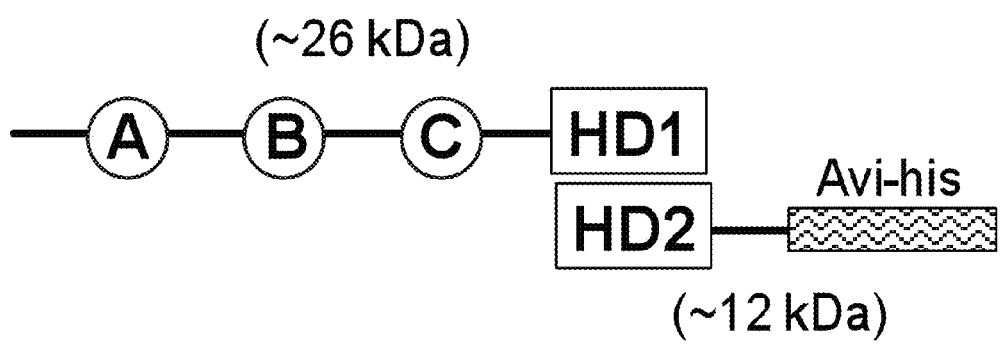
FIG. 1 shows a schematic diagram of recombinant, S1-cleaved, heterodimeric Notch3 NRR protein immunogen with Avi and His tags.

The present invention provides anti-Notch3 antibodies, or antigen-binding fragment thereof, and antibody-drug conjugates (ADCs) for the treatment of cancer. In order that the present invention is more readily understood, certain terms and general techniques are first defined.

All amino acid abbreviations used in this disclosure are those accepted by the United States Patent and Trademark Office as set forth in 37 C.F.R. §1.822 (d)(1).

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook J. & Russell D. *Molecular Cloning: A Laboratory Manual*, 3rd ed., Cold Spring Harbor Laboratory Press, Cold Spring Harbor, N.Y. (2000); Ausubel et al., *Short Protocols in Molecular Biology: A Compendium of Methods from Current Protocols in Molecular Biology*, Wiley, John & Sons, Inc. (2002); Harlow and Lane *Using Antibodies: A Laboratory Manual*, Cold Spring Harbor Laboratory Press, Cold Spring Harbor, N.Y. (1998); and Coligan et al., *Short Protocols in Protein Science*, Wiley, John & Sons, Inc. (2003).

"Notch3" or "Notch-3" refers to native, variants, isoforms and species homologs of human Notch3 protein. Native human Notch3 protein, for example, is made up of a leader peptide, a large epidermal growth factor (EGF)-like repeat region, three Lin12 repeats, a N terminal heterodimerization domain (HD-1), a C terminal heterodimerization domain (HD-2), a transmembrane (TM) sequence and an intracellular domain (Notch3$^{ICD}$). The NCBI/GenBank accession number of the full length human Notch3 is NM_000435.2.

"Notch3 negative regulatory region", or "Notch3 NRR" as used herein, unless otherwise indicated, refers to any native or synthetic polypeptide region of Notch3 consisting of the three Lin12 domains and the amino acid sequence or sequences located between the three Lin12 domains, plus the HD1 and HD2 domains of Notch3. In one embodiment, the "Notch3 NRR" includes the three Lin12 domains and two heterodimerization domains HD-1, and HD-2, wherein the HD-1 and HD-2 domains of Notch3 are covalently bonded and not yet cleaved by the furin-like protease (before S1 cleavage). In another embodiment, the "Notch3 NRR" includes the three Lin12 domains and the two heterodimerization domains HD-1, and HD-2, wherein the HD-1 and HD-2 domains are non-covalently bonded (after S1 cleavage). In one aspect of this embodiment, the S2 site within the HD-2 domain has not been cleaved by the ADAM-type metalloproteases. In another particular aspect of this embodiment, the S2 site within the HD-2 domain is being cleaved or has already been cleaved by the ADAM-type metalloproteases. (Gordon, W. R., et. al, Nature Structural & Molecular Biology, 2007, volume 14, 295-300).

An "antibody" or "Ab" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact polyclonal or monoclonal antibodies, but also any antigen binding portion (e.g., "antigen-binding fragment") thereof of an intact antibody that retains the ability to specifically bind to a given antigen (e.g., target Notch3) or single chain thereof, fusion proteins comprising an antibody, and any other modified configuration of the immunoglobulin molecule that comprises an antigen recognition site, for example without limitation, Fab; Fab'; F(ab')$_2$; an Fd fragment; an Fv fragment; a single domain antibody (dAb) fragment; an isolated complementarity determining region (CDR); single chain (scFv) and single domain antibodies (e.g., shark and camelid antibodies), maxibodies, minibodies, intrabodies, diabodies, triabodies, tetrabodies, v-NAR and bis-scFv (see, e.g., Hollinger and Hudson, 2005, Nature Biotechnology 23(9): 1126-1136). An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy chain (HC) constant regions that correspond to the different classes of immunoglobulins are called alpha, delta, epsilon, gamma, and mu, respectively. The subunit structures and three-dimensional configurations of different classes of immunoglobulins are well known.

An "isolated antibody" refers to an antibody that is substantially free of other antibodies having different antigenic specificities (e.g., an isolated antibody that specifically binds Notch3 is substantially free of antibodies that specifically bind antigens other than Notch3). An isolated antibody that specifically binds Notch3 may, however, have cross-reactivity to other antigens, such as Notch3 molecules from other species. Moreover, an isolated antibody may be substantially free of other cellular material and/or chemicals.

A "variable region" of an antibody refers to the variable region of the antibody light chain (VL) or the variable region of the antibody heavy chain (VH), either alone or in combination. As known in the art, the variable regions of the heavy and light chain each consist of four framework regions (FRs) connected by three complementarity determining regions (CDR1, CDR2, CDR3) also known as hypervariable regions, contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonincal class as the subject variable region (Chothia and Lesk, J Mol Biol 196(4): 901-917, 1987). When choosing FR to flank subject CDRs, e.g., when humanizing or optimizing an antibody, FRs from antibodies which contain CDR1 and CDR2 sequences in the same canonical class are preferred.

A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., 1989, Nature 342:877-883. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., 1996, J. Mol. Biol., 262:732-745. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

The terms "IgG Fc region", "Fc region", "Fc domain" and "Fc", as interchangeably used herein refer to the portion of an IgG molecule that correlates to a crystallizable fragment obtained by papain digestion of an IgG molecule. The Fc region consists of the C-terminal half of the two heavy chains of an IgG molecule that are linked by disulfide bonds. It has no antigen binding activity but contains the carbohydrate moiety and the binding sites for complement and Fc receptors, including the FcRn receptor (see below). The Fc fragment contains the entire second constant domain CH2 (residues 231-340 of human IgG1, according to the Kabat numbering system) and the third constant domain CH3 (residues 341-447).

By "engineered Fc polypeptide", "engineered Fc region" and "engineered Fc" as the terms are interchangeably used herein, is meant an Fc polypeptide, or portion thereof, comprising at least one mutation, e.g., an amino acid substitution, introducing a site for conjugation. Preferably, the mutation introduces a cysteine in place of the naturally-occurring amino acid residue at that position, where the mutation creates a reactive site (e.g., a reactive sulfhydryl group) for conjugation of a moiety to the Fc.

The term "monoclonal antibody" or "mAb" refers to an antibody that is derived from a single copy or clone, including e.g., any eukaryotic, prokaryotic, or phage clone, and not the method by which it is produced. Preferably, a monoclonal antibody of the invention exists in a homogeneous or substantially homogeneous population.

"Humanized" antibody refers to forms of non-human (e.g. rat) antibodies that are chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. Preferably, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity.

"Human antibody or fully human antibody" refers to those antibodies derived from transgenic mice carrying human antibody genes or from human cells.

The term "chimeric antibody" is intended to refer to antibodies in which the variable region sequences are derived from one species and the constant region sequences are derived from another species, such as an antibody in which the variable region sequences are derived from a rat antibody and the constant region sequences are derived from a human antibody.

A "therapeutic agent" is an agent that exerts a cytotoxic, cytostatic, and/or immunomodulatory effect on cancer cells or activated immune cells. Examples of therapeutic agents include cytotoxic agents, chemotherapeutic agents, cytostatic agents, and immunomodulatory agents.

A "chemotherapeutic agent" is a chemical compound useful in the treatment of cancer.

A "cytotoxic effect" refers to the depletion, elimination and/or the killing of a target cell(s). A "cytotoxic agent" refers to an agent that has a cytotoxic and/or cytostatic effect on a cell.

A "cytostatic effect" refers to the inhibition of cell proliferation. A "cytostatic agent" refers to an agent that has a cytostatic effect on a cell, thereby inhibiting the growth and/or expansion of a specific subset of cells.

"Antibody-drug conjugate" or "ADC" refers to antibodies or antibody fragments thereof, including antibody derivatives that bind to Notch3 and are conjugated to cytotoxic, cytostatic, and/or therapeutic agents.

"Anti-Notch3 antibody-drug conjugate" or "anti-Notch3 ADC" refers to an anti-Notch3 antibody or antigen binding fragment thereof, as described herein linked to a drug (D) via a linker (L).

"Linker (L)" describes the direct or indirect linkage of the antibody to the drug. Attachment of a linker to an antibody can be accomplished in a variety of ways, such as through surface lysines, reductive-coupling to oxidized carbohydrates, and through cysteine residues liberated by reducing interchain disulfide linkages. A variety of antibody-drug conjugate linkage systems are known in the art, including hydrazone-, disulfide- and peptide-based linkages.

"Drug (D)" is any substance having biological or detectable activity, for example, therapeutic agents, detectable labels, binding agents, etc., and prodrugs, which are metabolized to an active agent in vivo. The terms drug, payload and compound are used interchangeably.

"L-D" is a linker-drug moiety resulting from a drug (D) linked to a linker (L).

The term "epitope" refers to that portion of a molecule capable of being recognized by and bound by an antibody at one or more of the antibody's antigen-binding regions. Epitopes often consist of a chemically active surface grouping of molecules such as amino acids or sugar side chains and have specific three-dimensional structural characteristics as well as specific charge characteristics. The term "antigenic epitope" as used herein, is defined as a portion of a polypeptide to which an antibody can specifically bind as determined by any method well known in the art, for example, by conventional immunoassays. A "nonlinear epitope" or "conformational epitope" comprises noncontiguous polypeptides (or amino acids) within the antigenic protein to which an antibody specific to the epitope binds. Once a desired epitope on an antigen is determined, it is possible to generate antibodies to that epitope, e.g., using the techniques described in the present specification. During the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another e.g., the antibodies compete for binding to the antigen.

The term "binding affinity ($K_D$)" as used herein, is intended to refer to the dissociation rate of a particular antigen-antibody interaction. The $K_D$ is the ratio of the rate of dissociation, also called the "off-rate ($k_d$)", to the association rate, or "on-rate ($k_a$)". Thus, $K_D$ equals $k_d/k_a$ and is expressed as a molar concentration (M). It follows that the smaller the $K_D$, the stronger the affinity of binding. Therefore, a $K_D$ of 1 µM indicates weak binding affinity compared to a $K_D$ of 1 nM. $K_D$ values for antibodies can be determined using methods well established in the art. One method for determining the $K_D$ of an antibody is by using surface plasmon resonance, typically using a biosensor system such as a Biacore® system.

An antibody, an antibody conjugate, or a polypeptide that "preferentially binds" or "specifically binds" (used interchangeably herein) to a target (e.g., Notch3 protein) is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a Notch3 epitope is an antibody that binds this epitope with greater affinity, avidity, more readily, and/or with greater duration than it binds to other Notch3 epitopes or non-Notch3 epitopes. It is also understood that by reading this definition, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "$EC_{50}$" is a measurement of binding capacity and is defined as the half maximal effective concentration of an antibody or antibody-drug conjugate that is needed to produce a response halfway between the baseline and maximum.

"Pharmaceutically acceptable salt" as used herein refers to pharmaceutically acceptable organic or inorganic salts of a molecule or macromolecule.

The term "potency" is a measurement of biological activity and may be designated as $IC_{50}$, or inhibitory concentration of an antibody or antibody drug conjugate to the antigen Notch3, needed to inhibit 50% of Notch3-dependent reporter gene activity or growth of a Notch3 positive cell line as described in Examples 9 and 12 respectively.

The phrase "effective amount" or "therapeutically effective amount" as used herein refers to an amount necessary (at dosages and for periods of time and for the means of administration) to achieve the desired therapeutic result. An effective amount is at least the minimal amount, but less than a toxic amount, of an active agent which is necessary to impart therapeutic benefit to a subject.

The terms "inhibit" or "neutralize" as used herein with respect to bioactivity of an antibody of the invention mean the ability of the antibody to substantially antagonize, prohibit, prevent, restrain, slow, disrupt, eliminate, stop, reduce or reverse e.g. progression or severity of that which is being inhibited including, but not limited to, a biological activity.

The term "compete" or "competes", as used herein with regard to an antibody, means that a first antibody, or an antigen-binding fragment thereof, binds to an epitope in a manner sufficiently similar to the binding of a second antibody, or an antigen-binding fragment thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or fragment thereof), the skilled artisan would appreciate, based upon the teachings provided herein, that such competing and/or cross-competing antibodies are encompassed and can be useful for the methods disclosed herein.

The terms "polynucleotide" or "nucleic acid molecule", as used herein, are intended to include DNA molecules and RNA molecules. A nucleic acid molecule may be single-stranded or double-stranded, but preferably is double-stranded DNA.

The polynucleotides that encode the antibodies of the present invention may include the following: only the coding sequence for the variant, the coding sequence for the variant and additional coding sequences such as a functional polypeptide, or a signal or secretory sequence or a pro-protein sequence; the coding sequence for the antibody and non-coding sequence, such as introns or non-coding sequence 5' and/or 3' of the coding sequence for the antibody. The term 'polynucleotide encoding an antibody" encompasses a polynucleotide which includes additional coding sequence for the variant but also a polynucleotide which includes additional coding and/or non-coding sequence. It is known in the art that a polynucleotide sequence that is optimized for a specific host cell/expression system can readily be obtained from the amino acid sequence of the desired protein (see GENEART AG, Regensburg, Germany).

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

The term "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The term "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

The polynucleotides encoding the antibodies of the present invention will typically include an expression control polynucleotide sequence operably linked to the antibody coding sequences, including naturally-associated or heterologous promoter regions known in the art. Preferably, the expression control sequences will be eukaryotic promoter systems in vectors capable of transforming or transfecting eukaryotic host cells, but control sequences for prokaryotic hosts may also be used. Once the vector has been incorporated into the appropriate host cell line, the host cell is propagated under conditions suitable for expressing the nucleotide sequences, and, as desired, for the collection and purification of the antibodies. Preferred eukaryotic cell lines include CHO cell lines, various COS cell lines, HeLa cells, myeloma cell lines, transformed B-cells, or human embryonic kidney cell lines. The most preferred host cell is a CHO cell line.

Antibodies

Antibodies of the invention can be produced using techniques well known in the art, e.g., recombinant technologies, phage display technologies, synthetic technologies or combinations of such technologies or other technologies readily known in the art (see, for example, Jayasena, S. D., Clin. Chem., 45: 1628-50 (1999) and Fellouse, F. A., et al, J. Mol. Biol., 373(4):924-40 (2007)).

An embodiment of the invention is an antibody that specifically binds to the same Notch3 epitope as an antibody comprising a first amino acid sequence that is at least 90%, 92%, 94%, 95%, 96%, 97%, 98% or 99% identical to SEQ ID NO: 13 and a second amino acid sequence that is at least 90%, 92%, 94%, 95%, 96%, 97%, 98% or 99% identical to SEQ ID NO: 25.

Another embodiment of the invention is an antibody that specifically binds to the same Notch3 epitope as an antibody comprising a first amino acid sequence that is at least 90%, 92%, 94%, 95%, 96%, 97%, 98% or 99% identical to SEQ ID NO: 37 and a second amino acid sequence that is at least 90%, 92%, 94%, 95%, 96%, 97%, 98% or 99% identical to SEQ ID NO: 49.

In some embodiments, the antibody, or antigen-binding fragment thereof, specifically binds to Notch3, and the antibody, or antigen-binding fragment thereof, competes with the binding of an antibody comprising a first amino acid sequence that is at least 90%, 92%, 94%, 95%, 96%, 97%, 98% or 99% identical to SEQ ID NO: 13 and a second amino acid sequence that is at least 90%, 92%, 94%, 95%, 96%, 97%, 98% or 99% identical to SEQ ID NO: 25.

In some embodiments, the antibody, or antigen-binding fragment thereof, specifically binds to Notch3, and the antibody, or antigen-binding fragment thereof, competes with the binding of an antibody comprising a first amino acid sequence that is at least 90%, 92%, 94%, 95%, 96%, 97%, 98% or 99% identical to SEQ ID NO: 37 and a second amino acid sequence that is at least 90%, 92%, 94%, 95%, 96%, 97%, 98% or 99% identical to SEQ ID NO: 49.

Conjugation of a Drug to an Antibody

The drug has, or is modified to include, a group reactive with a conjugation point on the antibody. For example, a drug can be attached by alkylation (e.g., at the epsilon-amino group lysines or the N-terminus of antibodies), reductive amination of oxidized carbohydrate, transesterification between hydroxyl and carboxyl groups, amidation at amino groups or carboxyl groups, and conjugation to thiols. In some embodiments, the number of drug, p, conjugated per antibody molecule ranges from an average of 1 to 12, 1 to 11, 1 to 10, 1 to 9, 1 to 8; 1 to 7, 1 to 6, 1 to 5, 1 to 4, 1 to 3, or 1 to 2. In some embodiments, p ranges from an average of 2 to 12, 2 to 11, 2 to 10, 2 to 9, 2 to 8, 2 to 7, 2 to 6, 2 to 5, 2 to 4 or 2 to 3. In other embodiments, p is an average of 1, 2, 3, 4, 5, 6, 7, 8, 9, 10, 11 or 12. In some embodiments, p ranges from an average of about 1 to about 12, about 1 to about 11, about 1 to about 10, about 1 to about 9, about 1 to about 8; about 1 to about 7, about 1 to about 6, about 1 to about 5, about 1 to about 4, about 1 to about 3, or about 1 to about 2. In some embodiments, p ranges from about 2 to about 12, about 2 to about 11, about 2 to about 10, about 2 to about 9, about 2 to about 8, about 2 to about 7, about 2 to about 6, about 2 to about 5, about 2 to about 4 or about 2 to about 3. For examples of chemistries that can be used for conjugation, see, e.g., Current Protocols in Protein Science (John Wiley & Sons, Inc.), Chapter 15 (Chemical Modifications of Proteins).

Linkers

A linker is a bifunctional compound which can be used to link a drug and an antibody to form an antibody drug conjugate (ADC). Such conjugates are useful, for example, in the formation of immunoconjugates directed against tumor associated antigens. Such conjugates allow the selective delivery of cytotoxic drugs to tumor cells. Suitable linkers include, for example, cleavable and non-cleavable linkers. A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit), a phenylalanine-lysine (phe-lys) linker, or maleimido-caproyl-valine citrulline-p-aminobenzyloxycarbonyl (vc) linker. Another linker is Sulfosuccinimidyl-4-[N-maleimidomethyl]cyclohexane-1-carboxylate (smcc). Sulfo-smcc conjugation occurs via a maleimide group which reacts with sulfhydryls (thiols, —SH), while its Sulfo-NHS ester is reactive toward primary amines (as found in Lysine and the protein or peptide N-terminus). Yet another linker is maleimidocaproyl (mc). Other suitable linkers include linkers hydrolyzable at a specific pH or a pH range, such as a hydrazone linker. Additional suitable cleavable linkers include disulfide linkers. The linker may be covalently bound to the antibody to such an extent that the antibody must be degraded intracellularly in order for the drug to be released e.g. the mc linker and the like.

Linkers of the present invention include maleimidocaproyl valine-citrulline-p-aminobenzyloxycarbonyl (vc) and maleimidocaproyl (mc), maleimido-heptanoyl (me) and maleimido-Peg6C2 (MalPeg6C2).

Engineered Fc Polypeptide

It has been previously reported that certain residues presumably present on the surface of the CH2 or CH3 domain of the heavy chain of antibodies, or on the constant domain of the light chain, or otherwise accessible, are suitable for the substitution of the naturally-occurring wild type amino acid with, for example, cysteine, and are therefore useful to engineer a site capable of conjugation to various agents, as described in International Publication No. WO/2013/093809, which is incorporated herein by reference.

Amino acid modifications can be made by any method known in the art and many such methods are well known and routine for the skilled artisan. For example, but not by way of limitation, amino acid substitutions, deletions and insertions may be accomplished using any well-known PCR-based technique. Amino acid substitutions may be made by site-directed mutagenesis (see, for example, Zoller and Smith, 1982, Nucl. Acids Res. 10:6487-6500; and Kunkel, 1985, Proc. Natl. Acad. Sci USA 82:488).

In some embodiments, the engineered Fc polypeptide of the disclosure may be used to prepare an antibody, or antigen binding fragment thereof, such that the antibody or fragment thereof thereby comprises the engineered Fc region which can be used to conjugate, at the engineered residue (i.e., the amino acid substituted compared to wild type unmodified Fc), a wide variety of moieties.

In some embodiments, the engineered kappa light chain constant polypeptide of the disclosure may be used to prepare an antibody, or antigen binding fragment thereof, such that the antibody or fragment thereof thereby comprises an engineered CL region comprising an amino acid mutation, or fragment thereof, which can be used to conjugate, at the engineered amino acid residue, a wide variety of moieties.

It should be noted that a single substitution in an Fc polypeptide, for example of a cysteine residue, normally results in the display of two corresponding residues in the resultant IgG antibody due to the homodimeric nature of IgG antibody molecules. Thus, the resultant engineered IgG antibodies of the invention may display at least 1, 2, 3, 4, or more reactive groups for the purpose of conjugation to a drug or compound. In an embodiment, one or more of the substitutions is with a cysteine residue, and the resulting engineered antibodies may display at least 1, 2, 3, 4, or more thiol groups for the purpose of conjugation to a drug or compound.

In some embodiments, the engineered Fc polypeptide of the present invention comprises one or more substitutions selected from the positions 443 and 392, of the heavy chain of an antibody, and wherein the numbering system of the constant region is that of the EU index as set forth in Kabat et al. (supra).

In some embodiments, the engineered Fc polypeptide comprises one amino acid substitution (L443C) as provided in SEQ ID NO: 61. In another embodiment, the engineered Fc polypeptide comprises two amino acid substitutions (L443C/K392C) as provided in SEQ ID NO: 65.

Engineered Cκ Polypeptide

The anti-Notch3 antibodies of the present invention may encompass an engineered antibody light chain constant region (LC), or a fragment thereof, where 1, 2, or 3 amino acids of the antibody light chain, wherein the numbering system of the light chain constant region is that of the Kabat numbering system as set forth in Kabat et al. (1991, NIH Publication 91-3242, National Technical Information Service, Springfield, Va., hereinafter "Kabat"), of a parent, native, or wild type antibody, substituted with another amino acid (including natural and non-natural/synthetic amino acids).

In other embodiments, due to the dimeric nature of many antibodies (e.g., IgGs comprise two light chains and two heavy chains each heavy chain comprising an Fc polypeptide), an antibody of the invention may comprise at least one engineered Fc polypeptide and may further comprise at least one engineered light chain constant polypeptide thereby providing at least two site-specific conjugation sites—one in the Fc polypeptide and another in the CL polypeptide.

In some embodiments, the engineered Cκ polypeptide of the present invention comprises at least one substitution at position 183 of the light chain of the antibody. In some embodiments, the engineered Cκ polypeptide comprises one amino acid substitution (κK183C) as provided in SEQ ID NO. 63.

Therapy for Cancer

Cancers, including, but not limited to, a tumor, metastasis, or other disease or disorder characterized by uncontrolled cell growth, can be treated or prevented by administration of an antibody, or antigen-binding fragment thereof, or antibody-drug conjugate (ADC) of the present invention.

Exemplary anti-Notch3 antibodies, or antigen-binding fragments thereof, and antibody-drug conjugates are useful for treating cancer in which Notch3 is expressed or over-expressed, relative to a reference subject or standard (e.g., non-cancerous or normal tissue). Treatment or prevention of a Notch3-expressing cancer, according to the methods described herein, can be achieved by administering to a subject in need of such treatment an effective amount of an anti-Notch3 antibody, or antigen-binding fragment thereof, and/or antibody-drug conjugate. In some embodiments, an anti-Notch3 full length antibody, or antigen-binding fragment thereof, that is conjugated to a cytotoxic agent will be administered. In some exemplary embodiments, an anti-Notch3 antibody-drug conjugate of the present invention will (i) bind to Notch3 expressing cancer cells, and (ii) exert a cytotoxic or cytostatic effect to, for example, inhibit the proliferation of the Notch3 expressing cancer cells, or kill Notch3 expressing cancer cells.

In other embodiments, the anti-Notch3 antibodies, or antigen-binding fragment thereof, and/or anti-Notch3 antibody-drug conjugates are co-administered with another therapeutic agent, or administered sequentially with another therapeutic agent. In some embodiments, the anti-Notch3 antibodies, or antigen-binding fragment thereof, and/or anti-Notch3 antibody-drug conjugates are co-administered with chemotherapeutics, including standard of care chemotherapeutics, or administered sequentially.

In some embodiments, the other therapeutic agent will be an agent that is standard of care for the specific disease to be treated or is part of a salvage regimen for the specific disease to be treated. Anti-cancer agents and chemotherapeutic regimens include, for example, anti-cancer antibodies, including, for example, anti-CD52 antibodies (e.g., Alemtuzumab), anti-CD20 antibodies (e.g., Rituximab), and anti-CD40 antibodies (e.g., SGN40); chemotherapeutic regimens including, for example, CHOP (cyclophosphamide, doxorubicin, vincristine, and prednisone); CVP (cyclophosphamide, vincristine, and prednisone); RCVP (Rituximab+CVP); RCHOP (Rituximab+CHOP); RICE (Rituximab+ifosamide, carboplatin, etoposide); RDHAP, (Rituximab+ dexamethasone, cytarabine, cisplatin); RESHAP (Rituximab+etoposide, methylprednisolone, cytarabine, cisplatin); gemcitabine; combination treatment with vincristine, prednisone, and anthracycline, with or without asparaginase; combination treatment with daunorubicin, vincristine, prednisone, and asparaginase; combination treatment with teniposide and Ara-C (cytarabine); combination treatment with methotrexate and leucovorin; combination treatment with bleomycin, doxorubicin, etoposide, mechlorethamine, prednisone, vinblastine, and vincristine; small molecule inhibitors; and proteosome inhibitors including, for example, bortezomib.

In some embodiments, methods for treating cancer including administering to a patient in need thereof an effective amount of an anti-Notch3 antibody, or antigen-binding fragment thereof, and/or anti-Notch3 antibody-drug conjugate in combination with radiation treatment, and optionally another therapeutic agent. In some embodiments, the anti-Notch3 antibody, or antigen-binding fragment thereof, and/or anti-Notch3 antibody-drug conjugate is administered concurrently or sequentially with an anticancer agent (e.g., a chemotherapeutic agent) and/or with radiation therapy. In some embodiments, the chemotherapeutic agent or radiation therapy is administered at least an hour, five hours, 12 hours, a day, a week, a month, several months (e.g., up to three months), prior or subsequent to administration of a compound of the present invention.

Generally, for administration of an anti-Notch3 antibody and/or an anti-Notch3 antibody-drug conjugate, an initial candidate dosage can be about 2 mg/kg. For the purpose of the present invention, a typical daily dosage might range from about any of 3 µg/kg to 30 µg/kg to 300 µg/kg to 3 mg/kg, to 30 mg/kg, to 100 mg/kg or more, depending on the factors mentioned above. For example, dosage of about 1 mg/kg, about 2.5 mg/kg, about 5 mg/kg, about 10 mg/kg, and about 25 mg/kg may be used. For repeated administrations over several days or longer, depending on the condition, the treatment is sustained until a desired suppression of symptoms occurs or until sufficient therapeutic levels are achieved, for example, to inhibit or delay tumor growth/progression or metastasis of cancer cells. An exemplary dosing regimen comprises administering an initial dose of about 2 mg/kg, followed by a weekly maintenance dose of about 1 mg/kg of the anti-Notch3 antibody or anti-Notch3 antibody-drug conjugate, or followed by a maintenance dose of about 1 mg/kg every other week. Other exemplary dosing regimens comprise administering increasing doses (e.g., initial dose of 1 mg/kg and gradual increase to one or more higher doses every week or longer time period). Other dosing regimens may also be useful, depending on the pattern of pharmacokinetic decay that the practitioner wishes to achieve. For example, in some embodiments, dosing from one to four times a week is contemplated. In other embodiments dosing once a month or once every other month or every three months is contemplated as well as weekly, bi-weekly and every three weeks. The progress of this therapy may be monitored by conventional techniques and assays. The dosing regimen (including the anti-Notch3 antibody or the anti-Notch3 antibody-drug conjugate used) can vary over time.

For the purpose of the present invention, the appropriate dosage of an anti-Notch3 antibody or an anti-Notch3 antibody-drug conjugate will depend on the anti-Notch3 antibody or the anti-Notch3 antibody-drug conjugate (or compositions thereof) employed, the type and severity of symptoms to be treated, whether the agent is administered for therapeutic purposes, previous therapy, the patient's clinical history and response to the agent, the patient's clearance rate for the administered agent, and the discretion of the attending physician. The clinician may administer an anti-Notch3 antibody or an anti-Notch3 antibody-drug conjugate until a dosage is reached that achieves the desired result and beyond. Dose and/or frequency can vary over course of treatment, but may stay constant as well. Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of symptoms, e.g., tumor growth inhibition or delay, etc. Alternatively, sustained continuous release formulations of anti-Notch3 antibodies or anti-Notch3 antibody-drug conjugates may be appropriate. Various formulations and devices for achieving sustained release are known in the art.

In one embodiment, dosages for anti-Notch3 antibody or anti-Notch3 antibody-drug conjugate may be determined empirically in individuals who have been given one or more administration(s) of the anti-Notch3 antibody or its anti-Notch3 antibody-drug conjugate. Individuals are given incremental dosages of an anti-Notch3 antibody or a Notch3 antagonist. To assess efficacy, an indicator of the disease can be followed.

Administration of an anti-Notch3 antibody or an anti-Notch3 antibody-drug conjugate in accordance with the method in the present invention can be continuous or intermittent, depending, for example, upon the recipient's physiological condition, whether the purpose of the administration is therapeutic or prophylactic, and other factors known to skilled practitioners. The administration of an anti-Notch3 antibody or an anti-Notch3 antibody-drug conjugate may be essentially continuous over a preselected period of time or may be in a series of spaced doses.

In some embodiments, more than one anti-Notch3 antibody or anti-Notch3 antibody-drug conjugate may be present. At least one, at least two, at least three, at least four, at least five different or more anti-Notch3 antibody or anti-Notch3 antibody-drug conjugate can be present. Generally, those anti-Notch3 antibodies or anti-Notch3 antibody-drug conjugates may have complementary activities that do not adversely affect each other. For example, one or more of the following anti-Notch3 antibody may be used: a first anti-Notch3 antibody directed to one epitope on Notch3 and a second anti-Notch3 antibody directed to a different epitope on Notch3.

The anti-Notch3 antibodies, or antigen-binding fragment thereof, and/or anti-Notch3 antibody-drug conjugates of the present invention can be in the form of a pharmaceutical composition for administration that are formulated to be appropriate for the selected mode of administration, and pharmaceutically acceptable diluent or excipients, such as buffers, surfactants, preservatives, solubilizing agents, isotonicity agents, stabilizing agents, carriers, and the like. Remington's Pharmaceutical Sciences, Mack Publishing Co., Easton Pa., 18$^{th}$ ed., 1995, provides a compendium of formulation techniques as are generally known to practitioners.

These pharmaceutical compositions may be administered by any means known in the art that achieve the generally intended purpose to treat cancer. The in one embodiment, the route of administration is parenteral, defined herein as referring to modes of administration that include but not limited to intravenous, intramuscular, intraperitoneal, subcutaneous, and intraarticular injection and infusion. The dosage administered will be dependent upon the age, health, and weight of the recipient, kind of concurrent treatment, if any, frequency of treatment, and the nature of the effect desired.

Compositions within the scope of the invention include all compositions wherein an anti-Notch3 antibody, or antigen-binding fragment thereof, and/or anti-Notch3 antibody-drug conjugate is present in an amount that is effective to achieve the desired medical effect for treating cancer. While individual needs may vary from one patient to another, the determination of the optimal ranges of effective amounts of all of the components is within the ability of the clinician of ordinary skill.

Diagnostic

The antibodies, or antigen-binding fragment thereof, of the invention can also be used to detect Notch3 in a biological sample in vitro or in vivo. In one embodiment, the anti-Notch3 antibodies, or antigen-binding fragment thereof, of the invention are used to determine the level of Notch3 in a tissue or in cells derived from the tissue. In a one embodiment, the tissue is a diseased tissue. In some embodiments, the tissue is a tumor or a biopsy thereof. In a one embodiment, the levels of Notch3 in a tissue or biopsy from a patient can be determined in an immunoassay with the antibodies, or antigen-binding fragment thereof, of the invention. The tissue or biopsy thereof can be excised from the patient and can be frozen or fixed. The same method can be used to determine other properties of the Notch3 protein, such as its level of cell surface levels, or cellular localization.

The above-described method can be used to diagnose a cancer in a subject known to or suspected to have a cancer, wherein the level of Notch3 measured in the patient is compared with that of a reference subject or standard. The method can then be used to determine whether a tumor expresses Notch3, which may suggest that the tumor will respond well to treatment with the antibody-drug conjugates of the present invention. In one embodiment of the invention, the tumor is a solid tumor cancer, including but not limited to, lung cancer, breast cancer, ovarian cancer, stomach cancer, esophageal cancer, cervical cancer, head and neck cancer, bladder cancer, liver cancer, skin cancer and sarcoma or a blood cancer, including but not limited to, T-cell malignancies, T-cell leukemia, T-cell lymphoma, T-cell acute lymphoblastic leukemia, multiple myeloma, B-cell malignancies, myeloid malignancies, acute myeloid leukemia and chronic myeloid leukemia in which Notch3 is expressed, and other cancers yet to be determined in which Notch3 is expressed predominantly.

An embodiment of the invention is a method of treating a Notch3 expressing cancer, the method comprising: determining the level of Notch3 in a biological sample comprising the steps of: contacting a sample obtained from a subject suspected to have cancer with an anti-Notch3 antibody, or antigen-binding fragment thereof; determining the cell surface levels of Notch3 in the sample; comparing the cell surface levels of Notch3 with that of a reference subject or standard; and administering an antibody-drug conjugate of the present invention to the subject. The method may optionally comprise a step of obtaining the sample from a subject suspected to have cancer;

Another embodiment of the invention is a method of treating a Notch3 expressing cancer the method comprising: determining the level of Notch3 in a biological sample comprising the steps of: subjecting a sample obtained from a subject suspected to have cancer to in-situ hybridization (ISH); determining the level of Notch3 mRNA in the sample; comparing the levels of Notch3 mRNA with that of a reference subject or standard; and administering an antibody-drug conjugate of the present invention to the subject. The method may optionally comprise a step of obtaining the sample from a subject suspected to have cancer.

The present invention further provides for monoclonal antibodies, humanized antibodies and epitope-binding fragments thereof that are further labeled for use in research or diagnostic applications. In some embodiments, the label is a radiolabel, a fluorophore, a chromophore, an imaging agent or a metal ion.

A method for diagnosis is also provided in which the labeled antibodies or epitope-binding fragments thereof are administered to a subject suspected of having a cancer, and the distribution of the label within the body of the subject is measured or monitored.

Kit

The present invention also includes kits, e.g. comprising a described cytotoxic conjugate and instructions for the use of the cytotoxic conjugate for killing of particular cell types. The instructions may include directions for using the cytotoxic conjugates in vitro, in vivo or ex vivo. Typically, the kit will have a compartment containing the cytotoxic conjugate. The cytotoxic conjugate may be in a lyophilized form, liquid form, or other form amendable to being included in a kit. The kit may also contain additional elements needed to practice the method described on the instructions in the kit, such a sterilized solution for reconstituting a lyophilized powder, additional agents for combining with the cytotoxic conjugate prior to administering to a patient, and tools that aid in administering the conjugate to a patient.

All publications and patent documents cited above or in the following Examples are hereby incorporated by reference in their entirety for all purposes to the same extent as if each were so individually denoted.

The invention will be further described with reference to the following examples; however, it is to be understood that the invention is not limited to such examples.

The following examples of specific aspects for carrying out the present invention are offered for illustrative purposes only, and are not intended to limit the scope of the present invention in any way.

Example 1

Generation of Recombinant Notch3 Protein Immunogens cDNA constructs encoding the human Notch3 NRR region with a signal peptide at N-terminus, and Avi and His6 tag at C-terminus, were cloned into the expression vector pSMED2. These constructs were transiently transfected into Chinese hamster ovary (CHO) cells and the secreted proteins in conditioned media were analyzed on SDS-PAGE. After processing at the S1 cleavage site, the N-terminal ~26 kDa (LNR-A, B, C and HD1) and C-terminal ~12 kDa (HD2 and Avi_His tag) halves of the Notch3 NRR domain remain associated through non-covalent interactions to form a heterodimeric complex, as shown in FIG. 1. S1 processing of the Notch3 NRR was determined to be about 50% or less in samples prepared from CHO cells. To enhance processing at the S1 cleavage site, the Notch3 NRR expression construct was transfected into CHO-PACE cells (Harrison et, al, Semin Hematol. 1998 April; 35(2 Suppl 2):4-10) and stable cell lines with the highest expression and complete processing of Notch3 NRR were selected. Culture of these cell lines was scaled up for the collection of conditioned media from which Notch3 NRR proteins were purified.

The amino acid and nucleotide sequences of purified human and mouse Notch3 NRR_Avi_His tag proteins (hereinafter "Notch3 NRR recombinant proteins") are provided in FIG. 2. Lower case type represents the Avi_His tag. SDS-PAGE analysis showed that >90% of the purified protein was correctly cleaved into the predicted Notch3 NRR N-terminal and C-terminal peptide sizes (data not shown).

Example 2

Generation and Cloning of Rat Anti-Notch3 Antibodies

A. Immunization and Hybridoma Generation

Sprague-Dawley rats were immunized by subcutaneous injections with a mixture containing 20 μg each of human (SEQ ID NO. 1) and mouse (SEQ ID NO. 3) Notch3 recombinant proteins in Freund's complete adjuvant. Immunizations were repeated at 2-week intervals for 12 weeks. Collected sera samples at day 0, 35, 49, and 63 after the first injection were tested for circulating anti-Notch3 antibody titer activity by enzyme-linked immunosorbent assay (ELISA). When optimal titers were reached, a final dose of the protein mixture was injected intravenously (tail vein) into a rat having optimal antibody titer 4 days before it was to be sacrificed for splenocyte collection. Total splenocytes ($2 \times 10^8$) from the rat were fused with mouse myeloma cell line P3×63.Ag8.653 ($2.5 \times 10^7$) using PEG 1500. Fused cells were plated out in 96-well plates (0.2 mL/well) and subjected to HAT selection (RPMI 1640 containing $5 \times 10^{-4}$ M Hypoxanthine, $1.6 \times 10^{-5}$ M Thymidine, $4 \times 10^{-4}$ M Aminopterin, and 20% Heat Inactivated FCS).

Fourteen days post fusion, hybridoma supernatants were harvested and tested for the presence of Notch3 binding activities. Two parental rat clones 28 and 75 (hereinafter r28 and r75, respectively) exhibited binding activity to human Notch3 NRR recombinant protein by ELISA and to the cell surface of U-2 OS cells stably over-expressing human full length Notch3 by a cell-based ELISA with an O.D. 450 nM value of 1 or above at 0.1-1 nM antibody concentrations. Further, r28, but not r75, exhibited binding activity to mouse Notch3 NRR recombinant protein by ELISA and to the cell surface of U-2 OS cells stably over-expressing mouse full length Notch3 by a cell-based ELISA with an O.D. 450 nM value of 1 or above at 0.1-1 nM antibody concentrations.

B. Cloning and Sequencing of Anti-Notch3 Antibodies r28 and r75 variable regions were subcloned for further analysis. RNAs from the subclones were extracted and the variable region DNA sequences from the expressed antibodies were obtained via RT-PCR cloning. One to five million of the subcloned hybridoma cells were homogenized for total RNA isolation with QIAGEN RNAeasy Mini kit. First strand cDNA was then produced using SuperScript III RT kit (Invitrogen). Double stranded cDNAs for variable regions of anti-Notch3 IgGs were subsequently generated and amplified by PCR using primers from the rat IgG heavy chain (IgG1, 2a, 2b) and light chain (kappa or lambda) constant regions, as described below. PCR cycling conditions: 1 cycle at 95° C. for 1 min; 25 cycles at 95° C. for 1 min, 63° C. for 1 min and 72° C. for 1 min. The resulting RT-PCR products were cloned into TOPO-Blunt cloning vector (Invitrogen) and sequenced by conventional methods. The amino acid and nucleotide sequences of r28 and r75 variable regions are provided in FIG. 3. CDRs are underlined.

Example 3

Generation and Characterization of Chimeric Anti-Notch3 Antibodies

Variable region cDNAs from r28 and r75 were subcloned into mammalian expression vectors where rat variable heavy chain (VH) were fused in frame with human IgG1 (hIgG1) and rat variable light chain (VL) were fused with human kappa. Rat-human chimeric antibodies 28 and 75 (hereinafter ch28 and ch75, respectively) were generated from these constructs by transient transfection in HEK293 cells and further analyzed.

ch28 and ch75 were tested for binding activity in recombinant protein ELISA. Purified human or mouse Notch3 NRR recombinant proteins were coated on CoStar hi-bound 96-well ELISA plates in 100 μl of PBS with Mg/Ca at a concentration of 1 μg/ml overnight. The plates were washed with PBS-Mg/Ca and blocked for 1 hour with 1% BSA in PBS-Mg/Ca. Blocking solution was decanted from the plate and 1:3 serial dilutions of antibodies in blocking solutions were applied to the plate. After incubation at room temperature for 1 hour, plates were washed again with PBS-Mg/Can before HRP (horse radish peroxidase)-conjugated secondary antibody diluted (1:20,000) in blocking buffer was applied. When the primary antibody tested was rat IgG, the secondary antibody was goat anti-rat IgG Fc (Bethyl Biotech); and when the primary antibody was human IgG, the secondary antibody was goat anti-human IgG Fc (Southern Biotech). After 1 hour incubation with the secondary antibody, plates were washed again, as described above, and TMB substrate solution was added. The developing reaction was allowed for 10 minutes before the stopping solution, 0.18M $H_2SO_4$, was added. Absorbance at O. D. 450 nM was measured and data was plotted and analyzed with Microsoft Excel and Graphpad-Prism software. ch28 and ch75 exhibited strong binding activity to human Notch3 NRR recombinant protein, having an EC50 of 1 nM or lower, and ch28, but not ch75, also exhibited strong binding activity to mouse Notch3 NRR recombinant with an EC50 of 1 nM or below. ch28 and ch75 were selected for further cell based ELISA, as described below.

Example 4

Humanization r28 and r75 were selected to be humanized for further development. Humanization was performed by CDR grafting onto human acceptor frameworks, DP-54 for heavy chain and DPK9 for light chain, followed by selected back mutations in human acceptor framework to recover full activity of parental rat antibodies. Table 1 shows selected back mutations in the human acceptor framework for different variants.

TABLE 1

Selected back mutations for humanized anti-Notch3 antibody variants.

| Variant | Back Mutations (Kabat) |
|---|---|
| VH | |
| hu28 VH1.0 | none |
| hu28 VH1.1 | A93T, V37I |
| VL | |

TABLE 1-continued

Selected back mutations for humanized anti-Notch3 antibody variants.

| Variant | Back Mutations (Kabat) |
|---------|------------------------|
| hu28 VL1.0 | none |
| hu28 VL1.1 | Y36F |
|  | VH |
| hu75 VH1.8 | R71V |
| hu75 VH 1.9 | V34M (CDR1), R71V |
|  | VL |
| hu75 VL 1.1 | S60D |
| hu75 VL 1.2 | S60D, T85F |
| hu75 VL 1.3 | S67Y | cDNAs containing grafted CDR donor sequences of r28 and r75 onto human acceptor frameworks, DP-54 and DPK9, with selected back mutations were synthesized by Genewiz. Synthesized cDNA products were subcloned and fused in frame with human IgG1 heavy chain constant region for the heavy chain and human kappa for the light chain in mammalian expression vectors pSMED2 and pSMEN3, respectively.

Humanized r28 variant VH1.0/VL1.0 (hereinafter hu28) fully retained the antigen binding epitope and affinity of ch28 and lacked potent signaling inhibition activity observed in ch28. The CDRs of the VH and VL regions of hu28 are the same as the CDRs of the VH and VL regions of r28, respectively. Humanized r75 variant VH1.9/VL1.3 (hereinafter hu75) fully retained the antigen binding epitope and affinity of ch75 and potent signaling inhibition activity observed in ch75. CDR2 and CDR3 of the VH region of hu75 are the same as CDR2 and CDR3 of the VH region of r75, respectively. CDR1 of the VH region of hu75 contains one back mutation V34M. The CDRs of the VL region of hu75 are the same as the CDRs of the VL region of r28.

FIGS. 4A-4C provide amino acid and nucleotide sequences of hu28 with CDRs identified (Kabat and Chothia), and FIGS. 5A-5C provide amino acid and nucleotide sequences of hu75 with CDRs identified (Kabat and Chothia).

Alignment of the VH and VL regions of the human acceptor framework for r28 and hu28, and r75 and hu75 are shown in Table 2. The Kabat CDRs are underlined. The differences in residues of the framework between rat and humanized sequences are indicated by lower case text. The homology between the human acceptor framework for r28 and hu28 variable regions are 73% for VH and 76% for VL. The homology between the human acceptor framework for r75 and hu75 variable regions are 46% for VH and 64% for VL. Kabat CDRs are underlined.

TABLE 2

Alignment of human acceptor frameworks for anti-Notch3 antibodies.

r28 VH:

```
DP54_JH4   EVQLVESGGGLVQPGGSLRLSCAASGFTFS SYWMS WVRQAPGKGLEWVA NIKQDGSEKYYVDSVKG RFTISRDNAKNSLY
r28VH      EVQLVESGGGLVQPGRSLTLSCVASGFTFR DYGMT WVRQAPGKGLTWVA YISSGSNYIYYAEAVKG RFTISRDNAKNTLY
hu28VH1.0  EVQLVESGGGLVQPGGSLRLSCAASGFTER DYGMT WVRQAPGKGLEWVA YISSGSNYIYYAEAVKG RFTISRDNAKNSLY
DP54_JH4   LQMNSLRAEDTAVYYCAR ----YFDY WGQGTLVTVSS (SEQ ID NO: 67)
r28VH      LQMTSLRSEDTALYFCTR RGPFVLDA WGQGASVTVSS (SEQ ID NO: 5)
hu28VH1.0  LQMNSLRAEDTAVYYCAR RGPFVLDA WGQGTLVTVSS (SEQ ID NO: 13)
``` r28 VL:

```
DPK9_Jk4   DIQMTQSPSSLSASVGDRVTITC RASQSISSYLN WYQQKPGKAPKLLIY AASSLQS GVPSRFSGSGSGTDFTLTISSLQP
r28VL      DIQMTQSPSFLSASVGDRVTINC KASQSINRYLH WFQQKLGEAPKLLIY NANGLQT GIPSRFSGSGSGTDFTLTISSLQS
hu28VL1.0  DIQMTQSPSSLSASVGDRVTITC KASQSINRYLH WYQQKPGKAPKLLIY NANGLQT GVPSRFSGSGSGTDFTLTISSLQP
DPK9_Jk4   EDFATYYC QQSYSTPLT FGGGTVLEIK (SEQ ID NO: 68)
r28VL      EDVATYFC LQHNTWPDT FGAGTKLELK (SEQ ID NO: 7)
hu28VL1.0  EDFATYYC LQHNTWPDT FGGGTKVEIK (SEQ ID NO: 25)
``` r75 VH:

```
DP54_JH4   EVQLVESGGGLVQPGGSLRLSCAASGFTFS SYWmS WVRQAPGKGLEWVA NIKQDGSEKYYVDSVKG RFTISrDNAKNSLY
r75VH      QVKLLQSGAALVKPGASVKMSCKASGYAFT DYWvT WVKQSHGKSLEWIG EISPNSGGTNFNEKFKG KATLTvDKSTSTAY
hu75VH1.9  EVQLVESGGGLVQPGGSLRLSCAASGFTFS DYWmT WVRQAPGKGLEWVA EISPNSGGTNFNEKFKG RFTISvDNAKNSLY
DP54_JH4   LQMNSLRAEDTAVYYCAR ------YFDY WGQGTLVTVSS (SEQ ID NO: 67)
r75VH      MELSRLTSEDSAIYYCTR GEIRYNWFAY WGQGTLVTVSS (SEQ ID NO: 9)
hu75VH1.9  LQMNSLRAEDTAVYYCAR GEIRYNWFAY WGQGTLVTVSS (SEQ ID NO: 37)
``` r75 VL:

```
DPK9_Jk4   DIQMTQSPSSLSASVGDRVTITC RASQSISSYLN WYQQKPGKAPKLLIY AASSLQS GVPSRFSGSGsGTDFTLTISSLQP
r75VL      NIVMTQSPKSMSISVGDRVTMNC KASQNVGNNIA WYQQKPGQSPKLLIY YASNRYT GVPDRFTGGGyGTDFTLTINSMQA
hu75VL1.3  DIQMTQSPSSLSASVGDRVTITC KASQNVGNNIA WYQQKPGKAPKLLIY YASNRYT GVPSRFSGSGyGTDFTLTISSLQP
DPK9_Jk4   EDFATYYC QQSYSTPLT FGGGTKVEIK (SEQ ID NO: 68)
r75VL      EDAAFYYC QRLYNSPFT FGSGTKLEIK (SEQ ID NO: 11)
hu75VL1.3  EDFATYYC QRLYNSPFT FGGGTKVEIK (SEQ ID NO: 49)
```

Example 5

Characterization of hu28 and hu75

A. Cell-Based ELISA

Humanized hu28 and hu75, and rat-human chimeric, ch28 and ch75, anti-Notch3 antibodies were screened for cell surface Notch3 binding in a cell-based ELISA. U-2 OS cells stably over-expressing human or mouse full length Notch3 protein on cell surface (hereinafter U2OS/hNotch3 and U2OS/mNotch3, respectively) were plated at 50,000 cells/well in 96 well plates (white opaque, BD/VWR) the day before ELISA assay. On the day of the ELISA, culture media was removed from wells and serially diluted (1:3 in blocking buffer) antibody solutions were applied to the plate. Plates were incubated at room temperature for 2 hours before being washed with PBS-Mg/Ca. HRP-conjugated secondary antibody was then applied and incubated with cells for 1 hour as described above for recombinant protein ELISA. Plates were washed with PBS-Mg/Ca before being developed with Pico-Chemiluminescent developing kit (Thermal Scientific), and chemiluminescence measurements were performed per manufacturer's instructions. Data plotting and analyses were performed with Microsoft Excel and Graphpad-Prism software. $EC_{50}$ (nM) values were calculated from cell surface Notch3 binding ELISAs and provided in Table 3.

The data demonstrates that hu28 is similar to ch28 in binding to full-length human Notch3 expressed on the cell surface U2OS/hNotch3 cells. Further, the data demonstrates that hu28 fully retained the cross-reactivity of ch28 to mouse Notch3 expressed on the cell surface of U2OS/mNotch3 cells. The data also demonstrates that hu75 is similar to ch75 in binding to full-length human Notch3 expressed on the cell surface of U2OS/hNotch3 cells. Further, the data demonstrates that hu75 fully retained specificity of ch75 to human Notch3; no cross-reactivity was observed to mouse Notch3 expressed on the cell surface of U2OS/mNotch3 cells. N/B represents non-binding.

TABLE 3

$EC_{50}$ (nM) values of cell surface Notch3 binding ELISAs for anti-Notch3 antibodies.

| | $EC_{50}$ (nM) | | | |
|---|---|---|---|---|
| Antibody | ch28 | hu28 VH1.0/VL1.0 | ch75 | hu75 VH1.h9/VL1.3 |
| Full-length Human Notch3 | 0.098 | 0.093 | 0.20 | 0.22 |
| Full-length Mouse Notch3 | 0.13 | 0.13 | N/B | N/B |

B. Competition ELISA

Competition ELISAs were performed for hu28 and ch28, and hu75 and ch75 on cell surface expressed full-length human Notch3. 96 well cell culture plates were seeded with U2OS/hNotch3 cells (cell culture plate, Co-star). Serially diluted (1:3 in blocking buffer) antibody solutions, in the presence of 0.8 nM of ch28 (biotinylated) or ch75 (biotinylated) antibodies were applied to the plate. After incubation for 2 hours, the plates were washed, as described above, and HRP-conjugated streptavidin (Southern Biotech) diluted 1:5000 in blocking buffer was applied. After incubation with streptavidin for 30 minutes, the plates were washed again before being developed with TMB solution for 10 minutes. The developing reaction was stopped by adding 0.18M $H_2SO_4$ and absorbance at 450 nM was measured. Data plotting and analyses were performed with Microsoft Excel and Graphpad-Prism software.

Table 4 shows $EC_{50}$ (nM) values from competition ELISAs for binding to full-length human Notch3 expressed on the cell surface of U2OS/hNotch3 cells. The data shows that hu28 has a similar $EC_{50}$ value to the unlabelled r28, demonstrating that hu28 competes as well as unlabelled ch28 with biotinylated ch28 for binding to full-length human Notch3 expressed on the cell surface of U2OS/hNotch3 cells. The data indicates that hu28 binds to the same, or a highly similar, epitope on full-length human Notch3 expressed on the cell surface of U2OS/hNotch3 cells as ch28.

The data further shows that hu75 has a similar $EC_{50}$ value to unlabelled ch75, demonstrating that hu75 competes as well as unlabelled ch75 with biotinylated ch75 for binding to full-length human Notch3 expressed on the cell surface of U2OS/hNotch3 cells. The data indicates that hu75 binds to the same, or highly similar, epitope on full-length human Notch3 expressed on the cell surface of U2OS/hNotch3 cells as ch75.

TABLE 4

$EC_{50}$ (nM) values for competition ELISAs of anti-Notch3 antibodies.

| | $EC_{50}$ (nM) | | | | |
|---|---|---|---|---|---|
| Antibody | ch28 | hu28 VH1.0/ VL1.0 | ch75 | hu75 VH1.9/ VL1.3 | Anti-*E. Tenella* Control |
| Full-length Human Notch3 | 3.0 | 3.1 | 1.3 | 1.7 | Non-Competing |

C. Specificity of Binding to Other Human Notch Homologues

Other members of the Notch receptor family play important roles in biological processes. For example, a Notch1 or Notch2 deficiency leads to embryonic death in mouse models. In contrast, a Notch4 deficiency results in no detectable phenotype in mouse models. The closest homologues of the Notch3 NRR region are Notch1 and Notch2 (~50% homology), and Notch4 is a more distant homologue (~30% homology). Cross-reactivity of anti-Notch3 antibodies to other members of the Notch family, especially Notch1 and 2, may lead to undesired effects in patients. Therefore, the potential cross-reactivity of r28 and hu28, along with r75 and hu75 to other Notch family members were assessed.

Expression constructs encoding human Notch1 and Notch2 NRR regions, fused with human IgG1 Fc fragments were stably introduced into CHO-PACE cells. Conditioned media from these cells expressing NRR-Fc fusions were collected. Human Notch2 NRR-Fc and human Notch1 NRR-Fc were purified by protein A affinity followed by size exclusion chromatography (SEC). Purified preparations were dialysed into TBS with 1 mM $CaCl_2$ and analyzed on analytical SEC to be >99% in purity.

As shown in Table 5, r28 and hu28, along with r75 and hu75 all lacked detectable binding to human Notch2 NRR-Fc fusion proteins. Further, hu28 and hu75 also lacked detectable binding to full-length human Notch1 NRR-Fc. This demonstrates that hu28 and hu75 do not cross-react with Notch1 or Notch2. N/B represents non-binding.

TABLE 5

Binding of anti-Notch3 antibodies to Notch2 NRR-Fc and Notch1 NRR-Fc.

| | Antibody | Binding |
|---|---|---|
| Notch2 NRR-Fc | ch28 | N/B |
| | hu28 VH1.0/V1.0 | N/B |
| | ch75 | N/B |
| | hu75 VH1.9/V1.3 | N/B |
| Notch1 NRR-Fc | ch28 | N/B |
| | hu28 VH1.0/V1.0 | N/B |
| | ch75 | N/B |
| | hu75 VH1.9/V1.3 | N/B |

D. Binding Affinity to Human Notch3 NRR

The kinetic constants of the anti-Notch3 NRR interactions were determined by surface plasmon resonance (Biacore®

T100, Biacore Inc., Piscataway, N.J.). Flow cells of a CM5 chip were immobilized with approximately 10,000 response units (RU) of anti-human IgG-Fc (Biacore®) in 10 mM Glycine, pH 5.0 at 10 μl/min for 600 seconds. 10 μg/ml of anti-Notch3 antibodies ch28 and hu28, and ch75 and hu75 were diluted in TBS with 1 mM $CaCl_2$ were captured at 10 μl/min. Association of four concentrations of human Notch3 NRR recombinant protein (from 3.7-100 nM) and a zero concentration (running buffer) at 100 μl/min were recorded for 3 minutes in TBS with 1 mM $CaCl_2$. Dissociation of the complexes was measured for 10 minutes. The surface of the chip was regenerated by injecting 3M $MgCl_2$ with 3 mM EGTA for 60 seconds at 10 μl/min. Curves obtained after subtraction of the reference and buffer signals were fitted to a 1:1 Langmuir binding model with Biacore® T100 Evaluation Software (Biacore®).

$K_a$, $K_d$ and $K_D$ are shown in Table 6. Kinetic analysis shows similar ka (on) and kd (off) rates for ch28 and hu28. Further, a higher $k_a$ (on) and lower $k_d$ (off) rates for hu75 than ch75 were observed, resulting in a lower $K_D$ value for hu75.

TABLE 6

Kinetic analysis of anti-Notch3 antibodies.

| Antibody | $k_a$ (1/Ms) | $k_d$ (1/s) | $K_D$ (nM) |
|---|---|---|---|
| ch28 | 4.09E+05 | 2.49E−04 | 0.61 |
| hu28 VH1.0/VL1.0 | 3.86E+05 | 3.47E−04 | 0.90 |
| ch75 | 5.70E+04 | 9.92E−04 | 17.40 |
| hu75 VH1.9/VL1.3 | 3.48E+04 | 3.40E−04 | 9.76 |

D. Thermal Stability

There is a positive correlation between the thermal stability of a protein or protein domain with the overall stability of the protein or protein domain. A higher melting point of a protein or protein domain often provides improved manufacturability and longer shelf life. Differential scanning calorimetry (DSC) was used to assess the thermal stability of hu28 and hu75 versus ch28 and ch75, respectively. Protein samples were diluted in PBS to 0.3 mg/ml in a volume of 250 μl. The corresponding formulation buffer blank was used for the reference sample. Both samples were thoroughly degassed using a MicroCal ThermoVac Sample Degassing and Thermostat (Microcal, Inc., Northampton, Mass.) set to 8° C. Samples were dispensed into the appropriate cells of a MicroCal VP-DSC Capillary Cell Micro-Calorimter (MicroCal, Inc., Northampton, Mass.). Samples were equilibrated for 4 minutes at 15° C. and then scanned up to 100° C. at a rate of 100° C. per hour. A filtering period of 20 seconds was selected. Raw data was baseline corrected and the protein concentration was normalized. Origin Software (OriginLab Corporation, Northampton, Mass.) was used to fit the data to an MN2-State Model with an appropriate number of transitions.

As shown in Table 7 below, both hu28 and hu75 had higher thermostability, as displayed by higher melting point, in their Fab region (all above 77° C.) compared to ch28 and ch75, respectively.

TABLE 7

Thermal Stability (DSC) analysis of anti-Notch3 antibodies.

| | Tm (° C.) ± Standard Deviation | | |
|---|---|---|---|
| Antibody | CH2 | Fab | CH3 |
| ch28 | 70.20 ± 0.05 | 73.22 ± 0.73 | 84.24 ± 0.07 |
| hu28 VH1.0/VL1.0 | | 72.63 ± 0.03 | 83.45 ± 0.17 |
| ch75 | | 73.32 ± 0.01 | 84.59 ± 0.03 |
| hu75 VH1.9/VL1.3 | 70.46 ± 0.02 | 74.63 ± 0.17 | 84.17 ± 0.05 |

Example 6

Domain Swap Chimeric Constructs

As described in Example 3, both hu28 and hu75 lacked cross-reactivity with the Notch1 protein. Domain swap chimeric constructs for the Notch1 and Notch3 NRR were prepared for epitope mapping of the anti-Notch3 ch28 and ch75 antibodies. Expression constructs encoding human Notch1-Notch3 (hereinafter Notch 1-3) NRR region domain swap chimera with C-terminal Fc fusion (human IgG1 Fc fragment) were individually transfected into CHO-PACE and stable pools expressing each chimera were established. Conditioned media from each stable pool were applied to protein A affinity chromatography, followed by size exclusion chromatography (SEC) for the purification of the chimeric fusion protein. Purified preparations were dialysed into TBS with 1 mM $CaCl_2$ and analyzed on analytical SEC. FIG. 6 shows the recombinant NRR chimeric proteins consist of various Notch1 (shown in grey) and Notch3 (shown in black) domains fused to human Fc (not shown).

Relative binding capacities of ch28 and ch75 to Notch 1-3 NRR domain swap chimeras were tested in ELISAs as described in Examples 3 and 5. The Notch 1-3 NRR domain swap chimera were coated on ELISA plates at 1 ug/ml, followed by blocking with 1% BSA in PBS with 0.9 mM $Mg^{2+}$ and $Ca^{2+}$. ch28 and ch75 were then applied to the blocked plates at 5 ug/ml diluted in the blocking buffer. After 1 hour of incubation, plates were washed with PBS with 0.9 mM $Mg^{2+}$ and $Ca^{2+}$, before secondary goat anti-human Fc antibody conjugated with HRP were applied and incubated on the plates. After washing again, the plates were developed with TMB and the developing reactions were stopped by adding 0.18M $H_2SO_4$. O.D. 450 nM were read on plate reader and relative binding capacities indicated by O.D. values.

As shown in FIG. 6, the epitope binding profile of ch28 and ch75 to domains of the Notch3 NRR are distinct. More specifically, the binding of ch28 to the Notch3 NRR was more dependent on the LNR-C and HD-1 domains, while ch75 was more dependent on the LNR-A and both the HD-1 and HD-2 domains. The observed binding profile for ch28 and ch75 was consistent with the signaling inhibition activities of the antibodies. In particular, ch28 only interacted with the N-terminus of the Notch3 NRR heterodimer (HD-1) which would not maintain the Notch3 NRR region in the auto-inhibitory conformation that is required for inhibiting the activation of Notch3 signaling. In contrast, ch75 interacted with both the HD-1 and HD-2 domains of the Notch3 NRR heterodimer which would maintain the Notch3 NRR region in the auto-inhibitory conformation, thereby inhibiting the activation of Notch3 signaling.

Example 7

Identification of Notch3 Expressing Cancer Cell Lines

Expression of Notch3 was determined in a panel of cancer cell lines by western blot analysis to identify Notch3 positive cells for further analysis and testing of anti-Notch3 antibodies and anti-Notch3 antibody-drug conjugates. The panel included HCC2429 lung cancer cell line, OVCAR3 ovarian cancer cell line, MDA-MB-468 breast cancer cell line, N87 gastric cancer cell line, along with cell lines engineered to over-express human Notch3 including U-2 OS and MDA-MB-468 cells, hereinafter referred to as U2OS/hNotch3 and MDAMB468/hNotch3, respectively. Notch3 was detected with a rabbit monoclonal anti-Notch3 antibody D11B8 (Cell Signaling Technologies) or a mouse monoclonal 1G5 (Abnova) using standard western blot procedures.

Figure 7:
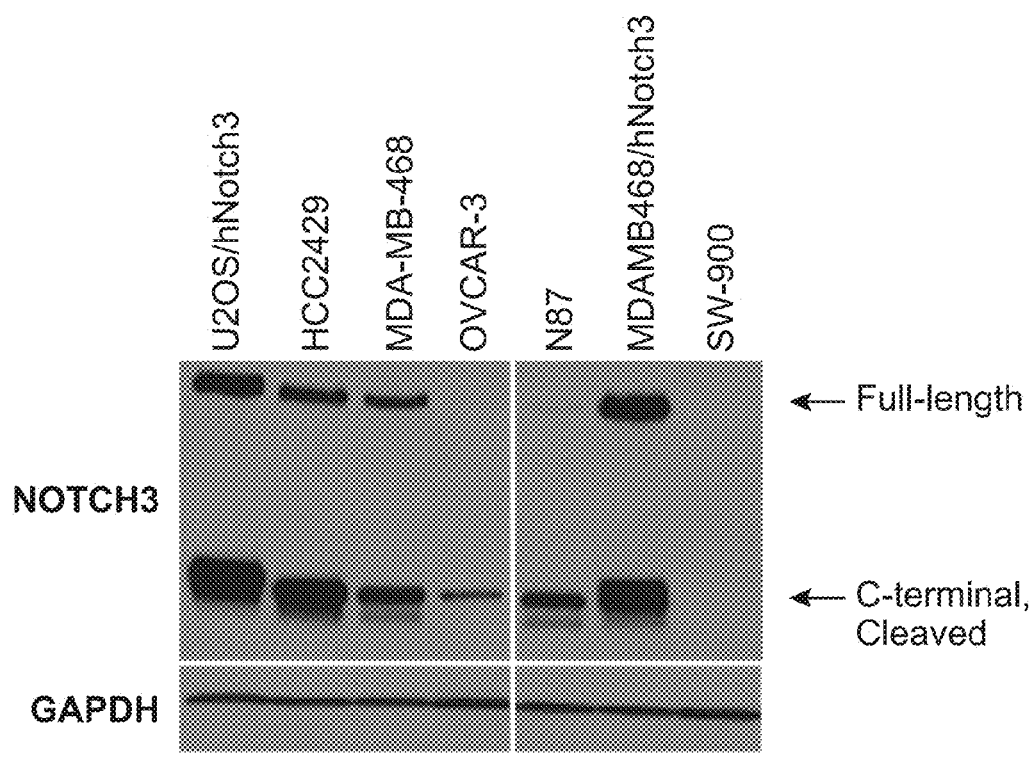
FIG. 7 shows Western blot analysis of Notch3 positive and negative cell lines using the D11B8 antibody.

The D11B8 anti-Notch3 antibody binds to an epitope surrounding Glu2312 within the C-terminal tail of the human Notch3 protein and recognizes both uncleaved, full-length Notch3 (~270 kDa) and cleaved, C-terminal domain containing Notch3 protein fragments at (~80-90 kDa). Notch3 bands at the ~80-90 kDa molecular weights represent the TMIC (Transmembrane and intracellular domain) and/or NEXT (Notch extracellular truncation) proteolytic fragments, as shown in FIG. 7. The 1G5 antibodies bind an epitope within amino acids 47-156 of the Notch3 extracellular domain (ECD) and recognize both the uncleaved, full-length (~270 kDa) and the cleaved, N-terminal fragment (~210 kDa) (data not shown).

Both the Notch3-ECD (data not shown) and the cleaved C-terminal domain containing Notch3 protein fragments were detected in HCC2429, OVCAR3, MDA-MB-468, N87, MDAMB468/hNotch3 and U2OS/hNotch3, as shown in FIG. 7. Further, Notch3 was not detected in the SW900 lung cancer cell line and thus represents a Notch3 negative control cell line.

Example 8

Internalization and Trafficking of Anti-Notch3 Antibodies

Anti-Notch3 antibody-drug conjugates consist of a peptide cleavable maleimidocaproyl-valine citrulline-p-aminobenzyloxycarbonyl (vc) linker or a non-cleavable, thio-ether-based maleimidocaproyl (mc) linker conjugated to a series of cytotoxic agents. Release of payloads from the antibody requires trafficking and localization of the antibody-drug conjugate to lysosomes that possess proteolytic enzymes, such as cathepsin B, to cleave the vc-type linker or late lysosomes for complete catabolism of the antibody in order to release the mc-linked payloads. The internalization and intracellular trafficking of anti-Notch3 antibodies to lysosomal vesicles were monitored by indirect and direct immunofluoresence microscopy-based assays. To directly visual intracellular trafficking of anti-Notch3 antibodies, they were conjugated to fluorescent dyes and incubated with live cells in the presence of pHrodo™ red dextran (Life Technologies) to stain acidic vesicles such as lysosomes. Live cell imaging was performed to identify co-localization of the fluorescence-labeled antibody with lysosomes and other acidic vesicles. Further, indirect immunofluorescence microscopy-based assays were performed on cells to confirm co-localization of anti-Notch3 antibodies and LAMP1, a lysosomal-associated protein.

A. Internalization and Lysosomal Trafficking

HCC2429 or MDA-MB-468 cells were cultured in a Lab Tec II 4 chambered coverglass with cover #1.5 borosilicate sterile slides (Thermo Fisher Scientific Inc.). On day 1, pHrodo™ red dextran (Life Technologies) was added to the medium at 10 µg/ml concentration and incubated for 16 hours in order to stain acidic vesicles such as lysosomes. On day 2, cells were washed twice with HBSS++ (Gibco Life Technologies). Anti-Notch3 antibody hu75 was conjugated to Alexa Fluor 488 (hereinafter "hu75-Alexa488") (Life Technologies Protein Labeling kit) and hu28 was directly conjugated to the DyLight650 maleimide reagent (hereinafter "hu28-DyLight650") (Thermo Scientific) according to manufacturer's instructions. Hu75-Alexa488 or hu28-DyLight650 labeled antibodies were added to the cells at a concentration 5 µg/ml in 2% bovine serum albumin (BSA)/HBSS++ for 25 minutes on wet ice. Cells were washed twice with ice cold HBSS++ on ice, placed in 2% BSA/HBSS++ and imaged on a spinning disk CSU-X1M 5000 microscope (Yokogawa) equipped with a eXcelon Evolve 512 camera (Photometrics) and a XL S Series chamber (Zeiss) for temperature, humidity and 5% $CO_2$ control, from 5 minutes to 12-18 hours. Images were captured every 5 minutes and combined using the Zen CZI file format (Zeiss). A Pearson's correlation coefficient was calculated using the Volocity v6.3 software (PerkinElmer) to determine the degree of colocalization between hu28-DyLight650 and pHrodo™ red dextran.

Figure 8A:
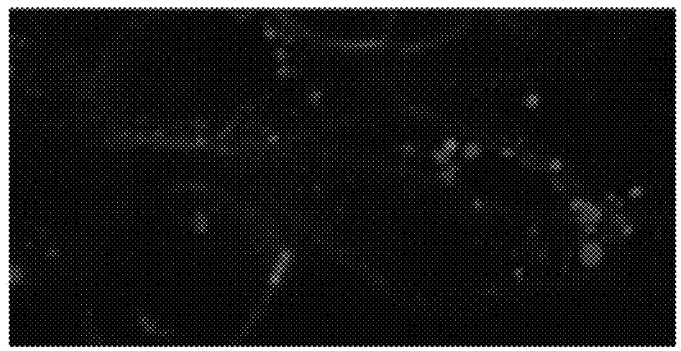
FIGS. 8A through 8E show [A] cell membrane localization of anti-Notch3 antibody hu75-Alexa 488 and labeling of acidic vesicles with pHrodo™ red dextran in MDA-MB-468 breast cancer cells at hour 0, [B] Intracellular trafficking of anti-Notch3 antibody hu75-Alexa 488 and co-localization with pHrodo™ red dextran in MDA-MB-468 breast cancer cells at hour 5 (arrows), [C] cell membrane localization of anti-Notch3 antibody hu28-DyLight650 and labeling of acidic vesicles with pHrodo™ red dextran (intracellular puncta) in MDA-MB-468 breast cancer cells at hour 0, [D] intracellular trafficking of anti-Notch3 antibody hu28-DyLight650 and co-localization with pHrodo™ red dextran in MDA-MB-468 breast cancer cells at hour 8 (arrows) and [E] Pearson's correlation coefficient demonstrating the degree of overlap or co-localization of hu28-DyLight650 and pHrodo™ red dextran fluorescent labels in MDA-MB-468 cells over time.
Figure 8B:
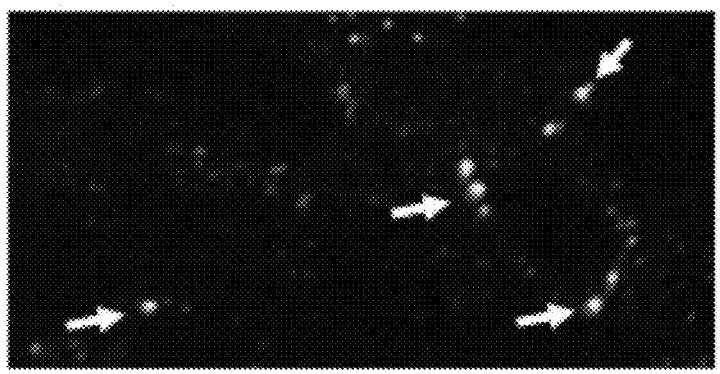

Once cells were prepared for live cell imaging, the earliest time point that could be assessed was 10 minutes due to set up and optimization of instrument setting for image acquisition. Approximately 10 minutes after cells were place in the humidified, 37° C., 5% $CO_2$ chamber, hu75-Alexa488 could be observed at the cell surface as well as in several punctuate-like structures inside the cells, as shown in FIG. 8A. This result indicates that anti-Notch3 antibody hu75 rapidly underwent internalization upon binding the Notch3 receptor at the cell membrane. At the early time points (10 minutes to about 65 minutes), intracellular anti-Notch3 antibody hu75-Alexa488 and acidic vesicles that were stained with pHrodo™ red dextran appeared as discrete puncta that did not co-localize. From time about 70 minutes and later, anti-Notch3 antibody hu75 and pHrodo™ red dextran-labeled vesicles co-localized to the same discrete punctate-like structures, as shown by arrows in FIG. 8B. This data suggests that anti-Notch3 antibody hu75 internalized and trafficked to acidic vesicles such as lysosomes in Notch3 expressing HCC2429 (data not shown) and MDA-MB-468 cells, as shown in FIG. 8B.

Figure 8C:
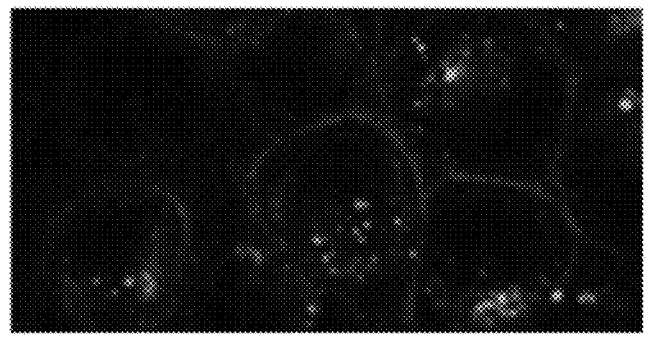
Figure 8D:
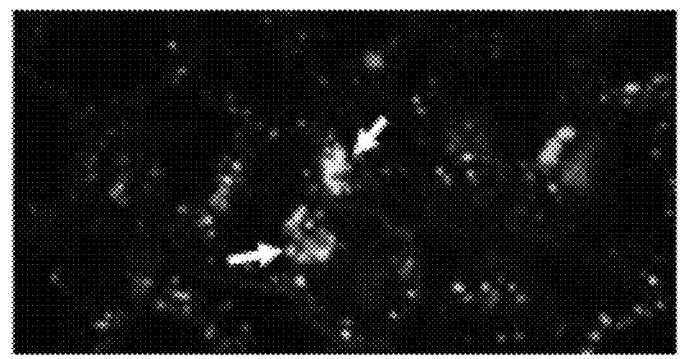
Figure 8E:
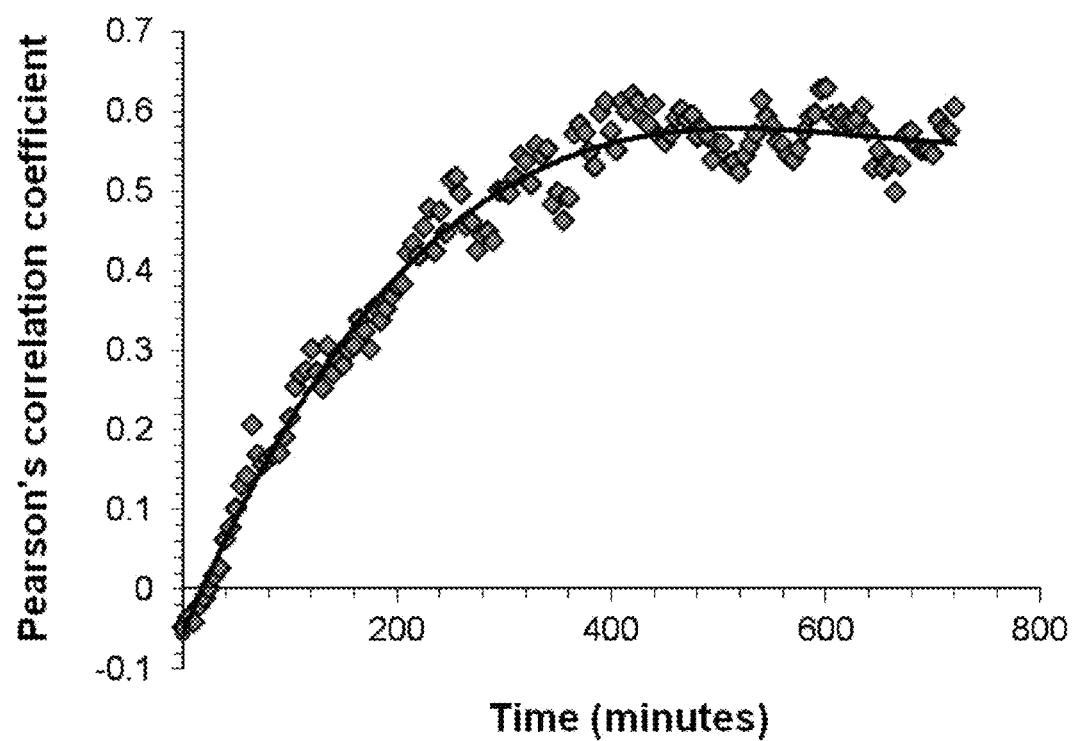

About 10 minutes after cells were place in the humidified, 37° C., 5% $CO_2$ chamber, hu28-DyLight650 could be observed at the cell surface, as shown in FIG. 8C. Intracellular anti-Notch3 antibody hu28-DyLight650 and pHrodo™ red dextran-stained acidic vesicles appeared as discrete puncta and gradually co-localized over time, as shown by arrows in FIG. 8D. A Pearson's correlation coefficient (PCC) was calculated to determine the degree of overlap or co-localization between hu28-DyLight650 and pHrodo™ red dextran fluorescent labels in MDA-MB-468 cells over time. The higher the PCC number, the greater degree of co-localization between the hu28-DyLight650 and pHrodo™ red dextran fluorescence labels. FIG. 8E demonstrates a steady increase in co-localization up to about 360 minutes and a maximal colocalization between hu28-DyLight650 and pHrodo™ red dextran occurs at about 420 minutes and then plateaus. The data suggests that anti-Notch3 antibody hu28-DyLight650 internalized and trafficked to acidic vesicles such as lysosomes in Notch3 expressing MDA-MB-468 cells.

B. Co-Localization with Lysosomal-Associated Membrane Protein 1 (LAMP1)

HCC2429 or MDA-MB-468 cells were cultured in a Lab Tec II 4 chambered coverglass with cover #1.5 borosilicate sterile slides (Thermo Fisher Scientific Inc.). For binding and internalization assays, cells were washed twice with HBSS++ and unconjugated anti-Notch3 antibodies, hu75 and hu28, were added to the cells at a concentration 10 µg/ml in 2% bovine serum albumin (BSA)/HBSS++ for 25 minutes on ice. To visual membrane binding at time 0 minutes, control cells were washed with ice cold HBSS++ and then fixed in 4% paraformaldehyde in PBS for 10 minutes. For antibody internalization, cells were washed twice with ice cold HBSS++ and then pre-warmed complete growth media was added to the cells and placed inside a humidified 37° C., 5% $CO_2$ incubator. Cells were removed from the incubator, washed and fixed as before at multiple time points from 5 minutes to 18 hours. Cells were then washed 3 times with PBS, and permeabilized for 10 minutes with 0.3% Triton X-100 in PBS. Cells were washed 3 times with PBS for 5 minutes each time and then blocked for 1 hour in 3% BSA/PBS. Anti-LAMP-1 mouse monoclonal antibody (H4A3, Abcam) was added at 1:100 in 2% BSA/PBS for overnight incubation at 4° C. Cells were washed twice with PBS for 5 minutes each and then secondary goat anti-human Alexa Fluor 488 and goat anti-mouse Alexa Fluor 555 (Life technologies) were added for 45 minutes in the dark. Cells were washed three times with PBS and were imaged on Zeiss LSM510 confocal microscope or a CSU-X1M 5000 (Yokogawa) spinning disk confocal microscope.

In control cells incubated on ice with anti-Notch3 antibodies and then immediately fixed, both hu28 and hu75 were localized at the cell surface of Notch3 expressing cells and no staining was observed inside the cells. In control cells, lysosomes were stained with an anti-LAMP1 antibody and appeared as discrete punctuate-like structures inside the cells that did not co-localize with anti-Notch3 antibodies hu28 and hu75. After incubation at 37° C. for 90 minutes, anti-Notch3 antibodies hu28 and hu75 were observed in punctuate-like structures inside the cells that co-localized with anti-LAMP1 antibodies. After incubation at 37° C., cell membrane staining of anti-Notch3 antibodies hu28 and hu75 was reduced and eventually became undetectable. This data suggested that anti-Notch3 antibodies hu28 and hu75 bound the cell surface after incubation with cells on ice and then underwent temperature-dependent internalization at 37° C. Once internalized, anti-Notch3 antibodies hu28 and hu75 co-localized with the LAMP1 protein indicating they trafficked specifically to the lysosome (data not shown).

Example 9

Effects of Anti-Notch3 Antibodies on Notch3 Signaling in Cell-Based Assays

Notch3 signaling is initiated by ligand-induced proteolysis. The mature Notch3 heterodimer after furin-like protease cleavage at site S1 is held in an auto-inhibited state by the juxtamembrane negative regulatory region (NRR). Binding of ligands, such as DLL4 or Jagged1, to the Notch3-ECD induces two successive additional cleavages at sites S2 and S3 that are catalyzed by ADAM-type metalloproteinase and gamma-secretase, respectively. The latter cleavage releases the intracellular domain of Notch3 (NICD3), permitting it to translocate to the nucleus and activate the transcription of target genes containing consensus DNA binding site motifs for the CSL protein.

The ability of anti-Notch3 chimeric antibodies, ch28-huIgG1 and ch75-huIgG1, and humanized antibodies, hu28 and hu75, to inhibit Notch3 signaling were tested in a Notch3-dependent reporter gene co-culture assay. Anti-Notch3 antibodies were pre-incubated with Notch3 reporter cells and then co-cultured with DLL4-HEK293 cells to activate Notch3 signaling or with parental HEK293 cells as a control.

A. Cell Line Construction for Notch3 Reporter Gene Co-Culture Assay

To generate the Notch3 reporter cell line, a series of three sequential, stable transfections were performed in the U-2 OS human osteosarcoma cell line (ATCC, Manassas, Va.). The first transfection used a vector for expression of full-length human Notch3 based on the pCMV6-Entry-Myc-Flag backbone (Origene), and the correct DNA sequence of the Notch3 insert was confirmed. Following transfection with the TransIT-LT1 transfection reagent (Mirus, Madison, Wis.), U-2 OS cells were selected in G418 and clonal lines were isolated. Second, stable Notch3-expressing U-2 OS clones were re-transfected with the pGL4.27 [luc2P/minP/Hygro] vector (Promega, Madison, Wis.) containing eight tandem copies of the CSL enhancer sequence (SEQ ID NO: 69 CGTGGGAAAAT), selected in Hygromycin B plus G418 and clonal lines were isolated. The 8xCSL Firefly-luciferase reporter construct is responsive to activated Notch signaling (for example, see, Jeffries et al., Mol. Cell. Biol. 22(11):3927-3941, 2002). Thirdly, the human Notch3 8xCSL Firefly-Luciferase U-2 OS cells were transduced with Cignal Lenti Renilla Control (luc) (Qiagen, CA) lentiviral particles, selected in Puromycin, Hygromycin B and G418, and clonal lines were isolated. The Cignal Lenti Renilla control (luc) vector encoded the Renilla-luciferase gene that is constitutively expressed from a CMV promoter and served as an internal control. The triple stable transfected U-2 OS line (hereinafter termed "Notch3 reporter cells") was maintained in McCoy's 5A medium (Gibco, Grand Island, N.Y.) containing 10% FBS, 1× Penicillin/Streptomycin/L-Glutamine (Gibco), 0.25 mg/ml G418 sulfate, 0.3 mg/ml Hygromycin B and 0.001 mg/ml Puromycin.

To generate the ligand-expressing cells, HEK293 cells (ATCC) were transfected with a vector for expression of human DLL4. The vector was based on the pCMV6-AC-HA-His backbone (Origene, Rockville, Md.), and the correct DNA sequence of the DLL4 insert was confirmed. Following transfection, HEK293 cells were selected in 0.5 mg/ml G418, and clonal lines were isolated, expanded and analyzed for DLL4 expression. Clones with high DLL4 expression and high induction of Notch3 reporter activity in the U-2 OS cells were used to assess the inhibitory effect of anti-Notch3 antibodies.

The luminescent readings from Firefly-luciferase were divided by the internal control Renilla-luciferase reading to normalize the signals (termed hereinafter "F/R ratio"). To calculate the fold-induction of Notch3 signaling, the F/R ratios generated from the DLL4-HEK293 co-culture reporter assays were divided by the F/R ratios from the parental HEK293 co-cultures and termed relative luciferase unit (RLU) or activity.

B. Reporter Gene Co-Culture Assays

Human Notch3 reporter cells were trypinized and harvested from culture plate in assay medium which consisted 50% complete McCoy's 5A media (McCoy's 5A with 10% FBS and penicillin, streptomycin, Invitrogen) and 50% of complete MEM media (MEM with 10% FBS and penicillin, streptomycin, Invitrogen) and counted. Appropriate dilutions of cells were made with the same medium to allow for 10,000 cells/well in a total volume of 45 μl/well on a 96 well culture plate (white opaque, BD/VWR), in the presence of serially diluted (1:3 in complete McCoy's 5A media) antibody solutions or hybridoma culture supernatants. The mixture of cells and antibody dilutions were incubated on the plates in a sterile hood at room temperature for 1 hr before 30,000/45 μl of human DLL4-HEK293 cells were added to each well. After addition of hDLL4-HEK293 cells, the plates were further incubated for 20 hrs in the incubator and Dual-Glo Luciferase assay system (Promega) was used to measure the firefly luciferase and internal control Renilla luciferase activity per manufacturer's instructions. Data was plotted and analyzed using Microsoft Excel and Graphpad-Prism software.

A titration of ch75-huIgG1 and hu75 in the human Notch3 reporter co-culture assay demonstrated potent inhibition of Notch3 signaling in a dose-dependent manner. Table 8 shows the inhibitory activities of ch75-huIgG1 and hu75 antibodies against Notch3 dependent signaling in human Notch3 reporter cells. ch75-huIgG1 and hu75 showed similar neutralization activities in human Notch3 dependent signaling reporter assays. Therefore, hu75 fully retained the inhibitory activity of ch75-huIgG1. Both ch28-huIgG1 and hu28 weakly inhibited Notch3 signaling at a level similar to control ch2H6-huIgG1 and huNeg8.8 antibodies. This indicates that the inhibitory activity of ch28-huIgG1 and hu28 were non-specific. Further, the data demonstrates that anti-Notch3 antibodies ch28-huIgG1 and hu28 do not inhibit Notch3 signaling and therefore are functionally distinct from ch75-huIgG1 and hu75.

C. Effect of Anti-Notch3 Antibodies on Site 2 Cleavage by Metalloprotease

To confirm that binding of anti-Notch3 antibody hu75, but not hu28, to the NRR domain of Notch3 is accompanied by a decrease in S2-cleavage, western blot analysis was performed. The rabbit monoclonal anti-Notch3 antibody D11B8 (Cell Signaling Technologies) recognizes the Notch3 C-terminal fragments that are products of S1 and S2 proteolytic cleavage events. As demonstrated by NRR domain swap experiments, the anti-Notch3 antibody hu75 bound simultaneously to LNR-A, HD-1 and HD-2 domains located on two non-covalently linked regions of the NRR that are separated by furin-cleavage at site 1 (S1). The anti-Notch3 antibody hu28 bound to LNR-C and HD1 domains that are located on a linear, covalently linked region of the NRR domain that is N-terminal to the S1-site. An inhibitory antibody is expected to decrease the detection of S2-cleaved Notch3 by stabilizing the NRR domain in an auto-inhibitory conformation thus preventing S2-cleavage, while a non-inhibitory antibody is not expected to have an effect on S2-cleavage.

Site 2 (S2)-cleavage of the Notch3 receptor was assessed by western blot analysis of the protein using the D11B8 (Cell Signaling Technologies) antibody which recognizes an epitope surrounding Glu2312 in the C-terminal domain. HCC2429 and MDA-MB-468 breast cancer cells were used to examine the effects of inhibitory anti-Notch3 antibody hu75 and non-inhibitory anti-Notch3 antibody hu28 on S2-cleavage. For the assay, $1-2.5\times10^6$ cells were plated in complete growth medium. Hu75, hu28 and huNeg8.8 control antibody were added at a concentration of 5 μg/ml. Cells were incubated at 37° C. in a 5% $CO_2$ incubator for 24 hours and then directly lysed in buffer. Extracts were resolved by denaturing SDS-PAGE on a 7.5% polyacrylamide gel (Bio-

TABLE 8

Dose-dependent inhibitory activity of humanized and chimeric antibodies.

| nM | hu28 VH1.0/VL1.0 | hu75 VH1.9/VL1.3 | huNeg-8.8 | ch28-hIgG1 | ch75-hIgG1 | ch2H6-hIgG1 |
|---|---|---|---|---|---|---|
| | | | % inhibition (SD) | | | |
| 0 | 100 (0) | 100 (0) | 100 (0) | 100 (0) | 100 (0) | 100 (0) |
| 0.27 | 99.9 (6.2) | 104.4 (4.9) | 84.5 (8.6) | 102.8 (6.1) | 88.4 (8.7) | 95.7 (6.9) |
| 0.82 | 88.6 (11.8) | 103.0 (17.8) | 88.2 (9.0) | 83.2 (11.7) | 70.6 (4.1) | 93.1 (11.0) |
| 2.47 | 77.7 (9.5) | 65.6 (12.3) | 84.6 (7.5) | 75.0 (5.2) | 48.4 (2.5) | 92.4 (9.0) |
| 7.41 | 71.9 (4.7) | 40.5 (4.1) | 79.3 (10.4) | 74.0 (2.9) | 26.8 (1.9) | 84.8 (9.4) |
| 22.2 | 68.6 (7.9) | 22.7 (3.2) | 83.5 (8.8) | 76.5 (6.2) | 20.3 (2.1) | 94.8 (8.6) |
| 66.7 | 66.8 (2.0) | 14.2 (1.1) | 81.4 (4.3) | 72.3 (8.9) | 13.2 (1.0) | 83.1 (2.8) |
| 200 | 71.1 (10.3) | 13.7 (0.9) | 75.7 (5.1) | 70.3 (4.1) | 13.9 (1.4) | 78.2 (5.1) |

The $IC_{50}$ (nM) values of ch75-huIgG1 and hu75 variants were calculated from the inhibition of Notch3-dependent signaling of the Notch3 reporter gene co-culture assays. $IC_{50}$ (nM) data from two or three independent experiments were averaged, as provided in Table 9. Both hu75 and ch75-huIgG1 have low $IC_{50}$ values indicating they are potent inhibitors of Notch3 signaling.

TABLE 9

$IC_{50}$ values (nM) for inhibitory activity of hu75 and ch75-hIgG1.

| Antibody | $IC_{50}$ (nM) | SD |
|---|---|---|
| hu75 VH1.9/VL1.3 | 4.43 | 2.36 |
| ch75-hIgG1 | 2.10 | 0.66 |

Rad criterion gel) and transferred to nitrocellulose paper using an iBlot Gel transfer system (Invitrogen). Notch3 was detected with D11B8 antibody and, as a loading control, anti-GAPDH (Sigma) using standard western blot procedures.

Figure 9:
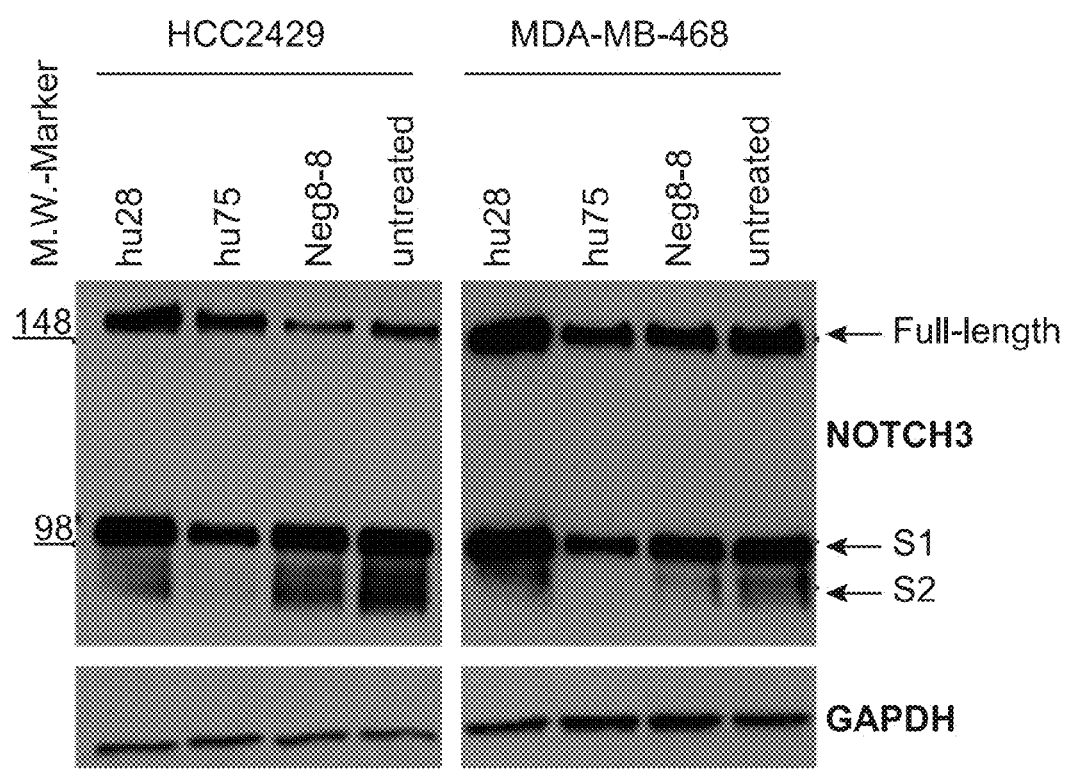
FIG. 9 shows Western blot analysis of S2-cleavage assay using HCC2429 and MDA-MB-468 cells treated with anti-Notch3 hu28 and hu75. M.W.=molecular weight.

FIG. 9 shows a Western blot analysis of the S2-cleavage assay. In untreated and control huNeg8.8-treated HCC2429 and MDA-MB-468 cells for 24 hours, both S1- and S2-cleaved C-terminal Notch3 protein fragments could be detected by western blot analysis with D11B8 antibody, as expected. Further, in cells treated with inhibitory anti-Notch3 antibody hu75, the S1-cleaved Notch3 C-terminal fragment was detected, but the S2-cleaved fragment was not detected indicating that metalloprotease cleavage was blocked by hu75. Furthermore, in cells treated with non-inhibitory anti-Notch3 antibody hu28, both S1- and S2-cleaved Notch3 C-terminal fragments were detected indicating that hu28 does not inhibit proteolysis of the receptor. Therefore, hu28 binds with high affinity to the Notch3-NRR as demonstrated in Example 5 and had a high binding activity to full-length Notch3 expressed on the cell surface, but does not inhibit Notch3 signaling indicating it is functionally distinct from inhibitory anti-Notch3-NRR antibodies, including hu75.

Example 10

Synthesis of Compounds

Compounds 0101, 6780, 0131, 3377 and 8261 were prepared according to the methods described in International Publication No. WO/2013/072813, which is incorporated herein by reference.

A. Experimental for Compound 0101 (#54 in the Schematic)

Preparation of 2-Methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#54)

Step 1. Synthesis of N-[(9H-fluoren-9-ylmethoxy)carbonyl]-2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#53). According to general procedure D (below), from #32 (2.05 g, 2.83 mmol, 1 eq.) in dichloromethane (20 mL, 0.1 M) and N,N-dimethylformamide (3 mL), the amine #19 (2.5 g, 3.4 mmol, 1.2 eq.), HATU (1.29 g, 3.38 mmol, 1.2 eq.)

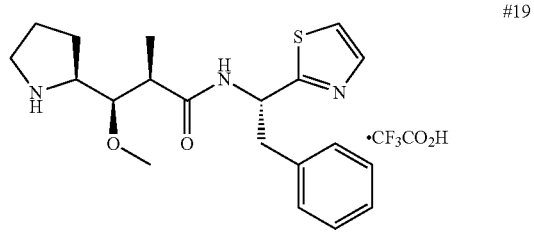

and triethylamine (1.57 mL, 11.3 mmol, 4 eq.) was synthesized the crude desired material, which was purified by silica

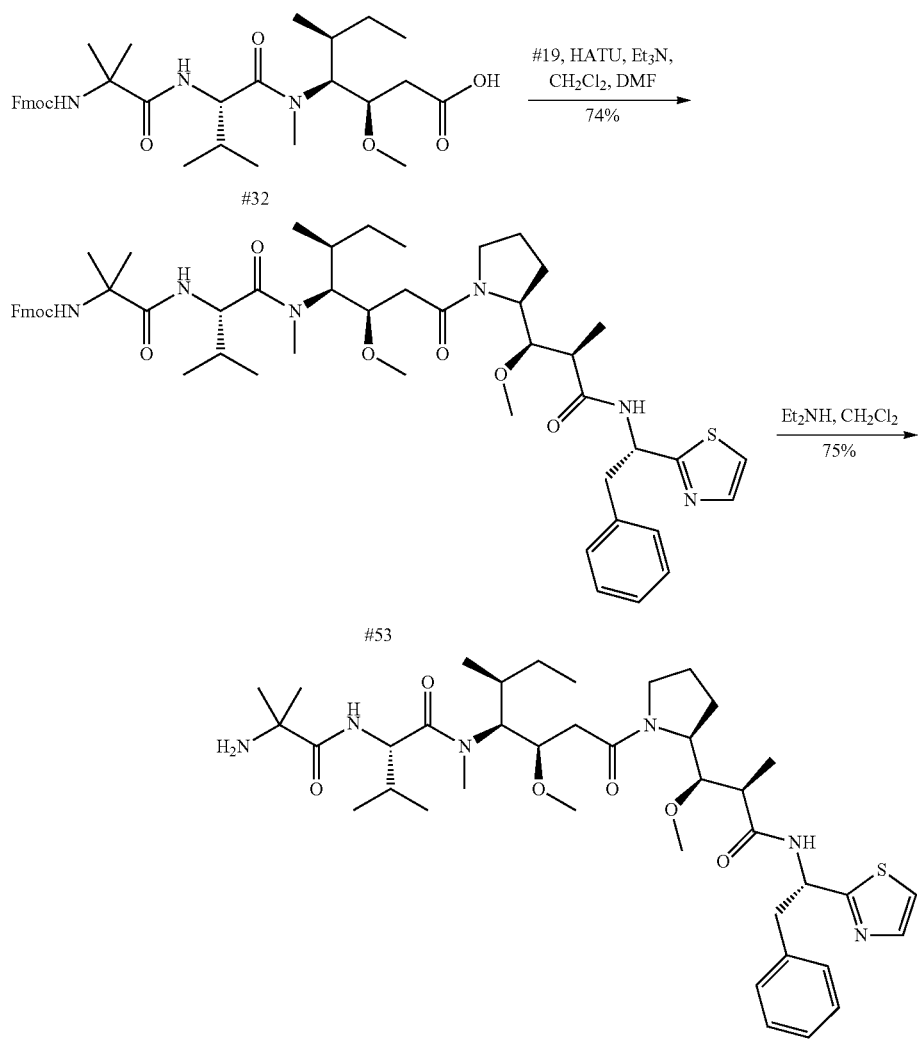

gel chromatography (Gradient: 0% to 55% acetone in heptane), producing #53 (2.42 g, 74%) as a solid. LC-MS: m/z 965.7 [M+H]$^+$, 987.6 [M+Na]$^+$, retention time=1.04 minutes; HPLC (Protocol A): m/z 965.4 [M+H]$^+$, retention time=11.344 minutes (purity >97%); $^1$H NMR (400 MHz, DMSO-d$_6$), presumed to be a mixture of rotamers, characteristic signals: δ 7.86-7.91 (m, 2H), [7.77 (d, J=3.3 Hz) and 7.79 (d, J=3.2 Hz), total 1H], 7.67-7.74 (m, 2H), [7.63 (d, J=3.2 Hz) and 7.65 (d, J=3.2 Hz), total 1H], 7.38-7.44 (m, 2H), 7.30-7.36 (m, 2H), 7.11-7.30 (m, 5H), [5.39 (ddd, J=11.4, 8.4, 4.1 Hz) and 5.52 (ddd, J=11.7, 8.8, 4.2 Hz), total 1H], [4.49 (dd, J=8.6, 7.6 Hz) and 4.59 (dd, J=8.6, 6.8 Hz), total 1H], 3.13, 3.17, 3.18 and 3.24 (4 s, total 6H), 2.90 and 3.00 (2 br s, total 3H), 1.31 and 1.36 (2 br s, total 6H), [1.05 (d, J=6.7 Hz) and 1.09 (d, J=6.7 Hz), total 3H].

Step 2. Synthesis of 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#54)

According to general procedure A (below), from #53 (701 mg, 0.726 mmol) in dichloromethane (10 mL, 0.07 M) was synthesized the crude desired material, which was purified by silica gel chromatography (Gradient: 0% to 10% methanol in dichloromethane). The residue was diluted with diethyl ether and heptane and was concentrated in vacuo to afford #54 (406 mg, 75%) as a white solid. LC-MS: m/z 743.6 [M+H]$^+$, retention time=0.70 minutes; HPLC (Protocol A): m/z 743.4 [M+H]$^+$, retention time=6.903 minutes, (purity >97%); $^1$H NMR (400 MHz, DMSO-d$_6$), presumed to be a mixture of rotamers, characteristic signals: δ [8.64 (br d, J=8.5 Hz) and 8.86 (br d, J=8.7 Hz), total 1H], [8.04 (br d, J=9.3 Hz) and 8.08 (br d, J=9.3 Hz), total 1H], [7.77 (d, J=3.3 Hz) and 7.80 (d, J=3.2 Hz), total 1H], [7.63 (d, J=3.3 Hz) and 7.66 (d, J=3.2 Hz), total 1H], 7.13-7.31 (m, 5H), [5.39 (ddd, J=11, 8.5, 4 Hz) and 5.53 (ddd, J=12, 9, 4 Hz), total 1H], [4.49 (dd, J=9, 8 Hz) and 4.60 (dd, J=9, 7 Hz), total 1H], 3.16, 3.20, 3.21 and 3.25 (4 s, total 6H), 2.93 and 3.02 (2 br s, total 3H), 1.21 (s, 3H), 1.13 and 1.13 (2 s, total 3H), [1.05 (d, J=6.7 Hz) and 1.10 (d, J=6.7 Hz), total 3H], 0.73-0.80 (m, 3H).

B. Experimental for Compound 6780 (#112 in the Schematic)

Preparation of 2-methylalanyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide (#112)

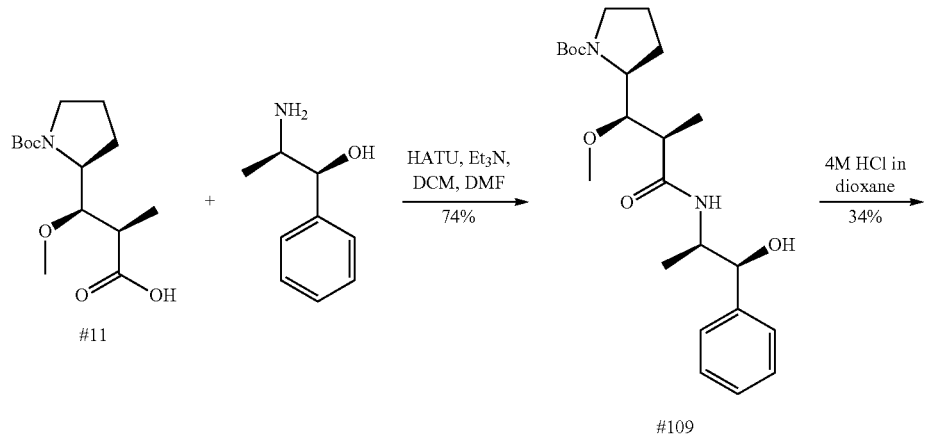

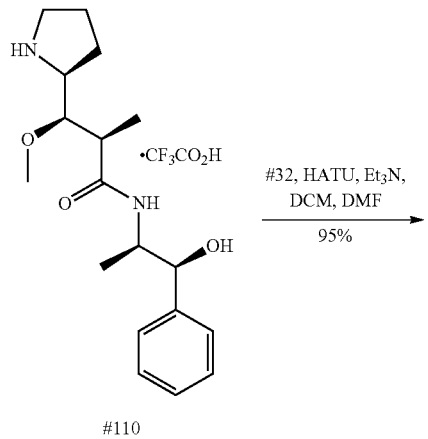

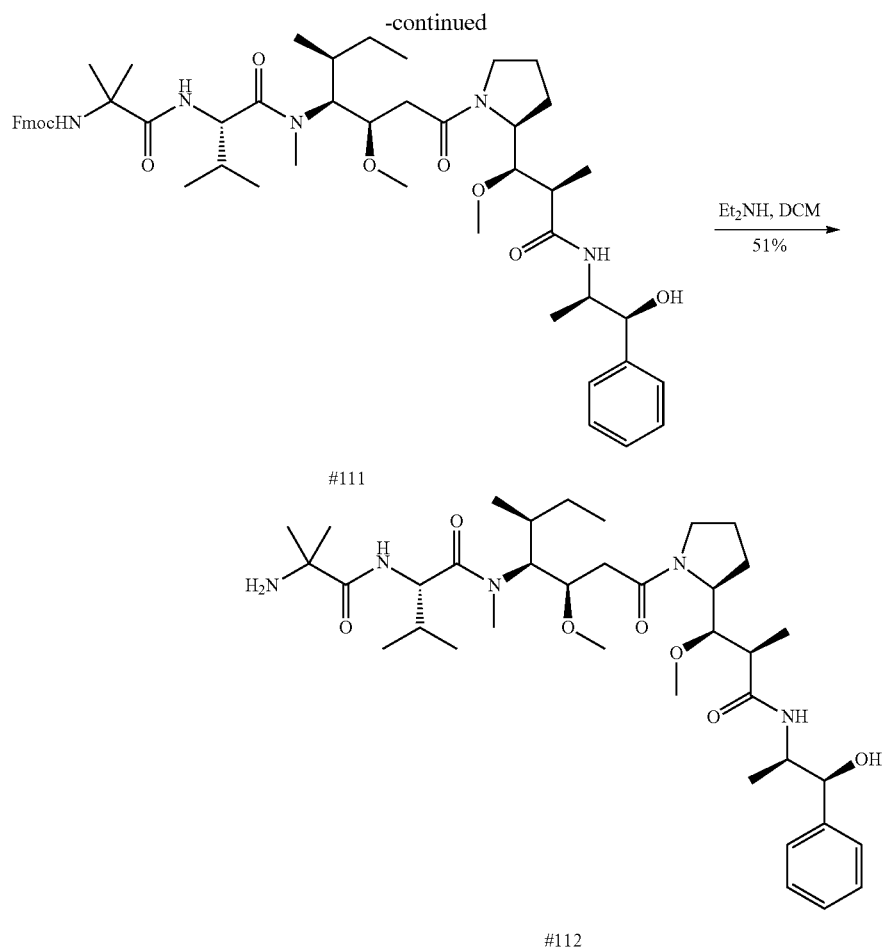

111

112

Step 1. Synthesis of tert-butyl (2S)-2-[(1R,2R)-3-{[(1S,2R)-1-hydroxy-1-phenylpropan-2-yl]amino}-1-methoxy-2-methyl-3-oxopropyl]pyrrolidine-1-carboxylate (#109). To a solution of #11 (2.00 g, 6.96 mmol, 1 eq.) in dichloromethane (21 mL, 0.3 M) and N,N-dimethylformamide (3 mL) was added HATU (3270 mg, 8.35 mmol, 1.2 eq.). After two minutes, the amine (1R,2S)-(+)-norephedrine (1.07 mg, 6.96 mmol, 1 eq.) and triethylamine (1.94 mL, 13.9 mmol, 2 eq.) were added. After two hours, the reaction mixture was diluted with ethyl acetate (100 mL), washed with a 1 M aqueous solution of hydrochloric acid and with brine, dried over sodium sulfate, filtered, concentrated in vacuo, and purified by silica gel chromatography (Gradient: 0% to 60% ethyl acetate in heptane) to provide #109 (2.18 g, 74%) as a white solid. LC-MS: m/z 321.3 [(M−Boc)+H$^+$], retention time=3.14 minutes; $^1$H NMR (400 MHz, DMSO-d$_6$), presumed to be a mixture of rotamers, characteristic signals: δ 7.64 (d, J=8.6 Hz, 1H), 7.24-7.33 (m, 4H), 7.15-7.21 (m, 1H), 5.35 (br d, J=5 Hz, 1H), 4.45 (br dd, J=5, 5 Hz, 1H), 3.91-4.00 (m, 1H), 3.30-3.39 (m, 1H), 3.26 (s, 3H), 2.94-3.07 (m, 1H), 2.04-2.14 (m, 1H), 1.46-1.78 (m, 4H), 1.40 (s, 9H), 0.97-1.04 (m, 6H).

Step 2. Synthesis of (2R,3R)—N-[(1S,2R)-1-hydroxy-1-phenylpropan-2-yl]-3-methoxy-2-methyl-3-[(2S)-pyrrolidin-2-yl]propanamide, trifluoroacetic acid salt (#110). According to general procedure C (below), at 0° C. from #109 (414 mg, 0.984 mmol, 1 eq.), dioxane (5 mL, 0.2 M) and a 4 M solution of hydrogen chloride in dioxane (15 mL, 60 mmol, 60 eq.) was synthesized the crude desired compound, which was purified by reverse phase chromatography (Method C) to give #110 (120 mg, 34%) as a viscous liquid. LC-MS: m/z 321.1 [M+H]$^+$, retention time=0.55 minutes; $^1$H NMR (400 MHz, DMSO-d$_6$), characteristic signals: δ 7.90 (d, J=8.6 Hz, 1H), 7.28-7.36 (m, 4H), 7.20-7.27 (m, 1H), 4.46 (d, J=6.2 Hz, 1H), 3.48 (dd, J=8.6, 2.3 Hz, 1H), 3.38 (s, 3H), 2.92-3.16 (m, 3H), 2.24-2.35 (m, 1H), 1.49-1.88 (m, 4H), 1.09 (d, J=6.6 Hz, 3H), 1.01 (d, J=6.6 Hz, 3H).

Step 3. Synthesis of N-[(9H-fluoren-9-ylmethoxy)carbonyl]-2-methylalanyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide (#111). According to general procedure D (below), from #32 (140 mg, 0.230 mmol, 1 eq.),

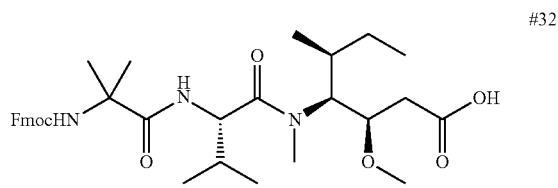

32

110 (110 mg, 0.253 mmol, 1.1 eq.), dichloromethane (3 mL, 0.08 M), N,N-dimethylformamide (0.5 mL), HATU (96.2 mg, 0.253 mmol, 1.1 eq) and triethylamine (96 μL, 0.69 mmol, 3 eq.) was synthesized the crude desired product, which was purified by silica gel chromatography (Gradient: 0% to 40% acetone in heptane) to give #111 (220 mg, 95%). LC-MS: m/z 912.4 [M+H$^+$], 935.4 [M+Na]$^+$, retention time=2.15 minutes; HPLC (Protocol B): m/z 912.5 [M+H$^+$], 934.5 [M+Na]$^+$, retention time=10.138 minutes (purity >94%); $^1$H NMR (400 MHz, DMSO-d$_6$), presumed to be a mixture of rotamers, characteristic signals: δ 7.89 (d, J=7.8 Hz, 2H), 7.66-7.75 (m, 2H), 7.41 (dd, J=7.4, 7.4 Hz, 2H), 7.12-7.20 (m, 1H), [5.33 (d, J=4.7 Hz) and 5.38 (d, J=4.7 Hz), total 1H], 3.15, 3.18, 3.22 and 3.23 (4 s, total 6H), 1.30, 1.33, 1.36 and 1.39 (4 s, total 6H), 0.95-1.06 (m, 6H).

Step 4. Synthesis of 2-methylalanyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide (#112). According to general procedure A (below), from #111 (210 mg, 0.230 mmol) in dichloromethane (5 mL, 0.05 M) and diethylamine (5 mL) was synthesized the crude desired material, which was purified by silica gel chromatography (Gradient: 0% to 10% methanol in dichloromethane) to give a mixture of an oil and solid. Diethyl ether and heptane were added and the mixture was concentrated in vacuo, producing #112 (81 mg, 51%) as a white solid. LC-MS: m/z 690.4 [M+H$^+$], retention time=1.10 minutes; HPLC (Protocol A): m/z 690.5 [M+H$^+$], 712.4 [M+Na]$^+$, retention time=7.229 minutes (purity >90%); $^1$H NMR (400 MHz, DMSO-d$_6$), presumed to be a mixture of rotamers, characteristic signals: δ [7.62 (br d, J=8 Hz), 7.88 (br d, J=8 Hz), 8.07 (br d, J=9 Hz) and 8.11 (br d, J=9 Hz), total 2H], 7.15-7.34 (m, 5H), [5.34 (d, J=4 Hz) and 5.41 (d, J=5 Hz), total 1H], 3.18, 3.21, 3.23 and 3.25 (4 s, total 6H), 2.93 and 3.08 (2 br s, total 3H), 1.15, 1.18, 1.21 and 1.25 (4 s, total 6H).

C, General Procedures

General Procedure A: Fmoc removal using diethylamine or piperidine. To a solution of the Fmoc-containing compound in dichloromethane or N,N-dimethylformamide (also referred to as DMF), was added an equal volume of diethylamine or piperidine. Reaction progress was monitored by LC-MS (or HPLC or TLC). Solvents were removed in vacuo, and in some cases the residue was azeotroped one to four times with heptane. Residue was usually diluted with dichloromethane and a small amount of methanol before being reduced down onto silica and purified by chromatography on silica gel, eluting with methanol in dichloromethane (or other appropriate mixture of solvents) to afford the desired material (or crude material was used as is).

General Procedure C: Boc removal or tert-butyl ester (also refers to t-Bu ester) cleavage using hydrochloric acid in dioxane. To either a solution of Boc-containing compound or tert-butyl ester-containing compound in dioxane (or in some cases no solution, or other relevant solvent) was added a 4 M solution of hydrochloric acid in dioxane. Reaction progress was monitored by LC-MS (or HPLC or TLC). The reaction was concentrated in vacuo and in some cases azeotroped one to four time with heptanes.

General Procedure D: coupling with O-(7-azabenzotriazol-1-yl)-N,N,N',N'-tetramethyluronium hexafluorophosphate (HATU). To a stirring solution of the amine (1.0 eq.) and acid (1.0-2.0 eq.) in dichloromethane, N,N-dimethylformamide (also referred to as DMF), or a mixture of both, HATU (1.0-2.0 eq.) was added followed by triethylamine (2.0-4.0 eq.) or diisopropylethylamine (2.0-4.0 eq., also referred to as Hunig's base). Reaction progress was monitored by LC-MS (or HPLC or TLC); the reaction was usually completed within three hours. Solvents were removed in vacuo. The residue was purified by silica gel or reverse phase chromatography or in some cases azeotroped three times with heptanes, diluted with a small amount of ethyl acetate before being reduced down onto silica or C18 bonded silica and purified by silica gel or reverse phase chromatography.

D. Other Compounds

Further compounds used in the present invention are described in International Publication No. WO/2013/072813 and shown below.

As used herein, compound 0131 or 2-methyl-L-prolyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt (#118) has the formula:

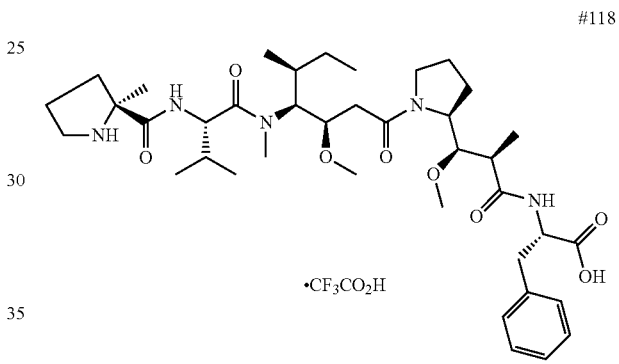

118

·CF$_3$CO$_2$H

As used herein, compound 3377 or N,2-dimethylalanyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide, trifluoroacetic acid salt (#115) has the formula:

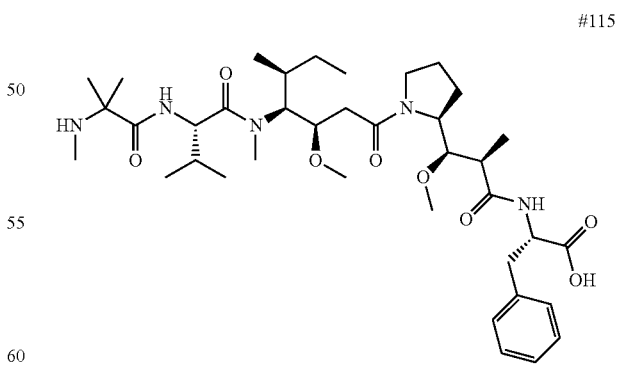

115

As used herein, compound 8261 or 2-Methylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide (#69) has the formula:

69

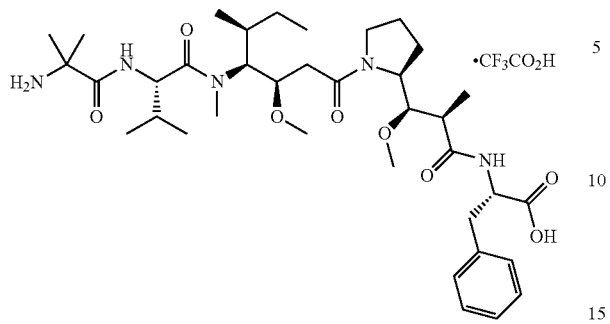

·CF₃CO₂H

Example 11

Preparation of Anti-Notch3 Antibody-Drug Conjugates (ADCs)

The ADCs of the present invention were prepared using a section of a linker having a reactive site for binding to a chemical compound and introducing another section of the linker unit having a reactive site for an antibody. In one aspect, the linker unit has a reactive site which has an electrophilic group that is reactive with a nucleophilic group present on an antibody unit, such as an antibody. Useful nucleophilic groups on an antibody include but are not limited to, sulfhydryl, hydroxyl and amino groups. The heteroatom of the nucleophilic group of an antibody is reactive to an electrophilic group on a linker unit and forms a covalent bond to a linker unit. Useful electrophilic groups on the linker include, but are not limited to, maleimide and haloacetamide groups.

The linker unit has a reactive site which has a nucleophilic group that is reactive with an electrophilic group present on an antibody unit. The electrophilic group on an antibody provides a convenient site for attachment to a linker unit. Useful electrophilic groups on an antibody include, but are not limited to, aldehyde and ketone carbonyl groups. The heteroatom of a nucleophilic group of a linker unit can react with an electrophilic group on an antibody and form a covalent bond to the antibody. Useful nucleophilic groups on a linker unit include, but are not limited to, hydrazide, oxime, amino, hydrazine, thiosemicarbazone, hydrazine carboxylate, and arylhydrazide.

As used herein, "mc-" also known as "MalC-" refers to:

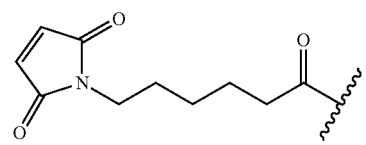 [SMILES: *C(=O)CCCCCN1C(=O)C=CC1=O]

As used herein, "vc-", also known as "mcValCitPABC-" or "MalCValCitPABC-" refers to:

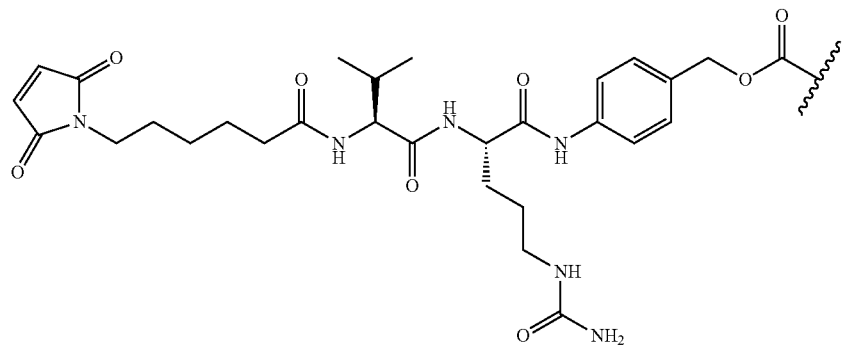 [SMILES: *C(=O)OCc1ccc(NC(=O)[C@H](CCCNC(N)=O)NC(=O)[C@@H](NC(=O)CCCCCN2C(=O)C=CC2=O)C(C)C)cc1]

As used herein, "me-" refers to

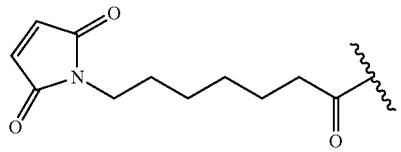 [SMILES: *C(=O)CCCCCCN1C(=O)C=CC1=O]

As used here, "MalPeg6C2-" refers to "MalPegXC2-" shown below, wherein X=6:

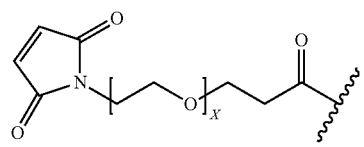

The ADCs of the present invention were prepared via partial reduction of the antibody with tris(2-carboxyethyl) phosphine (TCEP) followed by a reaction of reduced cysteine residues with the desired maleimide terminated linker-payload. Specifically, the antibodies were partially reduced via addition of about 2.3-3.0-fold molar excess of tris(2-carboxyethyl)phosphine (TCEP) in 100 mM HEPES (4-(2-hydroxyethyl)-1-piperazineethanesulfonic acid buffer), pH 7.0 and 1 mM diethylenetriaminepentaacetic acid (DTPA) for 2 hours at 37° C. The desired linker-payload was then added to the reaction mixture at a linker-payload/antibody molar ratio of about 7-8 and reacted for an additional 1 hour at 25° C. in the presence of 15% v/v of dimethylacetamide (DMA). After the 1 hour incubation period, 3-fold excess of N-ethylmaleimide was added to cap the unreacted thiols and was allowed to react for 15 minutes, followed by addition of 6-fold excess L-Cys to quench any unreacted linker-payload. The reaction mixture was dialyzed overnight at 4° C. in phosphate buffered saline (PBS), pH 7.4, and purified via SEC (AKTA explorer, Superdex 200). The hydrolysis of the succinimide ring was further achieved via incubating the purified ADC in a 100 mM borate, pH 9.2 buffer for 24-72 hours at 37° C. The ring opening was monitored via liquid chromatography electrospray ionization tandem mass spectrometry (LC-ESI MS) and purified via size exclusion chromatography (SEC). The ADC was further characterized via SEC for purity, hydrophobic interaction chromatography (HIC), and liquid chromatography electrospray ionization tandem mass spectrometry (LC-ESI MS) to calculate drug-antibody ratio (loading). The protein concentration was determined via UV spectrophotometer.

vc0101 (shows conjugation to antibody X through cysteine residue)

TABLE 10

Anti-Notch3 ADC nomenclature.

| ADC Nomenclature | Corresponding ADC Linker-Payload # |
|---|---|
| hu28-vc0101 | Notch3-28-v1010-hG1-(C)_mcValCitPABC-#54 |
| hu28-vc6780 | Notch3-28-v1010-hG1-(C)_mcValCitPABC-#112 |
| hu75-vc0101 | Notch3-75-v1913-hG1-(C)_mcValCitPABC-#54 |
| hu75-vc6780 | Notch3-75-v1913-hG1-(C)_mcValCitPABC-#112 |
| ch28-vc0101 | Notch3-28-cG1-(C)_mcValCitPABC-#54 |
| ch28-vc6780 | Notch3-28-cG1-(C)_mcValCitPABC-#112 |
| ch28-mc0101 | Notch3-28-cG1-(C)_mc-#54 |
| ch28-mc0131 | Notch3-28-cG1-(C)_mc-0#118 |
| ch28-mc3377 | Notch3-28-cG1-(C)_mc-#115 |
| ch28-mc8261 | Notch3-28-cG1-(C)_mc-#69 |
| ch28-MalPeg6C2-0131 | Notch3-28-cG1-(C)_MalPeg6C2-0#118 |
| ch28-MalPeg6C2-8261 | Notch3-28-cG1-(C)_MalPeg6C2-#69 |
| ch28-me0131 | Notch3-28-cG1-(C)_me-0#118 |
| ch28-m(H2O)c-0131 | Notch3-28-cG1-(C)_m(H2O)c-0#118 |
| ch75-vc0101 | Notch3-75-cG1-(C)_mcValCitPABC-#54 |

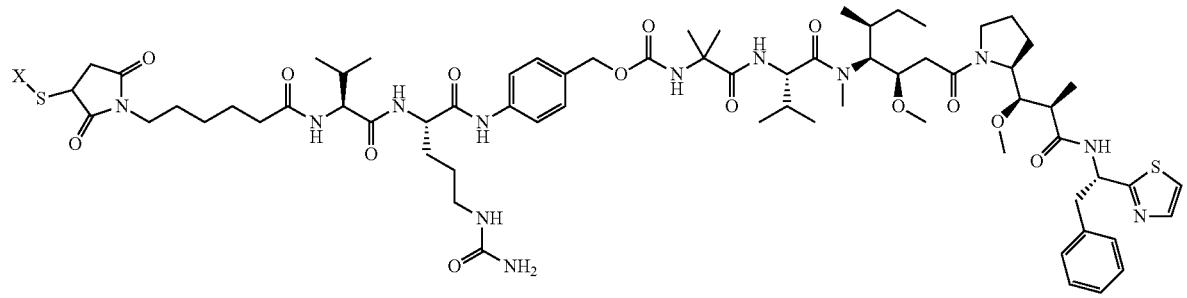

vc6780 (shows conjugation to antibody X through cysteine residue)

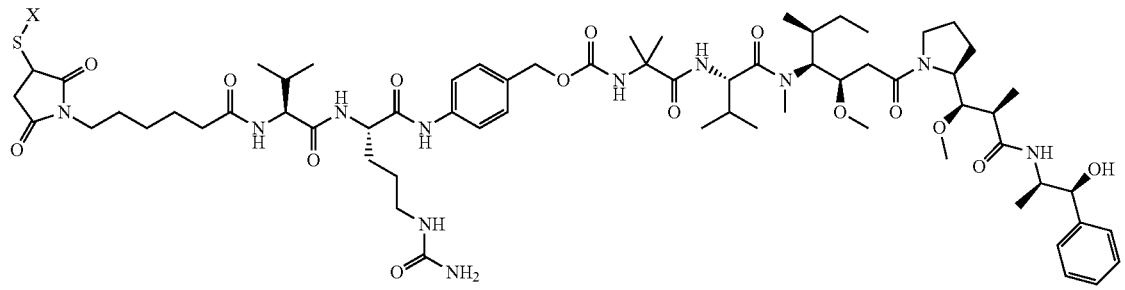

Humanized anti-Notch antibodies, hu28 and hu75, and rat-human chimeric anti-Notch antibodies, ch28 and ch75, were conjugated to various linker-payload combinations as provided in Table 10. The ADCs and elements thereof were prepared according to the methods of the present invention and according to International Publication No. WO/2013/072813.

TABLE 10-continued

Anti-Notch3 ADC nomenclature.

| ADC Nomenclature | Corresponding ADC Linker-Payload # |
|---|---|
| ch75-vc6780 | Notch3-75-cG1-(C)_mcValCitPABC-#112 |
| ch75-mc0131 | Notch3-75-cG1-(C)_mc-0#118 |
| ch75-mc3377 | Notch3-75-cG1-(C)_mc-#115 |

TABLE 10-continued

Anti-Notch3 ADC nomenclature.

| ADC Nomenclature | Corresponding ADC Linker-Payload # |
|---|---|
| ch75-MalPegC2-0131 | Notch3-75-cG1-(C)_MalPeg6C2-0#118 |
| ch75-MalPeg6C2-8261 | Notch3-75-cG1-(C)_MalPeg6C2-#69 |
| ch75-me0131 | Notch3-75-cG1-(C)_me-0#118 |
| ch75-m(H2O)c-0131 | Notch3-75-cG1-(C)_m(H2O)c-0#118 |
| huNeg8.8-vc0101 | huNeg8.8-(C)_mcValCitPABC-#54 |
| huNeg8.8-vc6780 | huNeg8.8-(C)_mcValCitPABC-#112 |
| huNeg8.8-mc0131 | huNeg8.8-(C)_mc-0#118 |
| huNeg8.8-mc3377 | huNeg8.8-(C)_mc-#115 |
| huNeg8.8-me0131 | huNeg8.8-(C)_me-0#118 |
| huNeg8.8-MalPeg6C2-8261 | huNeg8.8-(C)_MalPeg6C2-#69 |
| ch2H6-mc8261 | ch2H6-(C)_mc-#69 |

Example 12

Binding Activity and Specificity of Anti-Notch3 Antibodies and ADCs

A. Cell-Based ELISA

Unconjugated anti-Notch3 antibodies, anti-Notch3 ADCs and a negative control antibody (huNeg8.8) were screened for cell surface binding activity to Notch3 expressing cell lines in a cell-based ELISA. Over-expressing Notch3 cell line, U2OS/hNotch3, and endogenous Notch3 expressing cell lines, HCC2429 and MDA-MB-468, were plated at 50,000, 200,000 and 100,000 cells/well, respectively, in 96 well plates (white opaque, BD/VWR) the day before ELISA assay. On the day of the ELISA, culture media was removed from wells and serially diluted (1:3 in DPBS with calcium chloride and magnesium chloride (Ca/Mg) and 1% BSA) antibody and ADC solutions were applied to the plate. Plates were incubated at room temperature for 2 hours before washed with DPBS with Ca/Mg and 1% BSA. HRP-conjugated secondary antibody was then applied and incubated with cells for 1 hour. Plates were washed with DPBS with Ca/Mg and 1% BSA before being developed with Pico-Chemiluminescent developing kit (Thermal Scientific), and chemiluminescence measurements were performed per manufacturer's instructions. Data plotting and analyses were performed with Microsoft Excel and Graphpad-Prism software.

Table 11 shows $EC_{50}$ (nM) values and standard deviations (SD) calculated for two to four independent experiments from cell surface Notch3 binding ELISAs for unconjugated anti-Notch3 antibodies, hu28 and hu75, and anti-Notch3 ADCs, hu28-vc0101, hu28-vc6780, hu75-vc0101 and hu75-vc6780. The data demonstrates that hu28-ADCs and hu75-ADCs are similar to unconjugated antibodies hu28 and hu75, respectively, in binding to full-length human Notch3 expressed on the cell surface of U2OS/hNotch3, HCC2429 and MDA-MB-468 cells. Further, the data demonstrates that conjugation of various linker-payloads to the hu28 and hu75 antibodies did not affect or alter the binding characteristics. Furthermore, the data demonstrates that hu28 and both hu28-vc0101 and hu28-vc6780 have a higher binding capacity for cell surface Notch3, as demonstrated by their lower $EC_{50}$ values, than hu75 and hu75-vc0101 and hu75-vc6780. The negative control, unconjugated huNeg8.8 antibody, did not bind any of the cell lines tested. For the control antibody that lacked binding (LB), $EC_{50}$ values were not generated as indicated. (SD=Standard Deviation)

TABLE 11

$EC_{50}$ (nM) values for unconjugated anti-Notch3 antibodies and anti-Notch3 ADCs. (SD = Standard Deviation)

| | $EC_{50}$ (nM) and (SD) | | | | | |
|---|---|---|---|---|---|---|
| | HCC2429 | | MDA-MB-468 | | U2OS/hNotch3 | |
| | EC50 | SD | EC50 | SD | EC50 | SD |
| hu28 VH1.0/VL1.0 | 0.132 | 0.009 | 0.192 | 0.054 | 0.172 | 0.077 |
| hu28-vc0101 | 0.176 | 0.025 | 0.273 | 0.063 | 0.266 | 0.029 |
| hu28-vc6780 | 0.154 | 0.034 | 0.242 | 0.046 | 0.236 | 0.008 |
| hu75 VH1.9/VL1.3 | 0.335 | 0.053 | 1.284 | 0.176 | 0.585 | 0.160 |
| hu75-vc0101 | 0.427 | 0.115 | 2.022 | 0.167 | 0.798 | 0.057 |
| hu75-vc6780 | 0.343 | 0.063 | 1.804 | 0.062 | 0.723 | 0.041 |
| huNeg8.8 | LB | — | LB | — | LB | — |

B. Flow Cytometry

Unconjugated anti-Notch3 antibodies, hu28 and hu75, were examined for cell surface binding activity to Notch3 expressing cell lines by flow cytometry. Fluorescence activated cell sorting (FACS) analysis was conducted according to standard procedures. Cells were rinsed in HBSS with calcium chloride and magnesium chloride (herein termed HBSS++), harvested using trypsin without EDTA and neutralized with medium containing FBS. Cells were incubated on ice for 30 minutes with 4 µg/mL anti-Notch3 antibodies, hu28 and hu75, in HBSS++ containing 3% HICS (heat-inactivated calf serum). Cells were washed three times with cold HBSS++, 3% HICS buffer. Cells were incubated in allophycocyanin-conjugated AffiniPure F(ab')2 fragment goat anti-human IgG, Fc fragment secondary antibody (Jackson ImmunoResearch Laboratories, Inc., West Grove, Pa.) at 10 µg/mL for 30 minutes on ice in the dark. Cells were washed once with cold HBSS++/3% HICS buffer. Cells were resuspended in HBSS-++/3% HICS, 25 mM HEPES, 1 mM $MgCl_2$ and 25 µg/ml DNaseI. 7-AAD (7-Amino-Actinomycin D) was added for exclusion of non-viable cells. Live cells were analyzed on a BD FACSCalibur flow cytometer (BD Biosciences, San Jose, Calif.). Mean fluorescence intensity (MFI) from channel FL-4 was calculated with FlowJo flow cytometry analysis software (Ashland, Oreg.).

Table 12 shows the binding activity of unconjugated anti-Notch3 antibodies hu28 and hu75 by FACS analysis to a panel of Notch3 expressing cell lines. The U-2 OS cell line was used as a Notch3 negative/low control cell line. Both hu28 and hu75 had low levels of binding to U-2 OS that were minimally higher than the negative control huNeg8.8. Further, the data demonstrates that hu28 and hu75 bound specifically to the Notch3 over-expressing cell, U2OS/hNotch3 and MDAMB468/hNotch3, and Notch3 endogenously expressing cells MDA-MB-468, HCC2429 and OVCAR3. Furthermore, the data demonstrates that the binding activity of hu28 was greater than hu75 to all Notch3 expressing cell lines similar to the observation of binding activity by cell-based ELISA.

TABLE 12

MFI values by FACS analysis for anti-Notch3 antibodies.

| Cell line | MFI | | |
|---|---|---|---|
| | hu28 VH1.0/VL1.0 (anti-Notch3) | hu75 VH1.9/VL1.3 (anti-Notch3) | huNeg8.8 (negative control) |
| U2OS/hNotch3 (positive control) | 256 | 171 | 6 |
| MDA-MB-468 | 557 | 274 | 6 |
| MDA-MB-468/hNotch3 | 1192 | 530 | 6 |
| HCC2429 | 564 | 322 | 3 |
| OVCAR3 | 116 | 80 | 5 |
| U-2 OS (negative/low control) | 17 | 18 | 7 |

Example 13

In Vitro Cytotoxicity Assay

The effects of anti-Notch3 ADCs were assessed on 1) cell lines endogenously expressing Notch3 protein: HCC2429 (lung cancer), OVCAR3 (ovarian cancer) and MDA-MB-468 (breast cancer), 2) cell lines engineered to over-express full length human Notch3 protein: MDA-MB-468/hNotch3 and U2OS/hNotch3, and 3) a negative control cell line (SW900) using an MTS cellular viability indicator (Promega, Madison, Wis.). These cell lines were cultured with increasing concentrations of anti-Notch3 ADCs comprising rat-human chimeric anti-Notch3 antibodies, ch28 and ch75, and humanized anti-Notch3 antibodies, hu28 and hu75, conjugated to various linker-payload combinations of the present invention. As a specificity control for the anti-Notch3-ADCs, non-targeted control-ADCs (huNeg8.8-ADCs or ch2H6-ADCs) were also tested on the same cell lines. After four days, viability of each culture was assessed. $IC_{50}$ values were calculated by logistic non-linear regression, model #203 with XL fit v4.2 (IDBS, Guildford, Surry, UK) and presented as ng Ab/mL. The drug antibody ratio (DAR) is also provided.

Table 13 shows $IC_{50}$ (ng Ab/mL) values of the rat-human chimeric anti-Notch3 ADC treatments. For experiments with 2-4 individual repeats, average $IC_{50}$ values were calculated along with standard error of the mean (S.E.M.). The data demonstrates that the rat-human chimeric anti-Notch3 ADCs with various linker-payloads were active and induced cell death in the Notch3 expressing and over-expressing cancer cell lines HCC2429, OVCAR3, MDA-MB-468, MDA-MB-468/hNotch3, U2OS/hNotch3. The non-targeted control-ADCs either lacked potency (LP) and therefore $IC_{50}$ values were not generated as indicated, or were minimally active at the highest doses tested. Anti-Notch3 ADCs having $IC_{50}$ values equal to or higher than $IC_{50}$ values for control-ADCs were considered to lack potency in vitro and indicted as LP.

TABLE 13

$IC_{50}$ (ng Ab/mL) values of rat-human chimeric anti-Notch3 ADCs (nd = not determined).

| ADC | DAR | $IC_{50}$ (ng Ab/mL) ± S.E.M. | | | | |
|---|---|---|---|---|---|---|
| | | HCC2429 | OVCAR3 | MDA-MB-468 | MDA-MB-468/hNotch3 | U2OS/hNotch3 |
| ch28-mc8261 | 3.7 | LP | nd | 12147 ± 4806.4 | nd | nd |
| ch2H6-mc8261 | 4.1 | LP | nd | LP | nd | nd |
| ch28-MalPeg6C2-8261 | 4.3 | LP | nd | 83 ± 35.5 | nd | nd |
| ch75-MalPeg6C2-8261 | 3.8 | LP | nd | 4255 ± 2375 | nd | nd |
| huNeg8.8-MalPeg6C2-8261 | 4.1 | LP | nd | LP | nd | nd |
| ch28-mc0131 | 3.4 | 251 ± 77.5 | 6 ± 1.0 | 35 ± 18.5 | nd | 3 ± 0.5 |
| ch75-mc0131 | 3.3 | 671 ± 406.5 | 289 | 8202 ± 2773.0 | nd | 19 |
| huNeg8.8-mc0131 | 3.9 | nd | LP | LP | nd | LP |
| ch28-me0131 | 3.9 | 30 | 8 ± 2.0 | 24 ± 14.0 | nd | 3 ± 1.15 |
| ch75-me0131 | 3.5 | nd | nd | 259 | nd | nd |
| huNeg8.8-me0131 | 3.7 | nd | LP | LP | nd | LP |
| ch28-mc3377 | 3.7 | LP | 14 ± 5.5 | 27 ± 11.3 | nd | 3 ± 0.5 |
| ch75-mc3377 | 3.7 | nd | nd | 560 | nd | nd |
| huNeg8.8-mc3377 | 3.6 | nd | LP | LP | nd | LP |
| ch28-MalPeg6C2-0131 | 4.1 | LP | 10 ± 2.0 | 10 ± 1.0 | nd | 3 ± 0.85 |
| ch28-vc0101 | 3.8 | 3230 ± 1116.5 | 635 | 5443 ± 2630.9 | 4 ± 0.5 | 95 ± 18.2 |
| ch75-vc0101 | 2.7 | 2112 ± 826.0 | LP | 4064 ± 1793.9 | 24 ± 4.0 | LP |
| huNeg8.8-vc0101 | 3.7 | 15341 | LP | 4523 ± 2789.5 | 8833 | LP |
| ch28-vc6780 | 4.1 | 324 ± 78.9 | 90 ± 48.5 | 4407 ± 2128.2 | 3 ± 0.5 | LP |
| ch75-vc6780 | 2.8 | 1004 ± 177.0 | 922 | 6873 ± 4230.0 | 21 ± 3.5 | LP |
| huNeg8.8-vc6780 | 4.1 | LP | LP | LP | LP | LP |

Table 14 shows IC$_{50}$ (ng Ab/mL) values of the humanized anti-Notch3 ADC treatments. HCC2429 and MDA-MB-468/hNotch3 cell lines had two individual repeats. The data demonstrates that the humanized anti-Notch3 ADCs with various linker-payloads were active and induced cell death in the Notch3 expressing and over-expressing cancer cell lines HCC2429, OVCAR3, MDA-MB-468, MDA-MB-468/hNotch3, U2OS/hNotch3, but not in the negative control cell line SW900 lacking Notch3 expression. The non-targeted control-ADCs either lacked potency (LP) and therefore IC$_{50}$ values were not generated as indicated, or were minimally active at the highest doses tested. Anti-Notch3 ADCs having IC$_{50}$ values equal to or higher than IC$_{50}$ values for control-ADCs were considered to lack potency in vitro and indicted as LP. Unconjugated humanized anti-Notch3 antibodies hu28 and hu75 did not affect the viability of HCC2429 or MDAMB468/hNotch3, indicating cytotoxicity can be specifically attributed to payloads (data not shown).

determined as percentage of untreated control 96 hours after treatment IC$_{50}$ values were calculated by logistic non-linear regression, model #203 with XL fit v4.2 (IDBS, Guildford, Surry, UK) and presented as ng Ab/mL. For experiments with 2 individual repeats, average IC$_{50}$ values were calculated along with standard error of the mean (S.E.M.). Western blot analysis on extracts prepared from control and Notch3 siRNA-treated cells was performed to confirm that Notch3 knockdown occurred for up to 144 hours (data not shown). Cell lines that expressed Notch3 (herein termed control siRNA) or had reduced Notch3 expression after siRNA knockdown (herein termed Notch3 siRNA) were cultured with increasing concentrations of humanized anti Notch3 ADCs. As a specificity control for the anti-Notch3 ADCs, non-targeted control-ADCs (huNeg8.8-ADCs) were also tested on the same cell lines. After four days, viability of each culture was assessed. IC$_{50}$ values were calculated by logistic non-linear regression, model #203 with XL fit v4.2

TABLE 14

IC$_{50}$ (ng Ab/mL) values of humanized anti-Notch3 ADCs.

| ADC | DAR | HCC2429 | OVCAR3 | MDA-MB-468 | MDA-MB-468/hNotch3 | U2OS/hNotch3 | SW900 |
|---|---|---|---|---|---|---|---|
| hu28-vc0101 | 3.9 | 473 | 2940 | 306 | 6545 | 3.2 | 3 | 1330 | LP |
| hu75-vc0101 | 3.8 | 611 | 3295 | 515 | 7001 | 37 | 36 | 523 | LP |
| huNeg8.8-vc0101 | 3.7 | 18417 | 23978 | 3770 | LP | 5122 | LP | LP | 23379 |
| hu28-vc6780 | 3.9 | 148 | 2050 | 17 | LP | 1.3 | 3 | LP | LP |
| hu75-vc6780 | 4.2 | 214 | 630 | 254 | LP | 26 | 25 | LP | LP |
| huNeg8.8-vc6780 | 4.2 | LP | LP | 9238 | LP | LP | LP | LP | LP |

Notch3 knockdown with siRNAs was used to confirm that the in vitro cytotoxicity of anti-Notch3 ADCs was dependent on the expression of the Notch3 protein. siRNA transfections were generated using ON-TARGET plus SMART pool human Notch3 (L-011093-00), ON-TARGET plus Control Non-Targeting pool (D-001810-10) (Thermo Scientific Dharmacon) and Lipofectamine RNAiMAX Reagent (Invitrogen). Two to 2.5×10$^6$ cells of HCC2429, OVCAR3 and MDA-MB-468/hNotch3 cells were plated in 10 cm dishes in growth medium without antibiotics the day before transfection. The next day fresh medium without antibiotics was added. The siRNAs and the Lipofectamine RNAiMAX were diluted in OPTI-MEM media and used as per the manufacturer's specifications. Each of the cell lines was transfected with control and Notch3 siRNAs. The cells were incubated with the transfection mixture for 24 hours in a humidified, 37° C., 5% CO$_2$ incubator. After 24 hours, cells were trypsinized and plated for assessment using MTS cellular viability indicator (Promega, Madison, Wis.).

Depending on the cell line, cells were then seeded at a density of 2,500 to 5,000 cells per well 24 hours before treatment. Cells were treated with 3-fold serially diluted humanized anti-Notch3 ADCs in triplicates at 10 concentrations (range 0-30 µg Ab/ml). Relative cell viability was (IDBS, Guildford, Surry, UK) and presented as ng Ab/mL. The drug antibody ratio (DAR) is also provided.

Table 15 shows IC$_{50}$ (ng Ab/mL) values of humanized anti-Notch3 ADC treatments of a panel of control siRNA or Notch3 siRNA treated cancer cell lines. The data demonstrates that humanized anti-Notch3 ADCs with various linker-payloads were active and induced cell death in the Notch3-expressing cancer cell lines (control siRNA). In cells that had reduced Notch3 expression after siRNA knockdown (Notch3 siRNA), IC$_{50}$ values were greater than control siRNA indicating that a reduction in Notch3 expression was accompanied by a reduction in cytotoxicity of anti-Notch3 ADCs. Control-ADCs lacked potency (LP) and therefore IC$_{50}$ values were not generated as indicated, or were minimally active at the highest doses tested. The data further demonstrates that humanized anti-Notch3 ADCs specifically induced cell death on Notch3 expressing and over-expressing cancer cell lines. The observed cytotoxicity was dependent on Notch3 expression because Notch3 siRNA knockdown on the same cells reduced cell death by anti-Notch3 ADCs. Therefore, humanized anti-Notch3 ADCs were dependent on Notch3 expression for their in vitro cytotoxicity.

TABLE 15

IC$_{50}$ (ng Ab/ml) values of humanized anti-Notch3 ADCs.

| | | IC$_{50}$ (ng Ab/mL) ± S.E.M. | | | | | |
|---|---|---|---|---|---|---|---|
| | | HCC2429 | | OVCAR3 | | MDA-MB 468/ hNotch3 | |
| ADC | DAR | Control siRNA | Notch3 siRNA | Control siRNA | Notch3 siRNA | Control siRNA | Notch3 siRNA |
| hu28-vc0101 | 3.9 | 930 ± 529 | 7138 ± 827 | 684 ± 183 | 1994 ± 262 | 3.0 | 3340 |
| hu75-vc0101 | 3.8 | 956 ± 259 | 8972 ± 891 | 1056 ± 158 | 2408 ± 27.5 | 29.0 | 3187 |
| huNeg8.8-vc0101 | 3.7 | 17832 ± 2319 | 21374 ± 1614 | 3751 ± 922 | 2902 ± 654 | 4226 | 5580 |
| hu28-vc6780 | 3.9 | 259 ± 179 | 14120 ± 1175 | 189 ± 6.0 | 6100 ± 200 | 2.0 | LP |
| hu75-vc6780 | 4.2 | 236 ± 30.5 | LP | 690 ± 137 | 7300 ± 147 | 17.0 | 7981 |
| huNeg8.8-vc6780 | 4.2 | LP | LP | 8163 ± 1031 | 7674 ± 705 | LP | LP |

Example 14

In Vitro Assessment of Anti-Notch3 ADC Mechanism of Action

A. Anti-Notch3 ADC Disruption of Microtubules

Following internalization and intracellular release of the payload from the Notch3-ADC, the presumed mechanism of action of the released payload is disruption of microtubules that are required for cell division, thereby leading to cell cycle arrest, induction of apoptosis and cell death. To confirm this mechanism of action, OVCAR3 ovarian cancer cells were treated with hu28-vc0101, huNeg8.8-vc0101 (control ADC) or left untreated, and then subjected to immunofluorescence analysis by staining with an anti-alpha-tubulin antibody to mark microtubules and an anti-phospho-Histone H3 antibody to identify cells undergoing or arrested in mitosis.

OVCAR3 cells were seeded in a Lab Tec II 4 chambered coverglass with cover #1.5 borosilicate sterile slides (Thermo Fisher Scientific Inc.). Next day, cells were treated with 1.0 µg/ml of hu28-vc0101, control huNeg8.8-vc0101 or left untreated. Forty-eight hours later, cells were washed twice with HBSS++ and fixed in 4% paraformaldyhide for 10 minutes. Cells were washed three times with PBS and permeabilized with 0.5% Triton X-100 for 2 minutes. After washing cells three times with PBS, cells were blocked with 3% BSA/PBS for 30 minutes at room temperature. Cells were then incubated with 1:100 of anti-phospho-Histone H3 (Ser10) (Cell Signaling) and 2 µg/ml of anti-alpha-Tubulin, (Millipore) in 2% BSA/PBS for 2 hours at room temperature. After 2 hours, cells were washed twice with PBS and then incubated with a 1:500 dilution of goat anti-mouse Alexa Fluor 488 and goat anti-rabbit 555 for 45 minutes at room temperature. Cells were washed twice with PBS and samples were imaged on an LSM710 confocal microscope (Zeiss).

Figure 10:
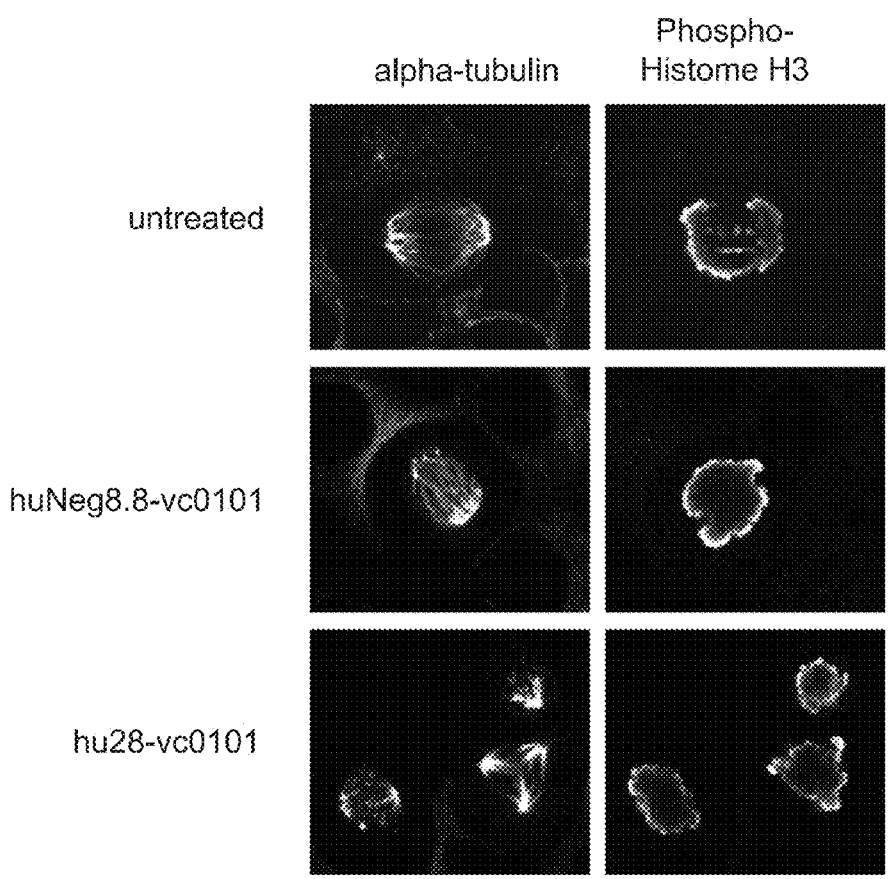
FIG. 10 shows the treatment of OVCAR3 ovarian cancer cells with anti-Notch3 hu28-vc0101 disrupts microtubules (stained with anti-alpha-tubulin antibody) in mitotic cells that were identified by phospho-Histone H3 staining.

As shown in FIG. 10, untreated OVCAR3 cells in the mitotic phase of the cell cycle stain positive for phospho-histone H3 and contain a normal bipolar spindle apparatus as demonstrated by anti-alpha-tubulin staining. Treatment with hu28-vc0101, but not control huNeg8.8-vc0101, disrupted the structure of the mitotic spindle apparatus as demonstrated by its abnormal morphology in phospho-Histone H3 stained cells. The data demonstrates that hu28-vc0101 inhibited cell proliferation by disrupting microtubules that are required during mitosis to complete cell division.

B. Anti-Notch3 ADC Induction of Apoptosis

Caspase-3 and caspase-7 (caspase-3/7) proteases are key members of the programmed cell death machinery responsible for mediating late apoptotic events in mammalian cells. The activity of caspase-3/7 was measured in Notch3 expressing cell lines that were treated with Notch3-ADCs.

OVCAR3, HCC2429 and MDA-MB-468/hNotch3 cells were seeded onto opaque white tissue culture plates and incubated overnight. OVCAR3 and HCC2429 were treated at 1.1 µg/ml and MDA-MB-468/hNotch3 cells were treated 1 µg/ml of hu28-vc0101 and huNeg8.8-vc010 (control ADC). After 48 hours incubation, cells were treated with the Caspase-Glo 3/7 reagent (Promega #G8090) for 2 hours at room temperature. Luminescence was measured with a luminometer and following subtraction of background, values were reported as relative luminescence units.

Table 16 shows that hu28-vc0101 induced the activity of caspase-3/7 in Notch3 expressing cell lines MDA-MB-468/hNotch3, HCC2429 and OVCAR3 cells from 2-3 fold over control Neg8.8-vc0101 treated cells. Thus, hu28-vc0101 inhibits cell growth by inducing apoptosis.

TABLE 16

Relative luminescence units for anti-Notch3 ADCs.

| | hu28-vc0101 | huNeg8.8-vc0101 |
|---|---|---|
| MDA-MB-468/hNotch3 | 78,622 ± 1160 | 47,362 ± 678 |
| HCC2429 | 128,518 ± 3483 | 55,255 ± 2965 |
| OVCAR3 | 209,715 ± 15572 | 118,150 ± 4280 |

Example 15

Notch3 Immunohistochemistry

The effects of anti-Notch3 ADCs were assessed in preclinical models that had detectable levels of Notch3 expression at the cell membrane of xenografted human tumor cells. To identify pre-clinical models expressing Notch3, immunohistochemistry (hereinafter "IHC") using an anti-Notch3 antibody was performed on a panel of xenograft models including: 37622A1 NSCLC (patient derived), HCC2429 lung cancer, MDA-MB-468 breast cancer and N87 gastric cancer xenograft models.

A tissue fragment from each xenograft was formalin-fixed and paraffin embedded (FFPE) using standard histological procedures. Five micron FFPE sections were cut, dewaxed and hydrated to distilled water. Antigens were retrieved in EDTA buffer pH 8.0 in a pressure cooker. Endogenous peroxidase was blocked with 3.0% H$_2$O$_2$ for 10 minutes. Sections were incubated with DAKO Protein block for 20 minutes. A 1:2000 dilution of rabbit anti-Notch3 (D11B8;

Cell Signaling Technologies) was applied to the sections for 1 hour at room temperature. Signalstain Boost anti-rabbit IgG-HRP polymer (Cell Signaling Technologies) was applied to the sections for 30 minutes at room temperature. DAB was used to develop color for 5 minutes. Sections were briefly counterstained in Mayer's hematoxylin, dehydrated, cleared and coverslipped. Table 17 shows the staining intensity and staining distribution grade that were scored on a scale of 0-4, with 0 being negative and 4 being the highest intensity.

TABLE 17

Staining intensity and staining distribution grade.

| Staining Intensity Grade | Staining Distribution Grade |
|---|---|
| 0 = negative | 0 = negative |
| 1 = minimal | 1 = 0-25% |
| 2 = mild | 2 = 26-50% |
| 3 = moderate | 3 = 51-75% |
| 4 = marked | 4 = 76-100% |

As shown in Table 18, Notch3 protein was detected on the cell membrane (Mem) and in the cytoplasm (Cyto) and/or nucleus (Nuc) of cells from the 37622A1 NSCLC, HCC2429, MDA-MB-468 and N87 xenografts. The data demonstrates that both HCC2429 and N87 xenografts had a homogenous distribution of Notch3 protein at the cell membrane of 76-100% of cells. Further, the data demonstrates that 37622A1 NSCLC and MDA-MB-468 xenografts had a heterogenous distribution of Notch3 protein at the cell membrane in 51-75% of cells. Furthermore, the detection of the Notch3 C-terminal intracellular domain in the nucleus of some epithelial tumor cells with the D11B8 antibody suggests that Notch3 signaling was active in these cells.

TABLE 18

Subcellular localization, intensity and distribution scores of Notch3 immunohistochemistry on a panel of xenograft models.

| Xenograft | Tissue Type | Cell type | Subcellular Localization | Intensity Score (Scale 0-4) | Distribution Grade (Scale 0-4) |
|---|---|---|---|---|---|
| 37622A1 NSCLC | Lung | Human epithelial | Cyto/Mem/Nuc | Cyto/Mem/Nuc = 1-3 | Cyto/Mem/Nuc = 3 |
| HCC2429 | Lung | Human epithelial | Cyto/Mem/Nuc | Cyto = 2-3<br>Mem = 2-4<br>Nuc = 1 | Cyto/Mem = 4<br>Nuc = 2 |
| MDA-MB-468 | Breast | Human epithelial | Cyto/Mem/Nuc | Cyto = 3-4<br>Mem/Nuc = 2 | Mem = 3<br>Cyto/Nuc = 4 |
| N87 | Gastric | Human epithelial | Cyto/Mem/Nuc | Cyto/Mem = 2-4<br>Nuc = 1-2 | Cyto/Mem/Nuc = 4 |
| OVCAR3 | Ovarian | Human epithelial | Cyto/Mem/Nuc | Cyto/Nuc = 1<br>Mem = 1-3 | Cyto/Nuc = 2<br>Mem = 4 |

Figure 11:
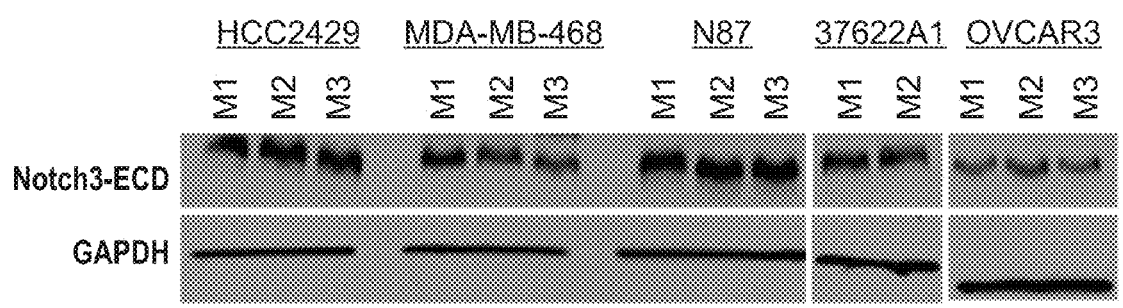
FIG. 11 shows Western blot analysis of Notch3-ECD from xenografts harvested from 2-3 mice (M).

As shown in FIG. 11, Western blot analysis confirmed the Notch3 expression levels in the panel of xenografts that were used for in vivo efficacy studies. An ~210 kDa Notch3 protein fragment of the extracellular domain (hereinafter Notch3-ECD) was detected in HCC2429, MDA-MB-468, N87 and 37622A1 xenograft extracts using a mouse monoclonal anti-Notch3 antibody 1G5 (Abnova). Therefore, the data from the IHC using the anti-Notch3 antibody D11B8 demonstrated Notch3 at the cell membrane of human epithelial tumor cells and the Western blot analysis using the anti-Notch3 antibody 1G5 demonstrated expression of the Notch3-ECD which contains the NRR domain, the target of anti-Notch3 ADCs.

Example 16

In Vivo Tumor Xenograft Models

Humanized anti-Notch3 antibodies, hu28 and hu75, and rat-human chimeric anti-Notch3 antibodies, ch28 and ch75, were conjugated to various linker-payload combinations and tested in 37622A1 non-small cell lung cancer (NSCLC), HCC2429 lung cancer, MDA-MB-468 breast cancer and N87 gastric cancer xenograft models. For each model described below the first dose was given on Day 0. The tumors were measured at least once a week and their volume was calculated with the formula: tumor volume (mm$^3$)=0.5× (tumor width$^2$)(tumor length). The mean tumor volumes (±S.E.M.) for each treatment group were calculated having a maximum of 10 animals and a minimum of 6 animals to be included.

A. 37622A1 Patient Derived NSCLC Xenografts

Figure 12:
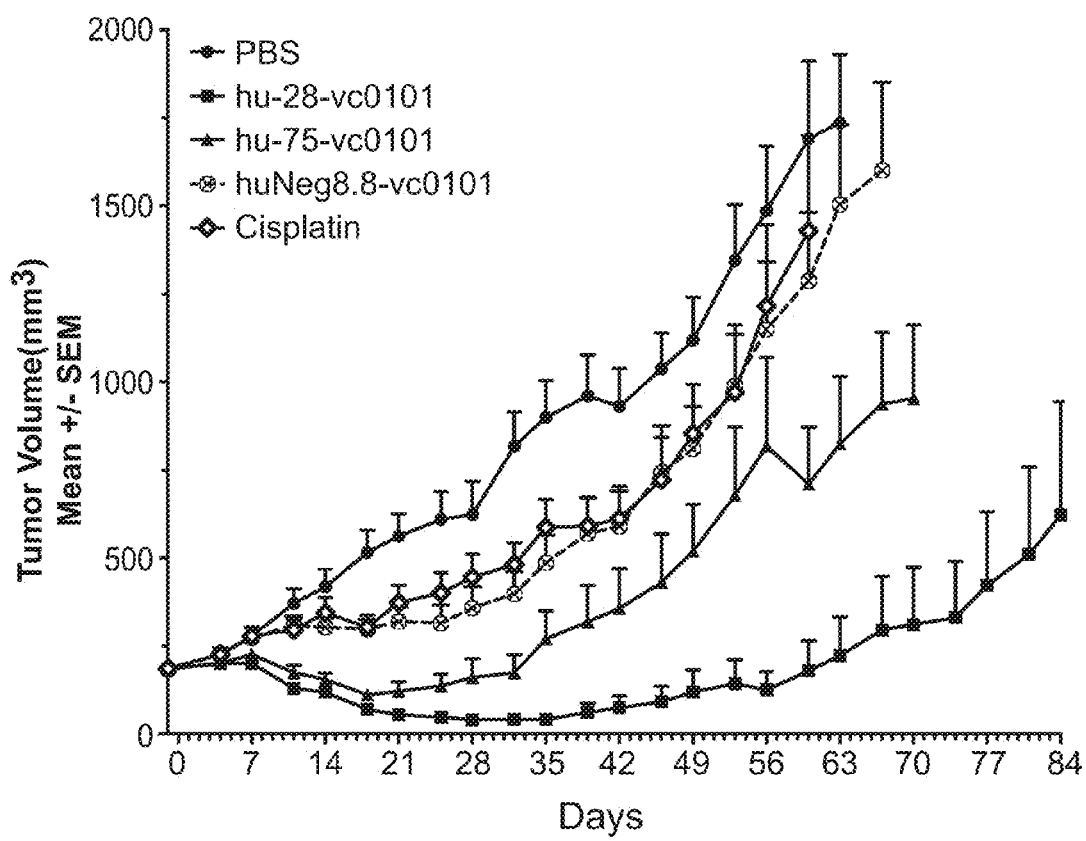
FIG. 12 shows the efficacy of anti-Notch3 hu28-vc0101 and hu75-vc0101 at a dose of 3 mg/kg compared to Cisplatin at a dose of 5 mg/kg in the 37622A1 NSCLC patient derived xenograft model.

The effects of anti-Notch3 ADCs were examined in immunodeficient mice on the in vivo growth of human tumor xenografts that were established from fragments of freshly resected 37622A1 NSCLC tumors obtained in accordance with appropriate consent procedures (Asterand). The 37622A1 NSCLC patient-derived xenografts were subcutaneously passaged in vivo as fragments from animal to animal in nude (Nu/Nu) female mice. When the tumors reached a volume of 150 to 300 mm$^3$, they were staged to ensure uniformity of the tumor size among various treatment groups. The 37622A1 NSCLC patient-derived xenografts model was dosed intravenously four times every four days (Q4d×4) with PBS vehicle, humanized anti-Notch3 ADCs, control huNeg-8.8 ADCs and cisplatin at the doses provided in Table 19. FIG. 12 shows a graph of the data from Table 19 of the ADCs with vc0101 linker-payloads at 3 mg/kg dose compared to Cisplatin (5 mg/kg) and PBS vehicle.

Cisplatin is a platinum-based anti-cancer agent used in the treatment of cancer and considered a standard-of-care therapy. Cisplatin cross-links DNA thereby inducing apoptosis and cell growth inhibition. The data demonstrates that anti-Notch3 ADCs hu28-vc0101, hu28-vc6780, hu75-vc0101 and hu75-vc6780 inhibited growth of 37622A1 NSCLC patient-derived xenograft tumors. The 3 mg/kg dose of hu28-vc0101 was the most potent ADC tested in this study, and by day 84, four out of nine animals still on study remained tumor-free. Further, the data shows that anti-Notch3 ADCs inhibited tumor growth more potently than control huNeg8.8-ADCs. Furthermore, the data shows that anti-Notch3 ADCs inhibited tumor growth more potently than cisplatin indicating a greater potency than a platinum-based standard-of-care chemotherapeutic drug (FIG. 12).

TABLE 19

Efficacy of anti-Notch3 ADCs in 37622A1 NSCLC xenografts.

37622A1 NSCLC patient-derived xenografts, tumor volume (mm³ ± SEM)

| | PBS | hu28-vc0101 | hu28-vc6780 | hu75-vc0101 | hu75-vc6780 | huNeg-8.8-vc0101 | huNeg-8.8-vc6780 | Cisplatin |
|---|---|---|---|---|---|---|---|---|
| | | | | | Dose mg/kg | | | |
| | 0 | 3 | 10 | 3 | 10 | 3 | 10 | 5 |
| DAY −1 | 187 ± 10 | 186 ± 13 | 182 ± 16 | 185 ± 17 | 183 ± 17 | 184 ± 18 | 182 ± 17 | 185 ± 11 |
| DAY 4 | 227 ± 19 | 202 ± 16 | 176 ± 13 | 200 ± 16 | 205 ± 23 | 225 ± 17 | 226 ± 26 | 226 ± 15 |
| DAY 7 | 279 ± 24 | 202 ± 15 | 176 ± 19 | 227 ± 16 | 195 ± 22 | 274 ± 18 | 265 ± 28 | 280 ± 29 |
| DAY 11 | 371 ± 42 | 130 ± 11 | 122 ± 10 | 175 ± 20 | 147 ± 23 | 309 ± 26 | 246 ± 30 | 301 ± 34 |
| DAY 14 | 419 ± 49 | 119 ± 11 | 95 ± 7 | 156 ± 19 | 118 ± 18 | 303 ± 26 | 277 ± 41 | 345 ± 47 |
| DAY 18 | 516 ± 63 | 71 ± 6 | 65 ± 6 | 112 ± 16 | 93 ± 14 | 298 ± 28 | 219 ± 31 | 309 ± 37 |
| DAY 21 | 562 ± 65 | 55 ± 6 | 56 ± 6 | 122 ± 27 | 98 ± 20 | 320 ± 41 | 218 ± 42 | 373 ± 50 |
| DAY 25 | 610 ± 78 | 49 ± 6 | 51 ± 6 | 137 ± 33 | 93 ± 24 | 315 ± 52 | 264 ± 52 | 401 ± 58 |
| DAY 28 | 624 ± 94 | 41 ± 7 | 51 ± 8 | 161 ± 53 | 99 ± 26 | 358 ± 61 | 246 ± 51 | 446 ± 64 |
| DAY 32 | 817 ± 99 | 42 ± 13 | 72 ± 15 | 175 ± 52 | 165 ± 45 | 398 ± 64 | 332 ± 77 | 482 ± 62 |
| DAY 35 | 900 ± 104 | 42 ± 11 | 92 ± 21 | 271 ± 79 | 229 ± 59 | 487 ± 79 | 384 ± 94 | 587 ± 80 |
| DAY 39 | 960 ± 117 | 62 ± 26 | 120 ± 31 | 319 ± 103 | 294 ± 78 | 569 ± 102 | 431 ± 114 | 591 ± 83 |
| DAY 42 | 931 ± 108 | 75 ± 34 | 151 ± 37 | 357 ± 113 | 318 ± 71 | 590 ± 101 | 495 ± 128 | 612 ± 92 |
| DAY 46 | 1037 ± 102 | 92 ± 44 | 172 ± 47 | 431 ± 137 | 412 ± 106 | 743 ± 133 | 610 ± 165 | 723 ± 119 |
| DAY 49 | 1119 ± 120 | 120 ± 63 | 248 ± 62 | 519 ± 135 | 521 ± 132 | 810 ± 121 | 718 ± 202 | 853 ± 139 |
| DAY 53 | 1345 ± 158 | 144 ± 67 | 339 ± 93 | 678 ± 195 | 629 ± 162 | 989 ± 146 | 848 ± 251 | 970 ± 193 |
| DAY 56 | 1485 ± 185 | 126 ± 51 | 376 ± 100 | 818 ± 251 | 808 ± 196 | 1149 ± 191 | 776 ± 184 | 1215 ± 231 |
| DAY 60 | 1691 ± 220 | 180 ± 85 | 503 ± 138 | 710 ± 162 | 917 ± 209 | 1287 ± 194 | 964 ± 232 | 1428 ± 273 |
| DAY 63 | 1736 ± 193 | 223 ± 111 | 604 ± 160 | 824 ± 191 | 917 ± 147 | 1503 ± 227 | 1097 ± 254 | — |
| DAY 67 | — | 296 ± 152 | 888 ± 272 | 938 ± 202 | 1116 ± 173 | 1600 ± 251 | 1167 ± 260 | — |
| DAY 70 | — | 312 ± 162 | 773 ± 235 | 953 ± 209 | 1181 ± 203 | — | 1352 ± 305 | — |
| DAY 74 | — | 331 ± 160 | 881 ± 264 | — | — | — | — | — |
| DAY 77 | — | 422 ± 210 | 1029 ± 325 | — | — | — | — | — |
| DAY 81 | — | 510 ± 248 | — | — | — | — | — | — |
| DAY 84 | — | 622 ± 322 | — | — | — | — | — | — |

B. HCC2429 Lung Xenografts

Similar in vivo experiments were performed with the HCC2429 lung cancer cell line as described above. To generate xenografts, nude (Nu/Nu) female mice were implanted subcutaneously with 3.5×10⁶ HCC2429 cells in 50% Matrigel (BD Biosciences). When the tumors reached a volume of 200 to 400 mm³, the tumors were staged to ensure uniformity of the tumor mass among various treatment groups. The HCC2429 lung model was dosed intravenously Q4d×4 with PBS vehicle, humanized anti-Notch3 ADCs and control huNeg-8.8 ADCs at the doses provided in Tables 20 and 21. The data demonstrates that anti-Notch3 ADCs hu28-vc0101, hu28-vc6780, hu75-vc0101 and hu75-vc6780 inhibited growth of HCC2429 lung xenografts in a dose-dependent manner. Further, the data shows that anti-Notch3 ADCs inhibited tumor growth more potently than control huNeg8.8-ADCs at the 1 and 3 mg/kg doses for anti-Notch3 ADCs with vc0101 linker-payloads and at the 3 and 10 mg/kg doses for anti-Notch3 ADCs with vc6780 linker-payloads. Furthermore, the data demonstrates that a 3 mg/kg dose of hu28-vc0101 was more potent than a 10 mg/kg dose of hu28-vc6780.

TABLE 20

Efficacy of anti-Notch3-vc0101 ADCs in HCC2429 lung xenografts.

HCC2429 Lung xenografts, tumor volume (mm³ +/− SEM)

| | PBS | hu28-vc0101 | | | hu75-vc0101 | | | huNeg-8.8-vc0101 | | |
|---|---|---|---|---|---|---|---|---|---|---|
| | | | | | Dose mg/kg | | | | | |
| | 0 | 3 | 1 | 0.3 | 3 | 1 | 0.3 | 3 | 1 | 0.3 |
| DAY −1 | 245 ± 24 | 245 ± 23 | 246 ± 26 | 246 ± 30 | 245 ± 28 | 246 ± 23 | 247 ± 29 | 244 ± 30 | 245 ± 33 | 246 ± 27 |
| DAY 1 | 529 ± 52 | 548 ± 52 | 532 ± 36 | 528 ± 50 | 498 ± 39 | 548 ± 37 | 524 ± 66 | 482 ± 59 | 519 ± 72 | 514 ± 50 |
| DAY 3 | 742 ± 73 | 606 ± 78 | 757 ± 68 | 733 ± 78 | 498 ± 44 | 753 ± 93 | 713 ± 74 | 695 ± 91 | 756 ± 97 | 724 ± 73 |
| DAY 6 | 1205 ± 120 | 723 ± 101 | 1095 ± 119 | 1112 ± 132 | 469 ± 70 | 1096 ± 146 | 1078 ± 74 | 1075 ± 132 | 1144 ± 100 | 1207 ± 100 |
| DAY 8 | 1720 ± 181 | 696 ± 100 | 1324 ± 173 | 1617 ± 172 | 407 ± 71 | 1428 ± 200 | 1499 ± 115 | 1404 ± 183 | 1598 ± 133 | 1683 ± 165 |
| DAY 10 | 2312 ± 197 | 620 ± 90 | 1606 ± 250 | 2027 ± 233 | 370 ± 81 | 1611 ± 189 | 1830 ± 120 | 1735 ± 253 | 1974 ± 185 | 2163 ± 260 |
| DAY 13 | 3235 ± 120 | 543 ± 92 | 1717 ± 223 | 2642 ± 297 | 273 ± 69 | 1803 ± 208 | 2408 ± 226 | 2162 ± 376 | 2676 ± 346 | 2589 ± 287 |
| DAY 15 | — | 512 ± 111 | 1865 ± 263 | — | 298 ± 88 | 1871 ± 232 | — | — | — | — |
| DAY 17 | — | 442 ± 114 | 2228 ± 333 | — | 250 ± 77 | 1948 ± 228 | — | — | — | — |
| DAY 20 | — | 428 ± 144 | — | — | 177 ± 44 | — | — | — | — | — |
| DAY 23 | — | 405 ± 149 | — | — | 160 ± 35 | — | — | — | — | — |
| DAY 27 | — | 422 ± 164 | — | — | 174 ± 51 | — | — | — | — | — |
| DAY 30 | — | 394 ± 182 | — | — | 196 ± 72 | — | — | — | — | — |
| DAY 34 | — | 505 ± 236 | — | — | 295 ± 121 | — | — | — | — | — |
| DAY 37 | — | 606 ± 283 | — | — | 433 ± 179 | — | — | — | — | — |
| DAY 41 | — | 750 ± 361 | — | — | 606 ± 259 | — | — | — | — | — |
| DAY 45 | — | 872 ± 415 | — | — | 836 ± 359 | — | — | — | — | — |
| DAY 49 | — | 558 ± 303 | — | — | 732 ± 350 | — | — | — | — | — |
| DAY 52 | — | 571 ± 310 | — | — | — | — | — | — | — | — |
| DAY 56 | — | 704 ± 399 | — | — | — | — | — | — | — | — |

TABLE 21

Efficacy of anti-Notch3-vc6780 ADCs in HCC2429 lung xenografts.

HCC2429 Lung xenografts, tumor volume (mm³ ± SEM)

| | PBS | hu28-vc6780 | | | hu75-vc6780 | | | huNeg-8.8-vc6780 | | |
|---|---|---|---|---|---|---|---|---|---|---|
| | | | | | Dose mg/kg | | | | | |
| | 0 | 10 | 3 | 1 | 10 | 3 | 1 | 10 | 3 | 1 |
| DAY −1 | 245 ± 28 | 244 ± 22 | 245 ± 24 | 245 ± 27 | 244 ± 19 | 246 ± 30 | 245 ± 16 | 244 ± 22 | 244 ± 26 | 245 ± 20 |
| DAY 1 | 398 ± 50 | 369 ± 31 | 379 ± 45 | 400 ± 66 | 407 ± 43 | 403 ± 51 | 418 ± 34 | 429 ± 56 | 427 ± 49 | 402 ± 53 |
| DAY 3 | 701 ± 102 | 318 ± 31 | 493 ± 65 | 579 ± 113 | 339 ± 36 | 526 ± 74 | 629 ± 65 | 619 ± 62 | 689 ± 83 | 655 ± 97 |
| DAY 5 | 949 ± 140 | 228 ± 28 | 609 ± 82 | 826 ± 191 | 251 ± 33 | 615 ± 98 | 916 ± 97 | 808 ± 101 | 965 ± 114 | 837 ± 117 |
| DAY 7 | 1345 ± 200 | 172 ± 22 | 638 ± 86 | 1023 ± 259 | 225 ± 24 | 615 ± 115 | 1164 ± 131 | 1072 ± 154 | 1380 ± 136 | 1099 ± 172 |
| DAY 10 | 2045 ± 356 | 143 ± 22 | 784 ± 115 | 1439 ± 398 | 198 ± 24 | 717 ± 129 | 1705 ± 184 | 1452 ± 210 | 2082 ± 192 | 1722 ± 363 |
| DAY 12 | — | 134 ± 20 | 883 ± 132 | 1442 ± 487 | 166 ± 22 | 807 ± 130 | 2029 ± 270 | 1673 ± 290 | 2701 ± 228 | 1586 ± 337 |

TABLE 21-continued

Efficacy of anti-Notch3-vc6780 ADCs in HCC2429 lung xenografts.

HCC2429 Lung xenografts, tumor volume (mm³ ± SEM)

| | PBS | hu28-vc6780 | | | hu75-vc6780 | | | huNeg-8.8-vc6780 | | |
|---|---|---|---|---|---|---|---|---|---|---|
| | | | | | Dose mg/kg | | | | | |
| | 0 | 10 | 3 | 1 | 10 | 3 | 1 | 10 | 3 | 1 |
| DAY 14 | — | 115 ± 16 | 895 ± 175 | — | 150 ± 22 | 831 ± 145 | 2294 ± 287 | 1809 ± 314 | — | — |
| DAY 17 | — | 127 ± 18 | 1105 ± 253 | — | 158 ± 32 | 1017 ± 178 | — | — | — | — |
| DAY 20 | — | 149 ± 27 | 1219 ± 311 | — | 164 ± 48 | 1297 ± 231 | — | — | — | — |
| DAY 24 | — | 206 ± 60 | 1618 ± 468 | — | 261 ± 89 | 1813 ± 343 | — | — | — | — |
| DAY 27 | — | 290 ± 100 | — | — | 316 ± 135 | 1970 ± 462 | — | — | — | — |
| DAY 31 | — | 378 ± 150 | — | — | 438 ± 201 | — | — | — | — | — |
| DAY 34 | — | 551 ± 244 | — | — | 423 ± 177 | — | — | — | — | — |
| DAY 38 | — | 718 ± 332 | — | — | 504 ± 203 | — | — | — | — | — |
| DAY 42 | — | 1011 ± 504 | — | — | 655 ± 266 | — | — | — | — | — |
| DAY 46 | — | — | — | — | 793 ± 320 | — | — | — | — | — |
| DAY 49 | — | — | — | — | 901 ± 351 | — | — | — | — | — |
| DAY 53 | — | — | — | — | 1228 ± 472 | — | — | — | — | — |

The HCC2429 lung model was also dosed intravenously Q4d×4 with PBS vehicle, rat-human chimeric anti-Notch3 ADCs and control huNeg-8.8 ADCs, at a dose of 5 mg/kg as provided in FIG. 16A. The data demonstrates that anti-Notch3 ADCs with non-cleavable (mc) and cleavable (vc) linkers and various payload combinations inhibited growth of HCC2429 lung xenografts. Further, the data shows that rat-human chimeric anti-Notch3 ADCs inhibited tumor growth more potently than control huNeg8.8-ADCs. Furthermore, the data demonstrates that rat-human chimeric anti-Notch3 ADCs with vc0101 linker-payloads were more potent than the other anti-Notch3 ADCs tested.

Additional in vivo experiments were performed with the HCC2429 lung cancer cell line using an unconjugated rat-human chimeric anti-Notch3 antibody, ch75-hIgG1, to determine whether ch75-hIgG1's Notch3 signaling inhibition contributed to the observed potency of the anti-Notch3 hu75-ADCs. To generate xenografts, nude (Nu/Nu) female mice were implanted subcutaneously with 3.5×10⁶ HCC2429 cells in 50% Matrigel (BD Biosciences). When the tumors reached a volume of 75 to 200 mm³, the tumors were staged to ensure uniformity of the tumor mass among various treatment groups.

The HCC2429 lung model was dosed intravenously Q4d×4 with PBS vehicle, rat-human chimeric anti-Notch3 antibody, ch75-hIgG1, and humanized anti-Notch1 antibody, hu438 VH1.1/VL1.8, at the does provided in Table 22. From 8 animals, mean tumor masses (±SEM) for each treatment group were calculated and compared to the control PBS vehicle group. P-values based on analysis of variance (ANOVA) were calculated to determine statistical significance of observed growth inhibition of anti-Notch treatments versus control PBS using Excel built-in statistical functions. Percent (%) growth inhibition values were calculated from measurements on the final day of the study for drug-treated compared with vehicle-treated mice with the formula $100*\{1-[(\text{Treated}_{Day\ 14}-\text{Treated}_{Day\ 0})/(\text{Control}_{Day\ 14}-\text{Control}_{Day\ 0})]\}$.

The data demonstrates that anti-Notch1 humanized antibody hu438 VH1.1/VL1.8 inhibited tumor growth by 57% and unconjugated rat-human chimeric anti-Notch3 antibody ch75-hIgG1 did not inhibit tumor growth compared to PBS vehicle treated tumors. Further, the data demonstrates that the observed tumor growth inhibition reported in Tables 20, 21 and FIG. 16A in the HCC2429 xenografts with Notch3 ADCs generated with the ch75 antibodies were not due to signaling inhibition.

TABLE 22

Effects of inhibitory anti-Notch3 and anti-Notch1 antibodies in HCC2429 lung xenografts.

HCC2429 Lung xenografts, tumor volume (mm³ ± SEM)

| | PBS control | ch75-hIgG1 (anti-Notch3) | p-value (ch75 ch75-hIgG1 vs. PBS) | (hu438 VH1.1/VL1.8 (anti-Notch1) | p-value (hu438 VH1.1/VL1.8 vs. PBS) |
|---|---|---|---|---|---|
| DAY 0 | 110 ± 7 | 110 ± 5 | 0.54 | 112 ± 11 | 0.504757 |
| DAY 3 | 218 ± 24 | 211 ± 24 | 0.39 | 173 ± 26 | 0.036706 |

TABLE 22-continued

Effects of inhibitory anti-Notch3 and anti-Notch1 antibodies in HCC2429 lung xenografts.

| | HCC2429 Lung xenografts, tumor volume (mm³ ± SEM) | | | | |
|---|---|---|---|---|---|
| | PBS control | ch75-hIgG1 (anti-Notch3) | p-value (ch75 ch75-hIgG1 vs. PBS) | (hu438 VH1.1/VL1.8 (anti-Notch1) | p-value (hu438 VH1.1/VL1.8 vs. PBS) |
| DAY 5 | 397 ± 41 | 356 ± 41 | 0.22 | 254 ± 36 | 0.001177 |
| DAY 7 | 665 ± 61 | 574 ± 59 | 0.19 | 311 ± 60 | 0.000001 |
| DAY 10 | 1267 ± 139 | 1054 ± 104 | 0.19 | 518 ± 92 | 0.000001 |
| DAY 12 | 1615 ± 187 | 1441 ± 139 | 0.34 | 701 ± 132 | 0.000006 |
| DAY 14 | 1985 ± 234 | 1821 ± 175 | 0.42 | 909 ± 172 | 0.000048 |

C. MDA-MB-468 Breast Xenografts

Similar in vivo experiments were performed with the MDA-MB-468 breast cancer cell line as described above. MDA-MB-468 cells are classified as a triple-negative breast cancer (TNBC) basal-like subtype since they lack expression of the estrogen receptor, progesterone receptor and human epidermal growth factor receptor 2 (HER2) (Lehmann, B D, et al, *J Clin Invest.* 2011; 121(7):2750-2767). To generate xenografts, female SCID Hairless Outbred (SHO) mice were orthotopically implanted with 10×10⁶ MDA-MB-468 cells containing 50% Matrigel (BD Biosciences) in the mammary fat pad. When the tumors reached a volume of 250 to 450 mm³, the tumors were staged to ensure uniformity of the tumor mass among various treatment groups. The MDA-MB-468 breast model was dosed intravenously Q4d×4 with PBS vehicle, humanized anti-Notch3 ADCs and control huNeg-8.8 ADCs at the doses provided in Tables 23 and 24. FIGS. 13A and 13B show graphs of the data from Table 23 of anti-Notch3 ADCs with vc0101 linker-payloads compared to control huNeg-8.8 ADCs and PBS vehicle. FIGS. 14A and 14B show graphs of the data from Table 24 of the anti-Notch3 ADCs with vc6780 linker-payloads compared to control huNeg-8.8 ADC and PBS vehicle.

The data demonstrates that anti-Notch3 ADCs hu28-vc0101, hu28-vc6780, hu75-vc0101 and hu75-vc6780 inhibited growth of MDA-MB-468 breast xenografts in a dose-dependent manner. Further, the data shows that anti-Notch3 ADCs inhibited tumor growth more potently than control huNeg8.8-ADCs at the 1 and 3 mg/kg doses for ADCs with vc0101 linker-payloads and 1, 3 and 10 mg/kg doses for ADC with vc6780 linker-payloads. Furthermore, the data demonstrates that a 1 mg/kg dose of anti-Notch3 ADCs with vc0101 linker-payloads were more potent than a 3 mg/kg dose of anti-Notch3 ADCs with vc6780 linker-payloads.

TABLE 23

Efficacy of anti-Notch3-vc0101 ADCs in MDA-MB-468 breast xenografts.

| | MDA-MB-468 Breast xenografts, tumor volume (mm³ ± SEM) | | | | | | | | | |
|---|---|---|---|---|---|---|---|---|---|---|
| | PBS | hu28-vc0101 | | | hu75-vc0101 | | | huNeg-8.8-vc0101 | | |
| | | Dose mg/kg | | | | | | | | |
| | 0 | 3 | 1 | 0.3 | 3 | 1 | 0.3 | 3 | 1 | 0.3 |
| DAY 0 | 343 ± 12 | 347 ± 15 | 348 ± 22 | 336 ± 19 | 347 ± 20 | 347 ± 22 | 348 ± 21 | 334 ± 23 | 346 ± 16 | 344 ± 19 |
| DAY 4 | 441 ± 24 | 359 ± 24 | 439 ± 21 | 403 ± 28 | 444 ± 28 | 410 ± 32 | 439 ± 31 | 424 ± 29 | 447 ± 32 | 442 ± 19 |
| DAY 7 | 469 ± 32 | 326 ± 27 | 415 ± 25 | 395 ± 38 | 338 ± 20 | 383 ± 33 | 435 ± 27 | 411 ± 26 | 449 ± 20 | 438 ± 23 |
| DAY 11 | 495 ± 28 | 227 ± 27 | 372 ± 34 | 412 ± 42 | 277 ± 22 | 373 ± 33 | 504 ± 38 | 439 ± 36 | 538 ± 23 | 496 ± 37 |
| DAY 14 | 581 ± 35 | 147 ± 20 | 314 ± 27 | 488 ± 45 | 181 ± 19 | 350 ± 40 | 507 ± 30 | 445 ± 29 | 592 ± 47 | 560 ± 36 |
| DAY 18 | 639 ± 43 | 77 ± 10 | 261 ± 33 | 497 ± 55 | 90 ± 12 | 296 ± 33 | 587 ± 44 | 479 ± 42 | 619 ± 42 | 578 ± 36 |
| DAY 21 | 638 ± 46 | 16 ± 8 | 219 ± 41 | 509 ± 60 | 60 ± 9 | 260 ± 49 | 590 ± 55 | 481 ± 34 | 676 ± 46 | 627 ± 30 |
| DAY 26 | 707 ± 41 | 0 ± 0 | 253 ± 61 | 590 ± 66 | 16 ± 10 | 267 ± 59 | 652 ± 64 | 548 ± 41 | 793 ± 54 | 671 ± 56 |
| DAY 29 | 749 ± 59 | 0 ± 0 | 238 ± 64 | — | 8 ± 8 | 261 ± 62 | 675 ± 63 | — | 819 ± 73 | 669 ± 37 |
| DAY 32 | 812 ± 80 | 0 ± 0 | 266 ± 67 | — | 7 ± 7 | 264 ± 67 | 738 ± 70 | — | 913 ± 72 | 758 ± 44 |
| DAY 35 | 891 ± 79 | 0 ± 0 | 271 ± 73 | — | 0 ± 0 | 326 ± 86 | 821 ± 69 | — | 1023 ± 96 | 848 ± 58 |
| DAY 39 | 892 ± 84 | 0 ± 0 | 310 ± 88 | — | 0 ± 0 | 324 ± 81 | 864 ± 74 | — | — | 884 ± 64 |
| DAY 42 | 1037 ± 104 | 0 ± 0 | 349 ± 95 | — | 0 ± 0 | 381 ± 94 | 997 ± 84 | — | — | 1002 ± 55 |
| DAY 47 | 1173 ± 134 | 0 ± 0 | 394 ± 123 | — | 0 ± 0 | 442 ± 69 | — | — | — | 1145 ± 78 |

TABLE 23-continued

Efficacy of anti-Notch3-vc0101 ADCs in MDA-MB-468 breast xenografts.

MDA-MB-468 Breast xenografts, tumor volume (mm³ ± SEM)

| | PBS | hu28-vc0101 | | | hu75-vc0101 | | | huNeg-8.8-vc0101 | | |
|---|---|---|---|---|---|---|---|---|---|---|
| | | | | | Dose mg/kg | | | | | |
| | 0 | 3 | 1 | 0.3 | 3 | 1 | 0.3 | 3 | 1 | 0.3 |
| DAY 50 | — | 0 ± 0 | 377 ± 118 | — | 0 ± 0 | 484 ± 89 | — | — | — | 1120 ± 67 |
| DAY 53 | — | 0 ± 0 | 414 ± 127 | — | 0 ± 0 | 452 ± 78 | — | — | — | 1229 ± 100 |
| DAY 56 | — | 0 ± 0 | 470 ± 128 | — | 0 ± 0 | 535 ± 93 | — | — | — | 1314 ± 120 |
| DAY 60 | — | 0 ± 0 | 532 ± 140 | — | 0 ± 0 | 603 ± 98 | — | — | — | — |
| DAY 63 | — | 0 ± 0 | 509 ± 117 | — | 0 ± 0 | — | — | — | — | — |
| DAY 67 | — | 0 ± 0 | 611 ± 148 | — | 0 ± 0 | — | — | — | — | — |
| DAY 70 | — | 0 ± 0 | — | — | 0 ± 0 | — | — | — | — | — |
| DAY 76 | — | 0 ± 0 | — | — | 0 ± 0 | — | — | — | — | — |
| DAY 83 | — | 0 ± 0 | — | — | 0 ± 0 | — | — | — | — | — |
| DAY 90 | — | 0 ± 0 | — | — | 0 ± 0 | — | — | — | — | — |
| DAY 97 | — | 0 ± 0 | — | — | 0 ± 0 | — | — | — | — | — |
| DAY 103 | — | 0 ± 0 | — | — | 0 ± 0 | — | — | — | — | — |
| DAY 110 | — | 0 ± 0 | — | — | 0 ± 0 | — | — | — | — | — |
| DAY 118 | — | 0 ± 0 | — | — | 0 ± 0 | — | — | — | — | — |
| DAY 125 | — | 0 ± 0 | — | — | 0 ± 0 | — | — | — | — | — |

TABLE 24

Efficacy of anti-Notch3-vc6780 ADCs in MDA-MB-468 breast xenografts.

MDA-MB-468 Breast xenografts, tumor volume (mm³ ± SEM)

| | PBS | hu28-vc6780 | | | hu75-vc6780 | | | huNeg-8.8-vc6780 | | |
|---|---|---|---|---|---|---|---|---|---|---|
| | | | | | Dose mg/kg | | | | | |
| | 0 | 10 | 3 | 1 | 10 | 3 | 1 | 10 | 3 | 1 |
| DAY 0 | 342 ± 9 | 335 ± 9 | 342 ± 18 | 342 ± 16 | 343 ± 10 | 344 ± 11 | 340 ± 14 | 339 ± 18 | 341 ± 12 | 346 ± 16 |
| DAY 4 | 466 ± 20 | 395 ± 19 | 394 ± 33 | 462 ± 22 | 418 ± 15 | 406 ± 22 | 423 ± 27 | 432 ± 45 | 457 ± 23 | 466 ± 29 |
| DAY 7 | 481 ± 17 | 350 ± 19 | 399 ± 24 | 452 ± 30 | 370 ± 18 | 378 ± 21 | 434 ± 29 | 449 ± 45 | 529 ± 24 | 528 ± 25 |
| DAY 11 | 611 ± 44 | 248 ± 26 | 380 ± 25 | 512 ± 35 | 302 ± 21 | 403 ± 21 | 471 ± 39 | 504 ± 38 | 599 ± 23 | 621 ± 43 |
| DAY 14 | 610 ± 19 | 154 ± 23 | 401 ± 30 | 507 ± 38 | 228 ± 19 | 370 ± 28 | 470 ± 44 | 503 ± 64 | 622 ± 31 | 639 ± 48 |
| DAY 19 | 707 ± 34 | 65 ± 17 | 438 ± 39 | 538 ± 47 | 112 ± 23 | 339 ± 19 | 536 ± 49 | 437 ± 54 | 697 ± 36 | 713 ± 48 |
| DAY 22 | — | 25 ± 16 | 414 ± 41 | 551 ± 48 | 52 ± 21 | 360 ± 17 | 552 ± 44 | 415 ± 54 | 719 ± 40 | — |
| DAY 25 | — | 26 ± 19 | 491 ± 37 | 575 ± 55 | 63 ± 25 | 381 ± 23 | 597 ± 48 | 421 ± 76 | 773 ± 39 | — |
| DAY 28 | — | 15 ± 15 | 497 ± 68 | 654 ± 74 | 64 ± 26 | 443 ± 33 | 660 ± 53 | 451 ± 84 | 808 ± 58 | — |
| DAY 32 | — | 0 ± 0 | 524 ± 69 | 653 ± 82 | 71 ± 31 | 437 ± 28 | 634 ± 74 | 456 ± 94 | — | — |
| DAY 35 | — | 0 ± 0 | — | 734 ± 89 | 85 ± 38 | 495 ± 33 | 742 ± 80 | 541 ± 108 | — | — |
| DAY 40 | — | 0 ± 0 | — | 761 ± 99 | 125 ± 44 | 535 ± 41 | 794 ± 87 | 563 ± 109 | — | — |
| DAY 43 | — | 0 ± 0 | — | 816 ± 122 | 134 ± 42 | 619 ± 47 | 832 ± 82 | 581 ± 120 | — | — |

TABLE 24-continued

Efficacy of anti-Notch3-vc6780 ADCs in MDA-MB-468 breast xenografts.

| | MDA-MB-468 Breast xenografts, tumor volume (mm$^3$ ± SEM) | | | | | | | | | |
|---|---|---|---|---|---|---|---|---|---|---|
| | PBS | hu28-vc6780 | | | hu75-vc6780 | | | huNeg-8.8-vc6780 | | |
| | | Dose mg/kg | | | | | | | | |
| | 0 | 10 | 3 | 1 | 10 | 3 | 1 | 10 | 3 | 1 |
| DAY 46 | — | 0 ± 0 | — | 859 ± 126 | 143 ± 42 | 636 ± 38 | 868 ± 99 | 617 ± 116 | — | — |
| DAY 49 | — | 0 ± 0 | — | 948 ± 178 | 159 ± 44 | 723 ± 71 | 996 ± 109 | 733 ± 129 | — | — |
| DAY 53 | — | 0 ± 0 | — | 1008 ± 192 | 201 ± 63 | 795 ± 67 | — | 758 ± 163 | — | — |
| DAY 56 | — | 0 ± 0 | — | — | 211 ± 63 | 819 ± 77 | — | — | — | — |
| DAY 60 | — | 0 ± 0 | — | — | 240 ± 63 | 976 ± 115 | — | — | — | — |
| DAY 63 | — | 0 ± 0 | — | — | 201 ± 57 | — | — | — | — | — |
| DAY 67 | — | 0 ± 0 | — | — | — | — | — | — | — | — |
| DAY 70 | — | 0 ± 0 | — | — | — | — | — | — | — | — |
| DAY 76 | — | 0 ± 0 | — | — | — | — | — | — | — | — |
| DAY 83 | — | 0 ± 0 | — | — | — | — | — | — | — | — |
| DAY 90 | — | 0 ± 0 | — | — | — | — | — | — | — | — |
| DAY 96 | — | 0 ± 0 | — | — | — | — | — | — | — | — |
| DAY 103 | — | 0 ± 0 | — | — | — | — | — | — | — | — |
| DAY 111 | — | 0 ± 0 | — | — | — | — | — | — | — | — |
| DAY 118 | — | 0 ± 0 | — | — | — | — | — | — | — | — |
| DAY 124 | — | 0 ± 0 | — | — | — | — | — | — | — | — |

The MDA-MB-468 breast cancer model was also dosed intravenously Q4d×4 with PBS vehicle, rat-human chimeric anti-Notch3 ADCs and control huNeg-8.8 ADCs, at a dose of 5 mg/kg as provided in FIGS. 16B and 16C. The data demonstrates that rat-human chimeric anti-Notch3 ADCs with non-cleavable (mc) and cleavable (vc) linkers and various payload combinations inhibited growth of MDA-MB-468 breast xenografts. Further, the data shows that rat-human chimeric anti-Notch3 ADCs inhibited tumor growth more potently than control huNeg8.8-ADCs. Furthermore, the data demonstrates that rat-human chimeric anti-Notch3 ADCs with vc0101 linker-payloads were more potent than the other rat-human chimeric anti-Notch3 ADCs tested.

The MDA-MB-468 breast cancer model was used to examine the in vivo mechanism of action of hu28-vc0101. The pharmacodynamics of hu28-vc0101 was visualized at the cellular level by staining with the mitotic marker phospho-Histone H3 in ADC treated xenografts. Histone H3 is phosphorylated on Ser-10 residues (hereinafter "pHH3") within chromatin during the mitotic phase of the cell cycle.

Mice bearing MDA-MB-468 breast xenografts were given a single 3 mg/kg dose intravenously with anti-Notch3 ADC hu28-vc0101, huNeg-8.8-vc0101 (control ADC) or PBS. Three xenografts were harvested after 6, 24 and 96 hours and processed for standard immunohistochemistry. Five micrometer thick formalin fixed, paraffin embedded tissue sections were deparaffinized in xylene substitute, rehydrated with graded alcohols to distilled water. To expose antigenic sites, tissue sections were heated in 10 mM citrate buffer pH 6.0 (Labvision) in a pressure cooker (Retriever; Electron Microscopy Sciences) and cooled to room temperature. Endogenous peroxidase activity was inactivated with 3% hydrogen peroxide for 15 min. Non specific protein interactions were blocked by a 10 minute incubation with UV Block (Labvision). Tissue sections were incubated with anti-pHH3 antibody for one hour, detected with Signalstain Boost Reagent (8114, Cell Signaling Technologies) for 30 minutes and color was developed with DAB+ (DAKO) for 5 minutes. All sections were counterstained with Hematoxylin QS (Vector Laboratories), washed in tap water, dehydrated in graded alcohols, cleared in xylene substitute, and mounted with Permount Mounting Medium (FisherChemicals, Fair Lawn, N.J.).

Immunohistochemically stained slides were evaluated by image analysis. Slides were imaged at 20× using a Hamamatsu NanoZoomer automated slide scanner. Once digitized, the virtual slides were analyzed using Definiens Tissue Studio software. Each xenograft section was regionally segmented and classified based on cellularity and morphology. Individual nuclei were identified within the viable regions of the xenograft and the positivity was determined using the average brown chromogen intensity of each nuclei. Data is presented as percent (%) pHH3 positivity which is calculated using the following equation: (Number of pHH3 positive nuclei (viable region)/Total number of nuclei (viable region))*100. Determination of statistical significance was determined for each treatment group and time point compared to PBS control at 24 hour time point with Graph Pad Prism using a 2 tailed T test.

ADCs generated with microtubule inhibitors like hu28-vc0101 are expected to arrest proliferating cells in the mitotic phase of the cell cycle when histone H3 is phosphorylated on Ser-10 residues within chromatin. An accumulation of pHH3 staining in ADC treated xenografts indicates that cancer cells were arrested in mitosis. Table 25 contains percentages of pHH3 stained cells in anti-Notch3 hu28-vc0101 and huNeg-8.8-vc0101 (control ADC) treated MDA-MB-468 xenografts and untreated MDA-MB-468 xenografts. The data demonstrates that hu28-vc0101, but not control huNeg8.8-vc0101 resulted in a statistically significant 2 fold increase in the percentage of pHH3 stained nuclei in MDA-MD-468 cancer cells at 24 and 96 hours post-treatment compared to the PBS control. The data indicates that anti-Notch3 hu28-vc0101 inhibits in vivo tumor growth, at least in part, by arresting cells in the mitotic phase of the cell cycle, thus preventing proliferation.

TABLE 25

Percentage of pHH3 stained nuclei in Notch3 ADC treated MDA-MB-468 breast cancer xenografts (n.d. = not determined)

| | 6 hr | | 24 hr | | 96 hr | |
|---|---|---|---|---|---|---|
| | % pHH3 | p-value | % pHH3 | p-value | % pHH3 | p-value |
| PBS | n.d | n.d. | 2.62 | n.d. | n.d. | n.d. |
| hu28-vc0101 | 2.54 | 0.84 | 5.37 | 0.0046 | 5.19 | 0.0003 |
| huNeg8.8-vc0101 | 2.74 | 0.78 | 3.67 | 0.1025 | 3.01 | 0.0730 |

D. N87 Gastric Xenografts

Similar in vivo experiments were performed with the N87 gastric cancer cell line as described above. To generate xenografts, nude (Nu/Nu) female mice were implanted subcutaneously with $8 \times 10^6$ N87 cells in 50% Matrigel (BD Biosciences). When the tumors reached a volume of 250 to 450 mm³, the tumors were staged to ensure uniformity of the tumor mass among various treatment groups. The N87 gastric model was dosed intravenously Q4dx4 with PBS vehicle, humanized anti-Notch3 ADCs, control huNeg-8.8 ADCs and cisplatin at the doses provided in Tables 26 and 27. The data demonstrates that anti-Notch3 ADCs hu28-vc0101, hu28-vc6780, hu75-vc0101 and hu75-vc6780 inhibited growth of N87 gastric xenografts in a dose-dependent manner. Further, the data shows that anti-Notch3 ADCs inhibited tumor growth more potently than control huNeg8.8-ADCs at the 1, 3, 5 mg/kg doses for ADCs with vc0101 linker-payloads and 3 and 10 mg/kg doses for ADCs with vc6780 linker-payloads. By day 133, the 5 mg/kg dose group of hu28-vc0101 contained 6 out of 9 animals that were tumor-free, hu75-vc0101 had 4 out of 9 animals and control huNeg8-8-vc0101 had 1 out of 8 animals that were tumor-free. Furthermore, the data demonstrates that ADCs with vc0101 linker-payloads were in general more potent than cisplatin standard-of-care therapy and ADCs with vc6780 linker-payloads.

TABLE 26

Efficacy of anti-Notch3-vc0101 ADCs in N87 gastric xenografts.

| | N87 Gastric xenografts, tumor volume (mm³ ± SEM) | | | | | | | | | |
|---|---|---|---|---|---|---|---|---|---|---|
| | PBS | hu28-vc0101 | | | hu75-vc0101 | | | huNeg-8.8-vc0101 | | Cisplatin |
| | | Dose mg/kg | | | | | | | | |
| | 0 | 1 | 3 | 5 | 1 | 3 | 5 | 1 | 3 | 5 | 5 |
| DAY 0 | 327 ± 11 | 321 ± 21 | 326 ± 13 | 321 ± 8 | 321 ± 9 | 324 ± 19 | 320 ± 11 | 327 ± 18 | 324 ± 11 | 321 ± 16 | 328 ± 20 |
| DAY 4 | 526 ± 19 | 369 ± 18 | 339 ± 11 | 344 ± 14 | 392 ± 15 | 362 ± 35 | 315 ± 15 | 437 ± 34 | 478 ± 19 | 423 ± 32 | 414 ± 27 |
| DAY 7 | 706 ± 27 | 429 ± 43 | 302 ± 10 | 272 ± 7 | 417 ± 25 | 303 ± 21 | 246 ± 12 | 584 ± 54 | 625 ± 34 | 512 ± 34 | 520 ± 26 |
| DAY 11 | 854 ± 36 | 304 ± 30 | 182 ± 14 | 152 ± 13 | 331 ± 21 | 174 ± 14 | 156 ± 10 | 702 ± 60 | 716 ± 53 | 501 ± 38 | 501 ± 29 |
| DAY 14 | 887 ± 45 | 282 ± 25 | 191 ± 5 | 155 ± 13 | 305 ± 17 | 172 ± 10 | 151 ± 7 | 822 ± 65 | 823 ± 42 | 549 ± 37 | 637 ± 31 |
| DAY 18 | 1045 ± 68 | 263 ± 24 | 161 ± 7 | 138 ± 11 | 267 ± 17 | 151 ± 10 | 128 ± 6 | 823 ± 73 | 789 ± 33 | 491 ± 51 | — |
| DAY 21 | 1072 ± 76 | 227 ± 23 | 123 ± 15 | 110 ± 9 | 218 ± 23 | 130 ± 5 | 115 ± 7 | 857 ± 78 | 785 ± 35 | 413 ± 50 | — |
| DAY 26 | 1303 ± 140 | 205 ± 32 | 108 ± 16 | 69 ± 16 | 185 ± 24 | 92 ± 14 | 82 ± 10 | 895 ± 126 | 825 ± 62 | 343 ± 63 | — |
| DAY 29 | 1276 ± 139 | 180 ± 30 | 99 ± 14 | 50 ± 13 | 211 ± 37 | 104 ± 16 | 75 ± 12 | 957 ± 126 | 879 ± 72 | 411 ± 89 | — |
| DAY 33 | 1480 ± 183 | 211 ± 43 | 106 ± 17 | 43 ± 14 | 251 ± 53 | 91 ± 18 | 73 ± 12 | 988 ± 180 | 966 ± 98 | 411 ± 89 | — |
| DAY 36 | — | 215 ± 42 | 122 ± 22 | 52 ± 16 | 272 ± 59 | 86 ± 18 | 85 ± 9 | 884 ± 143 | 1023 ± 106 | 481 ± 86 | — |
| DAY 39 | — | 261 ± 54 | 128 ± 23 | 45 ± 14 | 304 ± 72 | 59 ± 16 | 72 ± 13 | 937 ± 167 | 1142 ± 121 | 535 ± 128 | — |
| DAY 42 | — | 283 ± 52 | 149 ± 25 | 34 ± 15 | 314 ± 73 | 81 ± 22 | 74 ± 13 | 1008 ± 179 | 1240 ± 143 | 596 ± 119 | — |
| DAY 47 | — | 262 ± 64 | 105 ± 19 | 25 ± 14 | 334 ± 95 | 80 ± 25 | 36 ± 8 | 1061 ± 210 | 1380 ± 153 | 621 ± 137 | — |
| DAY 53 | — | 302 ± 75 | 104 ± 30 | 29 ± 16 | 393 ± 115 | 86 ± 24 | 69 ± 13 | — | — | 757 ± 189 | — |

TABLE 26-continued

Efficacy of anti-Notch3-vc0101 ADCs in N87 gastric xenografts.

N87 Gastric xenografts, tumor volume (mm³ ± SEM)

| | PBS | hu28-vc0101 | | | hu75-vc0101 | | | huNeg-8.8-vc0101 | | | Cisplatin |
|---|---|---|---|---|---|---|---|---|---|---|---|
| | | Dose mg/kg | | | | | | | | | |
| | 0 | 1 | 3 | 5 | 1 | 3 | 5 | 1 | 3 | 5 | 5 |
| DAY 62 | — | 415 ± 111 | 116 ± 47 | 33 ± 18 | 463 ± 155 | 106 ± 35 | 50 ± 15 | — | — | 690 ± 122 | — |
| DAY 70 | — | 521 ± 135 | 139 ± 54 | 58 ± 30 | 658 ± 241 | 148 ± 54 | 76 ± 22 | — | — | 852 ± 150 | — |
| DAY 78 | — | 622 ± 169 | 172 ± 69 | 67 ± 40 | 531 ± 152 | 161 ± 60 | 90 ± 25 | — | — | 937 ± 168 | — |
| DAY 84 | — | 709 ± 200 | 149 ± 73 | 85 ± 49 | 602 ± 185 | 200 ± 76 | 96 ± 37 | — | — | 1178 ± 222 | — |
| DAY 91 | — | 848 ± 236 | 178 ± 94 | 104 ± 63 | 732 ± 246 | 225 ± 92 | 109 ± 46 | — | — | — | — |
| DAY 99 | — | — | 214 ± 108 | 118 ± 72 | — | 170 ± 75 | 130 ± 53 | — | — | — | — |
| DAY 103 | — | — | 123 ± 43 | 135 ± 90 | — | 184 ± 82 | 142 ± 62 | — | — | — | — |
| DAY 112 | — | — | 126 ± 50 | 166 ± 105 | — | 222 ± 108 | 174 ± 75 | — | — | — | — |
| DAY 120 | — | — | 128 ± 44 | 226 ± 140 | — | 240 ± 116 | 221 ± 103 | — | — | — | — |
| DAY 133 | — | — | 175 ± 74 | 258 ± 157 | — | — | 295 ± 139 | — | — | — | — |

TABLE 27

Efficacy of anti-Notch3-vc6780 ADCs in N87 gastric xenografts.

N87 Gastric xenografts, tumor volume (mm³ ± SEM)

| | PBS | hu28-vc6780 | | | hu75-vc6780 | | | huNeg8.8-vc6780 | |
|---|---|---|---|---|---|---|---|---|---|
| | | Dose mg/kg | | | | | | | |
| | 0 | 10 | 3 | 1 | 10 | 3 | 1 | 10 | 3 |
| DAY 0 | 345 ± 14 | 350 ± 14 | 349 ± 10 | 348 ± 13 | 349 ± 8 | 351 ± 20 | 357 ± 14 | 356 ± 20 | 344 ± 14 |
| DAY 4 | 600 ± 16 | 434 ± 24 | 552 ± 24 | 560 ± 26 | 468 ± 18 | 545 ± 37 | 546 ± 35 | 581 ± 60 | 537 ± 36 |
| DAY 8 | 675 ± 20 | 379 ± 12 | 545 ± 37 | 592 ± 44 | 351 ± 24 | 511 ± 31 | 563 ± 55 | 605 ± 67 | 670 ± 45 |
| DAY 11 | 763 ± 54 | 315 ± 18 | 511 ± 25 | 617 ± 48 | 316 ± 25 | 544 ± 43 | 582 ± 56 | 636 ± 79 | 706 ± 38 |
| DAY 14 | 886 ± 72 | 292 ± 24 | 564 ± 29 | 782 ± 60 | 269 ± 27 | 558 ± 36 | 667 ± 68 | 717 ± 118 | 917 ± 36 |
| DAY 18 | 997 ± 93 | 199 ± 18 | 479 ± 29 | 797 ± 88 | 224 ± 26 | 494 ± 41 | 638 ± 80 | 665 ± 112 | 958 ± 57 |
| DAY 21 | 1041 ± 107 | 194 ± 20 | 499 ± 34 | 839 ± 93 | 192 ± 19 | 534 ± 41 | 709 ± 103 | 637 ± 119 | 1002 ± 59 |
| DAY 25 | 1151 ± 144 | 181 ± 21 | 588 ± 40 | 878 ± 105 | 227 ± 32 | 628 ± 58 | 750 ± 122 | 647 ± 134 | 1075 ± 82 |
| DAY 28 | 1200 ± 155 | 204 ± 16 | 672 ± 48 | 904 ± 123 | 244 ± 35 | 645 ± 57 | 763 ± 145 | 674 ± 146 | 1148 ± 77 |
| DAY 33 | 1481 ± 206 | 196 ± 27 | 786 ± 65 | 1043 ± 152 | 267 ± 52 | 730 ± 66 | 991 ± 239 | 733 ± 195 | 1290 ± 128 |
| DAY 36 | — | 189 ± 37 | 827 ± 69 | 1108 ± 185 | 300 ± 64 | 850 ± 74 | — | 817 ± 222 | 1265 ± 111 |
| DAY 39 | — | 228 ± 44 | 847 ± 77 | 1204 ± 209 | 323 ± 69 | 881 ± 88 | — | 880 ± 247 | 1429 ± 121 |
| DAY 42 | — | 257 ± 60 | 959 ± 81 | — | 350 ± 78 | 1020 ± 99 | — | 797 ± 244 | — |
| DAY 46 | — | 253 ± 59 | 1018 ± 94 | — | 380 ± 78 | 1097 ± 129 | — | 874 ± 267 | — |
| DAY 50 | — | 253 ± 67 | 1111 ± 95 | — | 415 ± 77 | 1162 ± 134 | — | — | — |
| DAY 56 | — | 298 ± 85 | 1279 ± 108 | — | 504 ± 111 | 1331 ± 187 | — | — | — |
| DAY 63 | — | 345 ± 93 | 1368 ± 133 | — | 581 ± 121 | — | — | — | — |

TABLE 27-continued

Efficacy of anti-Notch3-vc6780 ADCs in N87 gastric xenografts.

N87 Gastric xenografts, tumor volume (mm³ ± SEM)

| | PBS | hu28-vc6780 | | | hu75-vc6780 | | | huNeg8.8-vc6780 | |
|---|---|---|---|---|---|---|---|---|---|
| | | Dose mg/kg | | | | | | | |
| | 0 | 10 | 3 | 1 | 10 | 3 | 1 | 10 | 3 |
| DAY 70 | — | 376 ± 117 | 1483 ± 154 | — | 726 ± 163 | — | — | — | — |
| DAY 77 | — | 388 ± 123 | — | — | 797 ± 184 | — | — | — | — |
| DAY 84 | — | 463 ± 149 | — | — | 995 ± 239 | — | — | — | — |
| DAY 91 | — | 523 ± 171 | — | — | — | — | — | — | — |
| DAY 98 | — | 701 ± 251 | — | — | — | — | — | — | — |

The N87 gastric model was also dosed intravenously Q4d×4 with PBS vehicle, rat-human chimeric anti-Notch3 ADCs and control huNeg-8.8 ADCs, at a dose of 5 mg/kg as provided in FIG. 16D. The data demonstrates that rat-human chimeric anti-Notch3 ADCs with non-cleavable (mc) and cleavable (vc) linkers and various payload combinations inhibited growth of N87 gastric xenografts. Further, the data shows that rat-human chimeric anti-Notch3 ADCs inhibited tumor growth more potently than control huNeg8.8-ADCs. Furthermore, the data demonstrates that rat-human chimeric anti-Notch3 ADCs with vc0101 linker-payloads were more potent than the other anti-Notch3 ADCs tested.

The N87 gastric model was also dosed intravenously Q4d×4 with PBS vehicle and rat-human chimeric anti-Notch3 ADCs ch28-mc0131, ch75-mc0131, ch28-m(H2O)c-0131 and ch75-m(H2O)c-0131 at a dose of 5 mg/kg as provided in FIG. 16E. The data demonstrates that rat-human chimeric anti-Notch3 ADCs having mc0131 and m(H2O)c-0131 linker-payloads inhibited growth of N87 gastric xenografts. Further, the data demonstrates that rat-human chimeric anti-Notch3 ADCs having m(H2O)c-0131 linker-payloads were more potent than rat-human chimeric anti-Notch3 ADCs having mc0131 linker-payloads.

E. OVCAR3 Ovarian Xenografts

Figure 15:
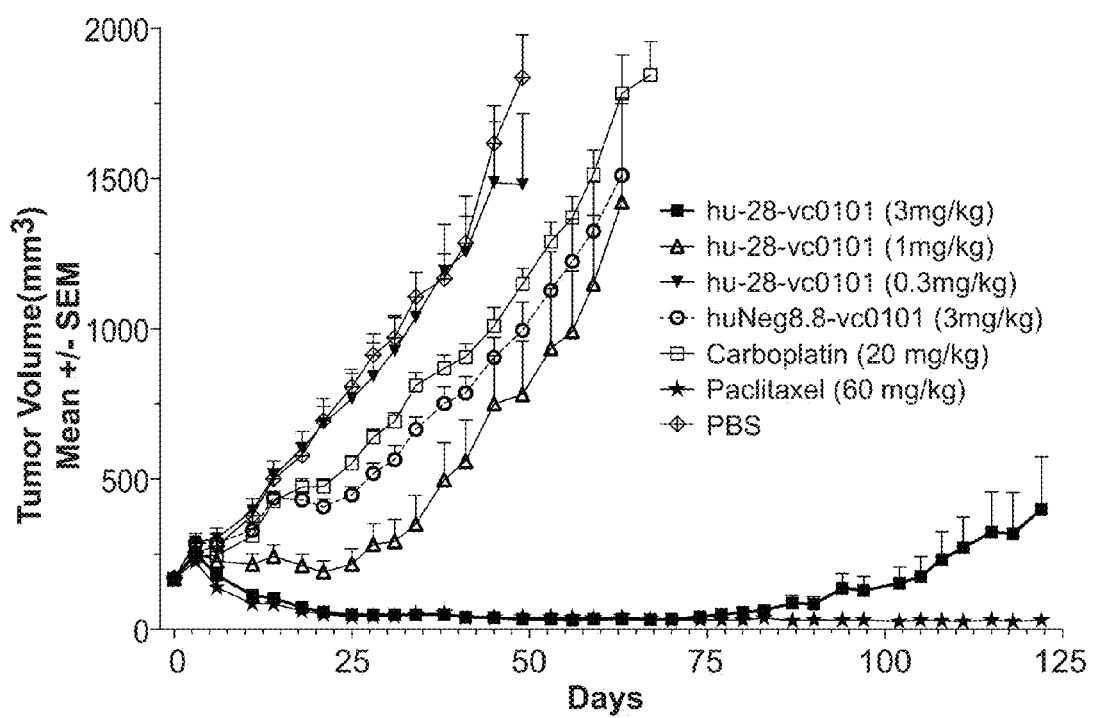
FIG. 15 shows the efficacy of anti-Notch3 hu28-vc0101 in the OVCAR3 ovarian model.

Similar in vivo experiments were performed with the OVCAR3 ovarian cell line as described above. To generate xenografts, SCID Hairless Outbred (SHO) female mice were implanted subcutaneously with 5×10⁶ OVCAR3 cells in 50% Matrigel (BD Biosciences). When the tumors reached a volume of 120 to 290 mm³, the tumors were staged to ensure uniformity of the tumor mass among various treatment groups. The OVCAR3 model was dosed intravenously Q4d×4 with PBS vehicle, humanized anti-Notch3 ADC hu28-vc0101, and control ADC huNeg-8.8-vc0101; and dosed intraperitoneally Q7d×4 with paclitaxel (30 mg/kg twice a day) and Q7d×8 with carboplatin at the doses provided in Table 28. FIG. 15 and Table 28 demonstrate that hu28-vc0101 inhibited growth of OVCAR3 ovarian xenografts in a dose-dependent manner. Further, the data shows that hu28-vc0101 inhibited tumor growth more potently than control huNeg8.8-vc0101 and carboplatin standard of care chemotherapy. Furthermore, the data demonstrates that hu28-vc0101 dosed at 3 mg/kg Q4d×4 had similar potency to paclitaxel dosed at 60 mg/kg, Q7d×4 which is the maximum tolerated dose of paclitaxel in SHO mice.

TABLE 28

Efficacy of anti-Notch3 ADC hu28-vc0101 in OVCAR3 ovarian xenografts.

OVCAR3 Ovarian Xenografts, tumor volume (mm3 ± S.E.M.)

| | PBS | hu28-vc0101 | | | huNeg8.8-vc0101 | | Carboplatin | Paclitaxel |
|---|---|---|---|---|---|---|---|---|
| | | Dose mg/kg | | | | | | |
| | 0 | 0.3 | 1 | 3 | 1 | 3 | 20 | 60 |
| DAY 0 | 170 ± 14 | 168 ± 18 | 169 ± 20 | 169 ± 18 | 171 ± 21 | 168 ± 14 | 167 ± 13 | 169 ± 13 |
| DAY 3 | 255 ± 18 | 291 ± 29 | 255 ± 31 | 253 ± 35 | 261 ± 36 | 286 ± 18 | 242 ± 20 | 225 ± 29 |
| DAY 6 | 277 ± 25 | 302 ± 35 | 226 ± 33 | 180 ± 19 | 267 ± 38 | 287 ± 30 | 246 ± 17 | 139 ± 13 |
| DAY 11 | 378 ± 18 | 394 ± 40 | 216 ± 35 | 113 ± 9 | 369 ± 68 | 329 ± 27 | 311 ± 25 | 85 ± 8 |
| DAY 14 | 501 ± 33 | 510 ± 50 | 242 ± 39 | 104 ± 9 | 467 ± 75 | 437 ± 23 | 426 ± 27 | 84 ± 7 |
| DAY 18 | 578 ± 43 | 601 ± 57 | 212 ± 38 | 72 ± 9 | 516 ± 101 | 431 ± 26 | 473 ± 29 | 61 ± 5 |
| DAY 21 | 693 ± 48 | 685 ± 83 | 190 ± 38 | 57 ± 6 | 587 ± 123 | 407 ± 26 | 475 ± 26 | 50 ± 4 |
| DAY 25 | 806 ± 59 | 767 ± 84 | 216 ± 52 | 49 ± 5 | 638 ± 131 | 447 ± 27 | 552 ± 25 | 41 ± 2 |

TABLE 28-continued

Efficacy of anti-Notch3 ADC hu28-vc0101 in OVCAR3 ovarian xenografts.

OVCAR3 Ovarian Xenografts, tumor volume (mm3 ± S.E.M.)

| | PBS | hu28-vc0101 | | | huNeg8.8-vc0101 | | Carboplatin | Paclitaxel |
|---|---|---|---|---|---|---|---|---|
| | | | | Dose mg/kg | | | | |
| | 0 | 0.3 | 1 | 3 | 1 | 3 | 20 | 60 |
| DAY 28 | 912 ± 71 | 841 ± 112 | 282 ± 69 | 47 ± 6 | 772 ± 171 | 518 ± 35 | 640 ± 26 | 44 ± 4 |
| DAY 31 | 970 ± 68 | 926 ± 118 | 292 ± 74 | 48 ± 4 | 854 ± 176 | 564 ± 48 | 692 ± 28 | 43 ± 3 |
| DAY 34 | 1105 ± 83 | 1038 ± 148 | 350 ± 95 | 48 ± 6 | 1002 ± 216 | 665 ± 41 | 811 ± 44 | 50 ± 3 |
| DAY 38 | 1166 ± 83 | 1191 ± 156 | 497 ± 124 | 49 ± 4 | 903 ± 88 | 751 ± 56 | 869 ± 44 | 55 ± 6 |
| DAY 41 | 1285 ± 89 | 1254 ± 188 | 559 ± 137 | 40 ± 6 | 979 ± 95 | 786 ± 56 | 906 ± 44 | 38 ± 3 |
| DAY 45 | 1616 ± 126 | 1486 ± 203 | 750 ± 160 | 39 ± 3 | 1109 ± 115 | 904 ± 67 | 1009 ± 62 | 39 ± 3 |
| DAY 49 | 1836 ± 142 | 1479 ± 236 | 781 ± 178 | 33 ± 4 | 1289 ± 129 | 994 ± 95 | 1149 ± 52 | 40 ± 4 |
| DAY 53 | — | — | 934 ± 200 | 34 ± 3 | 1486 ± 138 | 1127 ± 129 | 1290 ± 65 | 40 ± 5 |
| DAY 56 | — | — | 991 ± 201 | 30 ± 2 | 1481 ± 131 | 1224 ± 141 | 1370 ± 70 | 39 ± 4 |
| DAY 59 | — | — | 1149 ± 228 | 33 ± 4 | 1739 ± 182 | 1325 ± 163 | 1514 ± 81 | 37 ± 3 |
| DAY 63 | — | — | 1421 ± 328 | 35 ± 3 | — | 1510 ± 258 | 1783 ± 128 | 42 ± 4 |
| DAY 67 | — | — | — | 32 ± 3 | — | — | 1844 ± 112 | 33 ± 2 |
| DAY 70 | — | — | — | 33 ± 5 | — | — | — | 28 ± 2 |
| DAY 74 | — | — | — | 41 ± 8 | — | — | — | 32 ± 2 |
| DAY 77 | — | — | — | 50 ± 10 | — | — | — | 31 ± 3 |
| DAY 80 | — | — | — | 56 ± 15 | — | — | — | 31 ± 2 |
| DAY 83 | — | — | — | 63 ± 16 | — | — | — | 38 ± 4 |
| DAY 87 | — | — | — | 87 ± 26 | — | — | — | 28 ± 1 |
| DAY 90 | — | — | — | 84 ± 26 | — | — | — | 32 ± 2 |
| DAY 94 | — | — | — | 137 ± 49 | — | — | — | 30 ± 2 |
| DAY 97 | — | — | — | 129 ± 47 | — | — | — | 31 ± 3 |
| DAY 102 | — | — | — | 153 ± 55 | — | — | — | 26 ± 2 |
| DAY 105 | — | — | — | 176 ± 66 | — | — | — | 31 ± 2 |
| DAY 108 | — | — | — | 232 ± 93 | — | — | — | 28 ± 3 |
| DAY 111 | — | — | — | 271 ± 102 | — | — | — | 26 ± 2 |
| DAY 115 | — | — | — | 323 ± 134 | — | — | — | 31 ± 3 |
| DAY 118 | — | — | — | 318 ± 137 | — | — | — | 26 ± 4 |
| DAY 122 | — | — | — | 399 ± 176 | — | — | — | 31 ± 4 |

Example 17

Cysteine Mutant Generation for Site-Specific Conjugation

Anti-Notch3 ADCs described in the previous Examples were generated through conventional, non-specific conjugation of linker-payloads to cysteine amino acid residues of the target antibody. Site-specific conjugation of linker-payloads to antibodies was conducted to facilitate homogeneous drug loading and avoid ADC subpopulations with potentially altered antigen-binding or pharmacokinetics properties, which may be observed in some ADCs generated by conventional conjugation methods. One such site-specific conjugation strategy has been designed to introduce cysteine residues at specific sites in the amino acid sequence of the target antibody. A number of amino acid positions in the constant heavy chain and constant light chain were identified, as described in International Publication No. WO/2013/093809, and substituted with a cysteine residue at the specific amino acid position in the hu28 antibody.

Site-specific cysteine substitutions were engineered into the Fc polypeptide or human IgG1 heavy chain constant domain (Cγ) at positions L443 and K392 (herein L443C and K392C). Site-specific cysteine substitutions were engineered into the human kappa (κ) light chain constant domain (Cκ) polypeptide at position K183 (herein κK183C). CDRs of cysteine mutants remain the same as parental wildtype hu28. FIGS. 17A and 17B provide the amino acid and nucleotide sequences of the hu28 antibody with the site-specific cysteine substitutions described. Cysteine substitutions in the hu28 antibody resulted in the generation of the following antibodies: hu28-(L443C), hu28-(L443C/K392C) and hu28-(L443C/κK183C). All cysteine mutations were constructed by site-directed mutagenesis, as described in International Publication No. WO/2013/093809. Expression constructs for these mutant antibodies were generated in the site-specific integration (SSI) expression vector (Lonza) for stable expression in CHO cells. Stable pools of transfected CHO cells expressing the cysteine mutant antibodies were established and conditioned media generated. Standard Protein A affinity purification followed by size exclusion chromatography were employed to purify the anti-Notch3 cysteine mutant antibodies from conditioned media, as described in previous Examples.

Example 18

Characterization of Cysteine Mutants

Unconjugated cysteine mutant humanized anti-Notch3 antibodies were screened for cell surface binding activity to Notch3 expressing cell lines in a cell-based ELISA, as described in previous Examples. Table 29 shows $EC_{50}$ (nM) values calculated from cell surface Notch3 binding ELISAs for unconjugated cysteine mutants, hu28-(L443C), hu28-(L443/K382) and hu28-(L443/κK183C). The data demonstrates that the cysteine mutant antibodies have $EC_{50}$ values that are similar to the parental wildtype hu28 antibody in binding to full-length human Notch3 expressed on the cell surface of U2OS/hNotch3, HCC2429 and OVCAR3 cells. Further, the data demonstrates that substitution of cysteine amino acids into the constant regions of the heavy chain or both the heavy and light chains of the humanized hu28 antibody did not affect or alter their binding characteristics. The negative control huNeg8.8 antibody did not bind any of the cell lines tested. For the control antibody that lacked binding (LB), $EC_{50}$ values were not generated as indicated.

TABLE 29

$EC_{50}$ (nM) values for unconjugated cysteine mutant anti-Notch3 antibodies

| | $EC_{50}$ (nM Ab/ml) | | | |
|---|---|---|---|---|
| Antibody | U2OS/hNotch3 | HCC2429 | | OVCAR3 |
| hu28 VH1.0/VL1.0 | 0.3 | 0.26 | 0.10 | 0.46 |
| hu28-(L443C) | 0.28 | 0.30 | 0.08 | 0.20 |
| hu28-(L443C/κK183C) | 0.38 | 0.27 | 0.11 | 0.20 |

TABLE 29-continued $EC_{50}$ (nM) values for unconjugated cysteine mutant anti-Notch3 antibodies

| | $EC_{50}$ (nM Ab/ml) | | |
|---|---|---|---|
| Antibody | U2OS/hNotch3 | HCC2429 | OVCAR3 |
| hu28-(L443C/K392C) | 0.31 | 0.29 | 0.11 | 0.31 |
| huNeg8.8 | LB | — | LB | LB |

Example 19

In Vitro Cytotoxicity Assay of Cysteine Mutant ADCs

The conjugation of maleimide functionalized linker-payloads to the anti-Notch3 hu28 cysteine mutant antibodies was achieved via complete reduction of the antibodies with 100-fold molar excess of tris(2-carboxyethyl)phosphine (TCEP) in 100 mM HEPES (4-(2-hydroxyethyl)-1-piperazineethanesulfonic acid buffer), pH 7.0 and 1 mM diethylenetriaminepentaacetic acid (DTPA) for 2 hours at 37° C. followed by desalting to remove excess TCEP. The reduced antibodies were incubated in 2 mM dehydro ascorbic acid (DHA), 100 mM HEPES, pH 7.0 and 1 mM DTPA for 16 hours at 4° C. to reform the inter-chain disulfide bonds. After desalting, the vc0101 linker-payload was added to the reaction mixture at a linker-payload/antibody molar ratio of about 7 and reacted for an additional 1 hour at 25° C. in the presence of 15% v/v of dimethylacetamide (DMA). After the 1 hour incubation period, 6-fold excess L-Cys was added to quench any unreacted linker-payload. The reaction mixture was dialyzed overnight at 4° C. in phosphate buffered saline (PBS), pH 7.4, and purified via SEC (AKTA explorer, Superdex 200). The ADC was further characterized via SEC for purity, hydrophobic interaction chromatography (HIC), and liquid chromatography electrospray ionization tandem mass spectrometry (LC-ESI MS) to calculate drug-antibody ratio (loading). The protein concentration was determined via UV spectrophotometer. Additional conjugation techniques are described in International Publication No. WO/2013/093809.

This process generated the anti-Notch3 cysteine mutant ADCs: hu28-(L443C)-vc0101 and hu28-(L443C/κK183C)-vc0101. The activity of the anti-Notch3 cysteine mutant ADCs were assessed on cell lines endogenously expressing Notch3 protein: HCC2429 (lung cancer) and OVCAR3 (ovarian cancer) using an MTS cellular viability indicator as described in previous Examples.

Table 30 shows $IC_{50}$ (ng Ab/mL) values of the anti-Notch3 cysteine mutant ADC treatments. The data demonstrate that hu28-(L443C/κK183C)-vc0101 with a DAR=3.9 was active and had similar potency to the wildtype hu28-vc0101 ADC with DAR=3.9, and both induced cell death in the Notch3 expressing cancer cell lines HCC2429 and OVCAR3. The data further demonstrates that the single cysteine mutant hu28-(L443)-vc0101 with a DAR=2 and the non-targeted control huNeg8.8 ADC with DAR=4 were minimally active at the highest doses tested.

TABLE 30

$IC_{50}$ (ng Ab/mL) values of cysteine mutant humanized anti-Notch3 ADCs.

| | | $IC_{50}$ (ng Ab/ml) | | | | | |
|---|---|---|---|---|---|---|---|
| ADC | DAR | HCC2429 | | | OVCAR3 | | |
| hu28-vc0101 | 3.9 | 124 | 463 | 145 | 404 | 1450 | 1173 |
| hu28-(L443C)-vc0101 | 2 | 20308 | 16879 | 14324 | 13129 | 15840 | 12189 |

TABLE 30-continued

IC$_{50}$ (ng Ab/mL) values of cysteine mutant humanized anti-Notch3 ADCs.

| ADC | DAR | IC$_{50}$ (ng Ab/ml) | | | | | |
|---|---|---|---|---|---|---|---|
| | | HCC2429 | | | OVCAR3 | | |
| hu28-(L443C/κK183C)-vc0101 | 3.9 | 219 | 352 | 10 | 3020 | 3673 | 1250 |
| huNeg8.8-vc0101 | 4.0 | 18850 | 13944 | 18302 | 9944 | 9826 | 7564 |

Example 20

In Vivo Efficacy of Cysteine Mutant ADCs

Similar in vivo experiments were performed with the anti-Notch3 cysteine mutant ADCs using the OVCAR3 ovarian cell line as described in previous Examples. The OVCAR3 model was dosed intravenously Q4d×4 with PBS vehicle, hu28-vc0101, anti-hu28-(L443C)-vc0101, hu28-(L443C/κK183C)-vc0101, and control huNeg-8.8 ADC at the doses provided in Table 31. The data demonstrates that the double cysteine mutant hu28-(L443C/κK183C)-vc0101 inhibited growth of OVCAR3 ovarian xenografts with activity similar to wildtype hu28-vc0101 at the 3 mg/kg dose, but less at the 1 mg/kg dose. The data further demonstrates that the single cysteine mutant hu28-(L443C)-vc0101 with DAR=2 was efficacious in vivo, but was less active than the wildtype hu28-vc0101 and hu28-(L443C/κK183C)-vc0101 at both the 3 1 mg/kg and 3 mg/kg doses. The data indicates that anti-Notch3 cysteine mutant ADCs generated by site-specific conjugation are efficacious in vivo and inhibit tumor growth.

TABLE 31

In vivo efficacy of anti-Notch3 cysteine mutant ADCs in OVCAR3 ovarian xenograft OVCAR3 Ovarian Xenografts, tumor volume (mm3 ± S.E.M.)

| | PBS | hu28-vc0101 | | hu28-(L443C)-vc0101 | | hu28-(L443C/κK183C)-vc0101 | | huNeg8.8-vc0101 | |
|---|---|---|---|---|---|---|---|---|---|
| | 0 | 1 | 3 | 1 | 3 | 1 | 3 | 1 | 3 |
| DAY −2 | 161 ± 10 | 160 ± 13 | 160 ± 10 | 160 ± 10 | 160 ± 7 | 160 ± 11 | 159 ± 12 | 160 ± 11 | 160 ± 10 |
| DAY 2 | 248 ± 27 | 249 ± 28 | 246 ± 21 | 235 ± 17 | 244 ± 16 | 247 ± 31 | 247 ± 24 | 245 ± 34 | 265 ± 18 |
| DAY 6 | 312 ± 32 | 257 ± 30 | 219 ± 19 | 295 ± 23 | 259 ± 17 | 281 ± 39 | 223 ± 24 | 323 ± 43 | 325 ± 31 |
| DAY 9 | 404 ± 42 | 282 ± 29 | 192 ± 13 | 346 ± 26 | 240 ± 20 | 322 ± 35 | 169 ± 25 | 394 ± 51 | 386 ± 26 |
| DAY 12 | 477 ± 61 | 257 ± 28 | 133 ± 10 | 359 ± 35 | 198 ± 23 | 325 ± 41 | 133 ± 21 | 454 ± 60 | 400 ± 36 |
| DAY 15 | 590 ± 71 | 263 ± 24 | 99 ± 9 | 349 ± 49 | 142 ± 15 | 331 ± 51 | 98 ± 11 | 524 ± 72 | 433 ± 43 |
| DAY 19 | 655 ± 95 | 236 ± 34 | 73 ± 5 | 383 ± 63 | 115 ± 13 | 319 ± 62 | 76 ± 5 | 585 ± 89 | 466 ± 42 |
| DAY 22 | 742 ± 99 | 251 ± 40 | 63 ± 5 | 427 ± 77 | 94 ± 9 | 363 ± 89 | 68 ± 5 | 666 ± 101 | 452 ± 45 |
| DAY 26 | 831 ± 135 | 303 ± 49 | 63 ± 5 | 519 ± 101 | 85 ± 12 | 473 ± 123 | 63 ± 4 | 780 ± 108 | 497 ± 70 |
| DAY 29 | 1008 ± 171 | 396 ± 69 | 56 ± 4 | 624 ± 118 | 97 ± 14 | 583 ± 167 | 54 ± 3 | 834 ± 124 | 555 ± 80 |
| DAY 33 | 1168 ± 201 | 555 ± 96 | 58 ± 4 | 789 ± 138 | 114 ± 28 | 691 ± 194 | 58 ± 4 | 1007 ± 155 | 695 ± 88 |
| DAY 36 | 1207 ± 81 | 683 ± 125 | 56 ± 6 | 942 ± 164 | 146 ± 39 | 872 ± 246 | 48 ± 2 | 1152 ± 155 | 782 ± 93 |
| DAY 40 | 1330 ± 91 | 811 ± 144 | 58 ± 8 | 1046 ± 191 | 205 ± 56 | 1128 ± 311 | 46 ± 3 | 1328 ± 220 | 872 ± 131 |
| DAY 42 | 1363 ± 111 | 850 ± 157 | 55 ± 10 | 1130 ± 190 | 246 ± 71 | 955 ± 247 | 51 ± 5 | 1307 ± 200 | 910 ± 130 |
| DAY 47 | 1656 ± 98 | 1121 ± 197 | 76 ± 23 | 1493 ± 243 | 378 ± 103 | 1140 ± 255 | 44 ± 2 | 1470 ± 223 | 1032 ± 116 |
| DAY 50 | 1661 ± 95 | 1107 ± 204 | 74 ± 25 | — | 452 ± 131 | 1152 ± 248 | 40 ± 2 | — | 1101 ± 110 |
| DAY 54 | 2005 ± 140 | 1322 ± 228 | 102 ± 40 | — | 604 ± 184 | 1463 ± 317 | 48 ± 4 | — | 1272 ± 161 |
| DAY 57 | — | 1286 ± 235 | 117 ± 51 | — | 826 ± 264 | — | 43 ± 4 | — | 1270 ± 120 |
| DAY 61 | — | — | 152 ± 69 | — | 820 ± 248 | — | 63 ± 10 | — | 1610 ± 160 |
| DAY 64 | — | — | 182 ± 88 | — | — | — | 55 ± 9 | — | — |

TABLE 31-continued

In vivo efficacy of anti-Notch3 cysteine mutant ADCs in OVCAR3 ovarian xenograft OVCAR3 Ovarian Xenografts, tumor volume (mm3 ± S.E.M.)

| | PBS | hu28-vc0101 | | hu28-(L443C)-vc0101 | | hu28-(L443C/κK183C)-vc0101 | | huNeg8.8-vc0101 | |
|---|---|---|---|---|---|---|---|---|---|
| | 0 | 1 | 3 | 1 | 3 | 1 | 3 | 1 | 3 |
| DAY 68 | — | — | 217 ± 102 | — | — | — | 67 ± 15 | — | — |
| DAY 71 | — | — | 242 ± 120 | — | — | — | 73 ± 20 | — | — |
| DAY 75 | — | — | 286 ± 146 | — | — | — | 84 ± 24 | — | — |
| DAY 78 | — | — | — | — | — | — | 107 ± 32 | — | — |
| DAY 82 | — | — | — | — | — | — | 99 ± 36 | — | — |
| DAY 85 | — | — | — | — | — | — | 119 ± 50 | — | — |
| DAY 89 | — | — | — | — | — | — | 173 ± 63 | — | — |
| DAY 99 | — | — | — | — | — | — | 328 ± 130 | — | — |
| DAY 111 | — | — | — | — | — | — | 525 ± 203 | — | — |

What is claimed:

1. An isolated antibody, or antigen-binding fragment thereof, that binds to Notch3 comprising:
   a VH CDR1, a VH CDR2, and a VH CDR3 of a heavy chain variable region (VH) comprising the amino acid sequence set forth in SEQ ID NO: 13; and
   a VL CDR1, a VL CDR2, and a VL CDR3 of a light chain variable region (VL) comprising the amino acid sequence set forth in SEQ ID NO: 25.

2. The isolated antibody, or antigen-binding fragment thereof, of claim 1, wherein the antibody or antigen-binding fragment:
   (a) internalizes into a cell,
   (b) does not inhibit Notch3 signaling, or
   (c) does not activate Notch3 signaling.

3. The isolated antibody, or antigen-binding fragment thereof, of claim 1, wherein the antibody or antigen-binding fragment:
   (a) binds to the Lin 12/Notch repeat (LNR)-C and heterodimerization (HD)-1 domains of the Notch3 Negative Regulatory Region (NRR),
   (b) does not maintain the Notch3 NRR in an auto-inhibitory conformation, or
   (c) does not inhibit S2-cleavage.

4. The isolated antibody, or antigen-binding fragment thereof, of claim 1, comprising:
   a VH CDR1 comprising the amino acid sequence of SEQ ID NO: 15 or 16; a VH CDR2 comprising the amino acid sequence of SEQ ID NO: 19 or 20; a VH CDR3 comprising the amino acid sequence of SEQ ID NO: 23; a VL CDR1 comprising the amino acid sequence of SEQ ID NO: 27; a VL CDR2 comprising the amino acid sequence of SEQ ID NO: 29; and a VL CDR3 comprising the amino acid sequence of SEQ ID NO: 31.

5. The isolated antibody, or antigen-binding fragment thereof, of claim 1, comprising a heavy chain variable region having an amino acid sequence that is at least 90% identical to SEQ ID NO: 13 or a light chain variable region having an amino acid sequence that is at least 90% identical to SEQ ID NO: 25.

6. The isolated antibody, or antigen-binding fragment thereof, of claim 5, comprising a heavy chain variable region amino acid sequence of SEQ ID NO: 13.

7. The isolated antibody, or antigen-binding fragment thereof, of claim 6, comprising a heavy chain amino acid sequence of SEQ ID NO: 33.

8. The isolated antibody, or antigen-binding fragment thereof, of claim 5, comprising a light chain variable region amino acid sequence of SEQ ID NO: 25.

9. The isolated antibody, or antigen-binding fragment thereof, of claim 8, comprising a light chain amino acid sequence of SEQ ID NO: 35.

10. An antibody-drug conjugate comprising a cytotoxic agent conjugated to the antibody, or antigen-binding fragment thereof, of claim 1.

11. A pharmaceutical composition comprising the antibody-drug conjugate of claim 10 and a pharmaceutically acceptable carrier.

12. A composition comprising the antibody of claim 1.

13. An isolated antibody, or antigen-binding fragment thereof, that binds to Notch3 comprising:
   a VH CDR1, a VH CDR2, and a VH CDR3 of a heavy chain variable region (VH) comprising the amino acid sequence set forth in SEQ ID NO: 37; and
   a VL CDR1, a VL CDR2, and a VL CDR3 of a light chain variable region (VL) comprising the amino acid sequence set forth in SEQ ID NO: 49.

14. An isolated antibody, or antigen-binding fragment thereof, of claim 13, comprising:
   a VH CDR1 comprising the amino acid sequence of SEQ ID NO: 39 or 40; a VH CDR2 comprising the amino acid sequence of SEQ ID NO: 43 or 44; a VH CDR3 comprising the amino acid sequence of SEQ ID NO: 47; a VL CDR1 comprising the amino acid sequence of SEQ ID NO: 51; a VL CDR2 comprising the amino acid sequence of SEQ ID NO: 53; and a VL CDR3 comprising the amino acid sequence of SEQ ID NO: 55.

15. The isolated antibody, or antigen-binding fragment thereof, of claim 13, comprising a heavy chain variable region having an amino acid sequence that is at least 90% identical to SEQ ID NO: 37 or a light chain variable region having an amino acid sequence that is at least 90% identical to SEQ ID NO: 49.

16. The isolated antibody, or antigen-binding fragment thereof, of claim 15, comprising a heavy chain variable region amino acid sequence of SEQ ID NO: 37.

17. The isolated antibody, or antigen-binding fragment thereof, of claim 16, comprising a heavy chain amino acid sequence of SEQ ID NO: 57.

18. The isolated antibody, or antigen-binding fragment thereof, of claim 15, comprising a light chain variable region amino acid sequence of SEQ ID NO: 49.

19. The isolated antibody, or antigen-binding fragment thereof, of claim 18, comprising a light chain amino acid sequence of SEQ ID NO: 59.

20. An antibody-drug conjugate comprising a cytotoxic agent conjugated to the antibody, or antigen-binding fragment thereof, of claim 13.

21. A pharmaceutical composition comprising the antibody-drug conjugate of claim 20 and a pharmaceutically acceptable carrier.

22. A composition comprising the antibody of claim 13.

23. An antibody-drug conjugate of the formula:

Ab-(L-D)p, wherein:
   (a) Ab is an antibody, or antigen-binding fragment thereof, that binds to Notch3;
   (b) L-D is a linker-drug moiety, wherein L is a linker selected from the group consisting of maleimido-caproyl-valine-citrulline-p-aminobenzyloxycarbonyl (vc), maleimidocaproyl (mc), maleimido-heptanoyl (me) and maleimido-Peg6C2 (MalPeg6C2) and D is a drug selected from the group consisting of:

(i) 0101 having the formula:

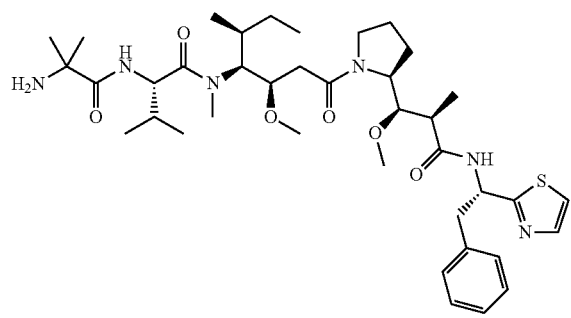

(ii) 6780 having the formula:

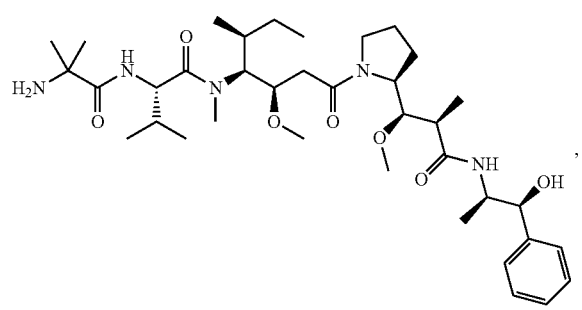 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)C(C)(C)N)C(C)C]

(iii) 0131 having the formula:

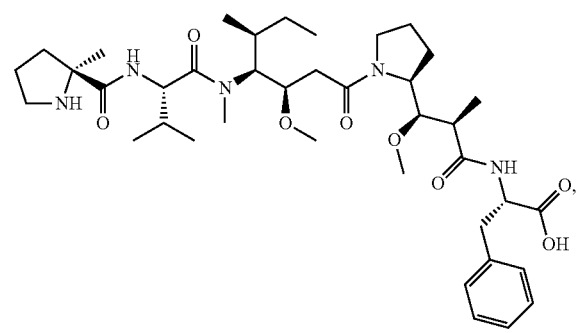 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@]1(C)CCCN1)C(C)C]

(iv) 3377 having the formula:

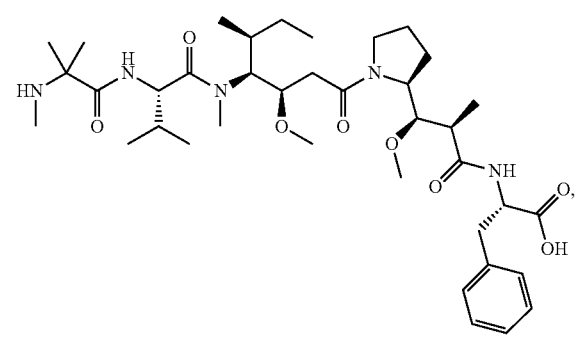 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)C(C)(C)NC)C(C)C]

and (v) 8261 having the formula:

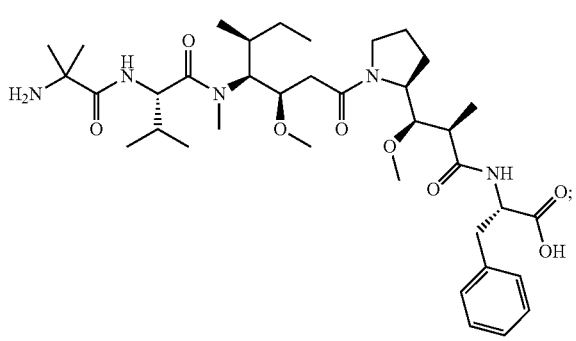 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)C(C)(C)N)C(C)C]

and (c) p is an integer from 1 to 12.

24. A pharmaceutical composition comprising the antibody-drug conjugate of claim 23 and a pharmaceutically acceptable carrier.

25. The antibody-drug conjugate of claim 23, wherein Ab comprises:

a VH CDR1, a VH CDR2, and a VH CDR3 of a heavy chain variable region (VH) comprising the amino acid sequence set forth in SEQ ID NO: 13; and a VL CDR1, a VL CDR2, and a VL CDR3 of a light chain variable region (VL) comprising the amino acid sequence set forth in SEQ ID NO: 25; or a VH CDR1, a VH CDR2, and a VH CDR3 of a heavy chain variable region (VH) comprising the amino acid sequence set forth in SEQ ID NO: 37; and a VL CDR1, a VL CDR2, and a VL CDR3 of a light chain variable region (VL) comprising the amino acid sequence set forth in SEQ ID NO: 49.

26. The antibody-drug conjugate of claim 23, wherein Ab comprises:

a VH CDR1 comprising the amino acid sequence of SEQ ID NO: 15 or 16; a VH CDR2 comprising the amino acid sequence of SEQ ID NO: 19 or 20; a VH CDR3 comprising the amino acid sequence of SEQ ID NO: 23; a VL CDR1 comprising the amino acid sequence of SEQ ID NO: 27; a VL CDR2 comprising the amino acid sequence of SEQ ID NO: 29; and a VL CDR3 comprising the amino acid sequence of SEQ ID NO: 31; or a VH CDR1 comprising the amino acid sequence of SEQ ID NO: 39 or 40; a VH CDR2 comprising the amino acid sequence of SEQ ID NO: 43 or 44; a VH CDR3 comprising the amino acid sequence of SEQ ID NO: 47; a VL CDR1 comprising the amino acid sequence of SEQ ID NO: 51; a VL CDR2 comprising the amino acid sequence of SEQ ID NO: 53; and a VL CDR3 comprising the amino acid sequence of SEQ ID NO: 55.

27. The antibody-drug conjugate of claim 26, wherein Ab comprises:

a heavy chain variable region having an amino acid sequence that is at least 90% identical to SEQ ID NO: 13 or a light chain variable region having an amino acid sequence that is at least 90% identical to SEQ ID NO: 25; or a heavy chain variable region having an amino acid sequence that is at least 90% identical to SEQ ID NO:

37 or a light chain variable region having an amino acid sequence that is at least 90% identical to SEQ ID NO: 49.

28. The antibody-drug conjugate of claim 27, wherein Ab comprises a heavy chain variable region amino acid sequence of SEQ ID NO: 13; or a heavy chain variable region amino acid sequence of SEQ ID NO: 37.

29. The antibody-drug conjugate of claim 28, wherein Ab comprises a heavy chain amino acid sequence of SEQ ID NO: 33; or a heavy chain amino acid sequence of SEQ ID NO: 57.

30. The antibody-drug conjugate of claim 27, wherein Ab comprises a light chain variable region amino acid sequence of SEQ ID NO: 25 or a light chain variable region amino acid sequence of SEQ ID NO: 49.

31. The antibody-drug conjugate of claim 30, wherein Ab comprises a light chain amino acid sequence of SEQ ID NO: 35; or a light chain amino acid sequence of SEQ ID NO: 59.

32. An antibody-drug conjugate of the formula:

Ab-(L-D)p, wherein:
(a) Ab is an antibody, or antigen-binding fragment thereof, that binds to Notch3,
(b) L-D is a linker-drug moiety, wherein L is a linker and D is a drug, wherein L-D is selected from the group consisting of:
vc0101 having the formula:

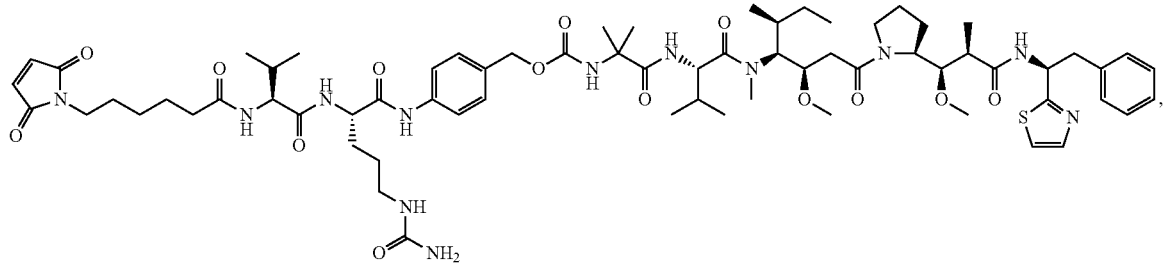 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)C(C)(C)NC(=O)OCc1ccc(NC(=O)[C@H](CCCNC(N)=O)NC(=O)[C@@H](NC(=O)CCCCCN2C(=O)C=CC2=O)C(C)C)cc1)C(C)C]

and vc6780 having the formula:

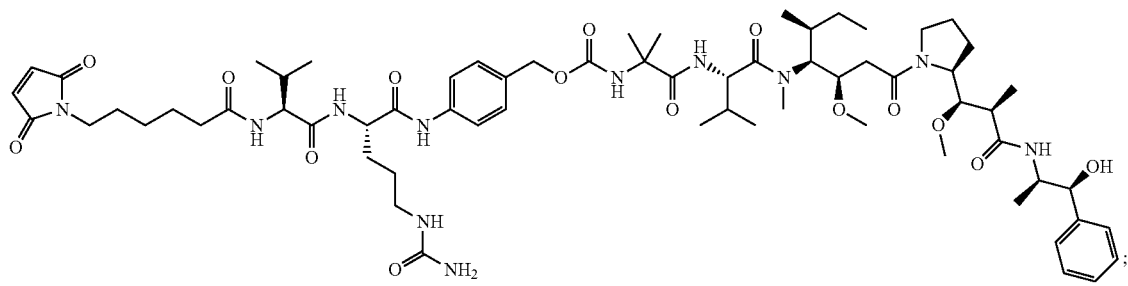 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)C(C)(C)NC(=O)OCc1ccc(NC(=O)[C@H](CCCNC(N)=O)NC(=O)[C@@H](NC(=O)CCCCCN2C(=O)C=CC2=O)C(C)C)cc1)C(C)C]

and
(c) p is an integer from 1 to 12.

33. A pharmaceutical composition comprising the antibody-drug conjugate of claim 32 and a pharmaceutically acceptable carrier.

34. The antibody-drug conjugate of claim 32, wherein Ab comprises:
a VH CDR1, a VH CDR2, and a VH CDR3 of a heavy chain variable region (VH) comprising the amino acid sequence set forth in SEQ ID NO: 13; and a VL CDR1, a VL CDR2, and a VL CDR3 of a light chain variable region (VL) comprising the amino acid sequence set forth in SEQ ID NO: 25; or
a VH CDR1, a VH CDR2, and a VH CDR3 of a heavy chain variable region (VH) comprising the amino acid sequence set forth in SEQ ID NO: 37; and a VL CDR1, a VL CDR2, and a VL CDR3 of a light chain variable region (VL) comprising the amino acid sequence set forth in SEQ ID NO: 49.

35. The antibody-drug conjugate of claim 32, wherein Ab comprises:
a VH CDR1 comprising the amino acid sequence of SEQ ID NO: 15 or 16; a VH CDR2 comprising the amino acid sequence of SEQ ID NO: 19 or 20; a VH CDR3 comprising the amino acid sequence of SEQ ID NO: 23; a VL CDR1 comprising the amino acid sequence of SEQ ID NO: 27; a VL CDR2 comprising the amino acid sequence of SEQ ID NO: 29; and a VL CDR3 comprising the amino acid sequence of SEQ ID NO: 31; or
a VH CDR1 comprising the amino acid sequence of SEQ ID NO: 39 or 40; a VH CDR2 comprising the amino acid sequence of SEQ ID NO: 43 or 44; a VH CDR3 comprising the amino acid sequence of SEQ ID NO: 47; a VL CDR1 comprising the amino acid sequence of SEQ ID NO: 51; a VL CDR2 comprising the amino acid sequence of SEQ ID NO: 53; and a VL CDR3 comprising the amino acid sequence of SEQ ID NO: 55.

36. The antibody-drug conjugate of claim 35, wherein Ab comprises:
a heavy chain variable region having an amino acid sequence that is at least 90% identical to SEQ ID NO: 13 or a light chain variable region having an amino acid sequence that is at least 90% identical to SEQ ID NO: 25; or
a heavy chain variable region having an amino acid sequence that is at least 90% identical to SEQ ID NO: 37 or a light chain variable region having an amino acid sequence that is at least 90% identical to SEQ ID NO: 49.

37. The antibody-drug conjugate of claim 36, wherein Ab comprises a heavy chain variable region amino acid sequence of SEQ ID NO: 13; or a heavy chain variable region amino acid sequence of SEQ ID NO: 37.

38. The antibody-drug conjugate of claim 37, wherein Ab comprises a heavy chain amino acid sequence of SEQ ID NO: 33; or a heavy chain amino acid sequence of SEQ ID NO: 57.

39. The antibody-drug conjugate of claim 36, wherein Ab comprises a light chain variable region amino acid sequence of SEQ ID NO: 25 or a light chain variable region amino acid sequence of SEQ ID NO: 49.

40. The antibody-drug conjugate of claim 39, wherein Ab comprises a light chain amino acid sequence of SEQ ID NO: 35; or a light chain amino acid sequence of SEQ ID NO: 59.

41. An antibody-drug conjugate of the formula:

Ab-(L-D)p, wherein:
(a) Ab is an antibody, or antigen-binding fragment thereof, that binds to Notch3 comprising a VH CDR1, a VH CDR2 and a VH CDR3 of a heavy chain variable region (VH) comprising the amino acid sequence set forth in SEQ ID NO: 13 and a VL CDR1, a VL CDR2 and VL CDR3 of a light chain variable region (VL) comprising the amino acid sequence set forth in SEQ ID NO: 25;
(b) L-D is a linker-drug moiety, wherein L is a linker, and D is a drug; and
(c) p is an integer from 1 to 12.

42. The antibody-drug conjugate of claim 41, wherein L is selected from the group consisting of maleimidocaproyl-valine-citrulline-p-aminobenzyloxycarbonyl (vc), maleimidocaproyl (mc), maleimido-heptanoyl (me) and maleimido-Peg6C2 (MalPeg6C2).

43. The antibody-drug conjugate of claim 42, wherein D is selected from the group consisting of:
(a) 0101 having the formula:

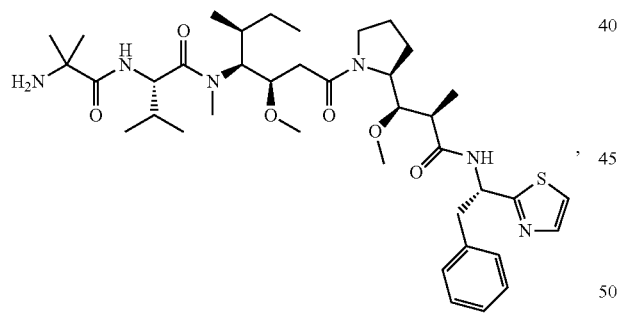

(b) 6780 having the formula:

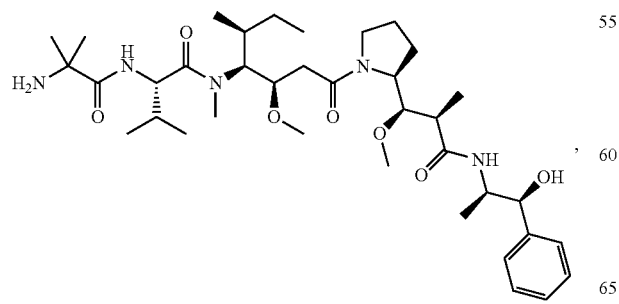

(c) 0131 having the formula:

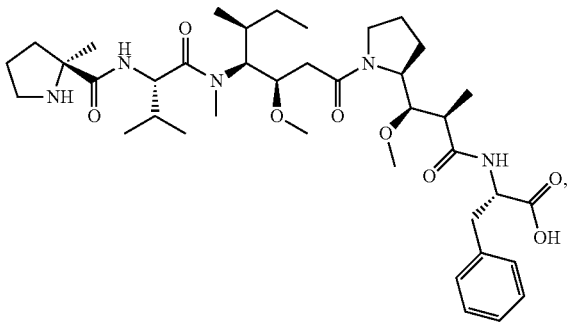 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@]1(C)CCCN1)C(C)C]

(d) 3377 having the formula:

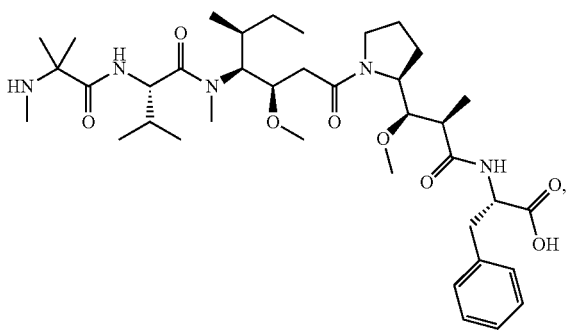 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)C(C)(C)NC)C(C)C]

and
(e) 8261 having the formula:

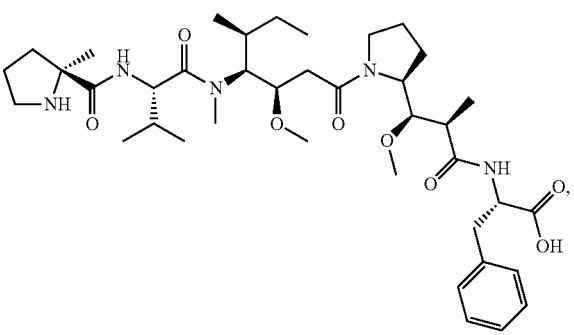 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@]1(C)CCCN1)C(C)C]

44. The antibody-drug conjugate of claim 41, wherein L-D is selected from the group consisting of:

vc0101 having the formula:

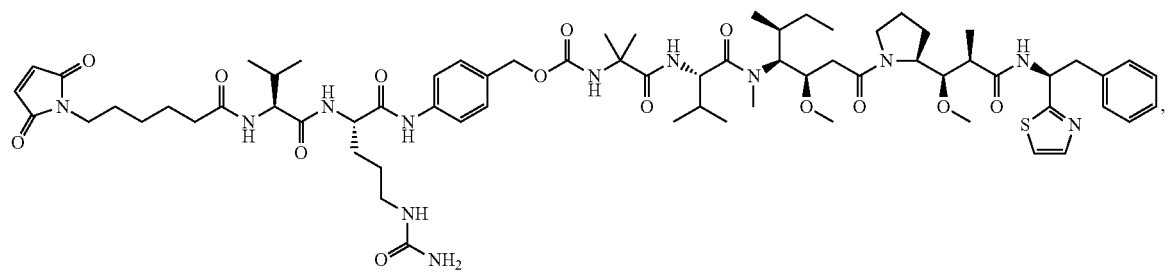 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)C(C)(C)NC(=O)OCc1ccc(NC(=O)[C@H](CCCNC(N)=O)NC(=O)[C@@H](NC(=O)CCCCCN2C(=O)C=CC2=O)C(C)C)cc1)C(C)C]

and vc6780 having the formula:

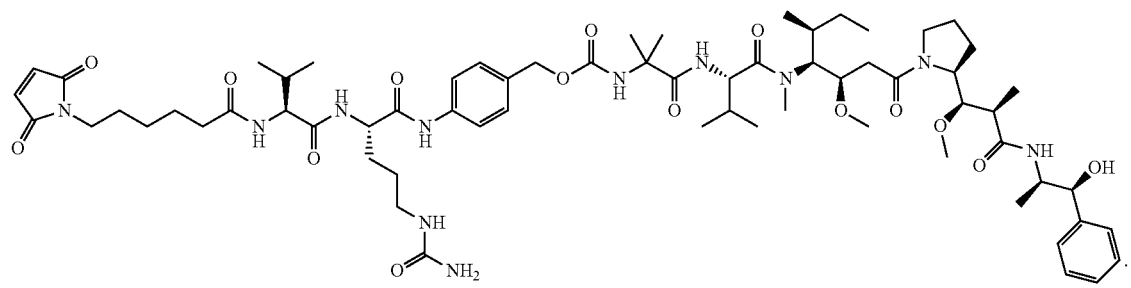 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)C(C)(C)NC(=O)OCc1ccc(NC(=O)[C@H](CCCNC(N)=O)NC(=O)[C@@H](NC(=O)CCCCCN2C(=O)C=CC2=O)C(C)C)cc1)C(C)C]

45. A pharmaceutical composition comprising the antibody-drug conjugate of claim 41 and a pharmaceutically acceptable carrier.

46. The antibody-drug conjugate of claim 41, wherein Ab comprises:
a VH CDR1 comprising the amino acid sequence of SEQ ID NO: 15 or 16; a VH CDR2 comprising the amino acid sequence of SEQ ID NO: 19 or 20; a VH CDR3 comprising the amino acid sequence of SEQ ID NO: 23; a VL CDR1 comprising the amino acid sequence of SEQ ID NO: 27; a VL CDR2 comprising the amino acid sequence of SEQ ID NO: 29; and a VL CDR3 comprising the amino acid sequence of SEQ ID NO: 31.

47. The antibody-drug conjugate of claim 41, wherein Ab comprises a heavy chain variable region having an amino acid sequence that is at least 90% identical to SEQ ID NO: 13 or a light chain variable region having an amino acid sequence that is at least 90% identical to SEQ ID NO: 25.

48. The antibody-drug conjugate of claim 47, wherein Ab comprises a heavy chain variable region amino acid sequence of SEQ ID NO: 13.

49. The antibody-drug conjugate of claim 48, wherein Ab comprises a heavy chain amino acid sequence of SEQ ID NO: 33.

50. The antibody-drug conjugate of claim 47, wherein Ab comprises a light chain variable region amino acid sequence of SEQ ID NO: 25.

51. The antibody-drug conjugate of claim 50, wherein Ab comprises a light chain amino acid sequence of SEQ ID NO: 35.

52. An antibody-drug conjugate of the formula:

Ab-(L-D)*p*, wherein:
(a) Ab is an antibody, or antigen-binding fragment thereof, that binds to Notch3 comprising a VH CDR1, a VH CDR2, and a VH CDR3 of a heavy chain variable region (VH) comprising the amino acid sequence set forth in SEQ ID NO: 37; and a VL CDR1, a VL CDR2, and a VL CDR3 of a light chain variable region (VL) comprising the amino acid sequence set forth in SEQ ID NO: 49;

(b) L-D is a linker-drug moiety, wherein L is a linker, and D is a drug; and (c) p is an integer from 1 to 12.

53. The antibody-drug conjugate of claim 52, wherein L is selected from the group consisting of maleimidocaproyl-valine-citrulline-p-aminobenzyloxycarbonyl (vc), maleimidocaproyl (mc), maleimido-heptanoyl (me) and maleimido-Peg6C2 (MalPeg6C2).

54. The antibody-drug conjugate of claim 53, wherein D is selected from the group consisting of:

(a) 0101 having the formula:

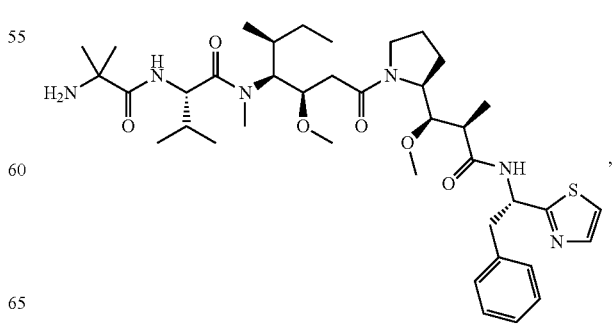

145
(b) 6780 having the formula:
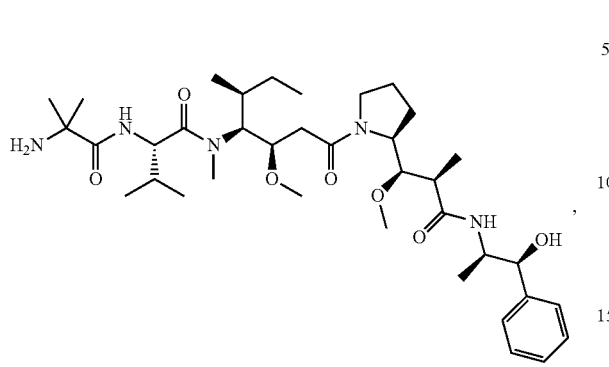
(c) 0131 having the formula:
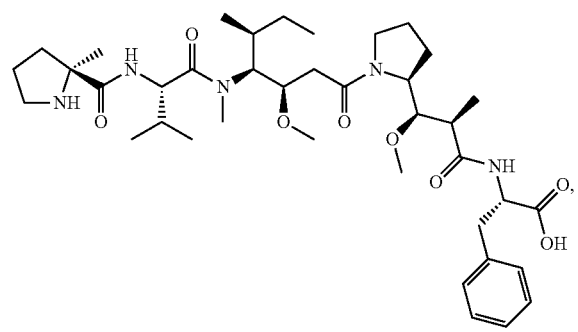 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@]1(C)CCCN1)C(C)C]
146
(d) 3377 having the formula:
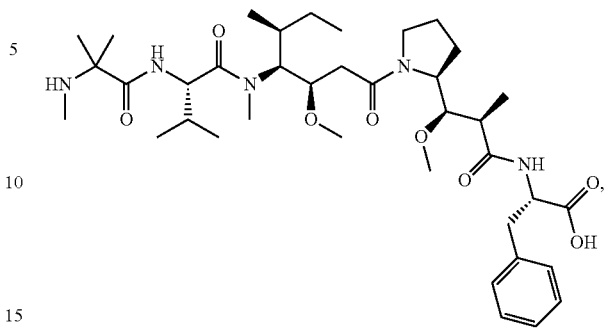
and
(e) 8261 having the formula:
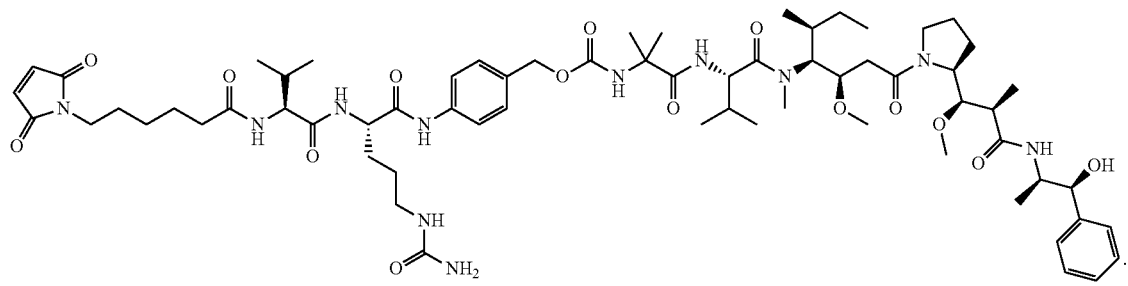 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)C(C)(C)NC(=O)OCc1ccc(NC(=O)[C@H](CCCNC(N)=O)NC(=O)[C@@H](NC(=O)CCCCCN2C(=O)C=CC2=O)C(C)C)cc1)C(C)C]
55. The antibody-drug conjugate of claim 52, wherein L-D is selected from the group consisting of:
vc0101 having the formula:
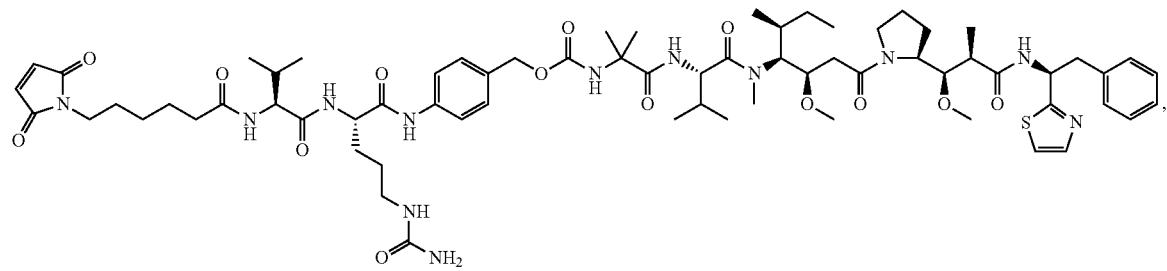 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)C(C)(C)NC(=O)OCc1ccc(NC(=O)[C@H](CCCNC(N)=O)NC(=O)[C@@H](NC(=O)CCCCCN2C(=O)C=CC2=O)C(C)C)cc1)C(C)C]
and vc6780 having the formula:
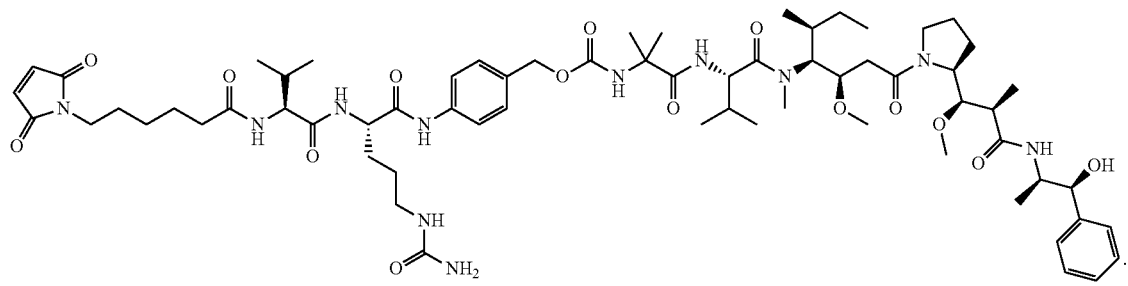 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)C(C)(C)NC(=O)OCc1ccc(NC(=O)[C@H](CCCNC(N)=O)NC(=O)[C@@H](NC(=O)CCCCCN2C(=O)C=CC2=O)C(C)C)cc1)C(C)C]

56. The antibody-drug conjugate of claim 52, wherein Ab comprises:
a VH CDR1 comprising the amino acid sequence of SEQ ID NO: 39 or 40; a VH CDR2 comprising the amino acid sequence of SEQ ID NO: 43 or 44; a VH CDR3 comprising the amino acid sequence of SEQ ID NO: 47; a VL CDR1 comprising the amino acid sequence of SEQ ID NO: 51; a VL CDR2 comprising the amino acid sequence of SEQ ID NO: 53; and a VL CDR3 comprising the amino acid sequence of SEQ ID NO: 55.

57. The antibody-drug conjugate of claim 52, wherein Ab comprises a heavy chain variable region having an amino acid sequence that is at least 90% identical to SEQ ID NO: 37 or a light chain variable region having an amino acid sequence that is at least 90% identical to SEQ ID NO: 49.

58. The antibody-drug conjugate of claim 57, wherein Ab comprises a heavy chain variable region amino acid sequence of SEQ ID NO: 37.

59. The antibody-drug conjugate of claim 58, wherein Ab comprises a heavy chain amino acid sequence of SEQ ID NO: 57.

60. The antibody-drug conjugate of claim 57, wherein Ab comprises a light chain variable region amino acid sequence of SEQ ID NO: 49.

61. The antibody-drug conjugate of claim 60, wherein Ab comprises a light chain amino acid sequence of SEQ ID NO: 59.

62. A pharmaceutical composition comprising the antibody-drug conjugate of claim 52 and a pharmaceutically acceptable carrier.

63. An antibody-drug conjugate of the formula:

Ab-(L-D)$p$, wherein:
(a) Ab is an antibody, or antigen-binding fragment thereof, comprising a heavy chain variable region amino acid sequence of SEQ ID NO: 13 and a light chain variable region amino acid sequence of SEQ ID NO 25;
(b) L-D is a linker-drug moiety, wherein L is a linker, and D is a drug, wherein the L-D is vc0101 having the formula

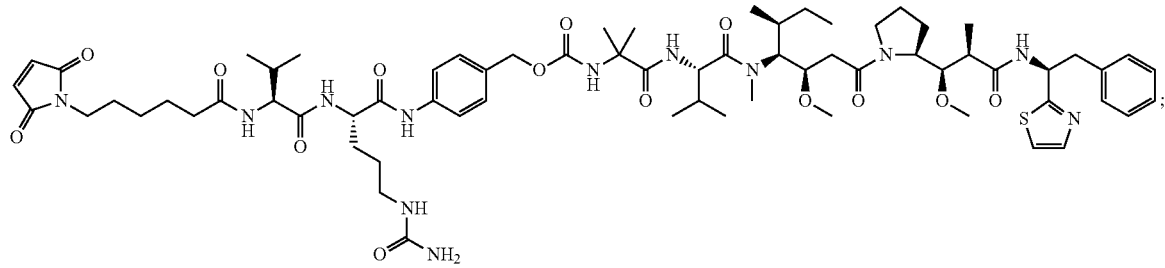 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)C(C)(C)NC(=O)OCc1ccc(NC(=O)[C@H](CCCNC(N)=O)NC(=O)[C@@H](NC(=O)CCCCCN2C(=O)C=CC2=O)C(C)C)cc1)C(C)C]

and
(c) p is an integer from 1 to 12.

64. A pharmaceutical composition comprising the antibody-drug conjugate of claim 63 and a pharmaceutically acceptable carrier.

* * * * *

SEQUENCE LISTING

<160> NUMBER OF SEQ ID NOS: 69

<210> SEQ ID NO 1
<211> LENGTH: 296
<212> TYPE: PRT
<213> ORGANISM: Artificial Sequence
<220> FEATURE:
<223> OTHER INFORMATION: Synthetic peptide sequence

<400> SEQUENCE: 1

```
Ala Pro Glu Val Ser Glu Glu Pro Arg Cys Pro Arg Ala Ala Cys Gln
1               5                   10                  15

Ala Lys Arg Gly Asp Gln Arg Cys Asp Arg Glu Cys Asn Ser Pro Gly
            20                  25                  30

Cys Gly Trp Asp Gly Gly Asp Cys Ser Leu Ser Val Gly Asp Pro Trp
        35                  40                  45

Arg Gln Cys Glu Ala Leu Gln Cys Trp Arg Leu Phe Asn Asn Ser Arg
    50                  55                  60

Cys Asp Pro Ala Cys Ser Ser Pro Ala Cys Leu Tyr Asp Asn Phe Asp
65                  70                  75                  80

Cys His Ala Gly Gly Arg Glu Arg Thr Cys Asn Pro Val Tyr Glu Lys
                85                  90                  95

Tyr Cys Ala Asp His Phe Ala Asp Gly Arg Cys Asp Gln Gly Cys Asn
            100                 105                 110

Thr Glu Glu Cys Gly Trp Asp Gly Leu Asp Cys Ala Ser Glu Val Pro
        115                 120                 125

Ala Leu Leu Ala Arg Gly Val Leu Val Leu Thr Val Leu Leu Pro Pro
    130                 135                 140

Glu Glu Leu Leu Arg Ser Ser Ala Asp Phe Leu Gln Arg Leu Ser Ala
145                 150                 155                 160

Ile Leu Arg Thr Ser Leu Arg Phe Arg Leu Asp Ala His Gly Gln Ala
                165                 170                 175
```

Met Val Phe Pro Tyr His Arg Pro Ser Pro Gly Ser Glu Pro Arg Ala
                180                 185                 190

Arg Arg Glu Leu Ala Pro Glu Val Ile Gly Ser Val Val Met Leu Glu
            195                 200                 205

Ile Asp Asn Arg Leu Cys Leu Gln Ser Pro Glu Asn Asp His Cys Phe
        210                 215                 220

Pro Asp Ala Gln Ser Ala Ala Asp Tyr Leu Gly Ala Leu Ser Ala Val
225                 230                 235                 240

Glu Arg Leu Asp Phe Pro Tyr Pro Leu Arg Asp Val Arg Gly Glu Pro
                245                 250                 255

Leu Glu Pro Pro Glu Pro Ser Val Pro Gly Gly Gly Ser Gly Gly Gly
            260                 265                 270

Leu Asn Asp Ile Phe Glu Ala Gln Lys Ile Glu Trp His Glu Gly Gly
        275                 280                 285

Pro Pro His His His His His His
            290                 295

<210> SEQ ID NO 2
<211> LENGTH: 888
<212> TYPE: DNA
<213> ORGANISM: Artificial Sequence
<220> FEATURE:
<223> OTHER INFORMATION: Synthetic nucleotide sequence

<400> SEQUENCE: 2
gcacccgagg tctcggagga gccgcggtgc ccgcgcgccg cctgccaggc caagcgcggg     60
gaccagcgct gcgaccgcga gtgcaacagc ccaggctgcg gctgggacgg cggcgactgc    120
tcgctgagcg tgggcgaccc ctggcggcaa tgcgaggcgc tgcagtgctg gcgcctcttc    180
aacaacagcc gctgcgaccc cgcctgcagc tcgcccgcct gcctctacga caacttcgac    240
tgccacgccg gtggccgcga gcgcacttgc aacccggtgt acgagaagta ctgcgccgac    300
cactttgccg acgccgctg cgaccagggc tgcaacacgg aggagtgcgg ctgggatggg    360
ctggattgtg ccagcgaggt gccggccctg ctggcccgcg cgtgctggt gctcacagtg    420 ctgctgccgc cggaggagct actgcgttcc agcgccgact ttctgcagcg gctcagcgcc    480
atcctgcgca cctcgctgcg cttccgcctg gacgcgcacg ccaggccat ggtcttccct    540 taccaccggc ctagtcctgg ctccgaaccc cgggcccgtc gggagctggc ccccgaggtg    600
atcggctcgg tagtaatgct ggagattgac aaccggctct gcctgcagtc gcctgagaat    660
gatcactgct tccccgatgc ccagagcgcc gctgactacc tgggagcgtt gtcagcggtg    720
gagcgcctgg acttcccgta cccactgcgg gacgtgcggg gggagccgct ggagcctcca    780
gaacccagcg tcccgggagg gggaagcgga ggcggactga cgacatctt cgaggctcag    840 aaaatcgaat ggcacgaagg tggcccacca catcatcatc atcatcac                 888

<210> SEQ ID NO 3
<211> LENGTH: 296
<212> TYPE: PRT
<213> ORGANISM: Artificial Sequence
<220> FEATURE:
<223> OTHER INFORMATION: Synthetic peptide sequence

<400> SEQUENCE: 3

Ala Pro Glu Val Pro Glu Glu Pro Arg Cys Pro Arg Ala Ala Cys Gln
1               5                   10                  15

Ala Lys Arg Gly Asp Gln Asn Cys Asp Arg Glu Cys Asn Thr Pro Gly
            20                  25                  30

```
Cys Gly Trp Asp Gly Asp Cys Ser Leu Asn Val Asp Asp Pro Trp
         35                  40                  45

Arg Gln Cys Glu Ala Leu Gln Cys Trp Arg Leu Phe Asn Asn Ser Arg
 50                  55                  60

Cys Asp Pro Ala Cys Ser Ser Pro Ala Cys Leu Tyr Asp Asn Phe Asp
 65                  70                  75                  80

Cys Tyr Ser Gly Gly Arg Asp Arg Thr Cys Asn Pro Val Tyr Glu Lys
                 85                  90                  95

Tyr Cys Ala Asp His Phe Ala Asp Gly Arg Cys Asp Gln Gly Cys Asn
                100                 105                 110

Thr Glu Glu Cys Gly Trp Asp Gly Leu Asp Cys Ala Ser Glu Val Pro
            115                 120                 125

Ala Leu Leu Ala Arg Gly Val Leu Val Leu Thr Val Leu Leu Pro Pro
        130                 135                 140

Glu Glu Leu Leu Arg Ser Ser Ala Asp Phe Leu Gln Arg Leu Ser Ala
145                 150                 155                 160

Ile Leu Arg Thr Ser Leu Arg Phe Arg Leu Asp Ala Arg Gly Gln Ala
                165                 170                 175

Met Val Phe Pro Tyr His Arg Pro Ser Pro Gly Ser Glu Ser Arg Val
            180                 185                 190

Arg Arg Glu Leu Gly Pro Glu Val Ile Gly Ser Val Val Met Leu Glu
        195                 200                 205

Ile Asp Asn Arg Leu Cys Leu Gln Ser Ala Glu Asn Asp His Cys Phe
    210                 215                 220

Pro Asp Ala Gln Ser Ala Ala Asp Tyr Leu Gly Ala Leu Ser Ala Val
225                 230                 235                 240

Glu Arg Leu Asp Phe Pro Tyr Pro Leu Arg Asp Val Arg Gly Glu Pro
                245                 250                 255

Leu Glu Ala Pro Glu Gln Ser Val Pro Gly Gly Ser Gly Gly Gly
            260                 265                 270

Leu Asn Asp Ile Phe Glu Ala Gln Lys Ile Glu Trp His Glu Gly Gly
        275                 280                 285

Pro Pro His His His His His His
    290                 295

<210> SEQ ID NO 4
<211> LENGTH: 888
<212> TYPE: DNA
<213> ORGANISM: Artificial Sequence
<220> FEATURE:
<223> OTHER INFORMATION: Synthetic nucleotide sequence

<400> SEQUENCE: 4
gcccctgagg tccccgagga gccacggtgc ccgcgagcgg cttgccaggc caagcgaggg      60
gaccagaact gcgatcgtga gtgcaacacc ccaggctgtg gctgggatgg cggtgactgc    120
tcactgaacg tggacgaccc ctggaggcag tgtgaggcac tgcagtgctg gcgtctcttc    180
aacaacagcc ggtgtgaccc ggcctgcagc tctccagcct gcctctatga caactttgac    240
tgctactctg gtggccgcga ccgcacctgc aaccctgttt atgagaagta ctgcgccgac    300
cactttgcag atggccgttg tgaccagggc tgcaacactg aggaatgcgg ctgggatggg    360
ctggactgtg ccagcgaggt cccggcccct ttggcccgag gggttctggt cctcacagtt    420
cttctgcctc ctgaagagtt gctgcgctcc agtgccgact tctgcagcg actcagcgct    480 attctgcgca cctcactgcg cttccgcttg gacgcacgtg gccaggccat ggtcttcccc    540
```

```
tatcaccggc caagccctgg ctctgaatcc cgggtccgtc gtgagctggg tcctgaggtg    600
atcggctctg tggtgatgct ggagattgac aaccggctct gtctgcagtc agctgagaat    660
gaccactgct tccctgatgc ccagagtgct gctgactacc tgggagcctt gtcagcagtg    720
gagcgacttg atttcccata cccacttcgg gatgtgcgag agagccgct ggaggccca     780 gagcagagcg tgccaggagg gggaagcgga ggcggactga acgacatctt cgaggctcag    840
aaaatcgaat ggcacgaagg tggcccacca catcatcatc atcatcac              888
```

<210> SEQ ID NO 5
<211> LENGTH: 117
<212> TYPE: PRT
<213> ORGANISM: Artificial Sequence
<220> FEATURE:
<223> OTHER INFORMATION: Synthetic peptide sequence

<400> SEQUENCE: 5

```
Glu Val Gln Leu Val Glu Ser Gly Gly Gly Leu Val Gln Pro Gly Arg
1               5                   10                  15

Ser Leu Thr Leu Ser Cys Val Ala Ser Gly Phe Thr Phe Arg Asp Tyr
            20                  25                  30

Gly Met Thr Trp Ile Arg Gln Ala Pro Gly Lys Gly Leu Thr Trp Val
        35                  40                  45

Ala Tyr Ile Ser Ser Gly Ser Asn Tyr Ile Tyr Tyr Ala Glu Ala Val
    50                  55                  60

Lys Gly Arg Phe Thr Ile Ser Arg Asp Asn Ala Lys Asn Thr Leu Tyr
65                  70                  75                  80

Leu Gln Met Thr Ser Leu Arg Ser Glu Asp Thr Ala Leu Tyr Phe Cys
                85                  90                  95

Thr Arg Arg Gly Pro Phe Val Leu Asp Ala Trp Gly Gln Gly Ala Ser
            100                 105                 110

Val Thr Val Ser Ser
        115
```

<210> SEQ ID NO 6
<211> LENGTH: 351
<212> TYPE: DNA
<213> ORGANISM: Artificial Sequence
<220> FEATURE:
<223> OTHER INFORMATION: Synthetic nucleotide sequence

<400> SEQUENCE: 6

```
gaggtgcaac tggtggagtc tggaggaggc ttagtgcagc ctggaaggtc cctgacactc     60
tcctgtgtag cctctggatt cactttcagg gactatggaa tgacctggat tcgccaggct    120
ccagggaagg ggctgacatg ggttgcatat attagtagtg gtagcaatta catctattat    180
gcagaagcgg tgaagggccg attcaccatc tccagagaca atgccaagaa caccctgtac    240
ctgcaaatga ccagtctgag gtctgaagac actgccttgt atttttgtac aagacgaggc    300
ccgtttgttt tggatgcctg gggtcaagga gcttcagtca ctgtctcctc a             351
```

<210> SEQ ID NO 7
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 7

Asp Ile Gln Met Thr Gln Ser Pro Ser Phe Leu Ser Ala Ser Val Gly
1               5                   10                  15

Asp Arg Val Thr Ile Asn Cys Lys Ala Ser Gln Ser Ile Asn Arg Tyr
            20                  25                  30

Leu His Trp Phe Gln Gln Lys Leu Gly Glu Ala Pro Lys Leu Leu Ile
        35                  40                  45

Tyr Asn Ala Asn Gly Leu Gln Thr Gly Ile Pro Ser Arg Phe Ser Gly
    50                  55                  60

Ser Gly Ser Gly Thr Asp Phe Thr Leu Thr Ile Ser Ser Leu Gln Ser
65              70                  75                  80

Glu Asp Val Ala Thr Tyr Phe Cys Leu Gln His Asn Thr Trp Pro Asp
                85                  90                  95

Thr Phe Gly Ala Gly Thr Lys Leu Glu Leu Lys
            100                 105

<210> SEQ ID NO 8
<211> LENGTH: 320
<212> TYPE: DNA
<213> ORGANISM: Artificial Sequence
<220> FEATURE:
<223> OTHER INFORMATION: Synthetic nucleotide sequence

<400> SEQUENCE: 8
gacatccaga tgacccagtc tccttcattc ctgtctgcat ctgtgggaga cagagtcact      60
atcaactgca aagcaagtca gagtattaac aggtacttac actggtttca gcagaaactt     120
ggagaagctc ccaaactcct gatatataat gcaaacggtt tgcaaacggg catcccatca     180
aggttcagtg gcagtggatc tggtactgat ttcacactta ccatcagcag cctgcagtct     240
gaagatgttg ccacatattt ctgcttgcag cataatacgt ggccggacac gtttggcgct     300
gggaccaagc tggaactgaa                                                 320

<210> SEQ ID NO 9
<211> LENGTH: 119
<212> TYPE: PRT
<213> ORGANISM: Artificial Sequence
<220> FEATURE:
<223> OTHER INFORMATION: Synthetic peptide sequence

<400> SEQUENCE: 9

Gln Val Lys Leu Leu Gln Ser Gly Ala Ala Leu Val Lys Pro Gly Ala
1               5                   10                  15

Ser Val Lys Met Ser Cys Lys Ala Ser Gly Tyr Ala Phe Thr Asp Tyr
            20                  25                  30

Trp Val Thr Trp Val Lys Gln Ser His Gly Lys Ser Leu Glu Trp Ile
        35                  40                  45

Gly Glu Ile Ser Pro Asn Ser Gly Gly Thr Asn Phe Asn Glu Lys Phe
    50                  55                  60

Lys Gly Lys Ala Thr Leu Thr Val Asp Lys Ser Thr Ser Thr Ala Tyr
65              70                  75                  80

Met Glu Leu Ser Arg Leu Thr Ser Glu Asp Ser Ala Ile Tyr Tyr Cys
                85                  90                  95

Thr Arg Gly Glu Ile Arg Tyr Asn Trp Phe Ala Tyr Trp Gly Gln Gly
            100                 105                 110

Thr Leu Val Thr Val Ser Ser
        115

<210> SEQ ID NO 10

<211> LENGTH: 357
<212> TYPE: DNA
<213> ORGANISM: Artificial Sequence
<220> FEATURE:
<223> OTHER INFORMATION: Synthetic nucleotide sequence

<400> SEQUENCE: 10

```
caggtcaagc tgctgcagtc tggggctgca ctggtgaagc ctggagcctc tgtgaagatg      60
tcttgcaaag cttctggtta tgcattcact gactactggg tgacctgggt gaagcagagt     120
catggaaaga gccttgagtg gattggggaa atttctccta acagtggtgg tactaacttc     180
aatgaaaagt tcaagggcaa ggccacattg actgtagaca atccaccag cacagcctat      240
atggagctca gcagattgac atctgaggac tctgcaatct attactgtac aagaggggaa     300
atccgttaca attggtttgc ttactgggggc caaggcactc tggtcactgt ctcctca       357
```

<210> SEQ ID NO 11
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 11

```
Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asn Val Gly Asn Asn
            20                  25                  30
Ile Ala Trp Tyr Gln Lys Pro Gly Lys Ala Pro Lys Leu Leu Ile
        35                  40                  45
Tyr Tyr Ala Ser Asn Arg Tyr Thr Gly Val Pro Ser Arg Phe Ser Gly
    50                  55                  60
Ser Gly Tyr Gly Thr Asp Phe Thr Leu Thr Ile Ser Ser Leu Gln Pro
65                  70                  75                  80
Glu Asp Phe Ala Thr Tyr Tyr Cys Gln Arg Leu Tyr Asn Ser Pro Phe
                85                  90                  95
Thr Phe Gly Gly Gly Thr Lys Val Glu Ile Lys
            100                 105
```

<210> SEQ ID NO 12
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 12

```
aacattgtga tgacccagtc tcccaaatcc atgtccatat cagtaggaga cagggtcacc      60
atgaactgca aggccagtca gaatgtgggt aataatatag cctggtatca acagaaacca     120
gggcagtctc ctaaactgtt gatctactat gcatctaacc ggtacactgg ggtccctgat     180
cgcttcacag gcggtggata tggacagat ttcactctca ccatcaatag tatgcaagct      240
gaagatgcag cctttttatta ctgtcagcgt ctttacaatt ctccattcac gttcggctca    300
gggacgaagt tggaaataaa g                                               321
```

<210> SEQ ID NO 13
<211> LENGTH: 117
<212> TYPE: PRT
<213> ORGANISM: Artificial Sequence
<220> FEATURE:

<223> OTHER INFORMATION: Synthetic peptide sequence

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Gly Met Thr Trp Val Arg Gln Ala Pro Gly Lys Gly Leu Glu Trp Val
        35                  40                  45

Ala Tyr Ile Ser Ser Gly Ser Asn Tyr Ile Tyr Tyr Ala Glu Ala Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Pro Phe Val Leu Asp Ala Trp Gly Gln Gly Thr Leu
            100                 105                 110

Val Thr Val Ser Ser
        115

<210> SEQ ID NO 14
<211> LENGTH: 351
<212> TYPE: DNA
<213> ORGANISM: Artificial Sequence
<220> FEATURE:
<223> OTHER INFORMATION: Synthetic nucleotide sequence

<400> SEQUENCE: 14
gaggtgcagc tggtggagtc tgggggaggc ttggtccagc ctggggggtc cctgagactc      60
tcctgtgcag cctctggatt cactttcagg gactatggaa tgacctgggt ccgccaggct     120
ccagggaagg ggctggagtg ggtggcctat attagtagtg gtagcaatta catctattat     180
gcagaagcgg tgaagggccg attcaccatc tccagagaca cgccaagaa ctcactgtat      240
ctgcaaatga acagcctgag agccgaggac acggctgtgt attactgtgc gagacgaggc     300
ccgtttgttt tggatgcctg gggccaggga accctggtca ccgtctcctc a              351

<210> SEQ ID NO 15
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 15

Asp Tyr Gly Met Thr
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 16

Gly Phe Thr Phe Arg Asp Tyr
1               5

<210> SEQ ID NO 17
<211> LENGTH: 15

```
<212> TYPE: DNA
<213> ORGANISM: Artificial Sequence
<220> FEATURE:
<223> OTHER INFORMATION: Synthetic nucleotide sequence

<400> SEQUENCE: 17
gactatggaa tgacc                                                      15

<210> SEQ ID NO 18
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 18
ggattcactt tcagggacta t                                               21

<210> SEQ ID NO 19
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 19

Tyr Ile Ser Ser Gly Ser Asn Tyr Ile Tyr Tyr Ala Glu Ala Val Lys
1               5                   10                  15

Gly

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 20

Ser Ser Gly Ser Asn Tyr
1               5

<210> SEQ ID NO 21
<211> LENGTH: 51
<212> TYPE: DNA
<213> ORGANISM: Artificial Sequence
<220> FEATURE:
<223> OTHER INFORMATION: Synthetic nucleotide sequence

<400> SEQUENCE: 21
tatattagta gtggtagcaa ttacatctat tatgcagaag cggtgaaggg c              51

<210> SEQ ID NO 22
<211> LENGTH: 18
<212> TYPE: DNA
<213> ORGANISM: Artificial Sequence
<220> FEATURE:
<223> OTHER INFORMATION: Synthetic nucleotide sequence

<400> SEQUENCE: 22
agtagtggta gcaattac                                                   18

<210> SEQ ID NO 23
<211> LENGTH: 8
<212> TYPE: PRT
<213> ORGANISM: Artificial Sequence
<220> FEATURE:
```

<223> OTHER INFORMATION: Synthetic peptide sequence

<400> SEQUENCE: 23

Arg Gly Pro Phe Val Leu Asp Ala
1               5

<210> SEQ ID NO 24
<211> LENGTH: 24
<212> TYPE: DNA
<213> ORGANISM: Artificial Sequence
<220> FEATURE:
<223> OTHER INFORMATION: Synthetic nucleotide sequence

<400> SEQUENCE: 24
cgaggcccgt ttgttttgga tgcc                                          24

<210> SEQ ID NO 25
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Ile Asn Arg Tyr
            20                  25                  30

Leu His Trp Tyr Gln Gln Lys Pro Gly Lys Ala Pro Lys Leu Leu Ile
        35                  40                  45

Tyr Asn Ala Asn Gly Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Thr Trp Pro Asp
                85                  90                  95

Thr Phe Gly Gly Gly Thr Lys Val Glu Ile Lys
            100                 105

<210> SEQ ID NO 26
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 26
gacatccaga tgacccagtc tccatcctcc ctgtctgcat ctgtaggaga cagagtcacc      60
atcacttgca aagcaagtca gagtattaac aggtacttac actggtatca gcagaaacca    120
gggaaagccc ctaagctcct gatctataat gcaaacggtt tgcaaacggg ggtcccatca    180
aggttcagtg gcagtggatc tgggacagat ttcactctca ccatcagcag tctgcaacct    240
gaagattttg caacttacta ctgtttgcag cataatacgt ggccggacac gtttggcgga    300
gggaccaagg tggagatcaa a                                              321

<210> SEQ ID NO 27
<211> LENGTH: 11
<212> TYPE: PRT
<213> ORGANISM: Artificial Sequence
<220> FEATURE:
<223> OTHER INFORMATION: Synthetic peptide sequence

```
<400> SEQUENCE: 27

Lys Ala Ser Gln Ser Ile Asn Arg Tyr Leu His
1               5                   10

<210> SEQ ID NO 28
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 28
aaagcaagtc agagtattaa caggtactta cac                            33

<210> SEQ ID NO 29
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 29

Asn Ala Asn Gly Leu Gln Thr
1               5

<210> SEQ ID NO 30
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 30
aatgcaaacg gtttgcaaac g                                         21

<210> SEQ ID NO 31
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 31

Leu Gln His Asn Thr Trp Pro Asp Thr
1               5

<210> SEQ ID NO 32
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 32
ttgcagcata atacgtggcc ggacacgttt                                30

<210> SEQ ID NO 33
<211> LENGTH: 446
<212> TYPE: PRT
<213> ORGANISM: Artificial Sequence
<220> FEATURE:
<223> OTHER INFORMATION: Synthetic peptide sequence

<400> SEQUENCE: 33

Glu Val Gln Leu Val Glu Ser Gly Gly Gly Leu Val Gln Pro Gly Gly
```

-continued

```
1               5                   10                  15
Ser Leu Arg Leu Ser Cys Ala Ala Ser Gly Phe Thr Phe Arg Asp Tyr
            20                  25                  30
Gly Met Thr Trp Val Arg Gln Ala Pro Gly Lys Gly Leu Glu Trp Val
            35                  40                  45
Ala Tyr Ile Ser Ser Gly Ser Asn Tyr Ile Tyr Ala Glu Ala Val
        50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Arg Gly Pro Phe Val Leu Asp Ala Trp Gly Gln Gly Thr Leu
            100                 105                 110
Val Thr Val Ser Ser Ala Ser Thr Lys Gly Pro Ser Val Phe Pro Leu
            115                 120                 125
Ala Pro Ser Ser Lys Ser Thr Ser Gly Gly Thr Ala Ala Leu Gly Cys
            130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
            195                 200                 205
Thr Lys Val Asp Lys Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
```

His Asn His Tyr Thr Gln Lys Ser Leu Ser Leu Ser Pro Gly
        435                 440                 445

<210> SEQ ID NO 34
<211> LENGTH: 1338
<212> TYPE: DNA
<213> ORGANISM: Artificial Sequence
<220> FEATURE:
<223> OTHER INFORMATION: Synthetic nucleotide sequence

<400> SEQUENCE: 34

| | | | | |
|---|---|---|---|---|
| gaggtgcagc tggtggagtc tgggggaggc ttggtccagc ctggggggtc cctgagactc | | | | 60 |
| tcctgtgcag cctctggatt cactttcagg gactatggaa tgacctgggt ccgccaggct | | | | 120 |
| ccagggaagg gctggagtg gtggcctat attagtagtg gtagcaatta catctattat | | | | 180 |
| gcagaagcgg tgaagggccg attcaccatc tccagagaca cgccaagaa ctcactgtat | | | | 240 |
| ctgcaaatga acagcctgag agccgaggac acggctgtgt attactgtgc gagacgaggc | | | | 300 |
| ccgtttgttt tggatgcctg gggccaggga accctggtca ccgtctcctc agcgtcgacc | | | | 360 |
| aagggcccat cggtcttccc cctggcaccc tcctccaaga gcacctctgg gggcacagcg | | | | 420 |
| gccctgggct gcctggtcaa ggactacttc cccgaaccgg tgacggtgtc gtggaactca | | | | 480 |
| ggcgccctga ccagcggcgt gcacaccttc ccggctgtcc tacagtcctc aggactctac | | | | 540 |
| tccctcagca gcgtggtgac cgtgccctcc agcagcttgg gcacccagac ctacatctgc | | | | 600 |
| aacgtgaatc acaagcccag caacaccaag gtggacaaga agttgagcc caaatcttgt | | | | 660 |
| gacaaaactc acacatgccc accgtgccca gcacctgaac tcctgggggg accgtcagtc | | | | 720 |
| ttcctcttcc ccccaaaacc caaggacacc ctcatgatct cccggacccc tgaggtcaca | | | | 780 |
| tgcgtggtgg tggacgtgag ccacgaagac cctgaggtca agttcaactg gtacgtggac | | | | 840 |
| ggcgtggagg tgcataatgc caagacaaag ccgcgggagg agcagtacaa cagcacgtac | | | | 900 |
| cgtgtggtca gcgtcctcac cgtcctgcac caggactggc tgaatggcaa ggagtacaag | | | | 960 |
| tgcaaggtct ccaacaaagc cctcccagcc cccatcgaga aaaccatctc caaagccaaa | | | | 1020 |
| gggcagcccc gagaaccaca ggtgtacacc ctgcccccat cccgggagga gatgaccaag | | | | 1080 |
| aaccaggtca gcctgacctg cctggtcaaa ggcttctatc ccagcgacat cgccgtggag | | | | 1140 |
| tgggagagca atgggcagcc ggagaacaac tacaagacca cgcctcccgt gctggactcc | | | | 1200 |
| gacggctcct tcttcctcta tagcaagctc accgtggaca agagcaggtg gcagcagggg | | | | 1260 |
| aacgtcttct catgctccgt gatgcatgag gctctgcaca accactacac gcagaagagc | | | | 1320 |
| ctctccctgt ccccgggt | | | | 1338 |

<210> SEQ ID NO 35
<211> LENGTH: 214
<212> TYPE: PRT
<213> ORGANISM: Artificial Sequence
<220> FEATURE:
<223> OTHER INFORMATION: Synthetic peptide sequence

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Ile Asn Arg Tyr
            20                  25                  30

Leu His Trp Tyr Gln Gln Lys Pro Gly Lys Ala Pro Lys Leu Leu Ile
        35                  40                  45

```
Tyr Asn Ala Asn Gly Leu Gln Thr Gly Val Pro Ser Arg Phe Ser Gly
     50                  55                  60
Ser Gly Ser Gly Thr Asp Phe Thr Leu Thr Ile Ser Ser Leu Gln Pro
 65              70                  75                  80
Glu Asp Phe Ala Thr Tyr Tyr Cys Leu Gln His Asn Thr Trp Pro Asp
                 85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
            195                 200                 205
Phe Asn Arg Gly Glu Cys
210
```

<210> SEQ ID NO 36
<211> LENGTH: 642
<212> TYPE: DNA
<213> ORGANISM: Artificial Sequence
<220> FEATURE:
<223> OTHER INFORMATION: Synthetic nucleotide sequence

<400> SEQUENCE: 36

```
gacatccaga tgacccagtc tccatcctcc ctgtctgcat ctgtaggaga cagagtcacc    60
atcacttgca aagcaagtca gagtattaac aggtacttac actggtatca gcagaaacca   120
gggaaagccc ctaagctcct gatctataat gcaaacggtt tgcaaacggg ggtcccatca   180
aggttcagtg gcagtggatc tgggacagat ttcactctca ccatcagcag tctgcaacct   240
gaagattttg caacttacta ctgtttgcag cataatacgt ggccggacac gtttggcgga   300
gggaccaagg tggagatcaa acggaccgtg gccgctcctt ccgtgttcat cttcccccct   360
tccgacgagc agctgaagtc tggcaccgcc tctgtggtgt gtctgctgaa caacttctac   420
cccggggagg ccaaggtgca gtggaaggtg gacaacgctc tgcagtccgg caactcccag   480
gagtctgtga ccgagcagga ctccaaggac agcacctact ccctgtcctc tacctgacc   540
ctgtccaagg ccgactacga gaagcacaag gtgtacgcct gtgaggtgac ccaccagggc   600
ctgtcctctc ctgtgaccaa gtccttcaac cggggcgagt gc                       642
```

<210> SEQ ID NO 37
<211> LENGTH: 119
<212> TYPE: PRT
<213> ORGANISM: Artificial Sequence
<220> FEATURE:
<223> OTHER INFORMATION: Synthetic peptide sequence

<400> SEQUENCE: 37

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Tyr Ala Phe Thr Asp Tyr
```

```
            20                  25                  30
Trp Met Thr Trp Val Arg Gln Ala Pro Gly Lys Gly Leu Glu Trp Val
        35                  40                  45

Ala Glu Ile Ser Pro Asn Ser Gly Gly Thr Asn Phe Asn Glu Lys Phe
    50                  55                  60

Lys Gly Arg Phe Thr Ile Ser Val Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Glu Ile Arg Tyr Asn Trp Phe Ala Tyr Trp Gly Gln Gly
            100                 105                 110

Thr Leu Val Thr Val Ser Ser
        115
```

<210> SEQ ID NO 38
<211> LENGTH: 357
<212> TYPE: DNA
<213> ORGANISM: Artificial Sequence
<220> FEATURE:
<223> OTHER INFORMATION: Synthetic nucleotide sequence

<400> SEQUENCE: 38

| | | | | | |
|---|---|---|---|---|---|
| gaggtgcagc | tggtggagtc | tgggggaggc | ttggtccagc | ctgggggtc | cctgagactc | 60 |
| tcctgtgcag | cctctggtta | tgcattcact | gactactgga | tgacctgggt | ccgccaggct | 120 |
| ccagggaagg | ggctggagtg | ggtggccgaa | atttctccta | acagtggtgg | tactaacttc | 180 |
| aatgaaaagt | tcaagggccg | attcaccatc | tccgttgaca | acgccaagaa | ctcactgtat | 240 |
| ctgcaaatga | acagcctgag | agccgaggac | acggctgtgt | attactgtgc | gagaggggaa | 300 |
| atccgttaca | attggtttgc | ttactggggc | cagggaaccc | tggtcaccgt | ctcctca | 357 |

<210> SEQ ID NO 39
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 39

Asp Tyr Trp Met Thr
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 40

Gly Tyr Ala Phe Thr Asp Tyr
1               5

<210> SEQ ID NO 41
<211> LENGTH: 15
<212> TYPE: DNA
<213> ORGANISM: Artificial Sequence
<220> FEATURE:
<223> OTHER INFORMATION: Synthetic nucleotide sequence

<400> SEQUENCE: 41
gactactgga tgacc                                                      15

<210> SEQ ID NO 42
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 42
ggttatgcat tcactgacta c                                        21

<210> SEQ ID NO 43
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 43

Glu Ile Ser Pro Asn Ser Gly Gly Thr Asn Phe Asn Glu Lys Phe Lys
1               5                   10                  15

Gly

<210> SEQ ID NO 44
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 44

Ser Pro Asn Ser Gly Gly
1               5

<210> SEQ ID NO 45
<211> LENGTH: 51
<212> TYPE: DNA
<213> ORGANISM: Artificial Sequence
<220> FEATURE:
<223> OTHER INFORMATION: Synthetic nucleotide sequence

<400> SEQUENCE: 45
gaaatttctc ctaacagtgg tggtactaac ttcaatgaaa agttcaaggg c        51

<210> SEQ ID NO 46
<211> LENGTH: 18
<212> TYPE: DNA
<213> ORGANISM: Artificial Sequence
<220> FEATURE:
<223> OTHER INFORMATION: Synthetic nucleotide sequence

<400> SEQUENCE: 46
tctcctaaca gtggtggt                                            18

<210> SEQ ID NO 47
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 47

Gly Glu Ile Arg Tyr Asn Trp Phe Ala Tyr
1               5                   10

```
<210> SEQ ID NO 48
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 48
ggggaaatcc gttacaattg gtttgcttac                                       30

<210> SEQ ID NO 49
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Asn Asn
            20                  25                  30

Ile Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Arg Leu Tyr Asn Ser Pro Phe
                85                  90                  95

Thr Phe Gly Gly Gly Thr Lys Val Glu Ile Lys
            100                 105

<210> SEQ ID NO 50
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 50
gacatccaga tgacccagtc tccatcctcc ctgtctgcat ctgtaggaga cagagtcacc      60
atcacttgca aggccagtca gaatgtgggt aataatatag cctggtatca gcagaaacca     120
gggaaagccc ctaagctcct gatctattat gcatctaacc ggtacactgg ggtcccatca     180
aggttcagtg gcagtggata tgggacagat ttcactctca ccatcagcag tctgcaacct     240
gaagattttg caacttacta ctgtcagcgt ctttacaatt ctccattcac gttcggcgga     300
gggaccaagg tggagatcaa a                                                321

<210> SEQ ID NO 51
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 51

Lys Ala Ser Gln Asn Val Gly Asn Asn Ile Ala
1               5                   10

<210> SEQ ID NO 52
```

```
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 52
aaggccagtc agaatgtggg taataatata gcc                              33

<210> SEQ ID NO 53
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 53

Tyr Ala Ser Asn Arg Tyr Thr
1               5

<210> SEQ ID NO 54
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 54
tatgcatcta accggtacac t                                           21

<210> SEQ ID NO 55
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 55

Gln Arg Leu Tyr Asn Ser Pro Phe Thr
1               5

<210> SEQ ID NO 56
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 56
cagcgtcttt acaattctcc attcacgttc                                  30

<210> SEQ ID NO 57
<211> LENGTH: 448
<212> TYPE: PRT
<213> ORGANISM: Artificial Sequence
<220> FEATURE:
<223> OTHER INFORMATION: Synthetic peptide sequence

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asp Tyr
            20                  25                  30

Trp Met Thr Trp Val Arg Gln Ala Pro Gly Lys Gly Leu Glu Trp Val
        35                  40                  45
```

```
Ala Glu Ile Ser Pro Asn Ser Gly Gly Thr Asn Phe Asn Glu Lys Phe
        50                  55                  60

Lys Gly Arg Phe Thr Ile Ser Val Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Glu Ile Arg Tyr Asn Trp Phe Ala Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445

<210> SEQ ID NO 58
<211> LENGTH: 1344
<212> TYPE: DNA
<213> ORGANISM: Artificial Sequence
<220> FEATURE:
<223> OTHER INFORMATION: Synthetic nucleotide sequence

<400> SEQUENCE: 58
gaggtgcagc tggtggagtc tgggggaggc ttggtccagc ctggggggtc cctgagactc      60
tcctgtgcag cctctggtta tgcattcact gactactgga tgacctgggt ccgccaggct     120
ccagggaagg ggctggagtg ggtggccgaa atttctccta acagtggtgg tactaacttc     180
aatgaaaagt tcaagggccg attcaccatc tccgttgaca cgccaagaa ctcactgtat      240
ctgcaaatga acagcctgag agccgaggac acggctgtgt attactgtgc gagaggggaa     300
atccgttaca attggtttgc ttactggggc cagggaaccc tggtcaccgt ctcctcagcg     360
tcgaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactcacac atgcccaccg tgcccagcac ctgaactcct ggggggaccg     720
tcagtcttcc tcttccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
```

-continued

```
gccaagggc agccccgaga accacaggtg tacaccctgc ccccatcccg ggaggagatg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctatagc aagctcaccg tggacaagag caggtggcag    1260
caggggaacg tcttctcatg ctccgtgatg catgaggctc tgcacaacca ctacacgcag    1320
aagagcctct ccctgtcccc gggt                                          1344
```

<210> SEQ ID NO 59
<211> LENGTH: 214
<212> TYPE: PRT
<213> ORGANISM: Artificial Sequence
<220> FEATURE:
<223> OTHER INFORMATION: Synthetic peptide sequence

<400> SEQUENCE: 59

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Asn Asn
            20                  25                  30

Ile Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Arg Leu Tyr Asn Ser Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 60
<211> LENGTH: 642
<212> TYPE: DNA
<213> ORGANISM: Artificial Sequence
<220> FEATURE:
<223> OTHER INFORMATION: Synthetic nucleotide sequence

<400> SEQUENCE: 60

```
gacatccaga tgacccagtc tccatcctcc ctgtctgcat ctgtaggaga cagagtcacc      60
atcacttgca aggccagtca gaatgtgggt aataatatag cctggtatca gcagaaacca     120
```

```
gggaaagccc ctaagctcct gatctattat gcatctaacc ggtacactgg ggtcccatca    180
aggttcagtg gcagtggata tgggacagat ttcactctca ccatcagcag tctgcaacct    240
gaagattttg caacttacta ctgtcagcgt ctttacaatt ctccattcac gttcggcgga    300
gggaccaagg tggagatcaa acggaccgtg gccgctcctt ccgtgttcat cttcccccct    360
tccgacgagc agctgaagtc tggcaccgcc tctgtggtgt gtctgctgaa caacttctac    420
ccccgggagg ccaaggtgca gtggaaggtg gacaacgctc tgcagtccgg caactcccag    480
gagtctgtga ccgagcagga ctccaaggac agcacctact ccctgtcctc taccctgacc    540
ctgtccaagg ccgactacga aagcacaag gtgtacgcct gtgaggtgac ccaccagggc    600
ctgtcctctc ctgtgaccaa gtccttcaac cggggcgagt gc    642
```

<210> SEQ ID NO 61
<211> LENGTH: 446
<212> TYPE: PRT
<213> ORGANISM: Artificial Sequence
<220> FEATURE:
<223> OTHER INFORMATION: Synthetic peptide sequence

<400> SEQUENCE: 61

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Gly Met Thr Trp Val Arg Gln Ala Pro Gly Lys Gly Leu Glu Trp Val
        35                  40                  45

Ala Tyr Ile Ser Ser Gly Ser Asn Tyr Ile Tyr Tyr Ala Glu Ala Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Pro Phe Val Leu Asp Ala Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270
```

```
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
        290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Cys Ser Pro Gly
        435                 440                 445
```

<210> SEQ ID NO 62
<211> LENGTH: 1338
<212> TYPE: DNA
<213> ORGANISM: Artificial Sequence
<220> FEATURE:
<223> OTHER INFORMATION: Synthetic nucleotide sequence

<400> SEQUENCE: 62

```
gaggtgcagc tggtggagtc tgggggaggc ttggtccagc ctggggggtc cctgagactc      60
tcctgtgcag cctctggatt cactttcagg gactatggaa tgacctgggt ccgccaggct     120
ccagggaagg ggctggagtg ggtggcctat attagtagtg gtagcaatta catctattat     180
gcagaagcgg tgaagggccg attcaccatc tccagagaca cgccaagaa ctcactgtat      240
ctgcaaatga acagcctgag agccgaggac acggctgtgt attactgtgc gagacgaggc     300
ccgtttgttt tggatgcctg gggccaggga accctggtca ccgtctcctc agcgtcgacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt      660
gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc ccatcgaga aaaccatctc caaagccaaa     1020
gggcagcccc gagaaccaca ggtgtacacc ctgcccccat cccgggagga gatgaccaag    1080
```

```
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta tagcaagctc accgtggaca agagcaggtg gcagcagggg    1260
aacgtcttct catgctccgt gatgcatgag gctctgcaca accactacac gcagaagagc    1320
ctctcctgct ccccgggt                                                  1338
```

<210> SEQ ID NO 63
<211> LENGTH: 214
<212> TYPE: PRT
<213> ORGANISM: Artificial Sequence
<220> FEATURE:
<223> OTHER INFORMATION: Synthetic peptide sequence

<400> SEQUENCE: 63

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Ile Asn Arg Tyr
            20                  25                  30

Leu His Trp Tyr Gln Gln Lys Pro Gly Lys Ala Pro Lys Leu Leu Ile
        35                  40                  45

Tyr Asn Ala Asn Gly Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Thr Trp Pro Asp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Cys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 64
<211> LENGTH: 642
<212> TYPE: DNA
<213> ORGANISM: Artificial Sequence
<220> FEATURE:
<223> OTHER INFORMATION: Synthetic nucleotide sequence

<400> SEQUENCE: 64

```
gacatccaga tgacccagtc tccatcctcc ctgtctgcat ctgtaggaga cagagtcacc     60
atcacttgca aagcaagtca gagtattaac aggtacttac actggtatca gcagaaacca    120
gggaaagccc ctaagctcct gatctataat gcaaacggtt tgcaaacggg ggtcccatca    180
aggttcagtg gcagtggatc tgggacagat ttcactctca ccatcagcag tctgcaacct    240
```

-continued

```
gaagattttg caacttacta ctgtttgcag cataatacgt ggccggacac gtttggcgga     300
gggaccaagg tggagatcaa acgaactgtg gctgcaccat ctgtcttcat cttcccgcca     360
tctgatgagc agttgaaatc tggaactgcc tctgttgtgt gcctgctgaa taacttctat     420
cccagagagc caaagtaca gtggaaggtg ataacgccc tccaatcggg taactcccag       480
gagagtgtca cagagcagga cagcaaggac agcacctaca gcctcagcag caccctgacg     540
ctgagctgcg cagactacga gaaacacaaa gtctacgcct gcgaagtcac ccatcagggc     600
ctgagctcgc ccgtcacaaa gagcttcaac aggggagagt gt                        642
```

<210> SEQ ID NO 65
<211> LENGTH: 446
<212> TYPE: PRT
<213> ORGANISM: Artificial Sequence
<220> FEATURE:
<223> OTHER INFORMATION: Synthetic peptide sequence

<400> SEQUENCE: 65

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Gly Met Thr Trp Val Arg Gln Ala Pro Gly Lys Gly Leu Glu Trp Val
        35                  40                  45

Ala Tyr Ile Ser Ser Gly Ser Asn Tyr Ile Tyr Tyr Ala Glu Ala Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Pro Phe Val Leu Asp Ala Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285
```

```
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Cys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Cys Ser Pro Gly
        435                 440                 445
```

<210> SEQ ID NO 66
<211> LENGTH: 1338
<212> TYPE: DNA
<213> ORGANISM: Artificial Sequence
<220> FEATURE:
<223> OTHER INFORMATION: Synthetic nucleotide sequence

<400> SEQUENCE: 66

```
gaggtgcagc tggtggagtc tgggggaggc ttggtccagc ctgggggtc cctgagactc      60
tcctgtgcag cctctggatt cactttcagg gactatggaa tgacctgggt ccgccaggct    120
ccagggaagg gctggagtg gtggcctat attagtagtg gtagcaatta catctattat     180
gcagaagcgg tgaagggccg attcaccatc tccagagaca cgccaagaa ctcactgtat    240
ctgcaaatga acagcctgag agccgaggac acggctgtgt attactgtgc gagacgaggc    300
ccgtttgttt tggatgcctg gggccaggga accctggtca ccgtctcctc agcgtcgacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc cggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660
gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
ggcagcccc gagaaccaca ggtgtacacc ctgcccccat cccgggagga tgaccaag    1080
aaccaggtca gcctgacctg cctggtcaaa ggcttctatc ccagcgacat cgccgtggag   1140
tgggagagca atgggcagcc ggagaacaac tactgcacca cgcctcccgt gctggactcc   1200
```

```
gacggctcct tcttcctcta tagcaagctc accgtggaca agagcaggtg gcagcagggg    1260
aacgtcttct catgctccgt gatgcatgag gctctgcaca accactacac gcagaagagc    1320
ctctcctgct ccccgggt                                                  1338
```

<210> SEQ ID NO 67
<211> LENGTH: 113
<212> TYPE: PRT
<213> ORGANISM: Artificial Sequence
<220> FEATURE:
<223> OTHER INFORMATION: Synthetic peptide sequence

<400> SEQUENCE: 67

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Phe Asp Tyr Trp Gly Gln Gly Thr Leu Val Thr Val Ser
            100                 105                 110

Ser
```

<210> SEQ ID NO 68
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 68

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105
```

<210> SEQ ID NO 69
<211> LENGTH: 11
<212> TYPE: DNA
<213> ORGANISM: Artificial Sequence
<220> FEATURE:
<223> OTHER INFORMATION: Synthetic nucleotide sequence

```
<400> SEQUENCE: 69
cgtgggaaaa t                                                                11
```